(12) United States Patent
Hutcheon et al.

(10) Patent No.: US 9,035,131 B2
(45) Date of Patent: May 19, 2015

(54) **ISOLATION AND USE OF FAD2 AND FAE1 FROM *CAMELINA***

(75) Inventors: Carolyn Hutcheon, Kirkland, WA (US); Renata F. Ditt, Seattle, WA (US); Christine K. Shewmaker, Woodland, CA (US)

(73) Assignee: Global Clean Energy Holdings, Inc, Long Beach, CA (US)

( * ) Notice: Subject to any disclaimer, the term of this patent is extended or adjusted under 35 U.S.C. 154(b) by 845 days.

(21) Appl. No.: 13/072,122

(22) Filed: Mar. 25, 2011

(65) Prior Publication Data

US 2011/0239323 A1 Sep. 29, 2011

Related U.S. Application Data

(60) Provisional application No. 61/318,273, filed on Mar. 26, 2010, provisional application No. 61/346,410, filed on May 19, 2010.

(51) Int. Cl.
| | | |
|---|---|---|
| *A01H 5/10* | (2006.01) | |
| *C12N 9/10* | (2006.01) | |
| *C12N 15/82* | (2006.01) | |
| *A01H 1/00* | (2006.01) | |
| *C12N 9/02* | (2006.01) | |
| *A01H 1/06* | (2006.01) | |

(52) U.S. Cl.
CPC .. *A01H 5/10* (2013.01); *A01H 1/00* (2013.01); *C12N 9/0004* (2013.01); *A01H 1/06* (2013.01); *C12N 9/0083* (2013.01); *C12N 9/1029* (2013.01); *C12N 15/8247* (2013.01)

(58) Field of Classification Search
None
See application file for complete search history.

(56) References Cited

U.S. PATENT DOCUMENTS

| | | | |
|---|---|---|---|
| 6,124,524 A * | 9/2000 | James et al. | 800/281 |
| 2002/0104124 A1 | 8/2002 | Green et al. | |
| 2008/0066203 A1 | 3/2008 | Lightner et al. | |

OTHER PUBLICATIONS

Buchsenschutz-Nothdurft and Friedt 1998 Industrial Crops and Products 7: p. 291-295.*
Lu and Kang 2008 Plant Cell Reports 27: p. 273-278.*
Smith et al 2000 Nature Sep. 21: p. 319-320.*
International Search Report based on International Patent Application No. PCT/US2011/029966, mailed on Aug. 8, 2011.
Hutcheon et al.: Polyploid genome of *Camelina sativa* revealed by isolation of fatty acid synthesis genes. BMC Plant Biology 2010 10:233.
Kang et al., Identification of three genes encoding microsomal oleate desaturases from the oilseed crop *Camelina sativa*. Plant Physiology and Biochemistry (2011) 49: 223-229.
Lu et al., A high-throughput screen for genes from castor that boost hydroxyl fatty acid accumulation in seed oils of transgenic *Arabidopsis*, The Plant Journal (2006) 45: 847-856.

* cited by examiner

*Primary Examiner* — Eileen B O Hara
*Assistant Examiner* — Matthew Keogh
(74) *Attorney, Agent, or Firm* — Saliwanchik, Lloyd & Eisenschenk

(57) ABSTRACT

The present invention provides isolated FAD2 and FAE1 genes and FAD2 and FAE1 protein sequences of *Camelina* species, e.g., *Camelina sativa*, mutations in *Camelina* FAD2 and FAE1 genes, and methods of using the same. In addition, methods of altering *Camelina* seed composition and/or improving *Camelina* seed oil quality are disclosed. Furthermore, methods of breeding *Camelina* cultivars and/or other closely related species to produce plants having altered or improved seed oil and/or meal quality are provided.

4 Claims, 16 Drawing Sheets

FIGURE 2A

```
CsFAD2_A    1   MGAGGRMPVP SSS.....KKSETDAIKRVPCEKPPFTLG LKKAIPP CFKRSIPRSFS
CsFAD2_B    1   MGAGGRMPVP SSS.....KKSETDAIKRVPCEKPPFTLG LKKAIPP CFKRSIPRSFS
CsFAD2_C    1   MGAGGRMPVP SSS.....KKSETDAIKRVPCEKPPFTLG LKKAIPP CFKRSIPRSFS
AtFAD2      1   MGAGGRMPVP SS......KKSETDTT KRVPCEKPPF VG LKKAIPPHCFKRSIPRSFS
BrFAD2      1   MGAGGRM QVSPPS.....KKSETDN IKRVPCE TPPFT G LKKAIPPHCFKRSIPRSFS
GmFAD2-3    1   MGAGGRTD VPPAN...... KSEVDP KRVPF EKPPF LSQ KKV IPPHCF QRS F RSFS
ZmFAD2      1   MGAGGRM TEKEREKQEQLA A GGAA M RS PVEKPPFTLG KKAIPPHCF ERS L SFS
                                                                         H1
CsFAD2_A   56   YLI DII IASCFYYVATNYFSLLPQPLSYLAWPLYWACQGCVLTGVWVIA HECGH HAFSD
CsFAD2_B   56   YLI DII ASCFYYVATNYFSLLPQPLSYLAWPLYWACQGCVLTGVWVIA HECGH HAFSD
CsFAD2_C   56   YLI DII ASCFYYVATNYFSLLPQPLSYLAWPLYWACQGCVLTGVWVIA HECGH HAFSD
AtFAD2     55   YLI DIIIASCFYYVATNYFSLLPQPLSYLAWPLYWACQGCVLTG WVIA HECGH HAFSD
BrFAD2     55   YLI WDIIIASCFYYVATT YF PLLP HPLSY F AWPLYWACQGCVLTGVWVIA HECGH HAFSD
GmFAD2-3   55   Y YD TIA C LYYVATH YF HLLPSPLS LAWP YWA VQGC LTGVWVIA HECGH HAFSD
ZmFAD2     61   Y HD VIAAALL Y F ALAIIPALPSL G Y AAWPLYW IAQGCV C TGVWVIA HECGH HAFSD
                                             H2
CsFAD2_A  116   YQWLDDTVGLIFHSFLLVPYFSWKYS HRRHH SNTGSLERDEVFVPKQKSAIKWYGKYLNN
CsFAD2_B  116   YQWLDDTVGLIFHSFLLVPYFSWKYS HRRHH SNTGSLERDEVFVPKQKSAIKWYGKYLNN
CsFAD2_C  116   YQWLDDTVGLIFHSFLLVPYFSWKYS HRRHH SNTGSLERDEVFVPKQKSAIKWYGKYLNN
AtFAD2    115   YQWLDDTVGLIFHSFLLVPYFSWKYS HRRHH SNTGSLERDEVFVPKQKSAIKWYGKYLNN
BrFAD2    115   YQWLDDTVGLIFHSFLLVPYFSWKYS HRRHH SNTGSLERDEVFVPK KKSD IKWYGKYLNN
GmFAD2-3  115   YC LDDI VGL LHS G LLVPYFSWKYS HRRHH SNTGSLERDEVFVPKQ KSC IKWY SKYLNN
ZmFAD2    121   YS LDDV VGL LHSS L VPYFSWKYS HRRHH SNTGSLERDEVFVPK KKEA LPWYTPY VYN

CsFAD2_A  176   . P AGRIMMLTVQFVLGWPLYLAFNVSGRPYDG. FACHFFPNAPIYNDRERLQIYLSDAGI
CsFAD2_B  176   . PP GRIMMLTVQFVLGWPLYLAFNVSGRPYDG. FACHFFPNAPIYNDRERLQIYLSDAGI
CsFAD2_C  176   . P AGRIMMLTVQFVLGWPLYLAFNVSGRPYDG. FACHFFPNAPIYNDRERLQIYLSDAGI
AtFAD2    175   . PL GRIMMLTVQFVLGWPLYLAFNVSGRPYDG. FACHFFPNAPIYNDRERLQIYLSDAGI
BrFAD2    175   . PL GRT V MLTVQFT LGWPLYLAFNVSGRPYDGG FACHF H PNAPIYNDRERLQIY SDAGI
GmFAD2-3  175   . PP GR V TLAV TLT LGWPLYLA L NVSGRPYD R. FAS H LDP YS PIY SDN ERLQIY SDAG
ZmFAD2    181   NP VGR L AH VVQ LTLGWPLYLAT NA SGRPY PR. FACHF DP Y P LYNDRERA QI SDAG V

CsFAD2_A  234   LAVCFGLYRYAAAQG ASMICLYGVPLLIVNAFLVLITYLQHTHPALPHYDSSEWDWLRG
CsFAD2_B  234   LAVCFGLYRYAAAQG ASMICLYGVPLLIVNAFLVLITYLQHTHPALPHYDSSEWDWLRG
CsFAD2_C  234   LAVCFGLYRYAAAQG ASMICLYGVPLLIVNAFLVLITYLQHTHPALPHYDSSEWDWLRG
AtFAD2    233   LAVCFGLYRYAAAQG ASMICLYGVPLLIVNAFLVLITYLQHTHPS LPHYDSSEWDWLRG
BrFAD2    234   LAVC GLYRYAA VQG ASM C F YGVPLLIVN F LVLITYLQHTHPS L PHYDSSEWDWLRG
GmFAD2-3  233   LAVC GL C LAMA KG AW CN YGVPLL VN FLVLIT LQHTHPALPHY T SSEWDWLRG
ZmFAD2    240   AAVA FGLY K LAAAF G WW VR Y VPLLIVNA LVLITYLQHTHPS LPHYDSSEWDWLRG
                                            H3
CsFAD2_A  294   ALA TVDRDYGILNKVFHNITDT HVAHH LFSTMPHYNAMEATKAIKPILGDYYQFDGTPWY
CsFAD2_B  294   ALATVDRDYGILNKVFHNITDT HVAHH LFSTMPHYNAMEATKAIKPILGDYYQFDGTPWY
CsFAD2_C  294   ALATVDRDYGILNKVFHNITDT HVAHH LFSTMPHYNAMEATKAIKPILGDYYQFDGTPWY
AtFAD2    293   ALATVDRDYGILNKVFHNITDT HVAHH LFSTMPHYNAMEATKAIKPILGDYYQFDGTPWY
BrFAD2    294   ALATVDRDYGILNKVFHNITDT HVAHH LFSTMPHY H AMEATKAIKPILG YYQFDGTP VV
GmFAD2-3  293   ALATVDRDYGILNKVFHNITDT HVAHH LFSTMPHY H AMEATKAIKPILG YY R FDGTP V
ZmFAD2    300   ALAT DRDYGILNK VFHNITDT HVAHH LFSTMPHY H AMEATKAI PILGDYY F PTPVA

CsFAD2_A  354   VAMYREAKECIYVEPDREGDKKGVYWYNNKL
CsFAD2_B  354   VAMYREAKECIYVEPDREGDKKGVYWYNNKL
CsFAD2_C  354   VAMYREAKECIYVEPDREGDKKGVYWYNNKL
AtFAD2    353   VAMYREAKECIYVEPDREGDKKGVYWYNNKL
BrFAD2    354   KAM REAKECIYVEPDR G KKGV YWYNNKL
GmFAD2-3  353   KAM REA ECIYVEPD QSTQS KGV YWYNNKL
ZmFAD2    360   KAT REA G ECIYVEP DR...KGV WYNK KF
```

FIGURE 2B

SEQUENCE LISTING

<160> NUMBER OF SEQ ID NOS: 82

<210> SEQ ID NO 1
<211> LENGTH: 2791
<212> TYPE: DNA
<213> ORGANISM: Camelina sativa

<400> SEQUENCE: 1

```
gcggaggagc ttcttcctcg tagggggttt cttcttcttc atcgttttta acgaaccatc    60
gttaagtcaa atctcccccc cccctacgt cagctccagg tccgtccttc tcatttccga   120
tttcgattca tttacgtctc gtctggtctg ttctgtgttt ttttttttct ttttctttct   180
cccgcactat ctcatttccg atgtttttt aaataaaaac cgatttcatt atatagatct   240
```

```
ggcttatatg tcttgcattc aaccttagat ctggtctcga tgctctgttt ttttctttag    300
ttgagaaatc tgatgttgtt acaatgagtt cttattcata taatgattac tagtgccttg    360
ggtcatccat gaaaacgata tgttaatgct atgatttttt tatttgtttt ctttgtcaaa    420
aatgaagtgc tgctttgacc cattcttctt tagatatttt tattttatttt ttgttgggtt    480 ggtagaatag tgagaatcac cataaaattc tcttatcagt ttcacgtccc tggttttttt    540
tattttttat ttatttaaag atctgtaata tattcagttt tccctaattt tgttgtgta    600 aaatttgctt tgaattgccg tgttgaatct cttatggatt tgacctatgc ctaccgggtc    660
ttaagattga tgataaaact ttttaaatag acaaaaaaaa aagtttcact gattgattct    720
cataaacttt acaatgaagt tggaattagg gtaattcagg atcagatgcg tagtagattc    780
agatgcaaaa taatgagttg catgacttgt taatattata gatccataaa gacatattta    840
aatatctgac atatgatgtc ggcaaaattc ggtggtatat agtatacatc acttagaaac    900
tgtttccttt ggacttgttt gccaacttgg ttgtattcag gaggatttgt gattttgatt    960
gatccattta ctttctctat tgttttttct ttttcttttg gggtctactt ggtggtattc   1020
ataagagaac ttttgttttt gattgaattt aattacaaga aactgatgat gataaccaca   1080
ataaagagat tgtgacctgt cgtattgaaa tcttattagt agtagcagtc gtgttctcaa   1140
cgtcaatggg tttcctttct ttggtttctt actttacgcc gcttctctgc tcttttttgtt   1200 cgttttggtc cacgcacttt ccttttttgt ggcaatccct ttcacaacct catctctgaa   1260
taataataat tattactagt ttgttgattt gatcattacc acctcgtttt ctagtgcatg   1320
caaaatttgt caattagtgt gataaacaaa caattccttt cttgagtttc agcttttga    1380 ttttctcttg ctctatgttt cttttgcaga atcatgggtg caggtggaag aatgccagtt   1440
ccttcttctt cttccaagaa atctgaaacc gatgccataa agcgtgtgcc ctgcgagaaa   1500
ccaccgttca cgctgggaga tctgaagaaa gcaatcccac cgcagtgttt caaacgctct   1560
atccctcgct ctttctccta ccttatcact gacatcatta ttgcctcctg cttctactac   1620
gtcgccacca attactttc tctcctccct cagcctctct cttacttggc ttggcccctc   1680
tattgggctt gtcaaggctg tgtcctaacc ggtgtctggg tcatagccca cgaatgcggt   1740
caccacgcat tcagcgacta ccagtggctc gatgacacag tcggtcttat cttccattcc   1800
ttccttctcg tccctttactt ctcctggaag tacagtcatc gccgtcacca ttccaacaca   1860
ggatccctcg aaagagatga agtatttgtc ccaaagcaga agtccgctat caagtggtat   1920
ggcaaatacc tcaacaaccc tgctggacgc atcatgatgt tgaccgtcca gtttgtcctc   1980
gggtggccct tgtacttggc ctttaacgtc tccggcagac catacgacgg gttcgcttgc   2040
catttcttcc ccaacgctcc catctacaac gaccgtgaac gcctccagat atatctctct   2100
gatgccggta ttctagcagt ctgttttggg ctttaccgtt acgccgctgc acaaggattg   2160
gcctcgatga tctgcctcta cggagtacca cttctgatag tgaacgcgtt cctcgtcttg   2220
atcacttact tgcagcacac tcatcctgcg ttgcctcact acgattcatc cgagtgggat   2280
tggcttaggg gagctttggc taccgtagac agagactatg gaatcttgaa taaggtgttc   2340
cacaacatca cggacacaca tgtggctcat catctgttct cgacaatgcc gcattataat   2400
gcgatggaag ctacaaaggc gataaagcca atactcggtg actattacca gttcgacgga   2460
acaccatggt atgtggccat gtataggagg gcaaaggagt gtatctatgt agaaccggac   2520
agggaaggtg acaagaaagg tgtgtactgg tacaacaata agttatgagg atgatggtga   2580
aagaacactg aagaaattgt cgatctttct ctagtctggt tctcttttgt ttaagaagtt   2640
```

```
atgttttgtt tcaataattt cagtgtccat tttgttgtgt tatgacattt tggcaaatta    2700
tgtgatgtgg aagttagtg ttcaaatgtt ttgtgtctgt attgttcttc tcatcgctgt    2760
tttgttggga tcgtagaaat gtgaccttcg g                                  2791
```

<210> SEQ ID NO 2
<211> LENGTH: 3875
<212> TYPE: DNA
<213> ORGANISM: Camelina sativa
<220> FEATURE:
<221> NAME/KEY: misc_feature
<222> LOCATION: (3864)..(3864)
<223> OTHER INFORMATION: n is a, c, g, or t
<220> FEATURE:
<221> NAME/KEY: misc_feature
<222> LOCATION: (3867)..(3867)
<223> OTHER INFORMATION: n is a, c, g, or t

<400> SEQUENCE: 2

```
gtggaggagc ttcttcctcg taggggtttt cttcttcttc atcgttatta acgaaccatc     60
gttgagtcaa atctcccaac cccctacgtc agctccaggt ccgtcctttc tcatttcata    120
ttccgattca tttacgtctc gtctgatctg ttctttgttt ttatttttt tttctttctc    180 ccgcactatc tcattttcga ttcttttttt ttttagaacc gatttgatga tatagatctg    240
gcttatatgt cttgcattca accttagatc tggtctcgat gctctgtttt ttctttagtt    300
gagaaatctg atgttgttgt tacaatgagt tcttattcat aataatgatt actagtgcct    360
tgggtcatcc atgaaaacga tatgttgtta tactatgatt ttttatttgt caaaaatgaa    420
gtgctgcttt gacccattct ctttagattt attattttg ttgggttggt agaatagtga    480
gaatcaccat aaaattctct tatcagttc acgtcctgtt tttttttcaa aaagatccgt    540
aatatattca gtttttttt atttgtgtgt aaaatttgct ttgtattgcc gtgttgaatc    600
tcttatggat ttgacctatg cctaccgggt cttatggatt gatgatataa ctttttaaac    660
agacaaaata agtttcactg aatgattctc ataaactata caataaagtt ggaattaggg    720
taattcagga tcagatgcgt agattcagat gcaaataatg agttgcatga catttttatta    780 ttatagatcc gtaaccgtaa agacatatta tgttctgttt taaatatctg atatatgatg    840
tcggcaaatt tcggtggttt atacatcact taaaaactgt ttcctttgga cttgtttgcc    900
aacttggtgc tattcaggag gatttctgat tttgattgat ccatttactt tctctattgt    960 ttttttttt tttgggggtc tacttgttgg tattcataaa agaattttg atcttgattg    1020 aatttaatta caagaaactg ctgatgataa ccacaataaa gagattgtga cctgtcgtat    1080
tgaaatctta ttagtagtag tagtcgtgtt ctcaacgtca atgggttttt ctttctttgg    1140
tttcttactt tacgccgctt ctctgctctt tttattcctt ttggtccacg ctctctcctt    1200
ttgtggcaat cccttctaca acctcatctc tgaataacaa taattattac tagtttgttg    1260
atttcatcat taccactcgt tttcagtgc atgcaaaatt tgtcaattag tgataaactg    1320
aaaattcctt tcttgatttt tctttgctct tggtttgttg cagaatcatg ggtgcaggtg    1380
gaagaatgcc agttccttct tcttcttcca agaaatcaga aaccgatgcc ataaagcgtg    1440
tgccctgcga gaaccaccg ttcacgttgg gagaattgaa gaaagcaatc ccaccgcagt    1500
gtttcaaacg ctctatccct cgctctttct cctaccttat cactgacatc attgttgcct    1560
cctgcttcta ctacgtcgcc accaattact tctctctcct ccctcagcct ctctcttact    1620
tggcttggcc tctctactgg gcttgtcaag gctgcgtcc aaccggtgtc tgggtcatag    1680
```

```
ctcacgaatg cggtcaccac gcattcagcg actaccaatg gcttgatgac acagttggtc    1740
ttatcttcca ttccttcctt ctcgtccctt acttctcctg gaagtacagt catcgccgtc    1800
accattccaa cacaggatct ctcgaaagag atgaagtatt tgtcccaaag cagaaatcag    1860
ctatcaagtg gtatggcaaa tacctcaaca accctcctgg acgcatcatg atgttaaccg    1920
tccagtttgt cctcgggtgg cccttgtact tggccttaa cgtctcgggc agaccgtacg    1980
acgggttcgc ttgccatttc ttccccaacg ctcccatcta caacgaccgt gaacgcctcc    2040
agatatatct ctcggatgcc ggtattctag cagtctgttt tgggctttac cgttacgctg    2100
ctgcacaagg aatggcctcg atgatctgcc tctacggagt accgcttctg atagtgaacg    2160
cgttcctcgt cttgatcact tacttgcagc acactcatcc tgcgttgcct cactacgatt    2220
catccgagtg ggattggctt aggggagctt tggctaccgt tgacagagac tatgaatct    2280 tgaacaaggt gttccacaac atcacggaca cacatgtggc tcatcatctg ttctcgacaa    2340
tgccacatta taatgcgatg gaagctcaa aggcgataaa gccaatactc ggtgactact    2400
accagttcga cggaacaccg tggtatgtgg cgatgtatag ggaggcaaag gagtgtatct    2460
atgtagaacc ggacagagaa ggtgacaaga aggtgtgta ctggtacaac aataagttat    2520
gaggatgatg atggtgaaag aacactgaag aaattgtcga actttctcta gtctggttct    2580
cttttgttta agaagttatg ttttgtttca ataatttcaa tgtccatttt gttgtgttat    2640
gacattttgg caaattatgt gatgtgggaa gttagtgttt aaatgttttg tgtctgtatt    2700
gttcttctca tcgctgtttt gctgggatcg tagaaatgtg accttcggac agtaaaactc    2760
tactaaaact atcttccttt cggtatcttc aaaagtgtta acttaactat gatgcacgta    2820
gtgaatcctg acttaaataa tcgacttctg tttaagacct atcaactgta agagggttac    2880
acgaatgttc ctttaacaaa ataaacataa caattgctct ctctaaatta ggttcgatgt    2940
ttttgtctgt ttgtttgatg catggtagtc ggagtagctg tcatgttcaa gttcaatctt    3000
cagtttagaa cttgtttcca ttgttttatg actagcactg aattccattg tactctctgt    3060
ctgtgatact gaagccaagc gtgacaaatg ttgaacatgc catgtcgatg tattaaaggg    3120
gattgagtta atagtgctgt tttggctggc aggtcacaat cacaattctt tcacactcca    3180
atcatgtggt taggcttacg attccttttt tttagaatta gcttttggta aagaactgag    3240
acctctggcc tttacatatg aaatatgaaa ccccttaac taaaattata tagcacgcca    3300
aatccattac ctctggtttc atctttgaga gggaacatta agagtaaaag aaagagaaat    3360
aaataaaaaa taatttttc cattacgaaa tcaccaaaag agaaggacaa caagaaagaa    3420
atgaggtgaa gaaacataga aaacaaaaga atgttctgta accaagtcga tcgatgaaca    3480
aaaggcttta ccaatacgga aacaatcttt catcccttcg atttaagcat aaacttagaa    3540
gcatttcctg tggactatgg atggccctga ctcatcatac tcacccttg atatccacat    3600 ctgtaaagca acaacattgt gtatgattaa caaatttcaa atgggtaaca agtaagtaa    3660 aaaagcacaa aaactcatag agaataaaga atgaagatat acctgttgg aaggtactga    3720 gggaagctaa aatggagcct ccaatccaga cactgtactt cctctcaggt ggtgcaacca    3780
ccttaatctt catgctgctt ggagccaaag cagtgatctc tttgctcatt ctatcagcaa    3840
ttccagggaa catggtggtt ccancantga gcaag                              3875
```

<210> SEQ ID NO 3
<211> LENGTH: 2725
<212> TYPE: DNA
<213> ORGANISM: Camelina sativa

<400> SEQUENCE: 3

```
gcggaggacc ttcttcctcg taggggtttt cttcttcttc atcgttatta acgaaccatc    60
gttaagtcaa atctcccccc ccccccccta cgtcagctcc aggtccgtcc ttctcatttc   120
cgatttcgat tctttaacgt atcgtctggt ctgttctgtg tttttatttt tttctttctt   180
tctcccgcac tatctcattt tcgattttt tttaataaaa aaaaaaccga tttcgtgata   240
tagatctggc ttatatgtct tgcattcaac cttagatctg gtctcgatgc tctgttttgt   300
tttttttttt ttgttgagaa atctgatgtt gttacaatga gttcttattc atataatgat   360
tactagtgcc ttgggtcatc catgataacg atatgttata ctatgatttt tattttattt   420
ttcttttgtc aaaaatgaag tgctgctttg acccattctc tttagatatt tttatttttt   480
tattttgtt gggttggtag aatagtgaga atcaccataa aattctctta tcagtttcac   540
gtcctggctt ttttcttgt ttttgttttt ttttaaagat ctgtaatata ttcagttttc   600
cctatttttg tttttgtaaa atttgctttg aattgccgtg ttgaatctct cttatggatt   660
tgacctatgc ctaccgaggt cttatggatt gatgatatga cttttaaat aaagttggaa   720
ttagggtaat tcaggatcag atgcgtagta gattcagatg caaataatga gttgcatgac   780
ttgaaaatat tatagatccg taaagacata tttaaatatc tgacatatga tgtcggcaaa   840
tttcggtggt ttatacatca ctcaaaactt aaaactgttt cttttggact tgtttggcaa   900
cttggtggta ttcaagagga tttgtgatt tgattgatcc atttactttc tctattgttt   960
tttcttttgg ggtctacttg ttggtattca taagagaact ttgtgatctt gattaaattt  1020
aattacaaga aactgatgat gatatccaca ataaagagat tgtgacctgt cgtattgaat  1080
atcttattag tagtagtagt cgtgttctca acgtcaatgg gtttctttct ttggtttctt  1140
actttacgcc gcttctctgc tctttttatt ccttttggtc cacgcacttt cctttgtgg  1200
caatcccttt cacaacctaa tcttcaattt ggatcatttc tctgaataat aataacaact  1260
agtttgttga tttgatcact accactcgtt ttctagtcca tgcaaaattt gtcaattcct  1320
ttattccttt gattttttg cagaaacatg ggtgcaggtg gaagaatgcc ggttccttct  1380
tcttcttcca agaaatcaga aaccgatgcc ataaagcgtg tgccttgcga gaaaccgccg  1440
ttcacactgg gagaattgaa gaaagcgatc ccaccgcagt gtttcaaacg ctctatccct  1500
cgctctttct cctaccttat cactgacatc attgttgcct cctgcttcta ctacgtcgcc  1560
accaattact tctctctcct ccctcagcct ctctcttact tggcttggcc cctctattgg  1620
gcttgtcaag gctgtgtcct aaccggtgtc tgggtcatag cccacgaatg cggtcaccac  1680
gcattcagcg actaccaatg gcttgatgac acagttggtc ttatcttcca ttccttcctt  1740
ctcgtccctt acttctcctg gaagtacagt catcgccgtc accattccaa cacaggatct  1800
ctcgaaagag atgaagtatt tgtcccaaag cagaagtccg ctatcaagtg gtatggcaaa  1860
tacctcaaca accctgctgg acgcatcatg atgttaaccg tccagtttgt cctcgggtgg  1920
cccttgtact tggcctttaa cgtctcgggc agaccatacg atgggttcgc ttgccatttc  1980
ttccccaacg ctcccatcta caacgaccgt gaacgcctcc agatatatct ctctgatgcc  2040
ggtattctag cagtctgttt tgggctttac cgttacgccg ctgcacaagg attggcctcg  2100
atgatctgcc tctacggagt accacttctg atagtaaacg cgttcctcgt cttgatcact  2160
tacttgcagc acactcatcc tgcgttgcct cactacgatt catccgagtg ggattggctt  2220
aggggagctt tggctaccgt agacagagac tatggaatct tgaacaaggt gttccacaac  2280
```

```
atcacggaca cacatgtggc tcatcatctg ttttcgacaa tgccgcatta taatgcgatg    2340
gaagctacaa aggcgataaa gccaatactc ggtgactatt accagttcga cggaacacca    2400
tggtatgtgg ccatgtatag ggaggcaaag gagtgtatct atgtagaacc ggacagggaa    2460
ggtgacaaga aggtgtgta ctggtacaac aataagttat gaggatgatg gtgaaagaac     2520
actgaagaaa ttgtcgatct ttctctagtc tggttctctt ttgtttaaga agttatgttt    2580
tatttcaata attccagtgt ccattttgtt gtgttatgac attttggcaa attatgtgat    2640
gtgggaagtt agtgttcaaa tgttttgtgt ctgtattgtt cttctcatcg ctgttttgtt    2700
gggatcgtag aaatgtgacc ttcgg                                          2725

<210> SEQ ID NO 4
<211> LENGTH: 5288
<212> TYPE: DNA
<213> ORGANISM: Camelina sativa

<400> SEQUENCE: 4
ggtatgaatt ggcttacacg gaagccaaag gaagaatgag gaaagggaac agagtttggc      60
agattgcttt tggaagcggg tttaagtgta acagcgcggt ttgggtggct ctccgcgatg     120
tcaagccctc ggttaacaat ccttgggaac attgcatcca tagatatcca gttaagatcg     180
atctttgaac tcgtaagaac cggtccgaaa acatggttag tcccctcca tgtaccaaaa      240 aaaaaagtt taactcttat atttttagtt ctttaccaat gggtcaagaa attctgttga      300
aggtaacact taaatgtatg tatgtgttta ttatattatt tattataatt aaaaaaatag    360
ttttatttcc ggatatacca aagttgaat ttttaaaaac aaatataaat tgttcaatct     420 ataaatatt caagctttag taatattatt ctttaaaaat aatatctatt gaattaaaaa     480
atttactaag taacgggtca aaatttgaat atttaaattc aatttcatat ttttttgttaa   540 atttatatat tttatatat ataataaact ttaaataatt tattttgaaa tatttttaat    600
atattgaaac ttgatataaa agttagaaac tataaacact ctattgaaat aaaagttatc     660
aataatattt cactataata tgaaagaatt tcaagaaacc aagtatatta aaacaaaacg    720
tataaaaata tattaaatta ctcataatat aatataactc acttttttaaa aaccaaattt   780 acaaaattat gttttataat gacattcaag tcatgatgta gaatatacat tgttgaaata    840
atttcacata cataaactaa tataacatat taaaatttta ttttaaaata taaaatatac    900
ataattttgt ataaataaaa tttaaccagt gttatagcac gggtaattat ctagaatcat    960
taacaatata aaactataa aataagtttt tttttcaag ctatcatatt tagcatatga     1020
ttttattgca taatgttta tccaaaaaac ttttaaaaac aagtatataa attacatttt   1080
atataaaaat tacaatataa ataaaataaa tttcaacacg tactctaaca cggatcttaa   1140
tctagtatgt tgtgtataaa ggtaacacta aaatgaccaa gaatggttac gaagtcaaaa    1200
gatgggacca aaagcgttga caaaatttta gttcttttct aaaaataaaa ttgtttgtat    1260
aataaaaatt gttaggtaga acttagaaca ctcaactaat atatccttgc gtacgaaaac    1320
atgtgttaag tgaagtgacc ttaatgtagt ggccaaaagt aagtctttaa tgcacaagac    1380
accatcacac cagagatcga gtctcgttcc ctacgaatgt agggattagt gtaatggtcc    1440
gacaaaaaaa acaaaacatg tattaaattt agaatacatg aaattactca caagttgcga    1500
atacatgtac ccctcggctc tgggatgcta aaccgggttc gtcttatact caaatataac    1560
atttaagttt gaatttttt tttgtcaata aaaataattt gtatactaaa aaattagtt     1620 aaaagtttaa aacaagtttt acttaaaaaa aaatatttgt gaaaaaatcc gaagtgttaa    1680
```

| | |
|---|---|
| atttagaaca cacaaaaata tgttggactt atgacacgaa gcttacagat ccgaaatgtt | 1740 |
| tagtcagatt aatcttcaag cgtatttaag tttaacactt aagtttgtaa atatacgaaa | 1800 |
| atattggtta aaaaaccttaa aattttagta tcgacaaaaa aaaaatctta aattttagtt | 1860 |
| taaaatctga aaagaaaaag tgaaaacctt tttgtttatt tgtaggaaaa atcaatcact | 1920 |
| taaaactaaa aaaaactaga aaagaaata aagaaagcaa tatacctctg cttgtgatat | 1980 |
| ggaagtggaa gaaatacaag atttgatcga ttctcatcat cttgagatga ctgaatagtc | 2040 |
| ggaaccatgg aaacaccaaa cacacaggat catgactggt tctctactct cactcgtcct | 2100 |
| cgttcctgca ttctcgcatc cttgagccgt cgttgatata tccaccgtgt gaaaacgttt | 2160 |
| cggtgatcgt agagaaaatt ttgacctaat ttaaatcgat gacgatcgga tgaagatgat | 2220 |
| gtagtcacga tttaacaaga gagattaatc acgaaaagag atgctctccg ctccgatcaa | 2280 |
| atatcaaaaa gagatcatct cttttttgtga ttgtgtaaga agttagagag aagacttgac | 2340 |
| gtcctgtaat cgtgatctcg atcgaatgaa gatatgtcgt cacgattaac atgaggatgg | 2400 |
| cgatcaatca atcacgaaca gagtcagaga tgcttcccct aatcttgaca gagatcacca | 2460 |
| acgcaaagct ttggatttgg tttctcaaag aagaagaaga agagagattt ggaaaacttt | 2520 |
| gacaaagaag aaaatgagag aatgaatgaa tgatgtgatg ttggagattt tttaacctaa | 2580 |
| tgactaaatg agccgtcttt tatatacgca acagctatat taatatttttt ttattttttta | 2640 |
| ttttctaatt tcagcaaatt taaataacga aattgtgatt gtttcctttg ttttcttttc | 2700 |
| cccacgagtt ctcaagttgt ttgttttctt attttggttg caaccaaaaa aaacaagaca | 2760 |
| gaaaaaacaa tttatctcaa gagtaacaaa aaggagattc gagatccttt ggagttactc | 2820 |
| aattacattc atatgtcacg agataaaaag gttaaacaat cactggatca gtgtgctcat | 2880 |
| ggtgttccag gtccaaaaca tgtgtcacga gataaaaaca aagagaaaca caactgaaaa | 2940 |
| tgattaccaa gatcacaact atatataaag gacttataaa aaatgaattt gaaagtggtt | 3000 |
| aaactaagtg attataagtg ttattgcagt taccccctta taggtttggt gaatcttatt | 3060 |
| agagataact tattcttaag atagttgcaa ttaaccaaaa aaaaaaattg tccggatagt | 3120 |
| ttgatgcaat taaatgatta atgagtgttc tatagggtct gattcttaat atttcgaaat | 3180 |
| atttggcctt aactaaactt ccaccatgat ttatttactg atctagttcg gggacagact | 3240 |
| ttgcgaataa aactcattac cgagaaacat tcatcccata attgctattt agtcagaggc | 3300 |
| taatcgacta tggcctttca gccaatcaaa gctacgaaca cgaatctccc taaaacatcc | 3360 |
| tcaagtattt tatttaatac acatgtatcg tattgagcac cactcataaa ctaatttcat | 3420 |
| acatttatca tactctttat ttgtaataat aaaagcatca acatattgta ggcaattaga | 3480 |
| atcaaaacaa aacatttttt ttttctttcc aaatttcaa aattggtaaa cgaaacttgg | 3540 |
| acctttaata cttatattgg caatataata atattgcaga gtggactatt tcccttattt | 3600 |
| tggcaacttt cagtggacta gtaatttatt tcaatgtgga tgcttgcatg agtgtgaata | 3660 |
| tacacatgtc tatatgcatg cctgcaaatc gtaacggacc acaaaaaagg atccatacaa | 3720 |
| atacctctta acggctcctc tctatcatac tctccgacac aaactgagca atgacgtccg | 3780 |
| ttaacgcaaa gctcctttac cattacgtcc taaccaactt tttcaacctt tgcttgtttc | 3840 |
| cgttaacggc gttacttgcc ggaaaagcct ctaggcttac ctcaaacgat ctctaccact | 3900 |
| tctattccca tctccaacac aaccttataa ccgtaatttt actctttgct ttcaccgctt | 3960 |
| tcggtttggt tctctacatt gtaacccggc ccaaaccggt ttacctcgtt gactactcgt | 4020 |

```
gctaccttcc accaccgcat ctcaaagtta gtgtttccaa ggcgatggat attttctacc    4080
aaataagaaa agctgatacc tcacggaacg tggcatgcga tgatccatcc tcgcttgatt    4140
tcctgaggaa gattcaagaa cgttcaggtc taggtgatga aacctacagt ccccagggac    4200
tcattaacgt gcccccacga aagacctttg cagcttcacg tgaagagaca gagcaggtaa    4260
tcatcggtgc gctagataag ctattcgaga ataccaaagt taaccctaga gaaattggta    4320
tacttgtggt caactcaagc atgtttaatc caactccttc gctatctgcg atggtcgtta    4380
atactttcaa gcttcgaagc aacatcaaaa gctttagtct cggaggaatg ggttgtagtg    4440
ctggtgtcat cgccattgat cttgcaaagg acttgttgca tgttcataaa aacacttatg    4500
cacttgtggt gagcactgag aacatcactc aaggcattta tgctggcgaa aatagatcca    4560
tgatggttag caattgcttg ttccgtgttg gtggcgcagc gattttgctc tccaacaagc    4620
caggagatcg gagacggtcc aagtacaagt tatgtcatac tgttcgaacg cataccggag    4680
ctgatgacat gtcttttcga tgtgtgcaac aaggagacga tgagcggt aaaatcggag    4740 tttgtctgtc aaaggacata accgttgttg cgggatagc gcttaagaaa aacatagcaa    4800
cgttgggtcc gttgattctt cctttaagcg aaaaatttct gttttagta accttcatcg    4860 ccaagaaact tttgaaggac aagatcaagc actattacgt cccggatttc aagcttgcta    4920
ttgaccattt ctgtattcat gcgggaggca gagccgtgat cgatgtgctt gagaagagct    4980
taggactatc tccaatcgat gtggaggcat ctagatcaac gttacacaga tttgggaata    5040
cttcgtctag ctcaatttgg tatgaattgg catacataga agcaaaagga aggatgaaga    5100
aagggaatag agcttggcag attgctttag ggtcaggatt taagtgtaac agtgcggttt    5160
gggtggctct atgcaatgtc aaggcttcgg cgaatagtcc ttgggaacat tgcatcgata    5220
gatatccggt tcaaattgat tctggttcat caaaatcaga tactcatgtc aaaaacggtc    5280
ggtcctaa                                                             5288

<210> SEQ ID NO 5
<211> LENGTH: 5097
<212> TYPE: DNA
<213> ORGANISM: Camelina sativa
<220> FEATURE:
<221> NAME/KEY: misc_feature
<222> LOCATION: (12)..(12)
<223> OTHER INFORMATION: n is a, c, g, or t

<400> SEQUENCE: 5
ggtatgaatt gncttacacg gaagccaaag gaagaatgag gaaagggaac agagtttggc      60
agattgcttt tggaagcggg tttaaatgta acagcgcggt ttgggtggct ctccgcgatg     120
tcgagccctc gttaaaaaat ccttgggaac attgcatcga tagatatccg gttaagatcg     180
atctttgaac tcgtaagaac ggtagattgg tctggaaaca tggttagtcc tccatgtacc     240
aaaaaaaaaa ggtaactct tatatctttt gttcttacc aagggtcaa gaaatcagt        300 ggaaggttaa tgtatgtttg tatatgttgt gtataaaggt aacccttaat taatgaccaa     360
gaatggttat gaagtcaaaa gataggacca aaagtgttga cctattaaaa tttaaaattt     420
tagttttttg gaaaaattaa atcatttgtg aaataaaaat ggtgagttag aaaaatcaaa     480
acaatttact tacttacaaa gaaccttaaa attaaactta agtgttaaat ttagaataaa     540
tgaaaaaatg ctaaacttat gacaccaaaa cctacgaact cttataagga cggggatact     600
aaatttgttt gtttgtttgt ttttttttttt ttttttgtaa atcaatccgg tttgttttca     660
atgtattcaa attaaagtcg ggttatgaca ccaacaccaa gcttacggat ctgaggaaga     720
```

```
cgggatgcta agtcgggtta gtcatcaagc gtattcaaat aactctgaag tcttagaact      780
ttttttgtta ataaaatatt ttgtataata aaaaaaattt agttaaaaaa atttaaaaca      840
atttttacat aaaatattat ttgtgaaaga acttttttaag tgttaaattt agaacactcg     900
aaaacatgtt agacttgtga caccaagctt attccaattt aacgcttaag tttgaaaact     960 tttttttgtca ataaaaaata tactatatga aaagattggt tataaaaacc ttaaatttag    1020
tttaaagtct gaaaataaaa ataaaaaata aaaaaaatta ttagttggaa aggaaataaa     1080
gaaagcaata tacctctggt tgtgatgtgg aagaaacaca agatttgatc gattctcatc    1140
agcttcagat gactgaatga atagtcggaa ccatggaaac accaccaaac acacaggatc    1200
atgactggtt cactactctc actcgtcctc gttcccgcat tctcgcatcc ttgagccgtc    1260
tttgacagat ggttaaaaca cgaacagagc tgaataagta aagaaaaaaa gagagagttt    1320
gagaagtttg atcgaatgaa taagaagaaa gactttttttt gacctggaat cgatctcgat   1380
tgaacagaga tgttttcctc tttaccgcat tagatcagat caatccaccg tgtgaaaacg    1440
tttcggtgat cgtagagcag attttgacct aattaattaa gatcgatcac gtacgatcgg    1500
atgacgataa tgtaagagat caatcacgaa aagagatgct ccgatcaaat atcaaaggga    1560
taataaagtt gatgcagaga tcatctctgt tcgtggttgt ttgagattag ggagaagact    1620
tgacctggaa tcaatctcga tcgaatgaag atgttgtcac gattaacatg gggatggcga    1680
tcagtcaatc acgaacagag tctgatatga ttcccctcc gatcttgaca gagatcacca     1740
acgcaaagct ttggatttgg tttctcaaag aagaagaaga agagagattt ggagaaactt    1800
tgatggtttt acaagaaga agagagaatg aatgaatgat ttggagattt tttaacctaa    1860
tgactaataa taatgagccg agtgtatgaa tgtatttaat ataagcaacg gctattttttt   1920 cttcttttct tttaacttta agcaaattta gaaaggaaa ttgtgattgt ttccttttttt     1980 ccccacgagc tctcaagttg aatccttttc ttatttgagt tgcaaccaat aataaaaaaa    2040
aaagatagaa aaacggaaat ttatcacaag agtaacaaaa aggagattcg agatcctttta   2100 gagtttactc aattacattc atatgtgcta gttgtgggag tgagaggagt tttctccttc    2160
cgaagtgatt tatgtatgga ggagttatc accgttaaga gttccgaatt gaaagagact    2220
atttgattgc taaaattgta tattactgtc tgagagaaaa aatattcgat cccccacaaa    2280 gtctccccccc ccttatatat ttatacagac caattaatta cccaattaat gcgtaattaa    2340
ttttacacga ttctcgcgtc ctaattaatt cacttgaatg ctagaatctt tgaccgaggt    2400
cgaactgcga gctgactaat atgacgcctc tccgcgctct cttcttctct ctgggcctga    2460
tgggccgacc agcgctacac ctttgacccg tttagcgtgc ccggcccagg tcctctgcct    2520
gttatccgag atgacgaatc gtgggtacaa cactagtgta tgacctttttg cctttatagg   2580 cactaaaaaa ctacccaaaa aaaatatgaa gaagaaaaaa aggttaaaca atcactggat    2640
cagtgtgctc atggtgttcc aggtccaaag catgtgtgtc acgagataaa aatagagaga    2700
aacacaactg attatgatca ccaagatcac gaatatatat aaaggactta taaaaaatga    2760
atttgaaagt ggttaaacta agtgattata tgtgtgattg ctcttagccc cttaggtgtg    2820
gtgaatctta ttatagagat gactattttt aaagatagtt gcaattaaaa aaaaaaatca    2880
gtgtccggat agtttgatgc aattaattag tgttctatag ggtctgattc ttaatattta    2940
tgcaaatatt atagtatttc aaagtatttg gccttaacta aacttccacc tgatttattt    3000
actgatctag ttcggggaca gactttgcga ataaaactcg ttcccgagaa acattcatcc    3060
```

```
cataactgct atttagtcag aggctaatcg actatagcct ttcagccaat caaatctacg    3120
aacacgaatc ccctaaaac atcctcaagt atttatttaa tacacatgta tcgtattgag     3180
caccactcat aaactatttt tttttttgtt tttaacaaaa aaaatttatc atactctttt    3240
gtaataatag atgcatcaac atattgtagg caacgttgaa gaaccagtac attcttttt     3300 tttttgctcc aaattttcaa aattggaaaa tgaaacttgg acgaaataaa tttaacactc    3360
tgtatatatt ggcaatataa tattgcagag tggactattt accttatttt ggcaactttc    3420
agtggactag taatttattt caatgtgtat gcttgcatga gtgtgaatat acacatgtct    3480
atatgcatgc ttgcaaatcg taacggacca caaaaaagga tccatacaaa tacctcttaa    3540
cggctcctct ctatcatact ctccgacaca aactgagcaa tgacgtccgt taacgcaaag    3600
ctcctttacc attacgttct aaccaacttt ttcaacctttt gcttgtttcc gttaacggcg    3660
ttacttgccg gaaaagcctc taagcttaca gcaaacgatc tctaccactt ctattcccat    3720
ctccaacaca accttataac cgtaatttta ctctttgctt tcaccgcttt cggtttggtt    3780
ctctacattg taacccggcc caaaccggtt tacctcgttg actactcgtg ctaccttcca    3840
ccaccgcatc tcaaagttag tgtttccaag gcgatggata ttttctacca aataagaaaa    3900
gctgatacct cacggaacgt ggcatgcgat gatccatcct cgcttgattt cctgaggaag    3960
attcaagaac gttcaggtct aggtgatgaa acgtacagtc cccagggact cattaacgtg    4020
cccccacaaa agacctttgc agcttcacgt gaagagacag agcaggtaat catcggtgcg    4080
ctagaaaagc tattcgagaa caccaaagta aaccctagag agattggtat acttgtggtg    4140
aactcaagca tgtttaatcc aactccttcg ctatctgcga tggtcgttaa cacttttcaag   4200 ctccgaagca acatcaaaag ctttagtctc ggaggaatgg gttgtagtgc tggtgttatc    4260
gccattgatc ttgcaaagga cttgttgcat gttcataaaa acacttatgc acttgtggtg    4320
agcactgaga acatcactca aggcatttat gctggcgaaa acagatccat gatggttagc    4380
aattgcttgt ttcgtgttgg tgggggcagcg atttttgctct ccaacaaact gggagatcgg    4440
agacggtcca agtacaagct atgtcatact gttcgaacgc ataccggagc tgatgacaag    4500
tcttttcgat gtgtgcaaca aggagacgat gagggcggta aaatcggagt ttgtctgtca    4560
aaggacataa ccgttgttgc ggggacagcg cttaagaaaa acatagcaac gttgggtccg    4620
ttgattcttc ctttaagcga aaagtttctg tttttagtta ccttcatcgc caagaaactt    4680
ttgaaggaca agatcaagca ctgttacgtc ccggatttca agcttgctat cgaccatttc    4740
tgtattcatg cgggaggcag agccgtgatc gatgtgcttg agaagagctt aggactatcg    4800
ccaatcgatg tggaggcatc tagatcaacg ttacatagat ttgggaatac ttcgtctagc    4860
tcaatttggt atgaattggc atacatgaa gcaaaaggaa ggatgaagaa agggaataga     4920
gcttggcaga ttgctttagg gtcagggttt aagtgtaaca gtgcggtttg ggtggctcta    4980
tgcaatgtca aggcttcggc gaatagtcct tgggaagatt gcatcgatag atatccggtt    5040
caaattgatt ctgattcatc aaaatcagag actcatgtca aaaacggtcg gtcctaa      5097
```

<210> SEQ ID NO 6
<211> LENGTH: 3583
<212> TYPE: DNA
<213> ORGANISM: Camelina sativa

<400> SEQUENCE: 6

```
gaggcgtcta aatgactttt gcatagattt ggaaacactt cctcgagctc gatatggtat    60
gaattggctt acacggaagc taaaggaaga atgaggaaag ggaacagagt ttggcagatt    120
```

-continued

```
gcttttggaa gcgggtttaa gtgtaacagc gcggtttgga tggctctccg cgatgtcgag    180
ccctcgttta aaatccttgg gaacattgca tcgatagata tccggttaag atcgatcttt    240
gaactcgtaa aacggtgga ttggtccgga acatggtta gtcctccatg taccaaaaaa     300
gaaagtgaac ttatatctct agttctttac taaggggtca agaaatcagt tgaaggttaa    360
tgtatgttta tatatgttgt gtataaaggt aacccttaaa tgaccaagac tgttgaccta    420
ttaaaattta aaatttaagt tctctcgaaa aattaaatcg tttgtaaaat aaaaattgtg    480
agttagaaaa atcaaaacaa tttacttacc tacaagaacc ttaaaattaa acttaagtat    540
taaattttga atacatgaaa aaatgttaaa cttatgacac caaaatttac gaactctgag    600
gacggaaatg cttaattcag tttgtttgtt ttttttgtttt gtaaatcaat ctggtttgtt    660
ttcaatgtat ctaaactaaa gtcgggttat gacaccaaca ccaagcttat ggagacagga    720
tgttaagtcg ggttagtcat caaggtattc aaataagtaa taacttttaa gttttagaac    780
ttttttgtca gtaaaatatt ttgtataata aaaaagttta gttaaaacat taaaacagtt    840
tttactgaaa atattatttg tgaaaaaact tcttttaagt gttaaattta gaacacgtaa    900
aaacatgtta gacttatgac accaagctta tagacccgaa aaggaaactg tgattgtttc    960
cttttcccca cgagttctaa gttgtttcct ttacttattt gggttgcaac caatataaaa    1020
agaaagaaaa atggaaattt atcacaaaaa ggagagtcga gatctctaga gttacattca    1080
tatgtgctag tgtctgacct tttgccttaa tttataggca ctaataaaaa aactaccaaa    1140
aaaaaaattg aagaagaaca aaaggttaaa caatcactgg atcagtgtgc tcatggtgtt    1200
ccaggtccaa aacatgtgtc acgagattaa aaaagagaga aacacaactg aaactattca    1260
ccaagatcac aactatatat ataaaggact tataaaaaat caatttgaaa gtggttaaac    1320
taaacgatta taagtgtgat tgcacttacc cccttatagg tttggtgaat cttattagag    1380
ataacttatt tttaagatag ttgcaattaa aaaaaaaaaa aaattgtccg gatagtttga    1440
tgcaattaat gagtgttcta tatggtctga ttcttaatat ttatgcaaat attatagtat    1500
ttcaaagtat ttggccttaa ctgacagact ttgcaaataa aactcattcc cgagaaacat    1560
tcatcccata attggtattt agtcagaggc taatcgacta tggcctttca gccaatcaaa    1620
gctacgaaca cgaatccccc taaaacatcc tcaagtattt atttaataca tcgtattgag    1680
caccactcat aaactaattc catacattta tcatactgtt tatttgtaat aataaaagca    1740
gcaacatatt gtagtttgta ggcaataaga aacaaaacaa aacatttttt tttctctcca    1800
aattttcaaa attggaaaac gaaacttgga ccttcaatac ttatatatta tatttgcaat    1860
ataaaattgc agagtggact atttcccttta ttttggcaac tttcagtgga ctagtaattt    1920
atttcaatgt gtatgcttgc atgagtgtga atatacacat gtctatatgc atgcctgcaa    1980
atcgtaacgg accacaaaaa aggatccata caaatatacc tctcaacggc tcctctctat    2040
tatgctctcc gacacaaact gagaaatgac gtccgttaac gcaaagctcc tttaccatta    2100
cgtcctaacc aacttttttca acctttgctt gtttccgtta acggcgttac ttgccggaaa    2160
agcctctacg cttaccacaa acgatctcta ccacttctat tcccatctcc aacacaacct    2220
tgtaaccgta atttactctc ttgctttctc ctctttcggt ttggttctct acgttgtaac    2280
ccggcgcaga ccggtttacc tcgttgacta ctcgtgctac cttccaccac cgcatctcaa    2340
agttagtgtt tctaaggtca tggatatttt ctaccaaata agaaaagctg atacctcacg    2400
aaacgtggca tgcgatgatc catcctcgct tgatttcctg aggaagattc aagaacgttc    2460
```

-continued

```
aggtctaggt gatgaaacct acagtccccc gggactcatt cacgtgcccc cacaaaagac    2520
ttttgcagct tcacgtgaag agacagagca ggtaatcatc ggtgcgttag aaaagttatt    2580
cgagaacacc aaagttaacc ctagagagat tggtatactt gtggtcaact caagcatgtt    2640
taatccaact ccttcgctat ctgcgatggt cgttaacact ttcaagctcc gaagcaacat    2700
caaaagcttt agtctcggag gaatgggttg tagtgctggt gtcatcgcca ttgatcttgc    2760
aaaggacttg ttgcatgttc ataaacacac ttatgcactt gtggtgagca ctgagaacat    2820
cactcaaggc atttatgctg gcgaaaatag atccatgatg gttagcaatt gcttgtttcg    2880
tgttggtggg gcagcgattt tgctatccaa caagccggga gatcggagac ggtccaagta    2940
caagctatgt cacacggttc ggactcatac cggagctgat gacaagtctt ttcgatgtgt    3000
gcaacaagga gacgatgaga gcggtaaaat cggagtttgt ctgtcaaagg acataacagt    3060
tgttgcgggg acagcgctta agaaaaacat agcaacgtta ggtccgttga ttcttccttt    3120
aagcgaaaag tttctgttct tagttacctt catcgccaag aaactttga aggacaagat    3180 caagcactat tacgtcccgg atttcaagct tgctattgac catttctgta ttcatgccgg    3240
aggcagagcc gtaatcgatg tgcttgagaa gagcttagga ctatcgccaa tcgatgtgga    3300
ggcatctaga tcaacgttac atagatttgg gaatacttcg tctagctcaa tttggtatga    3360
attggcatac atagaagcaa aaggaaggat gaagaaaggg aatagagctt ggcagattgc    3420
tttagggtca gggtttaagt gtaacagtgc ggttgggtg gctctatgca atgtcaaggc     3480
ttccgcgaat agtccttggg aacattgcat cgatagatat ccggttcaaa ttgattctga    3540
ttcatcaaaa tcagagactc atgtcaaaaa cggtcggtcc taa                      3583
```

<210> SEQ ID NO 7
<211> LENGTH: 384
<212> TYPE: PRT
<213> ORGANISM: Camelina sativa

<400> SEQUENCE: 7

```
Met Gly Ala Gly Gly Arg Met Pro Val Pro Ser Ser Ser Lys Lys
1               5                   10                  15

Ser Glu Thr Asp Ala Ile Lys Arg Val Pro Cys Glu Lys Pro Pro Phe
            20                  25                  30

Thr Leu Gly Asp Leu Lys Lys Ala Ile Pro Pro Gln Cys Phe Lys Arg
        35                  40                  45

Ser Ile Pro Arg Ser Phe Ser Tyr Leu Ile Thr Asp Ile Ile Ala
    50                  55                  60

Ser Cys Phe Tyr Tyr Val Ala Thr Asn Tyr Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
    130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175
```

```
Ala Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Cys His Phe Phe Pro Asn Ala Pro Ile Tyr Asn Asp Arg Glu Arg Leu
    210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Leu Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Asp Tyr Tyr Gln Phe Asp Gly Thr Pro Trp
            340                 345                 350

Tyr Val Ala Met Tyr Arg Glu Ala Lys Glu Cys Ile Tyr Val Glu Pro
        355                 360                 365

Asp Arg Glu Gly Asp Lys Lys Gly Val Tyr Trp Tyr Asn Asn Lys Leu
    370                 375                 380

<210> SEQ ID NO 8
<211> LENGTH: 384
<212> TYPE: PRT
<213> ORGANISM: Camelina sativa

<400> SEQUENCE: 8

Met Gly Ala Gly Gly Arg Met Pro Val Pro Ser Ser Ser Lys Lys
1               5                   10                  15

Ser Glu Thr Asp Ala Ile Lys Arg Val Pro Cys Glu Lys Pro Pro Phe
                20                  25                  30

Thr Leu Gly Glu Leu Lys Lys Ala Ile Pro Pro Gln Cys Phe Lys Arg
            35                  40                  45

Ser Ile Pro Arg Ser Phe Ser Tyr Leu Ile Thr Asp Ile Ile Val Ala
        50                  55                  60

Ser Cys Phe Tyr Tyr Val Ala Thr Asn Tyr Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
    130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175
```

```
Pro Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Cys His Phe Phe Pro Asn Ala Pro Ile Tyr Asn Asp Arg Glu Arg Leu
    210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Met Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Asp Tyr Tyr Gln Phe Asp Gly Thr Pro Trp
            340                 345                 350

Tyr Val Ala Met Tyr Arg Glu Ala Lys Glu Cys Ile Tyr Val Glu Pro
        355                 360                 365

Asp Arg Glu Gly Asp Lys Lys Gly Val Tyr Trp Tyr Asn Asn Lys Leu
    370                 375                 380

<210> SEQ ID NO 9
<211> LENGTH: 384
<212> TYPE: PRT
<213> ORGANISM: Camelina sativa

<400> SEQUENCE: 9

Met Gly Ala Gly Gly Arg Met Pro Val Pro Ser Ser Ser Ser Lys Lys
1               5                   10                  15

Ser Glu Thr Asp Ala Ile Lys Arg Val Pro Cys Glu Lys Pro Pro Phe
            20                  25                  30

Thr Leu Gly Glu Leu Lys Lys Ala Ile Pro Pro Gln Cys Phe Lys Arg
        35                  40                  45

Ser Ile Pro Arg Ser Phe Ser Tyr Leu Ile Thr Asp Ile Ile Val Ala
    50                  55                  60

Ser Cys Phe Tyr Tyr Val Ala Thr Asn Tyr Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
    130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
```

```
                    165                 170                 175
Ala Gly Arg Ile Met Met Leu Thr Val Gln Phe Val Leu Gly Trp Pro
                180                 185                 190

Leu Tyr Leu Ala Phe Asn Val Ser Gly Arg Pro Tyr Asp Gly Phe Ala
            195                 200                 205

Cys His Phe Phe Pro Asn Ala Pro Ile Tyr Asn Asp Arg Glu Arg Leu
        210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Leu Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Asp Tyr Tyr Gln Phe Asp Gly Thr Pro Trp
            340                 345                 350

Tyr Val Ala Met Tyr Arg Glu Ala Lys Glu Cys Ile Tyr Val Glu Pro
        355                 360                 365

Asp Arg Glu Gly Asp Lys Lys Gly Val Tyr Trp Tyr Asn Asn Lys Leu
    370                 375                 380

<210> SEQ ID NO 10
<211> LENGTH: 505
<212> TYPE: PRT
<213> ORGANISM: Camelina sativa

<400> SEQUENCE: 10

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
                20                  25                  30

Ala Ser Arg Leu Thr Ser Asn Asp Leu Tyr His Phe Tyr Ser His Leu
            35                  40                  45

Gln His Asn Leu Ile Thr Val Ile Leu Leu Phe Ala Phe Thr Ala Phe
        50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Ser Val Ser
                85                  90                  95

Lys Ala Met Asp Ile Phe Tyr Gln Ile Arg Lys Ala Asp Thr Ser Arg
            100                 105                 110

Asn Val Ala Cys Asp Asp Pro Ser Ser Leu Asp Phe Leu Arg Lys Ile
        115                 120                 125

Gln Glu Arg Ser Gly Leu Gly Asp Glu Thr Tyr Ser Pro Gln Gly Leu
    130                 135                 140

Ile Asn Val Pro Pro Arg Lys Thr Phe Ala Ala Ser Arg Glu Glu Thr
145                 150                 155                 160
```

```
Glu Gln Val Ile Ile Gly Ala Leu Asp Lys Leu Phe Glu Asn Thr Lys
            165                 170                 175

Val Asn Pro Arg Glu Ile Gly Ile Leu Val Asn Ser Ser Met Phe
        180                 185                 190

Asn Pro Thr Pro Ser Leu Ser Ala Met Val Val Asn Thr Phe Lys Leu
        195                 200                 205

Arg Ser Asn Ile Lys Ser Phe Ser Leu Gly Gly Met Gly Cys Ser Ala
        210                 215                 220

Gly Val Ile Ala Ile Asp Leu Ala Lys Asp Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Lys Leu Cys His Thr Val Arg Thr His Thr Gly Ala
        290                 295                 300

Asp Asp Met Ser Phe Arg Cys Val Gln Gln Gly Asp Glu Ser Gly
305                 310                 315                 320

Lys Ile Gly Val Cys Leu Ser Lys Asp Ile Thr Val Ala Gly Ile
                325                 330                 335

Ala Leu Lys Lys Asn Ile Ala Thr Leu Gly Pro Leu Ile Leu Pro Leu
                340                 345                 350

Ser Glu Lys Phe Leu Phe Leu Val Thr Phe Ile Ala Lys Lys Leu Leu
        355                 360                 365

Lys Asp Lys Ile Lys His Tyr Tyr Val Pro Asp Phe Lys Leu Ala Ile
        370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ser Ile Trp Tyr Glu
            420                 425                 430

Leu Ala Tyr Ile Glu Ala Lys Gly Arg Met Lys Lys Gly Asn Arg Ala
        435                 440                 445

Trp Gln Ile Ala Leu Gly Ser Gly Phe Lys Cys Asn Ser Ala Val Trp
        450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Ser Gly Ser Ser Lys Ser
                485                 490                 495

Asp Thr His Val Lys Asn Gly Arg Ser
                500                 505

<210> SEQ ID NO 11
<211> LENGTH: 505
<212> TYPE: PRT
<213> ORGANISM: Camelina sativa

<400> SEQUENCE: 11

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
            20                  25                  30
```

```
Ala Ser Lys Leu Thr Ala Asn Asp Leu Tyr His Phe Tyr Ser His Leu
         35                  40                  45

Gln His Asn Leu Ile Thr Val Ile Leu Leu Phe Ala Phe Thr Ala Phe
     50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Ser Val Ser
                 85                  90                  95

Lys Ala Met Asp Ile Phe Tyr Gln Ile Arg Lys Ala Asp Thr Ser Arg
                 100                 105                 110

Asn Val Ala Cys Asp Asp Pro Ser Ser Leu Asp Phe Leu Arg Lys Ile
                 115                 120                 125

Gln Glu Arg Ser Gly Leu Gly Asp Glu Thr Tyr Ser Pro Gln Gly Leu
             130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                 165                 170                 175

Val Asn Pro Arg Glu Ile Gly Ile Leu Val Val Asn Ser Ser Met Phe
             180                 185                 190

Asn Pro Thr Pro Ser Leu Ser Ala Met Val Val Asn Thr Phe Lys Leu
             195                 200                 205

Arg Ser Asn Ile Lys Ser Phe Ser Leu Gly Gly Met Gly Cys Ser Ala
         210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                 245                 250                 255

Tyr Ala Gly Glu Asn Arg Ser Met Met Val Ser Asn Cys Leu Phe Arg
             260                 265                 270

Val Gly Gly Ala Ala Ile Leu Leu Ser Asn Lys Leu Gly Asp Arg Arg
         275                 280                 285

Arg Ser Lys Tyr Lys Leu Cys His Thr Val Arg Thr His Thr Gly Ala
         290                 295                 300

Asp Asp Lys Ser Phe Arg Cys Val Gln Gln Gly Asp Asp Glu Gly Gly
305                 310                 315                 320

Lys Ile Gly Val Cys Leu Ser Lys Asp Ile Thr Val Ala Gly Thr
                 325                 330                 335

Ala Leu Lys Lys Asn Ile Ala Thr Leu Gly Pro Leu Ile Leu Pro Leu
             340                 345                 350

Ser Glu Lys Phe Leu Phe Leu Val Thr Phe Ile Ala Lys Lys Leu Leu
         355                 360                 365

Lys Asp Lys Ile Lys His Cys Tyr Val Pro Asp Phe Lys Leu Ala Ile
         370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                 405                 410                 415

Thr Leu His Arg Phe Gly Asn Thr Ser Ser Ser Ile Trp Tyr Glu
             420                 425                 430

Leu Ala Tyr Ile Glu Ala Lys Gly Arg Met Lys Lys Gly Asn Arg Ala
                 435                 440                 445
```

```
Trp Gln Ile Ala Leu Gly Ser Gly Phe Lys Cys Asn Ser Ala Val Trp
    450                 455                 460
Val Ala Leu Cys Asn Val Lys Ala Ser Ala Asn Ser Pro Trp Glu Asp
465                 470                 475                 480
Cys Ile Asp Arg Tyr Pro Val Gln Ile Asp Ser Asp Ser Ser Lys Ser
                485                 490                 495
Glu Thr His Val Lys Asn Gly Arg Ser
                500                 505

<210> SEQ ID NO 12
<211> LENGTH: 505
<212> TYPE: PRT
<213> ORGANISM: Camelina sativa

<400> SEQUENCE: 12

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
                20                  25                  30

Ala Ser Thr Leu Thr Thr Asn Asp Leu Tyr His Phe Tyr Ser His Leu
            35                  40                  45

Gln His Asn Leu Val Thr Val Ile Leu Leu Phe Ala Phe Ser Ser Phe
    50                  55                  60

Gly Leu Val Leu Tyr Val Val Thr Arg Arg Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Arg
                100                 105                 110

Asn Val Ala Cys Asp Asp Pro Ser Ser Leu Asp Phe Leu Arg Lys Ile
            115                 120                 125

Gln Glu Arg Ser Gly Leu Gly Asp Glu Thr Tyr Ser Pro Pro Gly Leu
    130                 135                 140

Ile His Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Glu Ile Gly Ile Leu Val Val Asn Ser Ser Met Phe
                180                 185                 190

Asn Pro Thr Pro Ser Leu Ser Ala Met Val Val Asn Thr Phe Lys Leu
            195                 200                 205

Arg Ser Asn Ile Lys Ser Phe Ser Leu Gly Gly Met Gly Cys Ser Ala
    210                 215                 220

Gly Val Ile Ala Ile Asp Leu Ala Lys Asp Leu Leu His Val His Lys
225                 230                 235                 240

His Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
                260                 265                 270

Val Gly Gly Ala Ala Ile Leu Leu Ser Asn Lys Pro Gly Asp Arg Arg
            275                 280                 285

Arg Ser Lys Tyr Lys Leu Cys His Thr Val Arg Thr His Thr Gly Ala
    290                 295                 300

Asp Asp Lys Ser Phe Arg Cys Val Gln Gln Gly Asp Asp Glu Ser Gly
305                 310                 315                 320
```

```
Lys Ile Gly Val Cys Leu Ser Lys Asp Ile Thr Val Ala Gly Thr
                325                 330                 335

Ala Leu Lys Lys Asn Ile Ala Thr Leu Gly Pro Leu Ile Leu Pro Leu
                340                 345                 350

Ser Glu Lys Phe Leu Phe Leu Val Thr Phe Ile Ala Lys Lys Leu Leu
                355                 360                 365

Lys Asp Lys Ile Lys His Tyr Tyr Val Pro Asp Phe Lys Leu Ala Ile
                370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
                420                 425                 430

Leu Ala Tyr Ile Glu Ala Lys Gly Arg Met Lys Lys Gly Asn Arg Ala
                435                 440                 445

Trp Gln Ile Ala Leu Gly Ser Gly Phe Lys Cys Asn Ser Ala Val Trp
                450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Ser Asp Ser Ser Lys Ser
                485                 490                 495

Glu Thr His Val Lys Asn Gly Arg Ser
                500                 505

<210> SEQ ID NO 13
<211> LENGTH: 24
<212> TYPE: DNA
<213> ORGANISM: Artificial Sequence
<220> FEATURE:
<223> OTHER INFORMATION: Primer FAD2 631F

<400> SEQUENCE: 13
tcaacaaccc tcttggacgc atca                                          24

<210> SEQ ID NO 14
<211> LENGTH: 24
<212> TYPE: DNA
<213> ORGANISM: Artificial Sequence
<220> FEATURE:
<223> OTHER INFORMATION: Primer FAD2 832R

<400> SEQUENCE: 14
cttgtgcagc agcgtaacgg taaa                                          24

<210> SEQ ID NO 15
<211> LENGTH: 25
<212> TYPE: DNA
<213> ORGANISM: Artificial Sequence
<220> FEATURE:
<223> OTHER INFORMATION: Primer AtFAE1 probe F

<400> SEQUENCE: 15
agacggtcca agtacaagct agttc                                         25

<210> SEQ ID NO 16
<211> LENGTH: 23
<212> TYPE: DNA
<213> ORGANISM: Artificial Sequence
<220> FEATURE:
```

<223> OTHER INFORMATION: Primer AtFAE1 probe R

<400> SEQUENCE: 16
ccaaatctat gtaacgttga tct                                              23

<210> SEQ ID NO 17
<211> LENGTH: 25
<212> TYPE: DNA
<213> ORGANISM: Artificial Sequence
<220> FEATURE:
<223> OTHER INFORMATION: Primer AtLFY probe F

<400> SEQUENCE: 17
gatgcggcgg ggaataacgg cggag                                            25

<210> SEQ ID NO 18
<211> LENGTH: 24
<212> TYPE: DNA
<213> ORGANISM: Artificial Sequence
<220> FEATURE:
<223> OTHER INFORMATION: Primer AtLFY probe R

<400> SEQUENCE: 18
cctgaagaag gaactcacgg catt                                             24

<210> SEQ ID NO 19
<211> LENGTH: 24
<212> TYPE: DNA
<213> ORGANISM: Artificial Sequence
<220> FEATURE:
<223> OTHER INFORMATION: Primer AtFAD2 start

<400> SEQUENCE: 19
aacatgggtg caggtggaag aatg                                             24

<210> SEQ ID NO 20
<211> LENGTH: 25
<212> TYPE: DNA
<213> ORGANISM: Artificial Sequence
<220> FEATURE:
<223> OTHER INFORMATION: Primer AtFAD2 stop2

<400> SEQUENCE: 20
tcataactta ttgttgtacc agtac                                            25

<210> SEQ ID NO 21
<211> LENGTH: 24
<212> TYPE: DNA
<213> ORGANISM: Artificial Sequence
<220> FEATURE:
<223> OTHER INFORMATION: Primer CaFAE1 start

<400> SEQUENCE: 21
atgacgtcca ttaacgtaaa gctc                                             24

<210> SEQ ID NO 22
<211> LENGTH: 21
<212> TYPE: DNA
<213> ORGANISM: Artificial Sequence
<220> FEATURE:
<223> OTHER INFORMATION: Primer CaFAE1 stop

<400> SEQUENCE: 22
ttaggaccga ccgttttggg c                                                21

```
<210> SEQ ID NO 23
<211> LENGTH: 26
<212> TYPE: DNA
<213> ORGANISM: Artificial Sequence
<220> FEATURE:
<223> OTHER INFORMATION: Primer AtKCS F

<400> SEQUENCE: 23
gggtggctct tcgcaatgtc gagccc                                          26

<210> SEQ ID NO 24
<211> LENGTH: 25
<212> TYPE: DNA
<213> ORGANISM: Artificial Sequence
<220> FEATURE:
<223> OTHER INFORMATION: Primer CsFAE1 5 prime RACE

<400> SEQUENCE: 24
gaggcttttc cggcaagtaa cgccg                                           25

<210> SEQ ID NO 25
<211> LENGTH: 24
<212> TYPE: DNA
<213> ORGANISM: Artificial Sequence
<220> FEATURE:
<223> OTHER INFORMATION: Primer AtKCS cons F

<400> SEQUENCE: 25
ggtatgaatt ggcttacacg gaag                                            24

<210> SEQ ID NO 26
<211> LENGTH: 24
<212> TYPE: DNA
<213> ORGANISM: Artificial Sequence
<220> FEATURE:
<223> OTHER INFORMATION: Primer CsKCSA F

<400> SEQUENCE: 26
tatgaattgg cttacacgga agcc                                            24

<210> SEQ ID NO 27
<211> LENGTH: 29
<212> TYPE: DNA
<213> ORGANISM: Artificial Sequence
<220> FEATURE:
<223> OTHER INFORMATION: Primer CsFAE1A R2

<400> SEQUENCE: 27
tatattgcca atataagtat taaaggtcc                                       29

<210> SEQ ID NO 28
<211> LENGTH: 24
<212> TYPE: DNA
<213> ORGANISM: Artificial Sequence
<220> FEATURE:
<223> OTHER INFORMATION: Primer AtKCS cons F

<400> SEQUENCE: 28
ggtatgaatt ggcttacacg gaag                                            24

<210> SEQ ID NO 29
<211> LENGTH: 29
<212> TYPE: DNA
<213> ORGANISM: Artificial Sequence
<220> FEATURE:
<223> OTHER INFORMATION: Primer CsFAE1B R
```

```
<400> SEQUENCE: 29
tatattgcca atataagtat taaaggtcc                                    29

<210> SEQ ID NO 30
<211> LENGTH: 24
<212> TYPE: DNA
<213> ORGANISM: Artificial Sequence
<220> FEATURE:
<223> OTHER INFORMATION: Primer AtKCS cons F

<400> SEQUENCE: 30
ggtatgaatt ggcttacacg gaag                                         24

<210> SEQ ID NO 31
<211> LENGTH: 24
<212> TYPE: DNA
<213> ORGANISM: Artificial Sequence
<220> FEATURE:
<223> OTHER INFORMATION: Primer CsFAE1C R

<400> SEQUENCE: 31
ggtagagatc gtttgtggta agcg                                         24

<210> SEQ ID NO 32
<211> LENGTH: 22
<212> TYPE: DNA
<213> ORGANISM: Artificial Sequence
<220> FEATURE:
<223> OTHER INFORMATION: Primer CsFAD2 start

<400> SEQUENCE: 32
atgggtgcag gtggaagaat gc                                           22

<210> SEQ ID NO 33
<211> LENGTH: 30
<212> TYPE: DNA
<213> ORGANISM: Artificial Sequence
<220> FEATURE:
<223> OTHER INFORMATION: Primer CsFAD2 stop

<400> SEQUENCE: 33
tcataactta ttgttgtacc agtacacacc                                   30

<210> SEQ ID NO 34
<211> LENGTH: 24
<212> TYPE: DNA
<213> ORGANISM: Artificial Sequence
<220> FEATURE:
<223> OTHER INFORMATION: Primer CsFAE1 start

<400> SEQUENCE: 34
atgacgtccg ttaacgcaaa gctc                                         24

<210> SEQ ID NO 35
<211> LENGTH: 24
<212> TYPE: DNA
<213> ORGANISM: Artificial Sequence
<220> FEATURE:
<223> OTHER INFORMATION: Primer CsFAE1 stop

<400> SEQUENCE: 35
ttaggaccga ccgttttttga catg                                        24

<210> SEQ ID NO 36
<211> LENGTH: 24
```

```
<212> TYPE: DNA
<213> ORGANISM: Artificial Sequence
<220> FEATURE:
<223> OTHER INFORMATION: Primer CsACT For

<400> SEQUENCE: 36
acaatttccc gctctgctgt tgtg                                          24

<210> SEQ ID NO 37
<211> LENGTH: 24
<212> TYPE: DNA
<213> ORGANISM: Artificial Sequence
<220> FEATURE:
<223> OTHER INFORMATION: Primer CsACT Rev

<400> SEQUENCE: 37
agggtttctc tcttccacat gcca                                          24

<210> SEQ ID NO 38
<211> LENGTH: 26
<212> TYPE: DNA
<213> ORGANISM: Artificial Sequence
<220> FEATURE:
<223> OTHER INFORMATION: Primer CsACT probe

<400> SEQUENCE: 38
tgtttcaaac gctctatccc tcgctc                                        26

<210> SEQ ID NO 39
<211> LENGTH: 23
<212> TYPE: DNA
<213> ORGANISM: Artificial Sequence
<220> FEATURE:
<223> OTHER INFORMATION: Primer CsFAD2 A For1

<400> SEQUENCE: 39
ctgcgagaaa ccaccgttca ccc                                           23

<210> SEQ ID NO 40
<211> LENGTH: 26
<212> TYPE: DNA
<213> ORGANISM: Artificial Sequence
<220> FEATURE:
<223> OTHER INFORMATION: Primer CsFAD2 all Rev

<400> SEQUENCE: 40
cacgagtagt caacgaggta aaccgg                                        26

<210> SEQ ID NO 41
<211> LENGTH: 29
<212> TYPE: DNA
<213> ORGANISM: Artificial Sequence
<220> FEATURE:
<223> OTHER INFORMATION: Primer CsFAD2 all probe

<400> SEQUENCE: 41
ccacttctat tcccatctcc aacacaacc                                     29

<210> SEQ ID NO 42
<211> LENGTH: 26
<212> TYPE: DNA
<213> ORGANISM: Artificial Sequence
<220> FEATURE:
<223> OTHER INFORMATION: Primer CsFAE1 all For

<400> SEQUENCE: 42
```
aacctttgct tgtttccgtt aacggc                                          26

<210> SEQ ID NO 43
<211> LENGTH: 26
<212> TYPE: DNA
<213> ORGANISM: Artificial Sequence
<220> FEATURE:
<223> OTHER INFORMATION: Primer CsFAE1 all Rev

<400> SEQUENCE: 43
cacgagtagt caacgaggta aaccgg                                          26

<210> SEQ ID NO 44
<211> LENGTH: 29
<212> TYPE: DNA
<213> ORGANISM: Artificial Sequence
<220> FEATURE:
<223> OTHER INFORMATION: Primer CsFAE1 all probe

<400> SEQUENCE: 44
ccacttctat tcccatctcc aacacaacc                                       29

<210> SEQ ID NO 45
<211> LENGTH: 1152
<212> TYPE: DNA
<213> ORGANISM: Capsella rubella

<400> SEQUENCE: 45
atgggtgcag gtggaagaat gccggttcct tcttcttcca agaagtcgga aaccaatgcc      60
atcaagcgtg tgccgtgcga gaaaccgcct ttcacggttg gagatctcaa gaaagcaatc     120
ccaccgcagt gtttcaaacg ctctatccct cgctctttct cctaccttat cactgacatc     180
attattgcct cctgcttcta ctacgtcgcc accaattact tctctctcct ccctcagcct     240
ctctcttact ttgcttggcc cctctactgg gcctgtcagg gctgtgtcct taccggtgtc     300
tgggtcattg cccacgaatg cggtcaccat gctttcagcg actaccaatg ctggatgac      360
acagttggtc ttatcttcca ctccttcctc ctcgtccctt acttctcctg aagtacagt      420
catcgccgcc accattccaa cacgggatct cttgaaaggg atgaagtatt tgttccaaag     480
cagaaatccg ctatcaagtg gtacggcaaa taccttaaca ccctttttgg acgtatcatg     540
atgttaaccg tccagtttgt cctcggatgg cccttgtact tggcctttaa cgtctcaggc     600
agaccttacg atgggttcgc ttgccatttc ttccccaacg ctcccatcta caacgaccgc     660
gaacgccttc agatctatat ctcggatgcc ggtattctag cagtctgtta tggtctttac     720
cgttacgctg ctgcacaagg aatggcctcg atgatctgcc tctacggagt accacttctg     780
atagtgaacg cgttccttgt cttgatcaca tacttgcagc acactcatcc tgcgttgcct     840
cactacgatt catccgagtg ggattggctt aggggagctt tggctaccgt agacagagac     900
tatggaatct tgaacaaggt gttccacaac atcacggaca cacatgtggc tcatcatctg     960
ttctcgacaa tgcctcatta caacgcgatg gaagctacaa aggcgataaa gcctatactc    1020
ggagactatt accagtttga tggaacaccg tggtatgtgg cgatgtatag ggaggcaaag    1080
gagtgtatct atgtagaacc ggacagggaa ggtgacaaga aggtgtgta ctggtacaac    1140
aataagttat ga                                                       1152

<210> SEQ ID NO 46
<211> LENGTH: 1152
<212> TYPE: DNA
<213> ORGANISM: Arabidopsis lyrata

<400> SEQUENCE: 46

| | | | | | |
|---|---|---|---|---|---|
| atgggtgcag | gtggaagaat | gccggttcct | acttcttcca | agaaatcgga | aaccgacacc | 60 |
| ataaagcgtg | tgccgtgcga | gaaaccgcct | ttctcggtgg | gagatctgaa | gaaagcaatc | 120 |
| ccccagcatt | gtttcaaacg | ctcaatccct | cgctctttct | cctaccttat | cggtgacatc | 180 |
| ataattgcct | catgcttcta | ctacgttgcc | accaattact | tctctctcct | acctcagcct | 240 |
| ctctcttact | tggcttggcc | actctattgg | gcctgtcaag | gctgtgtcct | aactggtgtc | 300 |
| tgggtcatag | cccacgaatg | cggtcaccac | gcattcagcg | actaccaatg | gctggatgac | 360 |
| acagtcggtc | ttatcttcca | ttccttcctc | ctcgtccctt | acttctcctg | gaagtatagt | 420 |
| catcgccgtc | accattccaa | cacgggatcc | ctcgaaagag | atgaagtatt | tgtcccaaaa | 480 |
| cagaaatccg | caatcaagtg | gtacggcaaa | tacctcaaca | ccctcttggg | acgcatcatg | 540 |
| atgttaaccg | tccagtttgt | cctcgggtgg | cccttgtact | tagcctttaa | cgtttcgggc | 600 |
| agaccgtatg | acgggttcgc | ttgccatttc | ttccccaacg | ctcccatcta | caatgaccgc | 660 |
| gaacgcctcc | agatatacct | ctcggatgcg | ggtattctag | ccgtctgttt | tggtctttac | 720 |
| cgttacgccg | ctgcacaagg | aatggcctct | atgatctgcc | tctacggagt | accgcttctg | 780 |
| atagtgaatg | cgttcctcgt | cttgatcact | tacttgcagc | acactcaccc | ctccttgcct | 840 |
| cactacgatt | catcagagtg | ggactggctc | aggggagctt | tggctaccgt | agacagagac | 900 |
| tatggaatct | tgaacaaggt | gttccacaac | attacagaca | cacgtggc | acatcacctg | 960 |
| ttctcgacaa | tgccgcatta | taacgcaatg | gaagctacaa | aggcgataaa | gccaatactg | 1020 |
| ggagactatt | accagttcga | tggaacaccg | tggtatgtgg | cgatgtatag | ggaggcaaag | 1080 |
| gagtgtatct | acgtagaacc | ggacagggaa | ggtgacaaga | aggtgtgta | ctggtacaac | 1140 |
| aataagttat | ga | | | | | 1152 |

<210> SEQ ID NO 47
<211> LENGTH: 1518
<212> TYPE: DNA
<213> ORGANISM: Arabidopsis lyrata

<400> SEQUENCE: 47

| | | | | | |
|---|---|---|---|---|---|
| atgacgtccg | ttaacgcaaa | gctcctttac | cattacgtct | taaccaactt | tttcaacctc | 60 |
| tgtttgttcc | cgttaacggc | gttcgtcgcc | ggaaaagcct | ctcggcatac | acaaacgat | 120 |
| ctccacaact | tcttttccta | tctccaacac | aaccttataa | ccgtagctat | actctttgct | 180 |
| ttcactgtct | ttggttttgt | tctctacatg | gtaacccgac | ccaaaccggt | ttatctcgtt | 240 |
| gactactcgt | gctaccttcc | accaccgcat | ctcagagcca | gtgtctccag | agtcatggat | 300 |
| gttttctatc | aaataagaaa | agctgatact | tcacggaacg | tggcatgcga | tgatccgtcc | 360 |
| tcgcttgatt | tcctgaggaa | gattcaagag | cgttcaggtc | taggtgatga | gacctacggt | 420 |
| cccgagggac | tccttcacgt | gcccccacgg | aagactttg | cagcggcacg | tgaagagaca | 480 |
| gagcaggtta | tcattggtgc | gctcgaaaat | ctattccaga | acaccaaagt | taacccctaga | 540 |
| gagattggta | tacttgtggt | gaactcaagc | atgtttaatc | caactccttc | gctttccgcg | 600 |
| atggtcgtta | atactttcaa | gctccgaagc | aacatcaaaa | gctttaatct | tggaggaatg | 660 |
| ggttgtagtg | ctggtgttat | cgccattgat | cttgcgaagg | acttgttgca | tgttcataaa | 720 |
| aacacttatg | ctcttgtggt | gagcactgag | aacatcactc | aagggattta | tgctggcgaa | 780 |
| aatagatcaa | tgatggttag | caattgcttg | ttccgtgttg | gtggggccgc | gattttgctc | 840 |

| | |
|---|---|
| tccaacaagc ctagagatcg gagacggtcc aagtacaagc tagctcacac ggttcgaacc | 900 |
| catacgggag ctgatgacaa gtcttttcga tgtgtgcaac aagaagacga tgagagtggt | 960 |
| aaaatcggtg tttgtctgtc aaaggacata accaatgttg cggggacaac gctaaagaaa | 1020 |
| aacatagcaa cattgggtcc gttgattctt cctttaagcg agaaatttct ttttttcgtt | 1080 |
| accttcgtcg ccaagaaact tttaaaggac agaatcaagc attactatgt cccggatttt | 1140 |
| aagcttgcta ttgaccattt ctgtattcat gccggaggca gagccgtgat cgatgagcta | 1200 |
| gagaagagct taggactatc accgatcgac gtggaggcat ctagatcaac gttacataga | 1260 |
| tttgggaata cgtcgtctag ctcaatttgg tatgaattgg catacataga ggcaaaagga | 1320 |
| agaatgaaga aagggaataa agcttggcag attgctttag gatcagggtt taagtgtaat | 1380 |
| agtgcggttt gggtggctct acgcaatgtc aagccttcgg caaatagtcc ttggcaacat | 1440 |
| tgcatcgata gatatccggc taaaattgat tctgatttgt caaagtcaga gactcatgtc | 1500 |
| aaaaacggtc ggtcctaa | 1518 |

<210> SEQ ID NO 48
<211> LENGTH: 1155
<212> TYPE: DNA
<213> ORGANISM: Camelina hispida

<400> SEQUENCE: 48

| | |
|---|---|
| atgggtgcag gtggaagaat gccagttcct tcttcttctt ccaagaaatc ggaaaccaat | 60 |
| gccataaagc gtgtgccctg cgagaaaccg ccgttcacgg ttggagaact gaagaaagca | 120 |
| atcccaccgc attgtttcaa cgctctatcc ctcgctcttt ctcctacct tatcactgac | 180 |
| atcattattg cctcctgctt ctactacgtc gccaccaatt acttctctct cctccctcag | 240 |
| cctctctctt acttggcttg gcctctctat tgggcctgtc aaggctgtgt cctaaccggt | 300 |
| gtctgggtca tagcccatga atgcggtcac cacgcattca gcgactacca atggctcgat | 360 |
| gacacagttg gtcttatctt ccattccttc cttctcgtcc cttacttctc ctggaagtac | 420 |
| agtcatcgcc gtcaccattc aacacagga tctcttgaaa gagatgaagt atttgtccca | 480 |
| aagcagaaat cagctatcaa gtggtatggc aaataccctca caacccctcc tggacgcatc | 540 |
| atgatgttaa ccgtccagtt tgtcctcggg tggcccttgt acttggcctt taacgtctcg | 600 |
| ggcagaccat acgacgggtt cgcttgccat ttcttcccca cgctcccat ctacaacgac | 660 |
| cgtgaacgcc tccagatata tctctctgat gctggtattc tagcagtctg ttttgggctt | 720 |
| taccgttatg ccgctgcaca aggattggct tcgatgatct gcctctacgg agtaccgctt | 780 |
| ctgatagtga acgcgttcct cgtcttgatc acttacttgc agcacactca tcctgcgttg | 840 |
| cctcactacg attcatccga gtgggattgg cttaggggag cttttggctac cgtagacaga | 900 |
| gactatggaa tcttgaacaa ggtgttccac aacatcacgg acacacatgt ggctcatcat | 960 |
| ctgttctcga caatgccgca ttataatgcg atggaagcta caaaggcgat aaagccaata | 1020 |
| ctcggtgact actaccagtt cgacggaaca ccgtggtatg tggcgatgta tagggaggca | 1080 |
| aaggagtgta tctatgtaga accggacagg gaaggtgaca agaaaggtgt gtactggtac | 1140 |
| aacaataagt tatga | 1155 |

<210> SEQ ID NO 49
<211> LENGTH: 1518
<212> TYPE: DNA
<213> ORGANISM: Camelina hispida

<400> SEQUENCE: 49

```
atgacgtccg ttaacgcaaa gctcctttac cattacgtcc taaccaactt tttcaacctt    60
tgcttgtttc cgttaacggc gttacttgtc ggaaaagtct ctcggcttac cgcaaacgat   120
ctctaccact tctatttcca tctccaacac aatctcataa ccgttattct actctttgct   180
ttcaccactt ttggtttggt tctctacatt gtaacccggc ccaaaccggt ttacctcgtt   240
gactactcgt gctaccttcc accaccgcat ctcaaagtta gtgtttccaa agtcatggat   300
attttctacc aaataagaaa agctgatact tcacggaacg tggcatgcga tgatccatcc   360
tcgcttgatt tcctgaggaa gattcaagaa cgttcaggtc taggtgatga aacctacagt   420
cccccgggac tcattcacgt gccaccacaa aagacccttg cagcgtcacg tgaagagaca   480
gagcaggtaa tcatcggtgc gctagaaaag ctattcgaga acactaaagt taaccctaga   540
gatattggta tacttgtggt caactcaagc atgtttaatc caactccttc gttatccgct   600
atggtcgtaa atactttcaa gcttcgaagc aacatcaaaa gctttagtct cggaggaatg   660
ggttgtagtg ctggtgttat cgccattgat cttgcaaagg acttgttgca tgttcataaa   720
aacacttatg cacttgtggt gagcactgag aacatcactc acggcattta ttctggcgaa   780
aatagatcca tgatggttag taattgcttg ttccgtgttg gtggggcagc gattttgctc   840
tccaacaagc caggagatcg tagacggtcc aagtacaagc tatgtcacac cgttcgaacg   900
cataccggag ctgatgacaa gtcttttcga tgtgtgcaac aaggagacga tgagagcggt   960
aaaattggag tttgtctgtc aaaggacata acagttgttg cggggacagc gcttaagaaa  1020
aacatagcaa cgttaggtcc attgattctt cctttaagcg aaaagtttct gtttttagta  1080
accttcatcg ccaagaaagt tttgaaggac aagatcaaga actattacgt cccggatttc  1140
aagcttgcta ttgaccactt ctgtattcat gcgggaggca gagccgtgat cgatgtgctt  1200
gagaagagct taggactatc tccaatcgat gtggaggcat ctagatcaac gttacataga  1260
tttgggaata cttcgtctag ctcaatttgg tatgaattgg catacataga agcaaaagga  1320
aggatgaaga aagggaatag agcttggcag attgctttag ggtcagggtt taagtgtaac  1380
agtgcggttt gggtggctct atgcaatgtc aaggcttcgg cgaatagtcc ttgggagcat  1440
tgcatcgata gatatccggt tcaaattgat tctgattcat caaaatcaga gactcatgtc  1500
aaaaacggtc ggtcctaa                                                 1518
```

<210> SEQ ID NO 50  
<211> LENGTH: 1518  
<212> TYPE: DNA  
<213> ORGANISM: Camelina hispida

<400> SEQUENCE: 50

```
atgacgtccg ttaacgcaaa gctcctttac cattacgtcc taaccaactt tttcaacctt    60
tgcttgtttc cgttaacggc gttacttgcc ggaaaagcct ctaggcttac cacaaacgat   120
ctctaccact tctattccca tctccaacac aaccttgtaa ccgtaatttt actctttgct   180
ttcacctctt tcggtttggt tctctacatt gtaacccggc ccaaaccggt ttacctcgtt   240
gactactcgt gctaccttcc accaccgcac ctcaaagtta gtgtttccaa ggtcatggat   300
attttctacc aaatcagaaa agctgatact tcacgaaacg tggcatgcga tgatccatcc   360
tcgcttgatt tcttgaggaa gattcaagaa cgttcaggtc taggtgatga aacctacagt   420
cccccgggac tcattaacgt gccccacaa aagacccttg cagcttcacg tgaagagaca   480
gagcaggtaa tcatcggtgc gctagaaaag ctattcgaga acaccaaagt taaccctaga   540
```

| | |
|---|---|
| gagattggta tacttgtggt gaactcaagc atgtttaatc caactccttc gctatctgcg | 600 |
| atggtcgtta acactttcaa gctccgaagc aacatcaaaa gcttaagtct cggaggaatg | 660 |
| ggttgtagtg ctggtgtcat cgccattgat cttgcaaagg acttgttgca tgttcataaa | 720 |
| aacacttatg ctcttgtggt gagcactgag aacatcactc aaggcatcta tgctggcgaa | 780 |
| aatagatcca tgatggttag caattgcttg ttccgtgttg gtggcgcagc gattttgctc | 840 |
| tccaacaagg cgggagatcg gagacggtct aagtacaagc tgtgtcacac tgttcgaacg | 900 |
| cataccggag ctgatgacaa gtcttttcga tgtgtgcaac aaggagacga tgagagcggt | 960 |
| aaaattggag tttgtctgtc aaaggacata accgttgttg cggggacagc gcttaagaaa | 1020 |
| aacatagcaa cgttgggtcc gttgattctt cctttaagcg aaaagtttct gttttagta | 1080 |
| accttcatcg ccaagaaact tttgaaggac aagatcaagc actattacgt ccccgatttc | 1140 |
| aagcttgcta ttgaccattt ctgtattcat gcgggaggca gagccgtaat cgatgttctt | 1200 |
| gagaagagct taggactatc tccaatagat gtggaggcct ctagatcaac gttacataga | 1260 |
| tttgggaata cttcgtctag ctcaatttgg tatgaattgg catacataga agcaaaagga | 1320 |
| aggatgaaga aagggaatag agcttggcag attgctttag ggtcagggtt taagtgtaac | 1380 |
| agtgcggttt gggtggctct atgcaatgtc aaggcttcgg cgaatagtcc ttgggaacat | 1440 |
| tgcatcgata gatatccggt tcaaattgat tctgattcat caaaatcaga gactcatgtc | 1500 |
| aaaaacggtc ggtcctaa | 1518 |

<210> SEQ ID NO 51
<211> LENGTH: 1158
<212> TYPE: DNA
<213> ORGANISM: Camelina laxa

<400> SEQUENCE: 51

| | |
|---|---|
| atgggtgcag gtggaagaat gccagttcct tcttcttctt cttccaagaa atctgaaacc | 60 |
| gatgccataa agcgtgtgcc ctgcgagaaa ccgccgttca cgcttggaga actgaagaaa | 120 |
| gcaatccccc cgcagtgttt caaacgctct atccctcgct cttctcctta ccttatcact | 180 |
| gacatcattg ttgcctcctg cttctactac gtcgccacca attacttctc tctcctccct | 240 |
| cagcctctct cttacttggc ttggcctctc tactgggcct gtcaaggctg tgtcctaacc | 300 |
| ggtgtctggg tcatagctca cgaatgcggt caccacgcat tcagcgacta ccaatggctt | 360 |
| gatgacacag ttggtcttat cttccattcc ttccttctcg tcccttactt ctcctggaag | 420 |
| tacagtcatc gtcgtcacca ttccaacaca ggatctctcg aaagagatga agtatttgtc | 480 |
| ccaaagcaga aatcagctat caagtggtat ggcaaatacc tcaacaaccc tcctggacgc | 540 |
| atcatgatgt taaccgtcca gtttgtcctc gggtggccct tgtacttggc ctttaacgtc | 600 |
| tcgggcagac cgtacgacgg gttcgcttgc catttcttcc ccaacgctcc catctacaac | 660 |
| gaccgcgaac gcctccagat atatctctct gatgccggta tcctagcagt ctgttttggg | 720 |
| ctttaccgtt acgttgctgc acaaggaatg gcctcgatga tctgcctcta cggagtaccg | 780 |
| cttctgatag tgaacgcgtt cctcgtcttg atcacttact tgcagcacac tcatcctgcg | 840 |
| ttgcctcact acgattcatc cgagtgggat tggcttaggg gagctttggc taccgttgac | 900 |
| agagactatg gaatcttgaa caaggtgttc cacaacatca cggacacaca tgtggctcat | 960 |
| catctgttct cgacaatgcc acattataat gcgatggaag ctacaaaggc gataaagcca | 1020 |
| atactcggtg actactacca gttcgacgga acaccgtggt atgtggcgat gtataggag | 1080 |
| gcaaaggagt gtatctatgt agaaccggac agagaaggtg acaagaaagg tgtgtactgg | 1140 |

<210> SEQ ID NO 52
<211> LENGTH: 1518
<212> TYPE: DNA
<213> ORGANISM: Camelina laxa

<400> SEQUENCE: 52

```
atgacgtccg ttaacgcaaa gctcctttac cattacgtcc taaccaactt tttcaacctt    60
tgcttgtttc cgttaacggc gttacttgtc ggaaaagtct ctcggcttac cgcaaacgat   120
ctctaccact tctatttcca tctccaacac aatctcataa ccgttattct actctttgct   180
ttcaccactt ttggtttggt tctctacatt gtaacccggc ccaaaccggt ttacctcgtt   240
gactactcgt gctaccttcc accaccgcat ctcaaagtta gtgtttccaa agtcatggat   300
atttctacc aaataagaaa agctgatact tcacggaacg tggcatgcga tgatccatcc   360
tcgcttgatt tcctgaggaa gattcaagaa cgttcaggtc taggtgatga aacctacagt   420
cccccgggac tcattcacgt gccaccacaa aagaccctttg cagcgtcacg tgaagagaca   480
gagcaggtaa tcatcggtgc gctagaaaag ctattcgaga acactaaagt taacccctaga  540
gatattggta tacttgtggt caactcaagc atgtttaatc caactccttc gttatccgct   600
atggtcgtaa atactttcaa gcttcgaagc aacatcaaaa gctttagtct cggaggaatg   660
ggttgtagtg ctggtgttat cgccattgat cttgcaaaag acttgttgca tgttcataaa   720
aacacttatg cacttgtggt gagcactgag aacatcactc acggcattta tgctggcgaa   780
aatagatcca tgatggttag caattgcttg ttccgtgttg gtggggcggc gattttgctc   840
tccaacaagc cgggagatcg gagacgggcc aagtacaagc tatgtcacac tgttcgaacg   900
cataccggag ctgatgacaa gtcttttcga tgtgtgcaac aaggagatga tgagagcggt   960
aaaatcggag tttgtctgtc aaaggacata accgctgttg cggggacagc gcttaagaaa  1020
aacatagcaa cgttaggtcc gttgattctt cctttaagcg aaaaatttct gtttttagta  1080
accttcatcg ccaagaaact tttgaaggac aagatcaagc actattacgt cccggatttc  1140
aaggttgcta ttgaccattt ctgtattcat gccggaggta gagccgtgat cgatgtgctt  1200
gagaagagct taggactatc tccaatcgat gtcgaggcat cgagatcaac gttacacaga  1260
tttgggaata cttcgtctag ctcaatttgg tatgaattgg catacataga agcaaaagga  1320
aggatgaaga aagggaataa agcttggcaa attgctttag ggtcagggtt taagtgtaac  1380
agtgcggttt gggtggctct atgcaatgtc aaggcttcgg cgaatagtcc ttgggaacat  1440
tgcatcgata gatatccggt tcaaatagat tttgattcat caaaatcaga cactcatgtc  1500
aaaaacggtc ggtcctaa                                                 1518
```

<210> SEQ ID NO 53
<211> LENGTH: 1518
<212> TYPE: DNA
<213> ORGANISM: Camelina laxa

<400> SEQUENCE: 53

```
atgacgtccg ttaacgcaaa gctcctttac cattacgtcc taaccaactt tttcaacctt    60
tgcttgtttc cgttaacggc gttacttgcc ggaaaagcct ctaggcttac cacaaacgat   120
ctctaccact tcaattccca tctccaacac aacattgtaa cggttgtttt actctttgct   180
tttaccgctt tcggtttggt tctttacgtt gtaacccggc ccaaaccggt ttacctcgtt   240
```

```
gactactcgt gctaccttcc accaccgcat ctcaaagtta gtgtttccaa ggtcatggat      300
attttctacc aaataagaaa agctgatacc acacgaaacg tggcatgcga tgatccatcc      360
tcgcttgatt tcctgaggaa gattcaagaa cgttcaggtc taggtgatga aacctacagt      420
ccccagggac tcattaacgt gcccccacaa aagacctttg cagcttcacg tgaagagaca      480
gagcaggtaa tcatcggtgc gctagaaaag ctattcgaga acaccaaagt taaccctaga      540
gagattggta tacttgtggt gaactcaagc atgtttaatc caactccttc gctatctgcg      600
atggtcgtta acactttcaa gctccgaagc aatatcaaaa gctttagtct cggaggaatg      660
ggttgtagtg ctggtgtcat cgccattgat cttgcaaaag acttgttgca tgttcataaa      720
aacacttatg cacttgtggt gagcactgag aacatcactc aaggcattta tgctggcgaa      780
aatagatcca tgatggttag caattgcttg ttccgtgttg gtggggcggc gattttgctc      840
tccaacaagc cgggagatcg gagacgggcc aagtacaagc tatgtcacac tgttcgaacg      900
cataccggag ctgatgacaa gtcttttcga tgtgtgcaac aaggagatga tgagagcggt      960
aaaatcggag tttgtctgtc aaaggacata accgctgttg cggggacagc gcttaagaaa     1020
aacatagcaa cgttaggtcc gttgattctt cctttaagcg aaaaatttct gttttagta     1080 accttcatcg ccaagaaact tttgaaggac aagatcaagc actattacgt cccggatttc     1140
aaggttgcta ttgaccattt ctgtattcat gccggaggta gagccgtgat cgatgtgctt     1200
gagaagagct taggactatc tccaatcgat gtcgaggcat cgagatcaac gttacacaga     1260
tttgggaata cttcgtctag ctcaatttgg tatgaattgg catacataga agcaaaagga     1320
aggatgaaga aagggaataa agcttggcaa attgctttag ggtcagggtt taagtgtaac     1380
agtgcggttt gggtggctct atgcaatgtc aaggcttcgg cgaatagtcc ttgggaacat     1440
tgcatcgata gatatccggt tcaaatagat tttgattcat caaaatcaga cactcatgtc     1500
aaaaacggtc ggtcctaa                                                   1518

<210> SEQ ID NO 54
<211> LENGTH: 1155
<212> TYPE: DNA
<213> ORGANISM: Camelina microcarpa

<400> SEQUENCE: 54
atgggtgcag gtggaagaat gccagttcct tcttcttctt ccaagaaatc tgaaaccgat       60
gccataaagc gtgtgccctg cgagaaacca ccgttcacgc tgggagatct gaagaaagca      120
atcccaccgc agtgtttcaa acgctctatc cctcgctctt tctcctacct tatcactgac      180
atcattattg cctcctgctt ctactacgtc gccaccaatt acttttctct cctccctcag      240
cctctctctt acttggcttg gccctctat tgggcttgtc aaggctgtgt cctaaccggt      300
gtctgggtca tagcccacga atgcggtcac cacgcattca gcgactacca gtggctcgat      360
gacacagtcg gtcttatctt ccattccttc cttctcgtcc cttacttctc ctggaagtac      420
agtcatcgcc gtcaccattc caacacagga tccctcgaaa gagatgaagt atttgtccca      480
aagcagaagt ccgctatcaa gtggtatggc aaatacctca caaccctgc tggacgcatc      540 atgatgttga ccgtccagtt tgtcctcggg tggcccttgt acttggcctt taacgtctcc      600
ggcagaccat acgacgggtt cgcttgccat ttcttcccca cgctcccat ctacaacgac      660 cgtgaacgcc tccagatata tctctctgat gccggtattc tagcagtctg tttttgggctt      720 taccgttacg ccgctgcaca aggattggcc tcgatgatct gcctctacgg agtaccactt      780
ctgatagtga acgcgttcct cgtcttgatc acttacttgc agcacactca tcctgcgttg      840
```

```
cctcactacg attcatccga gtgggattgg cttaggggag ctttggctac cgtagacaga    900
gactatggaa tcttgaataa ggtgttccac aacatcacgg acacacatgt ggctcatcat    960
ctgttctcga caatgccgca ttataatgcg atggaagcta caaaggcgat aaagccaata   1020
ctcggtgact attaccagtt cgacggaaca ccatggtatg tggccatgta tagggaggca   1080
aaggagtgta tctatgtaga accggacagg aaggtgaca agaaaggtgt gtactggtac   1140
aacaataagt tatga                                                     1155
```

<210> SEQ ID NO 55
<211> LENGTH: 1158
<212> TYPE: DNA
<213> ORGANISM: Camelina microcarpa

<400> SEQUENCE: 55

```
atgggtgcag gtggaagaat gccggttcct tcttcttctt cttccaagaa atcagaaacc     60
gatgccatga agcgtgtgcc ctgcgagaaa ccaccgttca cgctgggaga attgaagaaa    120
gcgatcccac cgcagtgttt caaacgctct atccctcgct ctttctccta ccttatcact    180
gacatcattg ttgcctcctg cttctactac gtcgccacca attacttctc tctcctccct    240
cagcctctct cttacttggc ttggcccctc tattgggcct gtcaaggctg tgtcctaacc    300
ggtgtctggg tcatagccca cgaatgcggt caccacgcat tcagtgacta ccaatggctt    360
gatgacacag ttggtcttat cttccattcc ttccttctcg taccttactt ctcctggaag    420
tacagtcatc gccgtcacca ttccaacaca ggatctctcg aaagagatga agtatttgtc    480
ccaaagcaga agtccgctat caagtggtat ggcaaatacc tcaacaaccc tcctggacgc    540
atcatgatgt taaccgtcca gtttgtcctc gggtggccct tgtacttggc ctttaacgtc    600
tcgggcagac catacgacgg gttcgcttgc catttctttc ccaacgctcc catctacaac    660
gaccgcgaac gcctccagat atatctctct gatgccggta ttctagcagt ctgtttttggg    720 cttttaccgtt acgcagctgc gcaaggaatg gcctcgatga tctgcctcta cggagtaccc    780
cttctgatag tgaacgcgtt cctcgtcttg atcacttact gcagcacac tcaccctgcg    840 ttgcctcact acgattcgtc cgagtgggat tggcttaggg gagctttggc taccgtagac    900
agagactacg gaatcttgaa caaggtgttc cataacatca cggacacaca tgtggctcat    960
catctgttct cgacaatgcc acattataat gctatggaag cgacaaaggc gataaagcca   1020
atactcggtg actactacca gttcgacgga acaccgtggt atgtggccat gtatagggag   1080
gcaaaggaat gtatctatgt agaaccggac agggaaggtg acaagaaagg tgtgtactgg   1140
tacaacaata agttatga                                                  1158
```

<210> SEQ ID NO 56
<211> LENGTH: 1155
<212> TYPE: DNA
<213> ORGANISM: Camelina microcarpa

<400> SEQUENCE: 56

```
atgggtgcag gtggaagaat gccggttcct tcttcttctt ccaagaaatc agaaaccgat     60
gccataaagc gtgtgccttg cgagaaaccg ccgttcacac tggagaatt gaagaaagcg    120 atcccaccgc agtgtttcaa acgctctatc cctcgctctt tctcctacct tatcactgac    180
atcattgttg cctcctgctt ctactacgtc gccaccaatt acttctctct cctccctcag    240
cctctctctt acttggcttg gcccctctat tgggcttgtc aaggctgtgt cctaaccggt    300
```

| | |
|---|---|
| gtctgggtca tagcccacga atgcggtcac cacgcattca gcgactacca atggcttgat | 360 |
| gacacagttg gtcttatctt ccattccttc cttctcgtcc cttacttctc ctggaagtac | 420 |
| agtcatcgcc gtcaccattc caacacagga tctctcgaaa gagatgaagt atttgtccca | 480 |
| aagcagaagt ccgctatcaa gtggtatggc aaatacctca caaccctgc tggacgcatc | 540 |
| atgatgttaa ccgtccagtt tgtcctcggg tggcccttgt acttggcctt taacgtctcg | 600 |
| ggcagaccat acgatgggtt cgcttgccat ttcttcccca acgctcccat ctacaacgac | 660 |
| cgtgaacgcc tccagatata tctctctgat gccggtattc tagcagtctg ttttgggctt | 720 |
| taccgttacg ccgctgcaca aggattggcc tcgatgatct gcctctacgg agtaccactt | 780 |
| ctgatagtaa acgcgttcct cgtcttgatc acttacttgc agcacactca tcctgcgttg | 840 |
| cctcactacg attcatccga gtgggattgg cttaggggag cttttggctac cgtagacaga | 900 |
| gactatggaa tcttgaacaa ggtgttccac aacatcacgg acacacatgt ggctcatcat | 960 |
| ctgttttcga caatgccgca ttataatgcg atggaagcta caaaggcgat aaagccaata | 1020 |
| ctcggtgact attaccagtt cgacggaaca ccatggtatg tggccatgta tagggaggca | 1080 |
| aaggagtgta tctatgtaga accggacagg gaaggtgaca agaaaggtgt gtactggtac | 1140 |
| aacaataagt tatga | 1155 |

<210> SEQ ID NO 57
<211> LENGTH: 1518
<212> TYPE: DNA
<213> ORGANISM: Camelina microcarpa

<400> SEQUENCE: 57

| | |
|---|---|
| atgacgtccg ttaacgcaaa gctcctttac cattacgtcc taaccaactt tttcaacctt | 60 |
| tgcttgtttc cgttaacggc gttacttgcc ggaaaagcct ctaggcttac ctcaaacgat | 120 |
| ctctaccact tctattccca tctccaacac aaccttataa ccgtaatttt actctttgct | 180 |
| ttcaccgctt tcggtttggt tctctacatt gtaacccggc ccaaaccggt ttacctcgtt | 240 |
| gactactcgt gctaccttcc accaccgcat ctcaaagtta gtgtttccaa ggcgatggat | 300 |
| attttctacc aaataagaaa agctgatacc tcacggaacg tggcatgcga tgatccatcc | 360 |
| tcgcttgatt tcctgaggaa gattcaagaa cgttcaggtc taggtgatga aacctacagt | 420 |
| ccccagggac tcattaacgt gcccccacga aagaccttg cagcttcacg tgaagagaca | 480 |
| gagcaggtaa tcatcggtgc gctagataag ctattcgaga ataccaaagt taaccctaga | 540 |
| gaaattggta tacttgtggt caactcaagc atgtttaatc caactccttc gctatctgcg | 600 |
| atggtcgtta atactttcaa gcttcgaagc aacatcaaaa gctttagtct cggaggaatg | 660 |
| ggttgtagtg ctggtgtcat cgccattgat cttgcaaagg acttgttgca tgttcataaa | 720 |
| aacacttatg cacttgtggt gagcactgag aacatcactc aaggcattta tgctggcgaa | 780 |
| aatagatcca tgatggttag caattgcttg ttccgtgttg gtggcgcagc gattttgctc | 840 |
| tccaacaagc caggagatcg gagacggtcc aagtacaagt tatgtcatac tgttcgaacg | 900 |
| cataccggag ctgatgacat gtcttttcga tgtgtgcaac aaggagacga tgagagcggt | 960 |
| aaaatcggag tttgtctgtc aaaggacata accgttgttg cggggatagc gcttaagaaa | 1020 |
| aacatagcaa cgttgggtcc gttgattctt cctttaaggg aaaaatttct gtttttagta | 1080 |
| accttcatcg ccaagaaact tttgaaggac aagatcaagc actattacgt cccggatttc | 1140 |
| aagcttgcta ttgaccattt ctgtattcat gcggaggca gagccgtgat cgatgtgctt | 1200 |
| gagaagagct taggactatc tccaatcgat gtggaggcat ctagatcaac gttacacaga | 1260 |

-continued

```
tttgggaata cttcgtctag ctcaatttgg tatgaattgg catacataga agcaaaagga    1320
aggatgaaga aagggaatag agcttggcag attgctttag ggtcaggatt taagtgtaac    1380
agtgcggttt gggtggctct atgcaatgtc aaggcttcgg cgaatagtcc ttgggaacat    1440
tgcatcgata gatatccggt tcaaattgat tctggttcat caaaatcaga tactcatgtc    1500
aaaaacggtc ggtcctaa                                                  1518
```

<210> SEQ ID NO 58
<211> LENGTH: 1518
<212> TYPE: DNA
<213> ORGANISM: Camelina microcarpa

<400> SEQUENCE: 58

```
atgacgtccg ttaacgcaaa gctcctttac cattacgttc taaccaactt tttcaacctt     60
tgcttgtttc cgttaacggc gttacttgcc ggaaaagcct ctaagcttac agcaaacgat    120
ctctaccact tctattccca tctccaacac aaccttataa ccgtaatttt actctttgct    180
ttcaccgctt tcggtttggt tctctacatt gtaacccggc ccaaaccggt ttacctcgtt    240
gactactcgt gctaccttcc accaccgcat ctcaaagtta gtgtttccaa ggcgatggat    300
attttctacc aaataagaaa agctgatacc tcacggaacg tggcatgcga tgatccatcc    360
tcgcttgatt cctgaggaa gattcaagaa cgttcaggtc taggtgatga tacgtacagt     420
ccccagggac tcattaacgt gccccacaa aagacctttg cagcttcacg tgaagagaca    480
gagcaggtaa tcatcggtgc gctagaaaag ctattcgaga acaccaaagt aaaccctaga    540
gagattggta tacttgtggt gaactcaagc atgtttaatc caactccttc gctatctgcg    600
atggtcgtta acactttcaa gctccgaagc aacatcaaaa gctttagtct cggaggaatg    660
ggttgtagtg ctggtgttat cgccattgat cttgcaaagg acttgttgca tgttcataaa    720
aacacttatg cacttgtggt gagcactgag aacatcactc aaggcattta tgctggcgaa    780
aacagatcca tgatggttag caattgcttg tttcgtgttg gtggggcagc gattttgctc    840
tccaacaaac tggagatcg gagacggtcc aagtacaagc tatgtcatac tgttcgaacg    900
cataccggag ctgatgacaa gtcttttcga tgtgtgcaac aaggagacga tgagggcggt    960
aaaatcggag tttgtctgtc aaaggacata accgttgttg cggggacagc gcttaagaaa   1020
aacatagcaa cgttgggtcc gttgattctt cctttaagcg aaaagtttct gttttttagtt   1080 accttcatcg ccaagaaact tttgaaggac aagatcaagc actgttacgt cccggatttc   1140
aagcttgcta tcgaccattt ctgtattcat gcgggaggca gagccgtgat cgatgtgctt   1200
gagaagagct taggactatc gccaatcgat gtggaggcat ctagatcaac gttacataga   1260
tttgggaata cttcgtctag ctcaatttgg tatgaattgg catacataga agcaaaagga   1320
aggatgaaga aagggaatag agcttggcag attgctttag ggtcagggtt taagtgtaac   1380
agtgcggttt gggtggctct atgcaatgtc aaggcttcgg cgaatagtcc ttgggaagat   1440
tgcatcgata gatatccggt tcaaattgat tctgattcat caaaatcaga gactcatgtc   1500
aaaaacggtc ggtcctaa                                                 1518
```

<210> SEQ ID NO 59
<211> LENGTH: 1518
<212> TYPE: DNA
<213> ORGANISM: Camelina microcarpa

<400> SEQUENCE: 59

```
atgacgtccg ttaacgcaaa gctcctttac cattacgttc taaccaactt tttcaacctt    60
tgcttgtttc cgttaacggc gttacttgcc ggaaaagcct ctaagcttac cgcaaacgat   120
ctctaccact tctattccca tctccaacac aaccttataa ccgtaatttt actctttgct   180
ttcaccgctt tcggtttggt tctctacatt gtaacccggg ccaaaccggt ttacctcgtt   240
gactactcgt gctaccttcc accaccgcat ctcaaagtta gtgtttccaa ggtgatggat   300
attttctacc aaataagaaa agctgatacc tcacggaacg tggcatgcga tgatccatcc   360
tcgcttgatt tcctgaggaa gattcaagaa cgttcaggtc taggtgatga aacctacggt   420
ccccaaggac tcattaatgt tccaccacaa aagacctttg cagcgtcacg tgaagagaca   480
gagcaggtaa tcatcggtgc gctagaaaag ctattcgaga cactaaagt taaccctaga   540 gagattggta tacttgtggt gaactcaagc atgtttaatc caactccttc gctatccgcg   600
atggtcgtta atactttcaa gctccgaagc aacatcaaaa gctttagtct cggaggaatg   660
ggttgtagtg ctggtgttat cgccattgat cttgcaaagg acttgttgca tgttcataaa   720
aacacttatg cacttgtggt gagcacagag aacatcactc aaggcattta tgctggcgaa   780
aatagatcca tgatggttag caattgcttg ttccgtgttg gtggggcagc gattttgctc   840
tccaacaagc cgggagatgg gagacggtcc aagtacaagc tatgtcatac tgttcgaaca   900
cataccggag ctgatgacaa gtcttttcga tgtgtgcaac aaggagacga tgagagcggt   960
aaaatcggag tatgtctgtc aaaggacata accgttgttg cggggacagc gcttaagaaa  1020
aacatagcaa cgttgggtcc gttgattctt cctttaagcg aaaagtttct cttttagtt  1080 accttcatcg ccaagaaact tttgaaggac aagatcaagc actattacgt cccggatttc  1140
aagcttgcta ttgaccattt ctgtattcat gccggaggca gagccgtaat cgatgtgctt  1200
gagaagagct taggactatc tccaatcgat gtggaggcat ctagatcaac gttacataga  1260
tttgggaata cttcgtctag ctcaatttgg tatgaattgg catacataga agcaaaagga  1320
aggatgaaga aagggaatag agcttggcag attgctttag ggtcagggtt taagtgtaac  1380
agtgcggttt gggtggctct atgcaatgtc aaggcttcgg cgaatagtcc ttgggaacat  1440
tgcatcgata gatatccggt tcaaattgat tctgattcat caaaattaga gactcatgtc  1500
aaaaacggtc ggtcctaa                                                1518

<210> SEQ ID NO 60
<211> LENGTH: 1155
<212> TYPE: DNA
<213> ORGANISM: Camelina rumelica

<400> SEQUENCE: 60
atgggtgcag gtggaagaat gccagttcct tcttcttctt ccaagaaatc tgaaaccgat    60
gccataaagc gtgtgccctg cgagaaaccg ccgttcacgg ttggagaact gaagaaagca   120
atcccaccgc attgtttcaa acgctctatc cctcgctctt tctcctacct tatcactgac   180
atcattgttg cctcctgctt ctactacgtc gccaccaatt acttctctct cctccctcag   240
cctctctctt acttggcttg gcctctctat gggcctgtc aaggctgtgt cctaaccggt   300
gtctgggtca tagcccacga atgcggtcac cacgcattca gcgactacca atggcttgat   360
gacacagttg gtcttatctt ccattccttc cttctcgtcc cttacttctc ctggaagtac   420
agtcatcgcc gtcaccattc caacacagga tctctcgaaa gagatgaagt atttgtccca   480
aagcagaaat cagctatcaa gtggtatggc aaatacctca caacccctcc tggacgcatc   540
atgatgttga ccgtccagtt tgtcctcggg tggcccttgt acttggcctt taacgtctcg   600
```

```
ggcagaccat acgacgggtt cgcttgccat ttcttcccca acgctcccat ctacaacgac      660
cgtgaacgcc tccagatata tctctccgat gccggtattc tagcagtctg ttttgggctt      720
taccgttacg cagctgcaca aggaatggcc tcgatgatct gcctctacgg agtaccactt      780
ctgatagtga acgcgttcct cgtcttgatc acttacttgc agcacactca tcctgcgttg      840
cctcactacg attcatccga gtgggattgg cttaggggag ctttggctac cgtagacaga      900
gactatggaa tcttgaacaa ggtgttccac aacatcacgg acacacatgt ggctcatcat      960
ctgttctcga caatgccgca ttataatgcg atggaagcga cgaaggcgat aaagccaata     1020
ctcggtgact actaccagtt cgacggaaca ccgtggtatg tggcgatgta tagggaggca     1080
aaggaatgta tctatgtaga accggacagg gaaggtgaca agaaaggtgt gtactggtac     1140
aacaataagt tatga                                                     1155

<210> SEQ ID NO 61
<211> LENGTH: 1155
<212> TYPE: DNA
<213> ORGANISM: Camelina rumelica

<400> SEQUENCE: 61
atgggtgcag gtggaagaat gccggttcct tcttcttctt ccaagaaatc tgaaaccgat       60
gccatgaagc gtgtgccctg cgagaaacca ccgttcacgc tgggagaact gaagaaagca      120
atcccaccgc agtgtttcaa acgctctatc cctcgctctt tctcctacct tatcactgac      180
atcattgttg cctcctgttt ctactacgtc gccaccaatt tcttctctct cctccctcag      240
cctctctctt acttggcttg gcctctctat tgggcttgtc aaggctgtgt cctaaccggt      300
gtctgggtca tagctcacga atgcggtcac cacgcattca gtgactacca atggcttgat      360
gacacagttg gtcttatctt ccattccttc cttctcgtcc cttacttctc ctggaagtac      420
agtcatcgcc gtcaccattc caacacagga tctctcgaaa gagatgaagt atttgtccca      480
aagcagaagt ccgctatcaa gtggtatggc aaatacctca acaaccctcc tggacgcatc      540
atgatgttaa ccgtccagtt tgtcctcggg tggcccttgt acttggcctt taacgtctcg      600
ggcagaccat acgacgggtt cgcttgccat ttcttcccca acgctcccat ctacaacgac      660
cgcgaacgcc tccagatata tctctctgat gccggtattc tagcagtctg ttttgggctt      720
taccgttacg cagctgcaca aggaatggcc tcgatgatct gcctctacgg agtaccactt      780
ctgatagtga acgcgttcct cgtcttgatc acttacttgc agcacactca ccctgcgttg      840
cctcactacg attcgtccga gtgggattgg cttaggggag ctttggctac cgtagacaga      900
gactacggaa tcttgaacaa ggtgttccat aacatcacgg acacacatgt ggctcatcat      960
ctgttctcga caatgccaca ttataatgct atggaagcga caaaggcgat aaagccaata     1020
ctaggtgact actaccagtt cgacggaaca ccgtggtatg tggccatgta tagggaggca     1080
aaggaatgta tctatgtaga accggacagg gaaggtgaca agaaaggtgt gtactggtac     1140
aacaataagt tatga                                                     1155

<210> SEQ ID NO 62
<211> LENGTH: 1518
<212> TYPE: DNA
<213> ORGANISM: Camelina rumelica

<400> SEQUENCE: 62
atgacgtccg ttaacgcaaa gctcctttac cattacgtcc taaccaactt tttcaaccct       60
```

```
tgcttgtttc cgttaacggc gttacttgcc ggaaaagcct ctaggcttac cacaaacgat    120
ctctaccact tctattccca tctccaacac aacctcataa ccgttattct actctttgct    180
tttaccgctt ttggtttggt tctctacatt gtaacccggc ccaaaccggt ttacctcgtt    240
gactactcgt gctaccttcc accaccgcat ctcaaagtta ctgtttccaa ggtcatggat    300
attttctacc aaataagaaa agctgatact tcacggaacg tggcatgcga tgatccatcc    360
tcgcttgatt tcctgaggaa gattcaagaa cgttcaggtc taggtgatga aacctacagt    420
cccccgggac tcattaacgt gcccccacaa aagacctttg cagcttcacg tgaagagaca    480
gagcaggtaa tcatccggtgc gctagaaaag ctattcgaga acaccaaagt taaccctaga    540
gagattggta tacttgtggt gaactcaagc atgtttaatc caactccttc gctatccgct    600
atggtcgtta acactttcaa gctccgaagc aatatcaaaa gctttagtct tggaggaatg    660
ggttgtagtg caggtgttat cgccattgat cttgcaaagg acttgttgca tgttcataaa    720
aacacttatg cacttgtggt gagcactgag aacatcactc aaggcattta tgctggcgaa    780
aatagatcca tgatggttag caattgcttg ttccgtgttg gtggggcagc cattttgctc    840
tccaacaagc caggagatcg gagacggtcc aagtaccagc tatgtcatac tgttcgaaca    900
cataccggag ctgatgacag gtcttttcga tgtgtgcaac aaggagacga tgagagcggt    960
aaaatcggag tttgtctgtc aaaggacata accgctgttg cggggacagc gcttaagaaa   1020
aacatagcaa cgttgggtcc attgattctt cctttaagcg aaaagtttct gtttttagta   1080
accttcatcg ccaagaaact tttgaagaac aagatcaagc actattacgt cccggatttc   1140
aagcttgcta ttgaccattt ctgtattcat gccggaggca gagccgtaat cgatgtgctt   1200
gagaagagct taggactatc gccaatcgat gtggaagcat ctagatcaac gttacataga   1260
tttgggaata cttcgtctag ctcaatttgg tatgaattgg catacataga agcaaaagga   1320
aggatgaaga aagggaatag agcttggcag attgctttag ggtcagggtt taagtgtaac   1380
agtgcggttt gggtggctct atgcaatgtc aaggcttcgg cgaatagtcc ttgggaacat   1440
tgcatcgata gatatccggt tcaacttaat tctgattcat caaaatcaga gactcatgtc   1500
aaaaacggtc ggtcctaa                                                 1518

<210> SEQ ID NO 63
<211> LENGTH: 1518
<212> TYPE: DNA
<213> ORGANISM: Camelina rumelica

<400> SEQUENCE: 63
atgacgtccg ttaacgcaaa gctcctttac cattacgttc taaccaactt tttcaacctt     60
tgcttgtttc cgttaacggc gttacttgcc ggaaaagcct ctaagcttac cgcaaacgat    120
ctctaccact tctattccca tctccaacac aaccttataa ccgtaatttt actctttgct    180
ttcacctctt tcggtttggt tctctacatt gtaacccggc ccaaaccggt ttacctcgtt    240
gattactcgt gctaccttcc accaccgcat ctcaaagtta gtgtttccaa ggtgatggat    300
attttctacc aaataagaaa agctgatacc tcacgaaacg tggcatgcga taatccatcc    360
tcgcttgatt tcctgaggaa gattcaagaa cgttcaggtc taggtgatga aacctacagt    420
cccccaagga ctcattaatgt tccaccacaa aagacctttg cagcgtcacg tgaagagaca    480
gagcaggtaa tcatccggtgc gctagaaaag ctattcgaga acactaaagt tagccctaga    540
gagattggta tacttgtggt gaactcaagc atgtttaatc caactccttc gctatccgcg    600
atggtcgtta atactttcaa gctccgaagc aacatcaaaa gctttagtct cggaggaatg    660
```

```
ggttgtagtg ctggtgttat cgccattgat cttgcaaagg acttgttgca tgttcataaa    720
aacacttatg cacttgtggt gagcactgaa aacatcactc aaggcattta tgctggcgaa    780
aatagatcca tgatggttag caattgcttg ttccgtgttg gtggcgcagc gattttgctc    840
tccaacaagc cgggagatcg gagacggtcc aagtacaagc tatgtcatac tgttcgaaca    900
cataccggag ctgacgacaa gtctttcga tgtgtgcaac aaggagacga tgagagcggt    960
aaaatcggag tatgtctgtc aaaggacata accgttgttg cggggatagc gcttaagaaa    1020
aacatagcaa cgttgggtcc gctgattctt cctttaagcg aaaaatttct gttttttagta    1080 agcttcatcg ccaagaaact tttgaaggac aagatcaagc actattacgt cccggatttc    1140
aagcttgcta ttgatcattt ctgtattcat gccggaggca gagccgtaat cgatgtgctt    1200
gagaagagct taggactatc tccaatcgat gtggaggcat ctagatcaac gttacataga    1260
tttgggaata cttcgtctag ctcaatttgg tatgaattgg catacacaga agcaaaagga    1320
aggatgaaga aagggaatag agcttggcag attgctttag ggtcagggtt taagtgtaac    1380
agtgcggttt gggtggctct atgcaatgtc aaggcttcgg cgaatagtcc ttgggaacat    1440
tgcatcgata gatatccggt taaaattgat tctgattcat caaaatcaga gactcatgtc    1500
aaaaacggtc ggtcctaa                                                  1518

<210> SEQ ID NO 64
<211> LENGTH: 383
<212> TYPE: PRT
<213> ORGANISM: Capsella rubella

<400> SEQUENCE: 64

Met Gly Ala Gly Gly Arg Met Pro Val Pro Ser Ser Lys Lys Ser
1               5                   10                  15

Glu Thr Asn Ala Ile Lys Arg Val Pro Cys Glu Lys Pro Pro Phe Thr
            20                  25                  30

Val Gly Asp Leu Lys Lys Ala Ile Pro Pro Gln Cys Phe Lys Arg Ser
        35                  40                  45

Ile Pro Arg Ser Phe Ser Tyr Leu Ile Thr Asp Ile Ile Ala Ser
    50                  55                  60

Cys Phe Tyr Tyr Val Ala Thr Asn Tyr Phe Ser Leu Leu Pro Gln Pro
65                  70                  75                  80

Leu Ser Tyr Phe Ala Trp Pro Leu Tyr Trp Ala Cys Gln Gly Cys Val
                85                  90                  95

Leu Thr Gly Val Trp Val Ile Ala His Glu Cys Gly His His Ala Phe
            100                 105                 110

Ser Asp Tyr Gln Trp Leu Asp Asp Thr Val Gly Leu Ile Phe His Ser
        115                 120                 125

Phe Leu Leu Val Pro Tyr Phe Ser Trp Lys Tyr Ser His Arg Arg His
    130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Phe
                165                 170                 175

Gly Arg Ile Met Met Leu Thr Val Gln Phe Val Leu Gly Trp Pro Leu
            180                 185                 190

Tyr Leu Ala Phe Asn Val Ser Gly Arg Pro Tyr Asp Gly Phe Ala Cys
        195                 200                 205

His Phe Phe Pro Asn Ala Pro Ile Tyr Asn Asp Arg Glu Arg Leu Gln
```

```
            210                 215                 220
Ile Tyr Ile Ser Asp Ala Gly Ile Leu Ala Val Cys Tyr Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
                260                 265                 270

Gln His Thr His Pro Ala Leu Pro His Tyr Asp Ser Ser Glu Trp Asp
                275                 280                 285

Trp Leu Arg Gly Ala Leu Ala Thr Val Asp Arg Asp Tyr Gly Ile Leu
            290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
                340                 345                 350

Val Ala Met Tyr Arg Glu Ala Lys Glu Cys Ile Tyr Val Glu Pro Asp
                355                 360                 365

Arg Glu Gly Asp Lys Lys Gly Val Tyr Trp Tyr Asn Asn Lys Leu
            370                 375                 380

<210> SEQ ID NO 65
<211> LENGTH: 383
<212> TYPE: PRT
<213> ORGANISM: Arabidopsis lyrata

<400> SEQUENCE: 65

Met Gly Ala Gly Gly Arg Met Pro Val Pro Thr Ser Ser Lys Lys Ser
1               5                   10                  15

Glu Thr Asp Thr Ile Lys Arg Val Pro Cys Glu Lys Pro Pro Phe Ser
                20                  25                  30

Val Gly Asp Leu Lys Lys Ala Ile Pro Gln His Cys Phe Lys Arg Ser
            35                  40                  45

Ile Pro Arg Ser Phe Ser Tyr Leu Ile Gly Asp Ile Ile Ala Ser
        50                  55                  60

Cys Phe Tyr Tyr Val Ala Thr Asn Tyr Phe Ser Leu Leu Pro Gln Pro
65                  70                  75                  80

Leu Ser Tyr Leu Ala Trp Pro Leu Tyr Trp Ala Cys Gln Gly Cys Val
                85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Phe His Ser
            115                 120                 125

Phe Leu Leu Val Pro Tyr Phe Ser Trp Lys Tyr Ser His Arg Arg His
        130                 135                 140

His Ser Asn Thr Gly Ser Leu Glu Arg Asp Glu Val Phe Val Pro Lys
145                 150                 155                 160

Gln Lys Ser Ala Ile Lys Trp Tyr Gly Lys Tyr Leu Asn Asn Pro Leu
                165                 170                 175

Gly Arg Ile Met Met Leu Thr Val Gln Phe Val Leu Gly Trp Pro Leu
                180                 185                 190

Tyr Leu Ala Phe Asn Val Ser Gly Arg Pro Tyr Asp Gly Phe Ala Cys
            195                 200                 205
```

```
His Phe Phe Pro Asn Ala Pro Ile Tyr Asn Asp Arg Glu Arg Leu Gln
    210                 215                 220

Ile Tyr Leu Ser Asp Ala Gly Ile Leu Ala Val Cys Phe Gly Leu Tyr
225                 230                 235                 240

Arg Tyr Ala Ala Ala Gln Gly Met Ala Ser Met Ile Cys Leu Tyr Gly
                245                 250                 255

Val Pro Leu Leu Ile Val Asn Ala Phe Leu Val Leu Ile Thr Tyr Leu
            260                 265                 270

Gln His Thr His Pro Ser Leu Pro His Tyr Asp Ser Ser Glu Trp Asp
        275                 280                 285

Trp Leu Arg Gly Ala Leu Ala Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr Asn Ala Met Glu Ala Thr Lys Ala Ile
                325                 330                 335

Lys Pro Ile Leu Gly Asp Tyr Tyr Gln Phe Asp Gly Thr Pro Trp Tyr
            340                 345                 350

Val Ala Met Tyr Arg Glu Ala Lys Glu Cys Ile Tyr Val Glu Pro Asp
        355                 360                 365

Arg Glu Gly Asp Lys Lys Gly Val Tyr Trp Tyr Asn Asn Lys Leu
370                 375                 380

<210> SEQ ID NO 66
<211> LENGTH: 505
<212> TYPE: PRT
<213> ORGANISM: Arabidopsis lyrata

<400> SEQUENCE: 66

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Phe Val Ala Gly Lys
            20                  25                  30

Ala Ser Arg His Thr Thr Asn Asp Leu His Asn Phe Phe Ser Tyr Leu
        35                  40                  45

Gln His Asn Leu Ile Thr Val Ala Ile Leu Phe Ala Phe Thr Val Phe
    50                  55                  60

Gly Phe Val Leu Tyr Met Val Thr Arg Pro Lys Pro Val Tyr Leu Val
65                  70                  75                  80

Asp Tyr Ser Cys Tyr Leu Pro Pro His Leu Arg Ala Ser Val Ser
                85                  90                  95

Arg Val Met Asp Val Phe Tyr Gln Ile Arg Lys Ala Asp Thr Ser Arg
                100                 105                 110

Asn Val Ala Cys Asp Asp Pro Ser Ser Leu Asp Phe Leu Arg Lys Ile
            115                 120                 125

Gln Glu Arg Ser Gly Leu Gly Asp Glu Thr Tyr Gly Pro Glu Gly Leu
        130                 135                 140

Leu His Val Pro Pro Arg Lys Thr Phe Ala Ala Ala Arg Glu Glu Thr
145                 150                 155                 160

Glu Gln Val Ile Ile Gly Ala Leu Glu Asn Leu Phe Gln Asn Thr Lys
                165                 170                 175

Val Asn Pro Arg Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205
```

Arg Ser Asn Ile Lys Ser Phe Asn Leu Gly Gly Met Gly Cys Ser Ala
    210                 215                 220

Gly Val Ile Ala Ile Asp Leu Ala Lys Asp Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Pro Arg Asp Arg Arg
        275                 280                 285

Arg Ser Lys Tyr Lys Leu Ala His Thr Val Arg Thr His Thr Gly Ala
    290                 295                 300

Asp Asp Lys Ser Phe Arg Cys Val Gln Gln Glu Asp Asp Glu Ser Gly
305                 310                 315                 320

Lys Ile Gly Val Cys Leu Ser Lys Asp Ile Thr Asn Val Ala Gly Thr
                325                 330                 335

Thr Leu Lys Lys Asn Ile Ala Thr Leu Gly Pro Leu Ile Leu Pro Leu
            340                 345                 350

Ser Glu Lys Phe Leu Phe Phe Val Thr Phe Val Ala Lys Lys Leu Leu
        355                 360                 365

Lys Asp Arg Ile Lys His Tyr Tyr Val Pro Asp Phe Lys Leu Ala Ile
    370                 375                 380

Asp His Phe Cys Ile His Ala Gly Gly Arg Ala Val Ile Asp Glu Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Lys Ala
        435                 440                 445

Trp Gln Ile Ala Leu Gly Ser Gly Phe Lys Cys Asn Ser Ala Val Trp
    450                 455                 460

Val Ala Leu Arg Asn Val Lys Pro Ser Ala Asn Ser Pro Trp Gln His
465                 470                 475                 480

Cys Ile Asp Arg Tyr Pro Ala Lys Ile Asp Ser Asp Leu Ser Lys Ser
                485                 490                 495

Glu Thr His Val Lys Asn Gly Arg Ser
            500                 505

<210> SEQ ID NO 67
<211> LENGTH: 384
<212> TYPE: PRT
<213> ORGANISM: Camelina hispida

<400> SEQUENCE: 67

Met Gly Ala Gly Gly Arg Met Pro Val Pro Ser Ser Ser Lys Lys
1               5                   10                  15

Ser Glu Thr Asn Ala Ile Lys Arg Val Pro Cys Glu Lys Pro Pro Phe
            20                  25                  30

Thr Val Gly Glu Leu Lys Lys Ala Ile Pro Pro His Cys Phe Lys Arg
        35                  40                  45

Ser Ile Pro Arg Ser Phe Ser Tyr Leu Ile Thr Asp Ile Ile Ile Ala
    50                  55                  60

Ser Cys Phe Tyr Tyr Val Ala Thr Asn Tyr Phe Ser Leu Leu Pro Gln

```
                65                  70                  75                  80
Pro Leu Ser Tyr Leu Ala Trp Pro Leu Tyr Trp Ala Cys Gln Gly Cys
                    85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
    130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175

Pro Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Cys His Phe Phe Pro Asn Ala Pro Ile Tyr Asn Asp Arg Glu Arg Leu
    210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Leu Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Asp Tyr Tyr Gln Phe Asp Gly Thr Pro Trp
            340                 345                 350

Tyr Val Ala Met Tyr Arg Glu Ala Lys Glu Cys Ile Tyr Val Glu Pro
        355                 360                 365

Asp Arg Glu Gly Asp Lys Lys Gly Val Tyr Trp Tyr Asn Asn Lys Leu
    370                 375                 380

<210> SEQ ID NO 68
<211> LENGTH: 505
<212> TYPE: PRT
<213> ORGANISM: Camelina hispida

<400> SEQUENCE: 68

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Val Gly Lys
                20                  25                  30

Val Ser Arg Leu Thr Ala Asn Asp Leu Tyr His Phe Tyr Phe His Leu
            35                  40                  45

Gln His Asn Leu Ile Thr Val Ile Leu Leu Phe Ala Phe Thr Thr Phe
        50                  55                  60
```

```
Gly Leu Val Leu Tyr Ile Val Thr Arg Pro Lys Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Ser Arg
            100                 105                 110

Asn Val Ala Cys Asp Asp Pro Ser Ser Leu Asp Phe Leu Arg Lys Ile
                115                 120                 125

Gln Glu Arg Ser Gly Leu Gly Asp Glu Thr Tyr Ser Pro Pro Gly Leu
            130                 135                 140

Ile His Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Asp Ile Gly Ile Leu Val Val Asn Ser Ser Met Phe
                180                 185                 190

Asn Pro Thr Pro Ser Leu Ser Ala Met Val Val Asn Thr Phe Lys Leu
            195                 200                 205

Arg Ser Asn Ile Lys Ser Phe Ser Leu Gly Gly Met Gly Cys Ser Ala
210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr His Gly Ile
                245                 250                 255

Tyr Ser Gly Glu Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
            275                 280                 285

Arg Ser Lys Tyr Lys Leu Cys His Thr Val Arg Thr His Thr Gly Ala
            290                 295                 300

Asp Asp Lys Ser Phe Arg Cys Val Gln Gln Gly Asp Asp Glu Ser Gly
305                 310                 315                 320

Lys Ile Gly Val Cys Leu Ser Lys Asp Ile Thr Val Val Ala Gly Thr
                325                 330                 335

Ala Leu Lys Lys Asn Ile Ala Thr Leu Gly Pro Leu Ile Leu Pro Leu
            340                 345                 350

Ser Glu Lys Phe Leu Phe Leu Val Thr Phe Ile Ala Lys Lys Val Leu
            355                 360                 365

Lys Asp Lys Ile Lys Asn Tyr Tyr Val Pro Asp Phe Lys Leu Ala Ile
370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
            405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Arg Ala
            435                 440                 445

Trp Gln Ile Ala Leu Gly Ser Gly Phe Lys Cys Asn Ser Ala Val Trp
            450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Ser Asp Ser Ser Lys Ser
```

485                 490                 495

Glu Thr His Val Lys Asn Gly Arg Ser
            500                 505

<210> SEQ ID NO 69
<211> LENGTH: 505
<212> TYPE: PRT
<213> ORGANISM: Camelina hispida

<400> SEQUENCE: 69

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
            20                  25                  30

Ala Ser Arg Leu Thr Thr Asn Asp Leu Tyr His Phe Tyr Ser His Leu
        35                  40                  45

Gln His Asn Leu Val Thr Val Ile Leu Leu Phe Ala Phe Thr Ser Phe
    50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Arg
            100                 105                 110

Asn Val Ala Cys Asp Asp Pro Ser Ser Leu Asp Phe Leu Arg Lys Ile
        115                 120                 125

Gln Glu Arg Ser Gly Leu Gly Asp Glu Thr Tyr Ser Pro Pro Gly Leu
    130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Ile Lys Ser Leu Ser Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Ala Gly Asp Arg Arg
        275                 280                 285

Arg Ser Lys Tyr Lys Leu Cys His Thr Val Arg Thr His Thr Gly Ala
    290                 295                 300

Asp Asp Lys Ser Phe Arg Cys Val Gln Gln Gly Asp Asp Glu Ser Gly
305                 310                 315                 320

Lys Ile Gly Val Cys Leu Ser Lys Asp Ile Thr Val Val Ala Gly Thr
                325                 330                 335

Ala Leu Lys Lys Asn Ile Ala Thr Leu Gly Pro Leu Ile Leu Pro Leu
            340                 345                 350

```
Ser Glu Lys Phe Leu Phe Leu Val Thr Phe Ile Ala Lys Leu Leu
        355                 360                 365

Lys Asp Lys Ile Lys His Tyr Tyr Val Pro Asp Phe Lys Leu Ala Ile
370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Arg Ala
        435                 440                 445

Trp Gln Ile Ala Leu Gly Ser Gly Phe Lys Cys Asn Ser Ala Val Trp
    450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Ser Asp Ser Ser Lys Ser
                485                 490                 495

Glu Thr His Val Lys Asn Gly Arg Ser
                500                 505

<210> SEQ ID NO 70
<211> LENGTH: 385
<212> TYPE: PRT
<213> ORGANISM: Camelina laxa

<400> SEQUENCE: 70

Met Gly Ala Gly Gly Arg Met Pro Val Pro Ser Ser Ser Ser Ser Lys
1               5                   10                  15

Lys Ser Glu Thr Asp Ala Ile Lys Arg Val Pro Cys Glu Lys Pro Pro
            20                  25                  30

Phe Thr Leu Gly Glu Leu Lys Lys Ala Ile Pro Pro Gln Cys Phe Lys
        35                  40                  45

Arg Ser Ile Pro Arg Ser Phe Ser Tyr Leu Ile Thr Asp Ile Ile Val
    50                  55                  60

Ala Ser Cys Phe Tyr Tyr Val Ala Thr Asn Tyr Phe Ser Leu Leu Pro
65                  70                  75                  80

Gln Pro Leu Ser Tyr Leu Ala Trp Pro Leu Tyr Trp Ala Cys Gln Gly
                85                  90                  95

Cys Val Leu Thr Gly Val Trp Val Ile Ala His Glu Cys Gly His His
            100                 105                 110

Ala Phe Ser Asp Tyr Gln Trp Leu Asp Asp Thr Val Gly Leu Ile Phe
        115                 120                 125

His Ser Phe Leu Leu Val Pro Tyr Phe Ser Trp Lys Tyr Ser His Arg
    130                 135                 140

Arg His His Ser Asn Thr Gly Ser Leu Glu Arg Asp Glu Val Phe Val
145                 150                 155                 160

Pro Lys Gln Lys Ser Ala Ile Lys Trp Tyr Gly Lys Tyr Leu Asn Asn
                165                 170                 175

Pro Pro Gly Arg Ile Met Met Leu Thr Val Gln Phe Val Leu Gly Trp
            180                 185                 190

Pro Leu Tyr Leu Ala Phe Asn Val Ser Gly Arg Pro Tyr Asp Gly Phe
        195                 200                 205

Ala Cys His Phe Phe Pro Asn Ala Pro Ile Tyr Asn Asp Arg Glu Arg
    210                 215                 220
```

-continued

```
Leu Gln Ile Tyr Leu Ser Asp Ala Gly Ile Leu Ala Val Cys Phe Gly
225                 230                 235                 240

Leu Tyr Arg Tyr Val Ala Ala Gln Gly Met Ala Ser Met Ile Cys Leu
            245                 250                 255

Tyr Gly Val Pro Leu Leu Ile Val Asn Ala Phe Leu Val Leu Ile Thr
                260                 265                 270

Tyr Leu Gln His Thr His Pro Ala Leu Pro His Tyr Asp Ser Ser Glu
            275                 280                 285

Trp Asp Trp Leu Arg Gly Ala Leu Ala Thr Val Asp Arg Asp Tyr Gly
            290                 295                 300

Ile Leu Asn Lys Val Phe His Asn Ile Thr Asp Thr His Val Ala His
305                 310                 315                 320

His Leu Phe Ser Thr Met Pro His Tyr Asn Ala Met Glu Ala Thr Lys
                325                 330                 335

Ala Ile Lys Pro Ile Leu Gly Asp Tyr Gln Phe Asp Gly Thr Pro
            340                 345                 350

Trp Tyr Val Ala Met Tyr Arg Glu Ala Lys Glu Cys Ile Tyr Val Glu
                355                 360                 365

Pro Asp Arg Glu Gly Asp Lys Lys Gly Val Tyr Trp Tyr Asn Asn Lys
            370                 375                 380

Leu
385

<210> SEQ ID NO 71
<211> LENGTH: 505
<212> TYPE: PRT
<213> ORGANISM: Camelina laxa

<400> SEQUENCE: 71

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Val Gly Lys
                20                  25                  30

Val Ser Arg Leu Thr Ala Asn Asp Leu Tyr His Phe Tyr Phe His Leu
            35                  40                  45

Gln His Asn Leu Ile Thr Val Ile Leu Leu Phe Ala Phe Thr Thr Phe
        50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Arg
                100                 105                 110

Asn Val Ala Cys Asp Asp Pro Ser Ser Leu Asp Phe Leu Arg Lys Ile
            115                 120                 125

Gln Glu Arg Ser Gly Leu Gly Asp Glu Thr Tyr Ser Pro Pro Gly Leu
        130                 135                 140

Ile His Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Asp Ile Gly Ile Leu Val Val Asn Ser Ser Met Phe
            180                 185                 190

Asn Pro Thr Pro Ser Leu Ser Ala Met Val Val Asn Thr Phe Lys Leu
```

```
            195                 200                 205
Arg Ser Asn Ile Lys Ser Phe Ser Leu Gly Gly Met Gly Cys Ser Ala
210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr His Gly Ile
            245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ala Lys Tyr Lys Leu Cys His Thr Val Arg Thr His Thr Gly Ala
290                 295                 300

Asp Asp Lys Ser Phe Arg Cys Val Gln Gln Gly Asp Asp Glu Ser Gly
305                 310                 315                 320

Lys Ile Gly Val Cys Leu Ser Lys Asp Ile Thr Ala Val Ala Gly Thr
                325                 330                 335

Ala Leu Lys Lys Asn Ile Ala Thr Leu Gly Pro Leu Ile Leu Pro Leu
            340                 345                 350

Ser Glu Lys Phe Leu Phe Leu Val Thr Phe Ile Ala Lys Lys Leu Leu
            355                 360                 365

Lys Asp Lys Ile Lys His Tyr Tyr Val Pro Asp Phe Lys Val Ala Ile
370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Lys Ala
            435                 440                 445

Trp Gln Ile Ala Leu Gly Ser Gly Phe Lys Cys Asn Ser Ala Val Trp
450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Phe Asp Ser Ser Lys Ser
                485                 490                 495

Asp Thr His Val Lys Asn Gly Arg Ser
                500                 505

<210> SEQ ID NO 72
<211> LENGTH: 505
<212> TYPE: PRT
<213> ORGANISM: Camelina laxa

<400> SEQUENCE: 72

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
                20                  25                  30

Ala Ser Arg Leu Thr Thr Asn Asp Leu Tyr His Phe Asn Ser His Leu
            35                  40                  45

Gln His Asn Ile Val Thr Val Leu Leu Phe Ala Phe Thr Ala Phe
        50                  55                  60
```

```
Gly Leu Val Leu Tyr Val Thr Arg Pro Lys Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Thr Arg
            100                 105                 110

Asn Val Ala Cys Asp Asp Pro Ser Ser Leu Asp Phe Leu Arg Lys Ile
            115                 120                 125

Gln Glu Arg Ser Gly Leu Gly Asp Glu Thr Tyr Ser Pro Gln Gly Leu
            130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Glu Ile Gly Ile Leu Val Val Asn Ser Ser Met Phe
            180                 185                 190

Asn Pro Thr Pro Ser Leu Ser Ala Met Val Val Asn Thr Phe Lys Leu
            195                 200                 205

Arg Ser Asn Ile Lys Ser Phe Ser Leu Gly Gly Met Gly Cys Ser Ala
210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
            275                 280                 285

Arg Ala Lys Tyr Lys Leu Cys His Thr Val Arg Thr His Thr Gly Ala
            290                 295                 300

Asp Asp Lys Ser Phe Arg Cys Val Gln Gln Gly Asp Asp Glu Ser Gly
305                 310                 315                 320

Lys Ile Gly Val Cys Leu Ser Lys Asp Ile Thr Ala Val Ala Gly Thr
                325                 330                 335

Ala Leu Lys Lys Asn Ile Ala Thr Leu Gly Pro Leu Ile Leu Pro Leu
            340                 345                 350

Ser Glu Lys Phe Leu Phe Leu Val Thr Phe Ile Ala Lys Lys Leu Leu
            355                 360                 365

Lys Asp Lys Ile Lys His Tyr Tyr Val Pro Asp Phe Lys Val Ala Ile
370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Lys Ala
            435                 440                 445

Trp Gln Ile Ala Leu Gly Ser Gly Phe Lys Cys Asn Ser Ala Val Trp
            450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Phe Asp Ser Ser Lys Ser
```

```
                485                 490                 495
Asp Thr His Val Lys Asn Gly Arg Ser
            500                 505

<210> SEQ ID NO 73
<211> LENGTH: 384
<212> TYPE: PRT
<213> ORGANISM: Camelina microcarpa

<400> SEQUENCE: 73

Met Gly Ala Gly Gly Arg Met Pro Val Pro Ser Ser Ser Lys Lys
1               5                   10                  15

Ser Glu Thr Asp Ala Ile Lys Arg Val Pro Cys Glu Lys Pro Phe
                20                  25                  30

Thr Leu Gly Asp Leu Lys Lys Ala Ile Pro Pro Gln Cys Phe Lys Arg
            35                  40                  45

Ser Ile Pro Arg Ser Phe Ser Tyr Leu Ile Thr Asp Ile Ile Ile Ala
            50                  55                  60

Ser Cys Phe Tyr Tyr Val Ala Thr Asn Tyr Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
                100                 105                 110

Phe Ser Asp Tyr Gln Trp Leu Asp Asp Thr Val Gly Leu Ile Phe His
            115                 120                 125

Ser Phe Leu Leu Val Pro Tyr Phe Ser Trp Lys Tyr Ser His Arg Arg
130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175

Ala Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
            195                 200                 205

Cys His Phe Phe Pro Asn Ala Pro Ile Tyr Asn Asp Arg Glu Arg Leu
            210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Leu Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
            275                 280                 285

Asp Trp Leu Arg Gly Ala Leu Ala Thr Val Asp Arg Asp Tyr Gly Ile
            290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Asp Tyr Tyr Gln Phe Asp Gly Thr Pro Trp
            340                 345                 350
```

```
Tyr Val Ala Met Tyr Arg Glu Ala Lys Glu Cys Ile Tyr Val Glu Pro
            355                 360                 365

Asp Arg Glu Gly Asp Lys Lys Gly Val Tyr Trp Tyr Asn Asn Lys Leu
    370                 375                 380
```

<210> SEQ ID NO 74
<211> LENGTH: 385
<212> TYPE: PRT
<213> ORGANISM: Camelina microcarpa

<400> SEQUENCE: 74

```
Met Gly Ala Gly Gly Arg Met Pro Val Pro Ser Ser Ser Ser Ser Lys
1               5                   10                  15

Lys Ser Glu Thr Asp Ala Met Lys Arg Val Pro Cys Glu Lys Pro Pro
            20                  25                  30

Phe Thr Leu Gly Glu Leu Lys Lys Ala Ile Pro Gln Cys Phe Lys
        35                  40                  45

Arg Ser Ile Pro Arg Ser Phe Ser Tyr Leu Ile Thr Asp Ile Ile Val
    50                  55                  60

Ala Ser Cys Phe Tyr Tyr Val Ala Thr Asn Tyr Phe Ser Leu Leu Pro
65                  70                  75                  80

Gln Pro Leu Ser Tyr Leu Ala Trp Pro Leu Tyr Trp Ala Cys Gln Gly
                85                  90                  95

Cys Val Leu Thr Gly Val Trp Val Ile Ala His Glu Cys Gly His His
            100                 105                 110

Ala Phe Ser Asp Tyr Gln Trp Leu Asp Asp Thr Val Gly Leu Ile Phe
        115                 120                 125

His Ser Phe Leu Leu Val Pro Tyr Phe Ser Trp Lys Tyr Ser His Arg
    130                 135                 140

Arg His His Ser Asn Thr Gly Ser Leu Glu Arg Asp Glu Val Phe Val
145                 150                 155                 160

Pro Lys Gln Lys Ser Ala Ile Lys Trp Tyr Gly Lys Tyr Leu Asn Asn
                165                 170                 175

Pro Pro Gly Arg Ile Met Met Leu Thr Val Gln Phe Val Leu Gly Trp
            180                 185                 190

Pro Leu Tyr Leu Ala Phe Asn Val Ser Gly Arg Pro Tyr Asp Gly Phe
        195                 200                 205

Ala Cys His Phe Phe Pro Asn Ala Pro Ile Tyr Asn Asp Arg Glu Arg
    210                 215                 220

Leu Gln Ile Tyr Leu Ser Asp Ala Gly Ile Leu Ala Val Cys Phe Gly
225                 230                 235                 240

Leu Tyr Arg Tyr Ala Ala Ala Gln Gly Met Ala Ser Met Ile Cys Leu
                245                 250                 255

Tyr Gly Val Pro Leu Leu Ile Val Asn Ala Phe Leu Val Leu Ile Thr
            260                 265                 270

Tyr Leu Gln His Thr His Pro Ala Leu Pro His Tyr Asp Ser Ser Glu
        275                 280                 285

Trp Asp Trp Leu Arg Gly Ala Leu Ala Thr Val Asp Arg Asp Tyr Gly
    290                 295                 300

Ile Leu Asn Lys Val Phe His Asn Ile Thr Asp Thr His Val Ala His
305                 310                 315                 320

His Leu Phe Ser Thr Met Pro His Tyr Asn Ala Met Glu Ala Thr Lys
                325                 330                 335

Ala Ile Lys Pro Ile Leu Gly Asp Tyr Tyr Gln Phe Asp Gly Thr Pro
            340                 345                 350
```

```
Trp Tyr Val Ala Met Tyr Arg Glu Ala Lys Glu Cys Ile Tyr Val Glu
            355                 360                 365

Pro Asp Arg Glu Gly Asp Lys Lys Gly Val Tyr Trp Tyr Asn Asn Lys
    370                 375                 380

Leu
385

<210> SEQ ID NO 75
<211> LENGTH: 384
<212> TYPE: PRT
<213> ORGANISM: Camelina microcarpa

<400> SEQUENCE: 75

Met Gly Ala Gly Gly Arg Met Pro Val Pro Ser Ser Ser Lys Lys
1               5                   10                  15

Ser Glu Thr Asp Ala Ile Lys Arg Val Pro Cys Glu Lys Pro Pro Phe
                20                  25                  30

Thr Leu Gly Glu Leu Lys Lys Ala Ile Pro Pro Gln Cys Phe Lys Arg
            35                  40                  45

Ser Ile Pro Arg Ser Phe Ser Tyr Leu Ile Thr Asp Ile Ile Val Ala
    50                  55                  60

Ser Cys Phe Tyr Tyr Val Ala Thr Asn Tyr Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
    130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175

Ala Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Cys His Phe Phe Pro Asn Ala Pro Ile Tyr Asn Asp Arg Glu Arg Leu
    210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Leu Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
```

```
             325                 330                 335
Ile Lys Pro Ile Leu Gly Asp Tyr Tyr Gln Phe Asp Gly Thr Pro Trp
            340                 345                 350

Tyr Val Ala Met Tyr Arg Glu Ala Lys Glu Cys Ile Tyr Val Glu Pro
            355                 360                 365

Asp Arg Glu Gly Asp Lys Lys Gly Val Tyr Trp Tyr Asn Asn Lys Leu
            370                 375                 380

<210> SEQ ID NO 76
<211> LENGTH: 505
<212> TYPE: PRT
<213> ORGANISM: Camelina microcarpa

<400> SEQUENCE: 76

Met Thr Ser Val Asn Ala Lys Leu Leu Tyr His Tyr Val Leu Thr Asn
  1               5                  10                  15

Phe Phe Asn Leu Cys Leu Phe Pro Leu Thr Ala Leu Leu Ala Gly Lys
             20                  25                  30

Ala Ser Arg Leu Thr Ser Asn Asp Leu Tyr His Phe Tyr Ser His Leu
         35                  40                  45

Gln His Asn Leu Ile Thr Val Ile Leu Leu Phe Ala Phe Thr Ala Phe
     50                  55                  60

Gly Leu Val Leu Tyr Ile Val Thr Arg Pro Lys Pro Val Tyr Leu Val
 65                  70                  75                  80

Asp Tyr Ser Cys Tyr Leu Pro Pro His Leu Lys Val Ser Val Ser
                 85                  90                  95

Lys Ala Met Asp Ile Phe Tyr Gln Ile Arg Lys Ala Asp Thr Ser Arg
                100                 105                 110

Asn Val Ala Cys Asp Asp Pro Ser Ser Leu Asp Phe Leu Arg Lys Ile
            115                 120                 125

Gln Glu Arg Ser Gly Leu Gly Asp Glu Thr Tyr Ser Pro Gln Gly Leu
        130                 135                 140

Ile Asn Val Pro Pro Arg Lys Thr Phe Ala Ala Ser Arg Glu Glu Thr
145                 150                 155                 160

Glu Gln Val Ile Ile Gly Ala Leu Asp Lys Leu Phe Glu Asn Thr Lys
                165                 170                 175

Val Asn Pro Arg Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Ile Lys Ser Phe Ser Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Lys Leu Cys His Thr Val Arg Thr His Thr Gly Ala
    290                 295                 300

Asp Asp Met Ser Phe Arg Cys Val Gln Gln Gly Asp Asp Glu Ser Gly
305                 310                 315                 320
```

```
Lys Ile Gly Val Cys Leu Ser Lys Asp Ile Thr Val Ala Gly Ile
                325                 330                 335

Ala Leu Lys Lys Asn Ile Ala Thr Leu Gly Pro Leu Ile Leu Pro Leu
        340                 345                 350

Arg Glu Lys Phe Leu Phe Leu Val Thr Phe Ile Ala Lys Lys Leu Leu
            355                 360                 365

Lys Asp Lys Ile Lys His Tyr Tyr Val Pro Asp Phe Lys Leu Ala Ile
370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
            405                 410                 415

Thr Leu His Arg Phe Gly Asn Thr Ser Ser Ser Ile Trp Tyr Glu
                420                 425                 430

Leu Ala Tyr Ile Glu Ala Lys Gly Arg Met Lys Lys Gly Asn Arg Ala
            435                 440                 445

Trp Gln Ile Ala Leu Gly Ser Gly Phe Lys Cys Asn Ser Ala Val Trp
        450                 455                 460

Val Ala Leu Cys Asn Val Lys Ala Ser Ala Asn Ser Pro Trp Glu His
465                 470                 475                 480

Cys Ile Asp Arg Tyr Pro Val Gln Ile Asp Ser Gly Ser Ser Lys Ser
                485                 490                 495

Asp Thr His Val Lys Asn Gly Arg Ser
            500                 505

<210> SEQ ID NO 77
<211> LENGTH: 505
<212> TYPE: PRT
<213> ORGANISM: Camelina microcarpa

<400> SEQUENCE: 77

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
            20                  25                  30

Ala Ser Lys Leu Thr Ala Asn Asp Leu Tyr His Phe Tyr Ser His Leu
        35                  40                  45

Gln His Asn Leu Ile Thr Val Ile Leu Leu Phe Ala Phe Thr Ala Phe
    50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Ser Val Ser
                85                  90                  95

Lys Ala Met Asp Ile Phe Tyr Gln Ile Arg Lys Ala Asp Thr Ser Arg
            100                 105                 110

Asn Val Ala Cys Asp Asp Pro Ser Ser Leu Asp Phe Leu Arg Lys Ile
        115                 120                 125

Gln Glu Arg Ser Gly Leu Gly Asp Asp Thr Tyr Ser Pro Gln Gly Leu
    130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Glu Ile Gly Ile Leu Val Val Asn Ser Ser Met Phe
            180                 185                 190
```

Asn Pro Thr Pro Ser Leu Ser Ala Met Val Val Asn Thr Phe Lys Leu
            195                 200                 205

Arg Ser Asn Ile Lys Ser Phe Ser Leu Gly Gly Met Gly Cys Ser Ala
        210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Leu Gly Asp Arg Arg
        275                 280                 285

Arg Ser Lys Tyr Lys Leu Cys His Thr Val Arg Thr His Thr Gly Ala
290                 295                 300

Asp Asp Lys Ser Phe Arg Cys Val Gln Gln Gly Asp Glu Gly Gly
305                 310                 315                 320

Lys Ile Gly Val Cys Leu Ser Lys Asp Ile Thr Val Val Ala Gly Thr
                325                 330                 335

Ala Leu Lys Lys Asn Ile Ala Thr Leu Gly Pro Leu Ile Leu Pro Leu
            340                 345                 350

Ser Glu Lys Phe Leu Phe Leu Val Thr Phe Ile Ala Lys Lys Leu Leu
        355                 360                 365

Lys Asp Lys Ile Lys His Cys Tyr Val Pro Asp Phe Lys Leu Ala Ile
370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Arg Ala
        435                 440                 445

Trp Gln Ile Ala Leu Gly Ser Gly Phe Lys Cys Asn Ser Ala Val Trp
        450                 455                 460

Val Ala Leu Cys Asn Val Lys Ala Ser Ala Asn Ser Pro Trp Glu Asp
465                 470                 475                 480

Cys Ile Asp Arg Tyr Pro Val Gln Ile Asp Ser Asp Ser Ser Lys Ser
                485                 490                 495

Glu Thr His Val Lys Asn Gly Arg Ser
            500                 505

<210> SEQ ID NO 78
<211> LENGTH: 505
<212> TYPE: PRT
<213> ORGANISM: Camelina microcarpa

<400> SEQUENCE: 78

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
            20                  25                  30

Ala Ser Lys Leu Thr Ala Asn Asp Leu Tyr His Phe Tyr Ser His Leu
        35                  40                  45

Gln His Asn Leu Ile Thr Val Ile Leu Leu Phe Ala Phe Thr Ala Phe

```
         50                  55                  60
Gly Leu Val Leu Tyr Ile Val Thr Arg Ala Lys Pro Val Tyr Leu Val
 65                  70                  75                  80

Asp Tyr Ser Cys Tyr Leu Pro Pro His Leu Lys Val Ser Val Ser
                 85                  90                  95

Lys Val Met Asp Ile Phe Tyr Gln Ile Arg Lys Ala Asp Thr Ser Arg
                100                 105                 110

Asn Val Ala Cys Asp Asp Pro Ser Ser Leu Asp Phe Leu Arg Lys Ile
                115                 120                 125

Gln Glu Arg Ser Gly Leu Gly Asp Glu Thr Tyr Gly Pro Gln Gly Leu
                130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Glu Ile Gly Ile Leu Val Val Asn Ser Ser Met Phe
                180                 185                 190

Asn Pro Thr Pro Ser Leu Ser Ala Met Val Val Asn Thr Phe Lys Leu
                195                 200                 205

Arg Ser Asn Ile Lys Ser Phe Ser Leu Gly Gly Met Gly Cys Ser Ala
210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
                260                 265                 270

Val Gly Gly Ala Ala Ile Leu Leu Ser Asn Lys Pro Gly Asp Gly Arg
                275                 280                 285

Arg Ser Lys Tyr Lys Leu Cys His Thr Val Arg Thr His Thr Gly Ala
                290                 295                 300

Asp Asp Lys Ser Phe Arg Cys Val Gln Gln Gly Asp Asp Glu Ser Gly
305                 310                 315                 320

Lys Ile Gly Val Cys Leu Ser Lys Asp Ile Thr Val Val Ala Gly Thr
                325                 330                 335

Ala Leu Lys Lys Asn Ile Ala Thr Leu Gly Pro Leu Ile Leu Pro Leu
                340                 345                 350

Ser Glu Lys Phe Leu Phe Leu Val Thr Phe Ile Ala Lys Lys Leu Leu
                355                 360                 365

Lys Asp Lys Ile Lys His Tyr Tyr Val Pro Asp Phe Lys Leu Ala Ile
                370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
                420                 425                 430

Leu Ala Tyr Ile Glu Ala Lys Gly Arg Met Lys Lys Gly Asn Arg Ala
                435                 440                 445

Trp Gln Ile Ala Leu Gly Ser Gly Phe Lys Cys Asn Ser Ala Val Trp
                450                 455                 460

Val Ala Leu Cys Asn Val Lys Ala Ser Ala Asn Ser Pro Trp Glu His
465                 470                 475                 480
```

```
Cys Ile Asp Arg Tyr Pro Val Gln Ile Asp Ser Asp Ser Ser Lys Leu
                485                 490                 495

Glu Thr His Val Lys Asn Gly Arg Ser
        500                 505

<210> SEQ ID NO 79
<211> LENGTH: 384
<212> TYPE: PRT
<213> ORGANISM: Camelina rumelica

<400> SEQUENCE: 79

Met Gly Ala Gly Gly Arg Met Pro Val Pro Ser Ser Ser Ser Lys Lys
1               5                   10                  15

Ser Glu Thr Asp Ala Ile Lys Arg Val Pro Cys Glu Lys Pro Pro Phe
            20                  25                  30

Thr Val Gly Glu Leu Lys Lys Ala Ile Pro His Cys Phe Lys Arg
        35                  40                  45

Ser Ile Pro Arg Ser Phe Ser Tyr Leu Ile Thr Asp Ile Ile Val Ala
    50                  55                  60

Ser Cys Phe Tyr Tyr Val Ala Thr Asn Tyr Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
    130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175

Pro Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Cys His Phe Phe Pro Asn Ala Pro Ile Tyr Asn Asp Arg Glu Arg Leu
    210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Met Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335

Ile Lys Pro Ile Leu Gly Asp Tyr Tyr Gln Phe Asp Gly Thr Pro Trp
```

```
                    340                 345                 350
Tyr Val Ala Met Tyr Arg Glu Ala Lys Glu Cys Ile Tyr Val Glu Pro
                355                 360                 365

Asp Arg Glu Gly Asp Lys Lys Gly Val Tyr Trp Tyr Asn Asn Lys Leu
                370                 375                 380

<210> SEQ ID NO 80
<211> LENGTH: 384
<212> TYPE: PRT
<213> ORGANISM: Camelina rumelica

<400> SEQUENCE: 80

Met Gly Ala Gly Gly Arg Met Pro Val Pro Ser Ser Ser Lys Lys
1               5                   10                  15

Ser Glu Thr Asp Ala Met Lys Arg Val Pro Cys Glu Lys Pro Pro Phe
                20                  25                  30

Thr Leu Gly Glu Leu Lys Lys Ala Ile Pro Pro Gln Cys Phe Lys Arg
            35                  40                  45

Ser Ile Pro Arg Ser Phe Ser Tyr Leu Ile Thr Asp Ile Ile Val Ala
        50                  55                  60

Ser Cys Phe Tyr Tyr Val Ala Thr Asn Phe Phe Ser Leu Leu Pro Gln
65                  70                  75                  80

Pro Leu Ser Tyr Leu Ala Trp Pro Leu Tyr Trp Ala Cys Gln Gly Cys
                85                  90                  95

Val Leu Thr Gly Val Trp Val Ile Ala His Glu Cys Gly His His Ala
            100                 105                 110

Phe Ser Asp Tyr Gln Trp Leu Asp Asp Thr Val Gly Leu Ile Phe His
        115                 120                 125

Ser Phe Leu Leu Val Pro Tyr Phe Ser Trp Lys Tyr Ser His Arg Arg
130                 135                 140

His His Ser Asn Thr Gly Ser Leu Glu Arg Asp Glu Val Phe Val Pro
145                 150                 155                 160

Lys Gln Lys Ser Ala Ile Lys Trp Tyr Gly Lys Tyr Leu Asn Asn Pro
                165                 170                 175

Pro Gly Arg Ile Met Met Leu Thr Val Gln Phe Val Leu Gly Trp Pro
            180                 185                 190

Leu Tyr Leu Ala Phe Asn Val Ser Gly Arg Pro Tyr Asp Gly Phe Ala
        195                 200                 205

Cys His Phe Phe Pro Asn Ala Pro Ile Tyr Asn Asp Arg Glu Arg Leu
    210                 215                 220

Gln Ile Tyr Leu Ser Asp Ala Gly Ile Leu Ala Val Cys Phe Gly Leu
225                 230                 235                 240

Tyr Arg Tyr Ala Ala Ala Gln Gly Met Ala Ser Met Ile Cys Leu Tyr
                245                 250                 255

Gly Val Pro Leu Leu Ile Val Asn Ala Phe Leu Val Leu Ile Thr Tyr
            260                 265                 270

Leu Gln His Thr His Pro Ala Leu Pro His Tyr Asp Ser Ser Glu Trp
        275                 280                 285

Asp Trp Leu Arg Gly Ala Leu Ala Thr Val Asp Arg Asp Tyr Gly Ile
    290                 295                 300

Leu Asn Lys Val Phe His Asn Ile Thr Asp Thr His Val Ala His His
305                 310                 315                 320

Leu Phe Ser Thr Met Pro His Tyr Asn Ala Met Glu Ala Thr Lys Ala
                325                 330                 335
```

```
Ile Lys Pro Ile Leu Gly Asp Tyr Tyr Gln Phe Asp Gly Thr Pro Trp
            340                 345                 350

Tyr Val Ala Met Tyr Arg Glu Ala Lys Glu Cys Ile Tyr Val Glu Pro
        355                 360                 365

Asp Arg Glu Gly Asp Lys Lys Gly Val Tyr Trp Tyr Asn Asn Lys Leu
    370                 375                 380

<210> SEQ ID NO 81
<211> LENGTH: 505
<212> TYPE: PRT
<213> ORGANISM: Camelina rumelica

<400> SEQUENCE: 81

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
            20                  25                  30

Ala Ser Arg Leu Thr Thr Asn Asp Leu Tyr His Phe Tyr Ser His Leu
        35                  40                  45

Gln His Asn Leu Ile Thr Val Ile Leu Leu Phe Ala Phe Thr Ala Phe
    50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Thr Val Ser
                85                  90                  95

Lys Val Met Asp Ile Phe Tyr Gln Ile Arg Lys Ala Asp Thr Ser Arg
            100                 105                 110

Asn Val Ala Cys Asp Asp Pro Ser Ser Leu Asp Phe Leu Arg Lys Ile
        115                 120                 125

Gln Glu Arg Ser Gly Leu Gly Asp Glu Thr Tyr Ser Pro Pro Gly Leu
    130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Asn Pro Arg Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205

Arg Ser Asn Ile Lys Ser Phe Ser Leu Gly Gly Met Gly Cys Ser Ala
    210                 215                 220

Gly Val Ile Ala Ile Asp Leu Ala Lys Asp Leu Leu His Val His Lys
225                 230                 235                 240

Asn Thr Tyr Ala Leu Val Val Ser Thr Glu Asn Ile Thr Gln Gly Ile
                245                 250                 255

Tyr Ala Gly Glu Asn Arg Ser Met Met Val Ser Asn Cys Leu Phe Arg
            260                 265                 270

Val Gly Gly Ala Ala Ile Leu Leu Ser Asn Lys Pro Gly Asp Arg Arg
        275                 280                 285

Arg Ser Lys Tyr Gln Leu Cys His Thr Val Arg Thr His Thr Gly Ala
    290                 295                 300

Asp Asp Arg Ser Phe Arg Cys Val Gln Gln Gly Asp Glu Ser Gly
305                 310                 315                 320

Lys Ile Gly Val Cys Leu Ser Lys Asp Ile Thr Ala Val Ala Gly Thr
                325                 330                 335
```

```
Ala Leu Lys Lys Asn Ile Ala Thr Leu Gly Pro Leu Ile Leu Pro Leu
            340                 345                 350

Ser Glu Lys Phe Leu Phe Leu Val Thr Phe Ile Ala Lys Lys Leu Leu
        355                 360                 365

Lys Asn Lys Ile Lys His Tyr Tyr Val Pro Asp Phe Lys Leu Ala Ile
    370                 375                 380

Asp His Phe Cys Ile His Ala Gly Gly Arg Ala Val Ile Asp Val Leu
385                 390                 395                 400

Glu Lys Ser Leu Gly Leu Ser Pro Ile Asp Val Glu Ala Ser Arg Ser
                405                 410                 415

Thr Leu His Arg Phe Gly Asn Thr Ser Ser Ser Ile Trp Tyr Glu
            420                 425                 430

Leu Ala Tyr Ile Glu Ala Lys Gly Arg Met Lys Lys Gly Asn Arg Ala
        435                 440                 445

Trp Gln Ile Ala Leu Gly Ser Gly Phe Lys Cys Asn Ser Ala Val Trp
    450                 455                 460

Val Ala Leu Cys Asn Val Lys Ser Ala Asn Ser Pro Trp Glu His
465                 470                 475                 480

Cys Ile Asp Arg Tyr Pro Val Gln Leu Asn Ser Asp Ser Ser Lys Ser
                485                 490                 495

Glu Thr His Val Lys Asn Gly Arg Ser
            500                 505

<210> SEQ ID NO 82
<211> LENGTH: 505
<212> TYPE: PRT
<213> ORGANISM: Camelina rumelica

<400> SEQUENCE: 82

Met Thr Ser Val Asn Ala Lys Leu Leu Tyr His Tyr Val Leu Thr Asn
1               5                   10                  15

Phe Phe Asn Leu Cys Leu Phe Pro Leu Thr Ala Leu Leu Ala Gly Lys
            20                  25                  30

Ala Ser Lys Leu Thr Ala Asn Asp Leu Tyr His Phe Tyr Ser His Leu
        35                  40                  45

Gln His Asn Leu Ile Thr Val Ile Leu Leu Phe Ala Phe Thr Ser Phe
    50                  55                  60

Gly Leu Val Leu Tyr Ile Val Thr Arg Pro Lys Pro Val Tyr Leu Val
65                  70                  75                  80

Asp Tyr Ser Cys Tyr Leu Pro Pro His Leu Lys Val Ser Val Ser
                85                  90                  95

Lys Val Met Asp Ile Phe Tyr Gln Ile Arg Lys Ala Asp Thr Ser Arg
            100                 105                 110

Asn Val Ala Cys Asp Asn Pro Ser Ser Leu Asp Phe Leu Arg Lys Ile
        115                 120                 125

Gln Glu Arg Ser Gly Leu Gly Asp Glu Thr Tyr Ser Pro Gln Gly Leu
    130                 135                 140

Ile Asn Val Pro Pro Gln Lys Thr Phe Ala Ala Ser Arg Glu Glu Thr
145                 150                 155                 160

Glu Gln Val Ile Ile Gly Ala Leu Glu Lys Leu Phe Glu Asn Thr Lys
                165                 170                 175

Val Ser Pro Arg Glu Ile Gly Ile Leu Val Val Asn Ser Ser Met Phe
            180                 185                 190

Asn Pro Thr Pro Ser Leu Ser Ala Met Val Val Asn Thr Phe Lys Leu
        195                 200                 205
```

-continued

```
Arg Ser Asn Ile Lys Ser Phe Ser Leu Gly Gly Met Gly Cys Ser Ala
    210             215             220

Gly Val Ile Ala Ile Asp Leu Ala Lys Asp Leu Leu His Val His Lys
225             230             235             240

Asn Thr Tyr Ala Leu Val Val Ser Thr Glu Asn Ile Thr Gln Gly Ile
                245             250             255

Tyr Ala Gly Glu Asn Arg Ser Met Met Val Ser Asn Cys Leu Phe Arg
                260             265             270

Val Gly Gly Ala Ala Ile Leu Leu Ser Asn Lys Pro Gly Asp Arg Arg
        275             280             285

Arg Ser Lys Tyr Lys Leu Cys His Thr Val Arg Thr His Thr Gly Ala
    290             295             300

Asp Asp Lys Ser Phe Arg Cys Val Gln Gln Gly Asp Asp Glu Ser Gly
305             310             315             320

Lys Ile Gly Val Cys Leu Ser Lys Asp Ile Thr Val Val Ala Gly Ile
                325             330             335

Ala Leu Lys Lys Asn Ile Ala Thr Leu Gly Pro Leu Ile Leu Pro Leu
            340             345             350

Ser Glu Lys Phe Leu Phe Leu Val Ser Phe Ile Ala Lys Lys Leu Leu
            355             360             365

Lys Asp Lys Ile Lys His Tyr Tyr Val Pro Asp Phe Lys Leu Ala Ile
    370             375             380

Asp His Phe Cys Ile His Ala Gly Gly Arg Ala Val Ile Asp Val Leu
385             390             395             400

Glu Lys Ser Leu Gly Leu Ser Pro Ile Asp Val Glu Ala Ser Arg Ser
                405             410             415

Thr Leu His Arg Phe Gly Asn Thr Ser Ser Ser Ile Trp Tyr Glu
                420             425             430

Leu Ala Tyr Thr Glu Ala Lys Gly Arg Met Lys Lys Gly Asn Arg Ala
            435             440             445

Trp Gln Ile Ala Leu Gly Ser Gly Phe Lys Cys Asn Ser Ala Val Trp
    450             455             460

Val Ala Leu Cys Asn Val Lys Ala Ser Ala Asn Ser Pro Trp Glu His
465             470             475             480

Cys Ile Asp Arg Tyr Pro Val Lys Ile Asp Ser Asp Ser Ser Lys Ser
                485             490             495

Glu Thr His Val Lys Asn Gly Arg Ser
                500             505
```

ISOLATION AND USE OF FAD2 AND FAE1 FROM *CAMELINA*

CROSS-REFERENCE TO RELATED APPLICATIONS

This application claims the benefit of U.S. Provisional Patent Application Ser. No. 61/318,273, filed Mar. 26, 2010, and U.S. Provisional Patent Application Ser. No. 61/346,410, filed May 19, 2010. The contents of the above applications are hereby incorporated by reference in their entireties for all purposes.

TECHNICAL FIELD

The invention relates to the identification, isolation and use of nucleic acid sequences, including genes, and nucleic acid fragments encoding fatty acid desaturase enzymes and/or fatty acid elongases, mutants thereof, and methods of altering lipid composition in *Camelina* species, e.g., *Camelina sativa*.

BACKGROUND

The current concern about our global dependence on fossil fuels and the consequent impact on climate change have brought biofuels to the forefront. This interest in biofuels has prompted researchers to critically evaluate alternative feedstocks for biofuel production. One important, emerging biofuel crop is *Camelina sativa* L. Cranz (Brassicaceae), commonly referred to as "false flax" or "gold-of-pleasure". Renewed interest in *C. sativa* as a biofuel feedstock is due in part to its drought tolerance and minimal requirements for supplemental nitrogen and other agricultural inputs (Putnam, Budin et al. 1993; Zubr 1997; Gehringer, Friedt et al. 2006; Gugel and Falk 2006). Similar to other non-traditional, renewable oilseed feedstocks such as *Jatropha curcas* L. ("*jatropha*"), *C. sativa* grows on marginal land. Unlike *jatropha*, which is a tropical and subtropical shrub, *C. sativa* is native to Europe and is naturalized in North America, where it grows well in the northern United States and southern Canada.

In addition to its drought tolerance and broad distribution, several other aspects of *C. sativa* biology make it well suited for development as an oilseed crop. First, *C. sativa* is a member of the family Brassicaceae, and thus is a relative of both the genetic model organism *Arabidopsis thaliana* and the oilseed crop *Brassica napus*. The close relationship between *C. sativa* and *A. thaliana* (Al-Shehbaz, Beilstein et al. 2006; Beilstein, Al-Shehbaz et al. 2006; Beilstein, Al-Shehbaz et al. 2008) makes the *A. thaliana* genome an ideal reference point for the development of genetic and genomic tools in *C. sativa*. Second, the oil content of *C. sativa* seeds is comparable to that of *B. napus*, ranging from 30 to 40% (w/w) (Budin, Breene et al. 1995; Gugel and Falk 2006), suggesting that agronomic lessons from the cultivation of *B. napus* are applicable to *C. sativa* cultivation. Finally, the properties of *C. sativa* biodiesel are already well described (Rice, Frohlich et al. 1997; Frohlich and Rice 2005; Worgetter, Prankl et al. 2006), and both seed oil and biodiesel from *C. sativa* were used as fuel in engine trials with promising results (Bernardo, Howard-Hildige et al. 2003; Frohlich and Rice 2005).

The quality of a biodiesel, regardless of its source, is dependent upon the fatty acid methyl ester (FAME) composition, which affects cold flow and oxidative stability (Knothe 2005; Durrett, Benning et al. 2008). For example, saturated FAMEs have poor cold flow properties since they can form crystals at lower temperatures, while the FAMEs from polyunsaturated fatty acids remain in solution at colder temperatures, and thus have good cold flow properties (Stournas 1995; Serdari, Lois et al. 1999). In contrast, the relationship between saturation and oxidative stability is exactly opposite that of cold flow. Fatty acid saturation is positively correlated with oxidative stability; saturated fatty acids have the best oxidative stability and fatty acids with 2 or greater double bonds have increasing oxidative instability (Knothe and Dunn 2003; Knothe 2005; Durrett, Benning et al. 2008). Additionally, polyunsaturated FAMEs can result in increased NOx emissions, e.g., NO, $NO_2$ et al (McCormick, Graboski et al. 2001), and thus affect the production of a monitored pollutant. Very long chain fatty acids (VLCFA; as used herein, refers to those fatty acids containing greater than 18 carbons) result in a biodiesel with a high distillation temperature that does not meet existing standards (American Society for Testing and Materials, ASTM), reducing marketability. Given these trade-offs, an ideal biodiesel blend is high in oleic acid (18:1; carbons:double bonds), low in polyunsaturated FAMEs, and with few long chain FAMEs. This blend is oxidatively stable, has a low cloud point, and meets biodiesel standards (ASTM; Knothe 2005; Durrett, Benning et al. 2008).

The naturally occurring oil composition of *C. sativa* negatively affects its biodiesel properties. Polyunsaturated fatty acids such as linoleic (18:2) and alpha-linolenic (18:3) acids account for 52.1-54.7% of *C. sativa* seed oil (Ní Eidhin, Burke et al. 2003; Abramovic and Abram 2005). This likely accounts for the low oxidative stability of *C. sativa* FAMEs (Bernardo, Howard-Hildige et al. 2003). *C. sativa* seeds also contain 21.4-22.4% VLCFA, of which 11-eicosenoic acid (20:1) at 14.9-16.2% are especially abundant (Zubr 2002; Ní Eidhin, Burke et al. 2003; Abramovic and Abram 2005), likely resulting in the high distillation temperature of the FAMEs. Most desirable for biodiesel is oleic acid (18:1), which accounts for 14.0-17.4% of *C. sativa* seed oil (Budin, Breene et al. 1995; Zubr 2002; Ní Eidhin, Burke et al. 2003; Abramovic and Abram 2005). There is therefore the potential to optimize *Camelina* oil for biodiesel production by decreasing both the amount of polyunsaturated fatty acids being produced from oleic acid and decreasing the production of fatty acids with chain length of 18 carbons or greater.

Genes affecting oil composition are well characterized in *Arabidopsis thaliana*, a close relative of *Camelina sativa*, as well as in some other plants. For example, oleic acid (18:1) is converted to linoleic acid (18:2) in the endoplasmic reticulum by the membrane bound delta-12-desaturase FATTY ACID DESATURASE 2 (FAD2). In *Arabidopsis* fad2 mutants, levels of 18:1 oleic acid in the seeds increase by a factor of 2-3.4 while levels of 18:2 linoleic acids are decreased by a factor of 4-10 (Okuley, Lightner et al. 1994). Thus, mutations affecting FAD2 have been shown to lead to higher levels of oleic acid in *A. thaliana* and other studies have shown FAD2 has a similar role in crops such as canola (Hu, Sullivan-Gilbert et al. 2006), sunflower (Hongtrakul, Slabaugh et al. 1998) and peanut (Patel, Jung et al. 2004).

Very long chain fatty acids are formed in the cytosol of *A. thaliana* by sequential addition of 2 carbon units to 18 carbon fatty acid CoA conjugates. The rate limiting step is thought to be initial condensation, catalyzed in the seed by FATTY ACID ELONGASE 1 (FAE1) (James Jr, Lim et al. 1995) (Kunst, Taylor et al. 1992). In wild type *Arabidopsis*, approximately 25% of fatty acids in seeds are long chain fatty acids, while fae1 mutants contain less than 1% long chain fatty acids. Interestingly, 18:1 content in seeds increases by a factor of 2 in *A. thaliana* fae1 (Kunst, Taylor et al. 1992). In *Brassica napus*, reductions in long chain fatty acids, particularly erucic acid (22:1), are linked to changes in FAE1 activity (Han, Labs et al. 2001; Katavic, Mietkiewska et al. 2002; Wang, Wang et al. 2008; Wu, Wu et al. 2008).

The close relationship between *A. thaliana* and *C. sativa* suggests that FAD2 and FAE1 may play similar roles in both species, making these genes good targets for manipulation of oil composition in *C. sativa*. To our knowledge, FAD2 and FAE1 gene sequences have not been previously reported for *C. sativa*. Indeed, published studies detailing the biology of *C. sativa* and its closest relatives in the genus *Camelina* are few. However, several important findings can be drawn from the literature. Taxonomic treatments describe 11 species in the genus with a center of diversity in Eurasia (Akeroyd J: *Camelina in Flora Europaea*. 2nd edn. Cambridge, UK: Cambridge University Press; 1993.) although *C. sativa, C. rumelica, C. microcarpa,* and *C. alyssum* are naturalized weeds with broad distributions. *Camelina* species can be annual or biennial, with some species requiring vernalization to induce flowering (Mirek Z: Genus *Camelina* in Poland—Taxonomy, Distribution and Habitats. *Fragmenta Floristica et Geobotanica* 1981, 27:445-503). Chromosome counts range from n=6 in *C. rumelica* (Brooks R E: Chromosome number reports LXXXVII *Taxon* 1985, 34:346-351; Baksay L: The chromosome numbers and cytotaxonomical relations of some European plant species. *Ann Hist-Nat Mus Natl Hung* 1957:169-174.) or n=7 in *C. hispida* (Maassoumi A: Cruciferes de la fore d'Iran: etude caryosystematique. Thesis. Strasbourg, France, 1980.), upwards to n=20 in *C. sativa, C. microcarpa,* and *C. alyssum* (Gehringer A, Friedt W, Luhs W, Snowdon R J: Genetic mapping of agronomic traits in false flax (*Camelina sativa* subsp. *sativa*). *Genome* 2006, 49:1555-1563; Francis A, Warwick S: The Biology of Canadian Weeds. 142. *Camelina alyssum* (Mill.) Thell.; *C. microcarpa* Andrz. ex DC.; *C. sativa* (L.) Crantz. *Canadian Journal of Plant Science* 2009, 89:791-810). Some *Camelina* species are interfertile; crosses of *C. sativa* with *C. alyssum*, and *C. sativa* with *C. microcarpa*, produce viable seed (Tedin O: Vererbung, Variation and Systematik in der Gattung *Camelina. Hereditas* 1925, 6:19-386). More recently, plastid simple sequence repeat (SSR) markers (Flannery M L, Mitchell F J, Coyne S, Kavanagh T A, Burke J I, Salamin N, Dowding P, Hodkinson T R: Plastid genome characterisation in *Brassica* and Brassicaceae using a new set of nine SSRs. *Theor Appl Genet.* 2006, 113:1221-1231.) and randomly amplified polymorphic DNA (RAPD) markers have been reported and a mapping study using amplified fragment length polymorphisms (AFLP) has been published (Gehringer A, Friedt W, Luhs W, Snowdon R J: Genetic mapping of agronomic traits in false flax (*Camelina sativa* subsp. *sativa*). *Genome* 2006, 49:1555-1563). Additionally, the sequences of a few *C. sativa* transcription factors are available from the literature (Martynov V V, Tsvetkov I L, Khavkin E E: Orthologs of *arabidopsis* CLAVATA 1 gene in cultivated Brassicaceae plants. *Ontogenez* 2004, 35:41-46.) and in GenBank.

As an oilseed crop in the Brassicaceae family, *Camelina sativa* has inspired renewed interest due to its potential for biofuels applications. Little is understood of the nature of the *C. sativa* genome, however. A study was undertaken by the present inventors to characterize two genes in the fatty acid biosynthesis pathway, fatty acid desaturase (FAD) 2 and fatty acid elongase (FAE) 1.

DESCRIPTION OF THE TEXT FILE SUBMITTED ELECTRONICALLY

The contents of the text file submitted electronically are incorporated herein by reference in their entirety: A computer readable format copy of the Sequence Listing (filename: TARG-005-02US_ST25.txt, date recorded: Jun. 3, 2011, file size 167 kilobyte).

SUMMARY OF THE INVENTION

*Camelina sativa* is a re-emerging oilseed with tremendous potential as an alternative biofuel crop and for which genomic information is becoming increasingly available. The inventors have characterized two genes encoding fatty acid biosynthesis enzymes and, in the process, have discovered unexpected complexity in the *C. sativa* genome.

The present inventors disclose herewith the sequences of three copies of both FAE1 and FAD2 recovered from *C. sativa*. Southern blots were used to determine whether the recovered copies are allelic or if they represent multiple loci. Moreover, the inventors performed phylogenetic analyses to infer the evolutionary history of the copies, and quantitative PCR (qPCR) to explore whether there is evidence of functional divergence among them. To better understand the *C. sativa* genome and to determine whether the multiple copies recovered are the result of polyploidization, the inventors also analyzed the genome sizes of *C. sativa* and its closest relatives in the genus *Camelina* by flow cytometry. Collectively the inventors' results indicate that *C. sativa* is an allohexaploid whose oil composition is likely influenced by more than one functional copy of FAE1 and FAD2. This should allow highly specialized blends of oil to be produced from *C. sativa* with mutations in FAE1 and FAD2, greatly increasing the utility of this emerging biofuel crop.

The present inventors unexpectedly discovered by Southern analysis that in *C. sativa*, there are three copies of both FAD2 and FAE1 as well as LFY, a known single copy gene in other species. All three copies of both FAD2 and FAE1 are expressed in developing seeds, and sequence alignments show that previously described conserved sites are present, suggesting that all three copies of both genes could be functional. The regions downstream of FAD2 and upstream of FAE1 demonstrate co-linearity with the *Arabidopsis* genome. In addition, results from flow cytometry indicate that the DNA content of *C. sativa* is approximately three-fold that of diploid *Camelina* relatives. Phylogenetic analyses further support a history of duplication and indicate that *C. sativa* and *C. microcarpa* might share a parental genome. FAD2 and FAE1 sequences from species in the tribe of Camelineae have been deposited in Genbank at the NCBI [Genbank: GU929417-GU929441, SEQ ID NOs: 1 to 6, and SEQ ID NOs 45-63, as listed below, which are incorporated by reference in their entireties].

| GenBank access # | Sequence Name | SEQ ID NO |
|---|---|---|
| GU929417 | *Camelina sativa* FAD2 A (upstream, coding and downstream genomic sequence) | 1 |
| GU929418 | *Camelina sativa* FAD2 B (upstream, coding and downstream genomic sequence) | 2 |
| GU929419 | *Camelina sativa* FAD2 C (upstream, coding and downstream genomic sequence) | 3 |
| GU929420 | *Camelina sativa* FAE1 A [upstream gene (KCS17), intergenic region and coding) | 4 |
| GU929421 | *Camelina sativa* FAE1 B (upstream gene (KCS17), intergenic region and coding) | 5 |
| GU929422 | *Camelina sativa* FAE1 C [upstream gene (KCS17), intergenic region and coding) | 6 |
| GU929423 | *Capsella rubella* FAD2 | 45 |
| GU929424 | *Arabidopsis lyrata* FAD2 | 46 |
| GU929425 | *Arabidopsis lyrata* FAE1 | 47 |

-continued

| GenBank access # | Sequence Name | SEQ ID NO |
|---|---|---|
| GU929426 | *Camelina hispida* FAD2 | 48 |
| GU929427 | *Camelina hispida* FAE1-1 | 49 |
| GU929428 | *Camelina hispida* FAE1-2 | 50 |
| GU929429 | *Camelina laxa* FAD2 | 51 |
| GU929430 | *Camelina laxa* FAE1-1 | 52 |
| GU929431 | *Camelina laxa* FAE1-2 | 53 |
| GU929432 | *Camelina microcarpa* FAD2 A | 54 |
| GU929433 | *Camelina microcarpa* FAD2 B | 55 |
| GU929434 | *Camelina microcarpa* FAD2 C | 56 |
| GU929435 | *Camelina microcarpa* FAE1 A | 57 |
| GU929436 | *Camelina microcarpa* FAE1 B | 58 |
| GU929437 | *Camelina microcarpa* FAE1 C | 59 |
| GU929438 | *Camelina rumelica* FAD2-1 | 60 |
| GU929439 | *Camelina rumelica* FAD2-2 | 61 |
| GU929440 | *Camelina rumelica* FAE1-1 | 62 |
| GU929441 | *Camelina rumelica* FAE1-2 | 63 |

The *C. sativa* genome appears to be organized in three copies, and can be considered to be an allohexaploid. The discovery of triplication and divergence of genes that in known diploids are present in single copy, the cytometrically determined genome size of *Camelina* species, the pattern of relationship and inferred duplication history in the gene trees, together with the previously known chromosome counts for this taxon, indicate a likely allohexaploid genomic constitution. The characterization of genes encoding key functions of fatty acid biosynthesis lays the foundation for future manipulations of this pathway in *Camelina sativa*, which allows for the future manipulation of oil composition of this emerging biofuel crop.

The present invention provides an isolated nucleic acid sequence comprising a sequence selected from the group consisting of SEQ ID NOs: 1 to 6 and 45 to 63, and fragments and variations derived from thereof, which encode a plant fatty acid synthesis gene.

In one embodiment, the present invention provides an isolated polynucleotide encoding plant fatty acid desaturase, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 1, 2, 3, 45, 46, 48, 51, 54, 55, 56, 60, and/or 61.

In another embodiment, the present invention provides an isolated polynucleotide encoding fatty acid elongase, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 4, 5, 6, 47, 49, 50, 52, 53, 57, 58, 59, 62, and/or 63.

The present invention further provides an isolated amino acid sequence (e.g., a peptide, polypeptide and the like) comprising a sequence selected from the group consisting of SEQ ID NOs: 7 to 12, and fragments and variations derived from thereof, which form a plant fatty acid synthesis protein.

In some embodiments, the present invention provides an isolated amino acid sequence which forms a protein that shares an amino acid sequence having at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 7, 8, 9, 64, 65, 67, 70, 73, 74, 75, 79, and/or 80.

In one embodiment, the present invention provides an isolated amino acid sequence which forms a protein that shares an amino acid having at least 85%, at least 86%, at lest 87%, at least 88%, at least 89%, at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 10, 11, 12, 66, 68, 69, 71, 72, 76, 77, 78, 81, and/or 82.

The present invention also provides a chimeric gene comprising the isolated nucleic acid sequence of any one of the polynucleotides described above operably linked to suitable regulatory sequences.

The present invention also provides a recombinant construct comprising the chimeric gene as described above.

The present invention further comprises interfering RNA (RNAi) based on the expression of the nucleic acid sequences of the present invention, wherein such RNAi includes but is not limited to microRNA (miRNA) and small interfering RNA (siRNA) which can be used in gene silencing constructs.

The present invention also provides a transformed host cell comprising the chimeric gene as described above. In one embodiment, said host cell is selected from the group consisting of bacteria, yeasts, filamentous fungi, algae, animals, and plants.

The present invention in another aspect, provides a plant comprising in its genome one or more genes as described herein, one or more genes with mutations as described herein, or the chimeric genes as described herein.

The present invention in another aspect, provides a plant seed obtained from the plants described herein, wherein the plants comprise in their genomes one or more genes as described herein, one or more genes with mutations as described herein, or the chimeric genes as described herein.

The present invention in another aspect, provides *Camelina* oil obtained from the seeds of a *Camelina* plant comprising the one or more genes described herein, one or more genes with mutations as described herein, or one or more chimeric genes as described herein.

The present invention in another aspect, provides meals made from *Camelina* plants comprising the one or more genes described herein, one or more genes with mutations as described herein, or one or more chimeric genes as described herein. In some embodiments, the meal is a byproduct of the extraction of the oil from said *Camelina* seeds. In some embodiments, said *Camelina* plant has reduced level of erucic acid (22:1) compared to a wild type *Camelina* plant. In some embodiments, said *Camelina* plant has less than 4%, less than 3%, less than 2%, less than 1%, or less than 0.1% erucic acid (22:1) compared to the wild type. In further embodiments, the *Camelina* meal is included in the diets of an animal for about 0.1%, about 0.5%, about 1%, about 2%, about 3%, about 4%, about 5%, about 6%, about 7%, about 8%, about 9%, or about 10% of their feed on a weight or volume basis.

Thus, the present invention provides methods of altering and/or improving *Camelina* fatty acids composition by disrupting and/or altering one, two, or all three copies of one or more fatty acid synthesis genes in *Camelina*. Methods of disrupting and/or altering gene function include but are not limited to mutagenesis (e.g., chemical mutagenesis, radiation mutagenesis, transposon mutagenesis, insertional mutagenesis, signature tagged mutagenesis, site-directed mutagenesis, and natural mutagenesis), antisense, knock-outs, and/or RNA interference.

In some embodiments, the methods comprise introducing mutations in one or more FAD2 genes and/or one or more FAE1 genes of *Camelina*. In some embodiments, the methods disclosed herein comprise utilizing *Camelina* mutants with mutations in all three FAD2 genes (e.g., FAD2 A, FAD2 B, and FAD2 C), and/or *Camelina* mutants with mutations in all three FAE1 genes (e.g., FAE1 A, FAE1 B, and FAE1 C).

The present invention provides mutants in FAD2 A, FAD2 B, FAD2 C, FAE1 A, FAE1 B, and FAE1 C, including but not limited to those as listed in Tables 7-12. In some embodiments, the methods of altering and/or improving *Camelina* fatty acids composition comprise utilizing one or more *Camelina* mutants for any one or more of the mutations listed in Tables 7 to 12 and as described in Example 11. In some embodiments, mutations in one or more copies of FAD2 genes and/or mutations in one or more copies of FAE1 genes as described in the Tables 7 to 12 are integrated together to create mutant plants with double, triple, quadruple et al. mutations in one, two, or all three copies of FAD2 and/or FAE1 genes. In some embodiments, the mutations described in the Tables 7-12 can be integrated into *Camelina sativa* cultivars other than Cs32 (commercial name as SO30) or other *Camelina* species by classic breeding methods, with or without the help of marker-facilitated inter-cultivar gene transfer methods. In some embodiments, mutations described in the Tables 7-12 can be integrated into species closely related to *Camelina sativa*. In still other embodiments, amino acids in conserved domains or sites compared to FAD2 or FAE1 orthologs in other species can be substituted or deleted to make mutants with reduced or abolished activity, mutants that lead to loss-of-function (e.g., protein instability), and/or mutants that lead to gain-of-function (e.g., more stable or more active protein).

In some embodiments, one, two, or all three copies of *Camelina* FAD2 and/or FAE1 genes, and one, two, or all three copies of other non-FAD, non-FAE fatty acid synthesis genes are disrupted. In still some embodiments, one, two, or all three copies of *Camelina* FAD2 and/or FAE1 genes are disrupted, while one or more non-FAD, non-FAE fatty acid synthesis genes are overexpressed. In still more embodiments, one, two, or all three copies of *Camelina* FAD2 and/or FAE1 genes are disrupted, while one or more non-fatty-acid-synthesis genes are disrupted and/or overexpressed.

In another aspect, the present invention provides methods of producing *Camelina* seed oil containing altered and/or increased levels of oleic acid (18:1), and/or altered or reduced levels of polyunsaturated fatty acids, and/or decreased very long chain fatty acids. Such methods comprising utilizing the *Camelina* plants comprising the chimeric genes as described herein, or *Camelina* plants with disrupted FAD2 and/or FAE1 genes as described herein. As used herein, the phrase "very long chain fatty acid" refers to a fatty acid with more than 18 carbons.

The present invention also provides methods of increasing the activity of a FAD2 and/or FAE1 protein in a *Camelina* plant cell, plant part, tissue culture or whole plant comprising transforming the plant cell, plant part, tissue culture or whole plant with a chimeric gene comprising one FAD2 and/or FAE1 gene encoding the polypeptide of the present invention, or functional variants thereof. In one embodiment, the chimeric gene is overexpressed. As used herein, a functional variant of a protein refers to a polypeptide comprising one or more amino acid modifications (e.g., substitution, deletion, modification, et al) compared to the original protein, but still maintains the activity of the original protein. In the present invention, "overexpression promoter" means a promoter capable of causing strong expression (large amount expression) of a gene that has been ligated thereto in host plant cells. The overexpression promoter of the present invention may be either an inducible promoter or a constitutive promoter. A promoter is a DNA comprising an expression control region generally located on the 5' upstream of a structural gene or a modified sequence thereof. In the present invention, any promoters appropriate for foreign gene expression in plant cells can be used as overexpression promoters. Non-limiting examples of such overexpression promoters to be used in the present invention include, but are not limited to, a cauliflower mosaic virus (CaMV) 35S promoter, a rice actin promoter, a modified 35S promoter, or an embryo-specific promoter. As used herein an "embryo-specific promoter" refers to a promoter of an embryo-specific gene. An embryo-specific gene is preferentially expressed during embryo development in a plant. For purposes of the present disclosure, embryo development begins with the first cell divisions in the zygote and continues through the late phase of embryo development (characterized by maturation, desiccation, dormancy), and ends with the production of a mature and desiccated seed. Embryo-specific genes can be further classified as "early phase-specific" and "late phase-specific". Early phase-specific genes are those expressed in embryos up to the end of embryo morphogenesis. Late phase-specific genes are those expressed from maturation through to production of a mature and desiccated seed. An early phase-specific promoter is a promoter that initiates expression of a protein prior to day 7 after pollination in *Arabidopsis* or an equivalent stage in another plant species. Non-limiting examples of promoter sequences that can be used in the present invention include a promoter for the amino acid permease gene (AAP1) (e.g., the AAP1 promoter from *Arabidopsis thaliana*, Hirner et al, Plant J. 14:535-544, 1998), a promoter for the oleate 12-hydroxylase:desaturase gene (e.g., the promoter designated LFAH 12 from *Lesquerella fendleri*, Broun et al, Plant J. 13:201-210, 1998), a promoter for the 2S2 albumin gene (e.g., the 2S2 promoter from *Arabidopsis thaliana*, Guerche et al, Plant cell 2:469-478, 1990), a fatty acid elongase gene promoter (FAE1) (e.g., the FAE1 promoter from *Arabidopsis thaliana*, Rossak et al, Plant Mol Biol. 46:717-715, 2001), and the leafy cotyledon gene promoter (LEC2) (e.g., the LEC2 promoter from *Arabidopsis thaliana*, Kroj et al Development 130:6065-6073, 2003). Other early embryo-specific promoters of interest include, but are not limited to, seedstick (Pinyopich et al, Nature 424:85-88, 2003), Fbp7 and Fbp11 (Petunia Seedstick) (Colombo et al, Plant Cell. 9:703-715, 1997), Banyuls (Devic et al, Plant J. 19:387-398, 1999), agl-15 and agl-18 (Lehti-Shiu et al, Plant Mol Biol. 58:89-107, 2005), Phel (Kohler et al, Genes Develop. 17:1540-1553, 2003), Perl (Haslekas et al, Plant Mol Biol. 36:833-845, 1998; Haslekas et al, Plant Mol Biol. 53:313-326, 2003), emb175 (Cushing et al, Planta 221:424-436, 2005), Lll (Kwong et al, Plant Cell 15:5-18, 2003), Lecl (Lotan et al, Cell 93:1195-1205, 1998), Fusca3 (Kroj et al, Development 130:6065-6073, 2003), tt12 (Debeaujon et al, Plant Cell 13:853-871, 2001), tt16 (Nesi et al, Plant Cell 14:2463-2479, 2002), A-RZf (Zou and Taylor, Gene 196:291-295, 1997), TtGl (Walker et al, Plant Cell 11:1337-1350, 1999; Tsuchiya et al, Plant J. 37:73-81, 2004), TtI (Sagasser et al, Genes Dev. 16:138-149, 2002), TT8 (Nesi et al, Plant Cell 12:1863-1878, 2000), Gea-8 (carrot) (Lin and Zimmerman, J. Exp. Botany 50:1139-1147, 1999), Knox (rice) (Postma-Haarsma et al, Plant Mol. Biol. 39:257-271, 1999), Oleosin (Plant et al, Plant Mol Biol. 25:193-205, 1994; Keddie et al, Plant Mol Biol. 24:121-14$, 1994), ABI3 (Ng et al, Plant Mol Biol. 54:25-38, 2004; Parcy et al, Plant Cell 6:1567-1582, 1994), and the like.

The present invention also provides methods of decreasing the activity of a FAD2 and/or FAE1 protein in a *Camelina* plant cell, plant part, tissue culture or whole plant comprising contacting the plant cell, plant part, tissue culture or whole plant with an inhibitory nucleic acid having complementarity to a gene encoding the FAD2 and/or FAE1 protein.

In one aspect, the present invention provides methods of breeding *Camelina* species producing altered levels of fatty acids in the seed oil and/or meal. In one embodiment, such methods comprise making a cross between a *Camelina* mutant with one or more mutations listed in Tables 7-12 with a second *Camelina* cultivar to produce an F1 plant; backcrossing the F1 plant to the second *Camelina* cultivar; and repeating the backcrossing step to generate an near isogenic line, wherein the one or more mutations are integrated into the genome of the second *Camelina* cultivar; wherein the near isogenic line derived from the second *Camelina* cultivar with the integrated mutations has altered seed oil composition. Optionally, such methods can be facilitated by molecular markers.

In another aspect, the present invention provides methods of breeding species close to *Camelina sativa*, wherein said species produces altered levels of fatty acids in the seed oil and/or meal. For example, intertribal somatic hybridizations are possible between *C. sativa* and *B. oleracea* (see, e.g., Lise N. Hansen, 1998, Euphytica, Volume 104, No. 3, pages 173-179). In one embodiment, such methods comprise making a cross between the *Camelina* mutants with one or more mutations listed in Tables 7-12 with a species that is closely related to the *Camelina* species containing the mutations to make an F1 plant; backcrossing the F1 plants to the species that is closely related to the *Camelina* species containing the mutations; and, repeating backcrossing step to generate an near isogenic line, wherein the one or more mutations are integrated into the genome of the species that is closely related to the *Camelina* species containing the mutations; wherein the near isogenic line derived from the species that is closely related to the *Camelina* species containing the mutations has integrated these mutations and has altered seed oil composition. Optionally, such method can be facilitated by molecular markers.

BRIEF DESCRIPTION OF THE DRAWINGS

FIG. 2 depicts FAD2 and FAE1 protein alignment. FIG. 2A shows amino acid sequence comparison of the three *Camelina sativa* FAD2 sequences, *Arabidopsis thaliana* FAD2 sequence [Genbank: NM_112047], *Brassica rapa* FAD2 sequence [Genbank: AJ459107], *Glycine max* FAD2-3 sequence [Genbank: DQ532371], *Zea mays* FAD2 sequence [Genbank: AB257309]. Blue underlines below the sequences indicate amino acids conserved in all 50 FAD2 sequences (Belo, Zheng et al. 2008) while the green underline indicates the ER localization signal (McCartney, Dyer et al. 2004). The three His boxes described by Tocher D R (1998) are indicated with red boxes. FIG. 2B shows amino acid sequence comparison of the three *Camelina sativa* FAE1 sequences, *Arabidopsis thaliana* FAE1 [Genbank: NM_119617], *Crambe abyssinica* [Genbank: AAX22298], *Brassica rapa* HEAC FAE1 [Genbank:Y14975], *Brassica rapa* LEAC FAE1 [Genbank: Y14974], *Limnanthes alba* (meadow foam) [Genbank: AF247134], *Tropaeolum majus* (nasturtium) [Genbank: ABD77097]. Blue underlines below the sequence indicate the asparagine at position 424 and the highly conserved histidine and cysteine residues described by Ghanevati and Jaworski (Ghanevati and Jaworski 2001; Ghanevati and Jaworski 2002). The red box indicates the region highly conserved among condensing enzymes in very long chain fatty acid biosynthesis (Moon, Smith et al. 2001) Abbreviations: Heac=High erucic acid, Leac=Low erucic acid.

DETAILED DESCRIPTION

Definition

Figure 1:
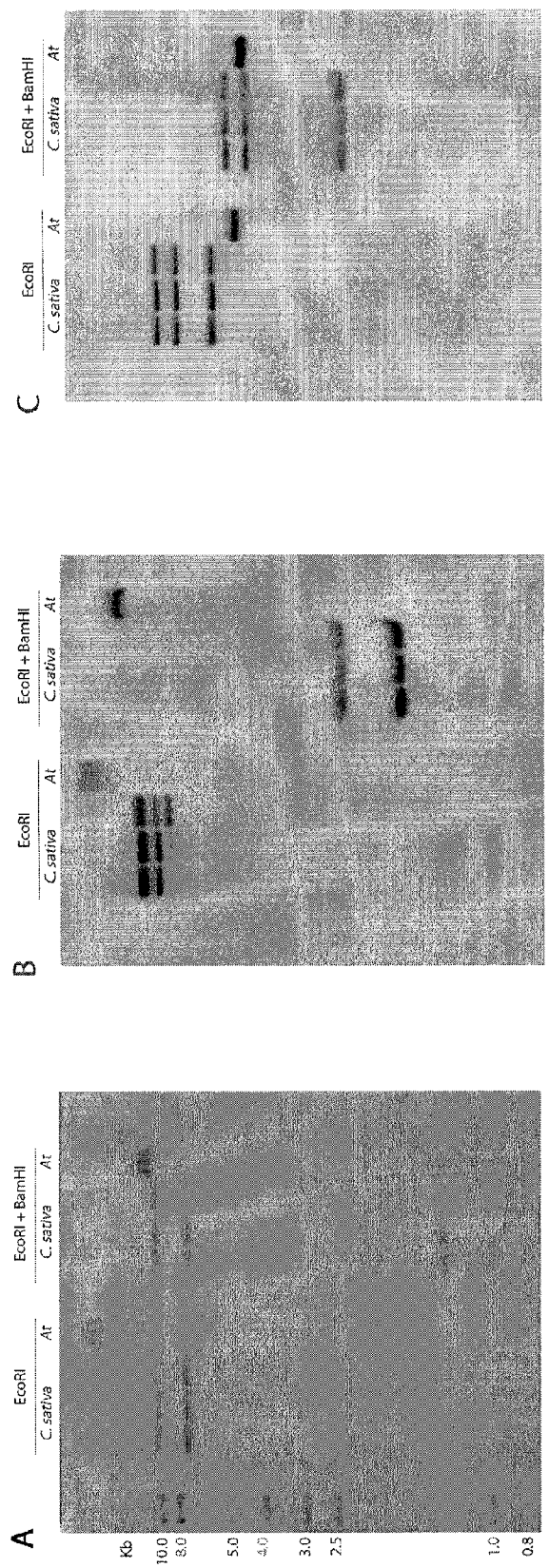
FIG. 1 depicts Southern blot analysis of *Camelina sativa* and *Arabidopsis thaliana*. A blot containing genomic DNA from *C. sativa* and *A. thaliana* digested with EcoRI or a combination of EcoRI and BamHI was hybridized with an α-32P dCTP-labeled (A) FAD2 probe, (B) FAE1 probe or (C) LFY probe obtained from PCR amplification of *C. sativa* DNA.

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom). This includes familiar organisms such as but not limited to trees, herbs, bushes, grasses, vines, ferns, mosses and green algae. The term refers to both monocotyledonous plants, also called monocots, and dicotyledonous plants, also called dicots. Examples of particular plants include but are not limited to corn, potatoes, roses, apple trees, sunflowers, wheat, rice, bananas, tomatoes, opo, pumpkins, squash, lettuce, cabbage, oak trees, guzmania, geraniums, hibiscus, clematis, poinsettias, sugarcane, taro, duck weed, pine trees, Kentucky blue grass, zoysia, coconut trees, brassica leafy vegetables (e.g. broccoli, broccoli raab, Brussels sprouts, cabbage, Chinese cabbage (Bok Choy and Napa), cauliflower, cavalo, collards, kale, kohlrabi, mustard greens, rape greens, and other brassica leafy vegetable crops), bulb vegetables (e.g. garlic, leek, onion (dry bulb, green, and Welch), shallot, and other bulb vegetable crops), citrus fruits (e.g. grapefruit, lemon, lime, orange, tangerine, citrus hybrids, pummelo, and other citrus fruit crops), cucurbit vegetables (e.g. cucumber, citron melon, edible gourds, gherkin, muskmelons (including hybrids and/or cultivars of cucumis melons), water-melon, cantaloupe, and other cucurbit vegetable crops), fruiting vegetables (including eggplant, ground cherry, pepino, pepper, tomato, tomatillo, and other fruiting vegetable crops), grape, leafy vegetables (e.g. romaine), root/tuber and corm vegetables (e.g. potato), and tree nuts (almond, pecan, pistachio, and walnut), berries (e.g., tomatoes, barberries, currants, elderberries, gooseberries, honeysuckles, mayapples, nannyberries, Oregon-grapes, see-buckthorns, hackberries, bearberries, lingonberries, strawberries, sea grapes, lackberries, cloudberries, loganberries, raspberries, salmonberries, thimbleberries, and wineberries), cereal crops (e.g., corn, rice, wheat, barley, sorghum, millets, oats, ryes, triticales, buckwheats, fonio, and quinoa), pome fruit (e.g., apples, pears), stone fruits (e.g., coffees, jujubes, mangos, olives, coconuts, oil palms, pistachios, almonds, apricots, cherries, damsons, nectarines, peaches and plums), vine (e.g., table grapes, wine grapes), fibber crops (e.g. hemp, cotton), ornamentals, and the like. For example, the plant is a species in the tribe of Camelineae, such as *C. alyssum, C. anomala, C. grandiflora, C. hispida, C. laxa, C. microcarpa, C. microphylla, C. persistens, C. rumelica, C. sativa, C. Stiefelhagenii*, or any hybrid thereof.

As used herein, the term "plant part" refers to any part of a plant including but not limited to the shoot, root, stem, seeds, stipules, leaves, petals, flowers, ovules, bracts, branches, petioles, internodes, bark, pubescence, tillers, rhizomes, fronds, blades, pollen, stamen, and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "chimeric protein" refers to a construct that links at least two heterologous proteins into a single macromolecule (fusion protein).

As used herein, the term "nucleic acid" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably.

As used herein, the terms "polypeptide," "peptide," and "protein" are used interchangeably herein to refer to polymers of amino acids of any length. These terms also include proteins that are post-translationally modified through reactions that include glycosylation, acetylation and phosphorylation.

As used herein, the term "homologous" or "homolog" or "ortholog" is known in the art and refers to related sequences that share a common ancestor or family member and are determined based on the degree of sequence identity. The terms "homology", "homologous", "substantially similar" and "corresponding substantially" are used interchangeably herein. They refer to nucleic acid fragments wherein changes in one or more nucleotide bases do not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologs" or "orthologs" are thought, believed, or known to be functionally related. A functional relationship may be indicated in any one of a number of ways, including, but not limited to: (a) degree of sequence identity and/or (b) the same or similar biological function. Preferably, both (a) and (b) are indicated. The degree of sequence identity may vary, but in one embodiment, is at least 50% (when using standard sequence alignment programs known in the art), at least 60%, at least 65%, at least 70%, at least 75%, at least 80%, at least 85%, at least 90%, at least about 91%, at least about 92%, at least about 93%, at least about 94%, at least about 95%, at least about 96%, at least about 97%, at least about 98%, or at least 98.5%, or at least about 99%, or at least 99.5%, or at least 99.8%, or at least 99.9%. Homology can be determined using software programs readily available in the art, such as those discussed in *Current Protocols in Molecular Biology* (F. M. Ausubel et al., eds., 1987) Supplement 30, section 7.718, Table 7.71. Some alignment programs are MacVector (Oxford Molecular Ltd, Oxford, U.K.) and ALIGN Plus (Scientific and Educational Software, Pennsylvania). Other non-limiting alignment programs include Sequencher (Gene Codes, Ann Arbor, Mich.), AlignX, and Vector NTI (Invitrogen, Carlsbad, Calif.).

As used herein, the term "nucleotide change" or "nucleotide modification" refers to, e.g., nucleotide substitution, deletion, and/or insertion, as is well understood in the art. For example, mutations containing alterations that produce silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "derived from" refers to the origin or source, and may include naturally occurring, recombinant, unpurified, or purified molecules. A nucleic acid or an amino acid derived from an origin or source may have all kinds of nucleotide changes or protein modification as defined elsewhere herein.

As used herein, the term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988).

As used herein, the term "suppression" or "disruption" of regulation refers to reduced activity of regulatory proteins, and such reduced activity can be achieved by a variety of mechanisms including antisense, mutation knockout or RNAi. Antisense RNA will reduce the level of expressed protein resulting in reduced protein activity as compared to wild type activity levels. A mutation in the gene encoding a protein may reduce the level of expressed protein and/or interfere with the function of expressed protein to cause reduced protein activity.

As used herein, the terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The term "primer" as used herein refers to an oligonucleotide which is capable of annealing to the amplification target allowing a DNA polymerase to attach, thereby serving as a point of initiation of DNA synthesis when placed under conditions in which synthesis of primer extension product is induced, i.e., in the presence of nucleotides and an agent for polymerization such as DNA polymerase and at a suitable temperature and pH. The (amplification) primer is preferably single stranded for maximum efficiency in amplification. Preferably, the primer is an oligodeoxyribonucleotide. The primer must be sufficiently long to prime the synthesis of extension products in the presence of the agent for polymerization. The exact lengths of the primers will depend on many factors, including temperature and composition (A/T and G/C content) of primer. A pair of bi-directional primers consists of one forward and one reverse primer as commonly used in the art of DNA amplification such as in PCR amplification.

As used herein, "coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence.

As used herein, "regulatory sequences" may include, but are not limited to, promoters, translation leader sequences, introns, and polyadenylation recognition sequences.

As used herein, "promoter" refers to a DNA sequence capable of controlling the expression of a coding sequence or functional RNA. The promoter sequence consists of proximal and more distal upstream elements, the latter elements often referred to as enhancers. Accordingly, an "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

As used herein, the "3' non-coding sequences" or "3' UTR (untranslated region) sequence" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht, I. L., et al. (1989) Plant Cell 1:671-680.

As used herein, the term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

As used herein, the term "vector", "plasmid", or "construct" refers broadly to any plasmid or virus encoding an exogenous nucleic acid. The term should also be construed to include non-plasmid and non-viral compounds which facilitate transfer of nucleic acid into virions or cells, such as, for example, polylysine compounds and the like. The vector may be a viral vector that is suitable as a delivery vehicle for delivery of the nucleic acid, or mutant thereof, to a cell, or the vector may be a non-viral vector which is suitable for the same purpose. Examples of viral and non-viral vectors for delivery of DNA to cells and tissues are well known in the art and are described, for example, in Ma et al. (1997, Proc. Natl. Acad. Sci. U.S.A. 94:12744-12746). Examples of viral vectors include, but are not limited to, recombinant plant viruses. Non-limiting examples of plant viruses include, TMV-mediated (transient) transfection into tobacco (Tuipe, T-H et al (1993), J. Virology Meth, 42: 227-239), ssDNA genomes viruses (e.g., family Geminiviridae), reverse transcribing viruses (e.g., families Caulimoviridae, Pseudoviridae, and Metaviridae), dsNRA viruses (e.g., families Reoviridae and Partitiviridae), (−) ssRNA viruses (e.g., families Rhabdoviridae and Bunyaviridae), (+) ssRNA viruses (e.g., families Bromoviridae, Closteroviridae, Comoviridae, Luteoviridae, Potyviridae, Sequiviridae and Tombusviridae) and viroids (e.g., families Pospiviroldae and Avsunviroidae). Detailed classification information of plant viruses can be found in Fauquet et al (2008, "Geminivirus strain demarcation and nomenclature". *Archives of Virology* 153:783-821, incorporated herein by reference in its entirety), and Khan et al. (Plant viruses as molecular pathogens; Publisher Routledge, 2002, ISBN 1560228954, 9781560228950). Examples of non-viral vectors include, but are not limited to, liposomes, polyamine derivatives of DNA, and the like.

Camelina Sativa

*Camelina* is a genus of flowering plants belonging to the Brassicaceae family. *Camelina sativa* is a particular species of the genus *Camelina* that is important historically and is a source of oil that can be used in, for example, biofuels and lubricants. *C. sativa* is being investigated for both biofuel and human utility. It is a crop that has not benefited much from molecular investigation in the past and as such, there is relatively little sequence information available. The utility of a plant oil either for biodiesel or food depends on its fatty acid composition. *Camelina* has a fatty acid composition with high levels of both polyunsaturated fatty acids such as 18:2 and 18:3 (52-54%) as well as long chain fatty acids such as 20:1 (11-15%) and 22:1 (2-5%). For biodiesel, the optimum fatty acid is 18:1 (oleic). Oleic has the best balance of characteristics for cloud point vs. oxidative stability. Polyunsaturated fatty acids such as 18:2 and 18:3 have poor oxidative stability. The long chain fatty acids such as 20:1 and 22:1 contribute to out of range distillation temperatures in biodiesel. For biodiesel utility it is therefore desirable to lower the level of polyunsaturated fatty acids and to lower the level of long chain fatty acids. The ultimate goal is to increase the percentage of 18:1 fatty acid. 18:1 is also considered a good fatty acid for food utility.

*Camelina* has not been intensively bred and the germplasm is somewhat limited genetically. An in-house field study of a significant number of cultivars showed little variation in the fatty acid composition. This agrees with published literature (e.g., Putnam et al., 1993. *Camelina*: A promising low-input oilseed. p. 314-322. In: J. Janick and J. E. Simon (eds.), New crops. Wiley, New York).

Fatty Acids Synthesis in Plants

Fatty acid biosynthesis in plants takes place within the endoplasmic reticulum and plastids, the latter of which is an organelle widely thought to have originated from a photosynthetic bacterial symbiont. Fatty acid metabolism in plants closely resembles that of bacteria.

During fatty acid biosynthesis, a repeated series of reactions incorporates acetyl moieties of acetyl-CoA into an acyl group 16 or 18 carbons long. The enzymes involved in this synthesis are acetyl-CoA carboxylase (ACCase), malonyl-CoA:ACP transacylase, 3-ketoacyl-ACP synthase I and III (KAS I and KAS III), 3-ketoacyl-ACP reductase, 2,3-trans-Enoyl-ACP reductase, 3-hydroxyacyl-ACP dehydratase (all referred as fatty acid synthase (FAS), except for ACCase). The name fatty acid synthase refers to a complex of several individual enzymes that catalyze the conversion of acetyl-CoA and malonyl-CoA to 16:0 and 18:0 fatty acids. Acyl-carrier protein (ACP), an essential protein cofactor, is generally considered a component of FAS.

The last three steps of the fatty acids synthesis cycle reduce a 3-ketoacyl substrate to form a fully saturated acyl chain. Each cycle of fatty acid synthesis adds two carbons to the acyl chain. Typically, fatty acid synthesis ends at 16:0 or 18:0, when one of several reactions stops the process. The most common reactions are hydrolysis of acyl moiety from ACP by a thioesterase, transfer of the acyl moiety from ACP directly onto a glycerolipid by an acyl transferase, or double-bond formation on the acyl moiety by an acyl-ACP desaturase. The thioesterase reaction yields a sulfhydryl ACP.

Figure 7:
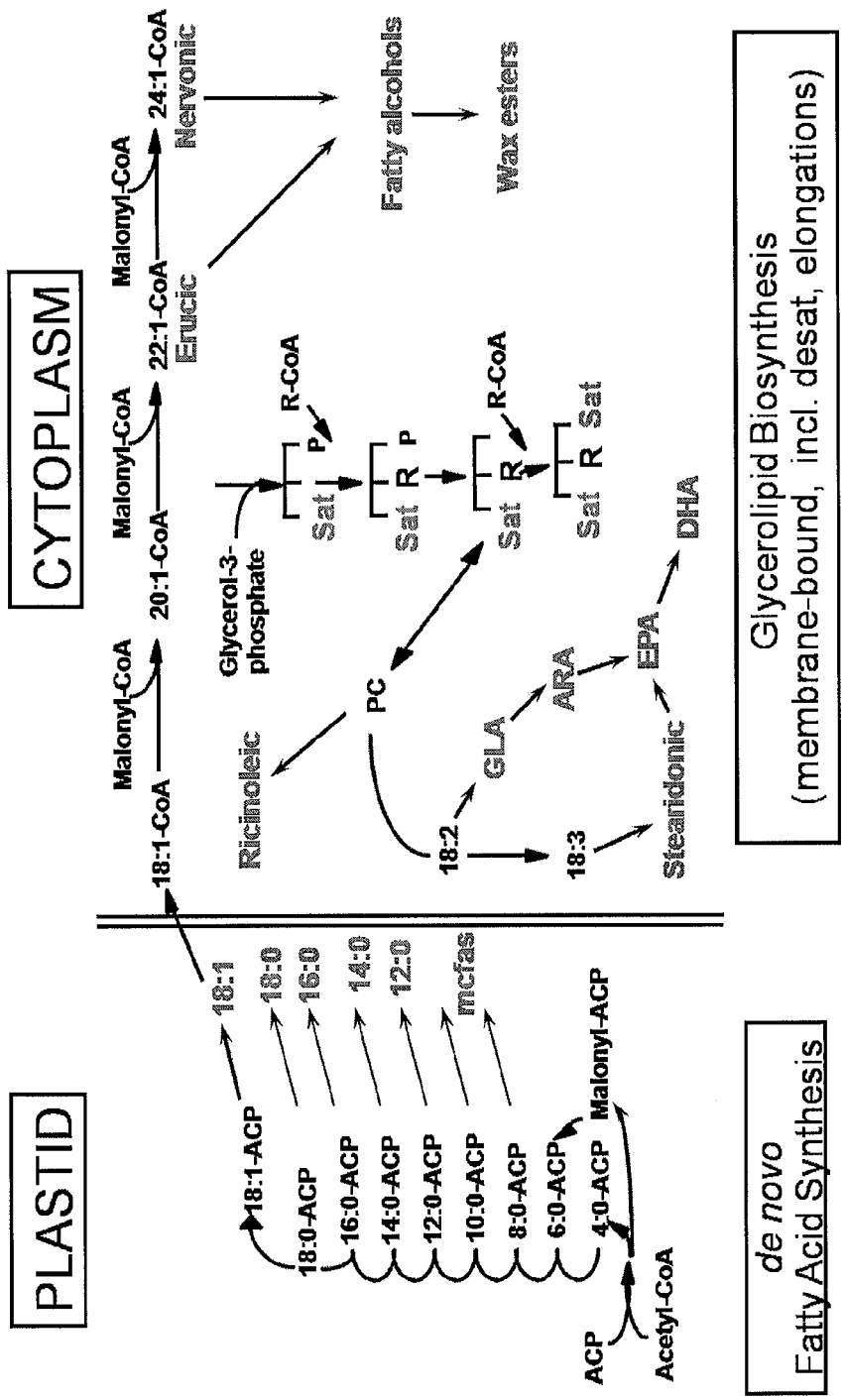
FIG. 7 depicts a simplified version of fatty acid synthesis pathways in plant.

Two principal types of acyl-ACP thioesterases occur in plants. For making storage lipids (triglycerides) in the ER, the FAT enzymes convert the fatty acid-ACP to a fatty acid-Co-A. The substrate for FAE1 is an R-CoA and it is an R-CoA that is added to various positions in the glycerol backbone during the Kennedy pathway portion of the synthesis of Triglycerides in the ER (FIG. 7). The major class, designated FatA, is most active with 18:1 delta9-ACP. A second class designated FatB, typified by 16:0-ACP thioesterase, is most active with shorter-chain, saturated acyl-ACPs. Thioesterases play important role in plants that have unusually short fatty acids, such as coconut, many species of *Cuphea*, and California bay. These plants have thioesterases that are especially active with C10 to C12 acyl-ACPs, by prematurely terminating fatty acid biosynthesis.

Unsaturated fatty acids are produced by desaturation of saturated lipids with the help of desaturases (FAD enzymes). Most fatty acid desaturases (FADs) in plants are integral membrane proteins, with the exception that plant contains a soluble, plastid-localized stearoyl-ACP desaturase. The number and properties of different FADs in plants are known from the isolation of a comprehensive collection of *Arabidopsis* mutants with defects in each of eight desaturase genes. The enzymes encoded by these genes differ in substrate specificity, subcellular location, mode of regulation, or some combination of these. A summary of the *Arabidopsis* FADs is shown below:

The biochemical defect of each class of mutants is shown by breaks in the pathway on page 480 of Buchanan et al., Biochemistry and Molecular Biology of Plants, American Society of Plant Physiologists, 2000, ISBN 0943088372, 9780943088372, which is incorporated by reference in its entirety.

Extensive surveys of the fatty acid composition of seed oils from different plant species have resulted in the identification of more than 200 naturally occurring fatty acids, which can broadly be classified into 18 structural classes, such as laballenic acid, stearolic acid, sterculynic acid, chaulmoogric acid, ricinoleic acid, vernolic acid, furan-containing fatty acid, et al. Less is known about the mechanisms responsible for the synthesis and accumulation of unusual fatty acids, or of their significance to the fitness of the plants that accumulate them. However, recent studies indicate that enzymes involved in the synthesis of unusual fatty acids are structurally similar to the desaturases and hydroxylases. Unusual fatty acids occur almost exclusively in seed oils and may serve a defense function.

Synthesis of structural lipids (e.g. cutin, suberin, epicuticular wax) has also been studied in *Arabidopsis*. Proposed pathways related to this is shown on page 512 of Buchanan et al., Biochemistry and Molecular Biology of Plants, American Society of Plant Physiologists, 2000, ISBN 0943088372, 9780943088372, which is incorporated by reference in its entirety.

Figure 13:
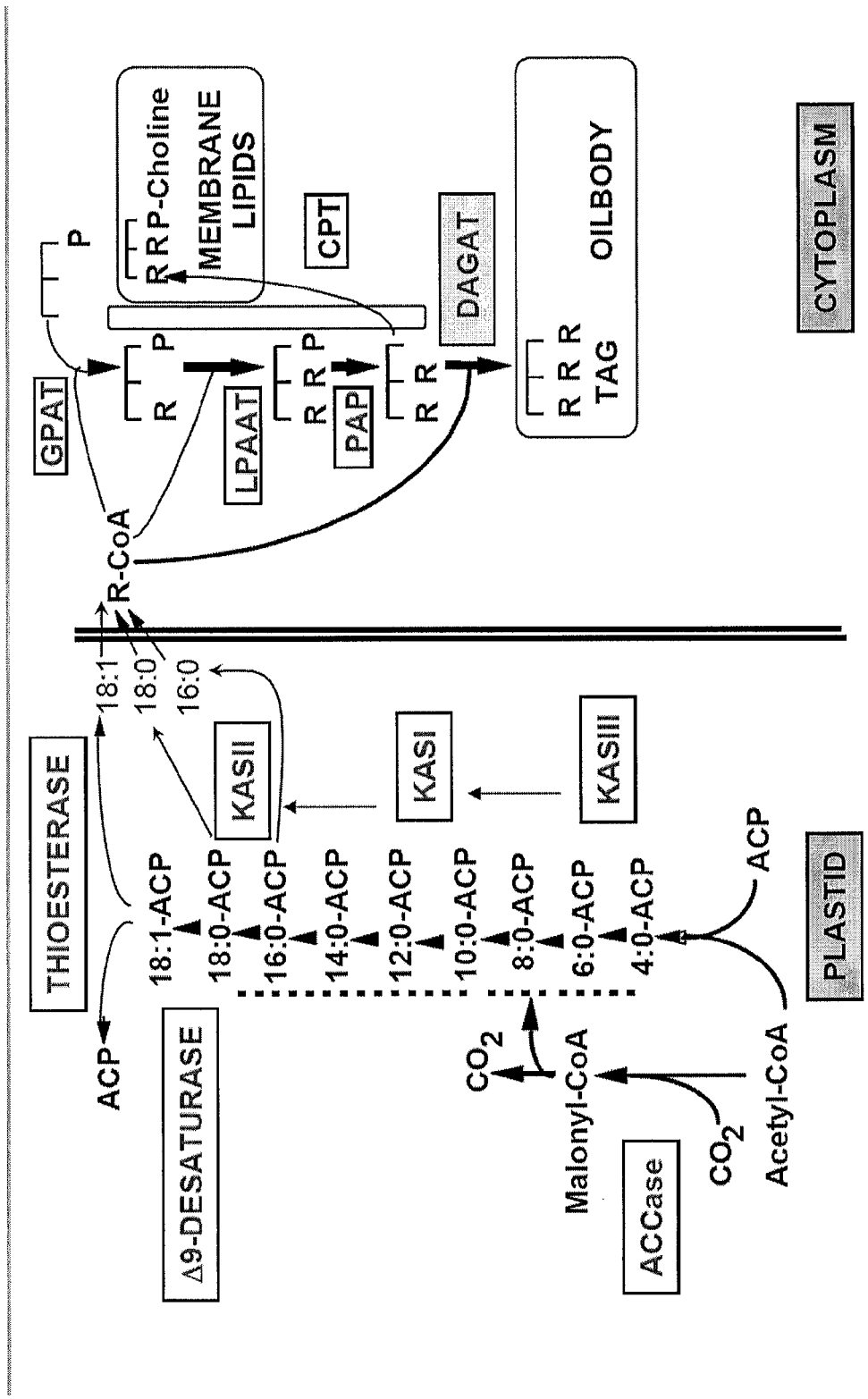
FIG. 13 depicts lipid synthesis in the plastid and cytoplasm of oilseeds. Key enzymes are in red text and boxed. ACCase=acetyl co-A carboxylase, KAS=β-ketoacyl-acyl carrier protein (ACP) synthase, GPAT=glycerol phosphate acyltransferase, LPAAT=lysophosphatidic acid acyltransferase, PAP=phosphatidate phosphatase, DAGAT=diacylglycerol acyltransferase, R=fatty acyl group, P=phosphate group, CPT=chloroplast

Thus, as used herein, the phrase "fatty acid synthesis genes" or "FAS gene" refers to any genes that are involved in synthesis of fatty acids, cuticle, and wax as described above. For example, such genes include, but are not limited to, malonyl-CoA:ACP transacylase, 3-ketoacyl-ACP synthase I and III (KAS I and KAS III), 3-ketoacyl-ACP reductase, 2,3-trans-Enoyl-ACP reductase, 3-hydroxyacyl-ACP dehydratase, acyl-ACP thioesterases, fatty acid desaturases (e.g., FAD2, FAD3), fatty acid elongases (e.g., FAE1), hydroxylases, and enzymes displayed in FIGS. 7 and 13.

Figure 11:
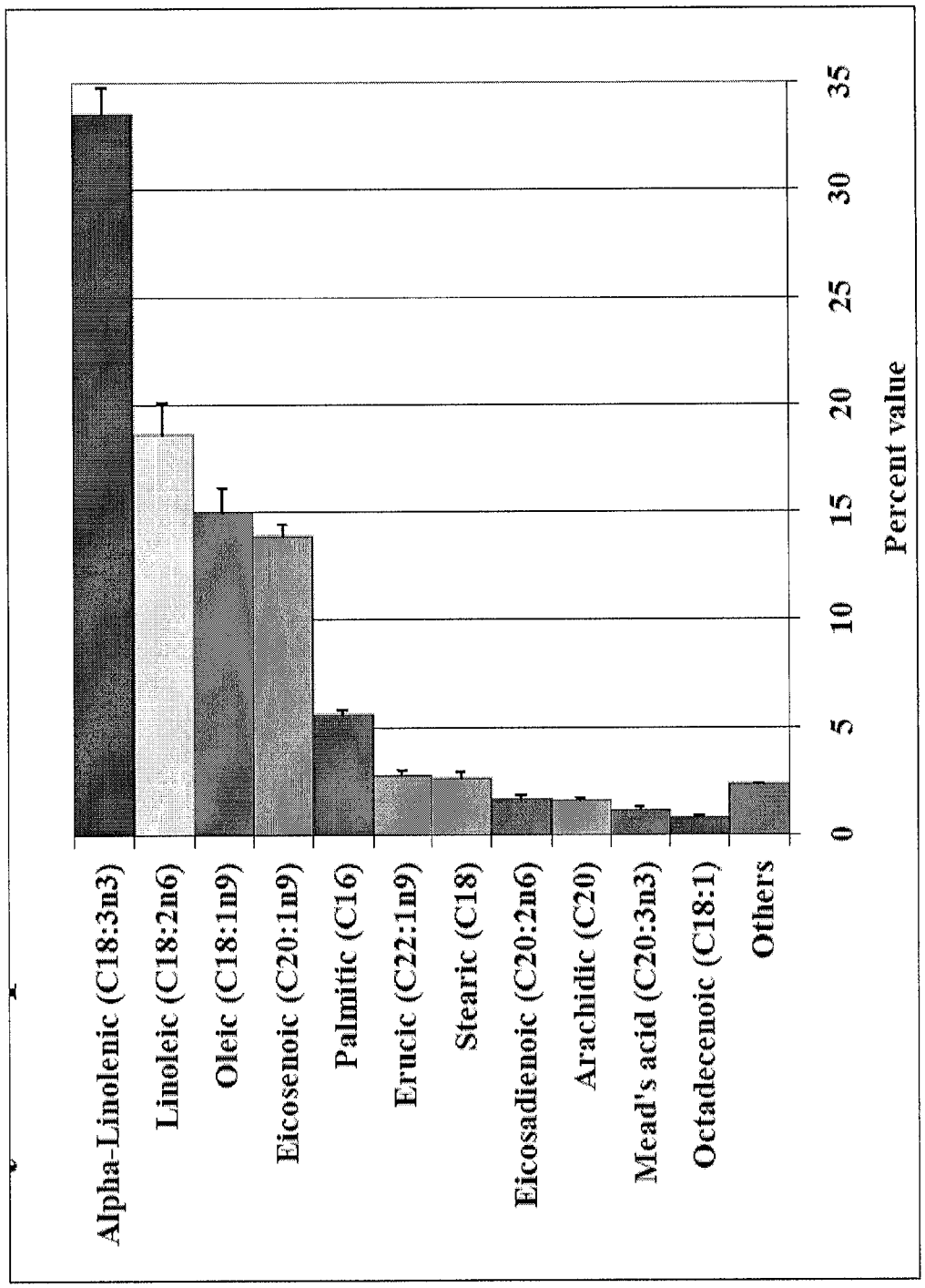
FIG. 11 depicts a representative composition of *Camelina sativa* seed oil.

Seed oil of *Camelina sativa* contains high levels (up to 45%) of omega-3 fatty acids, which is uncommon in vegetable sources. Over 50% of the fatty acids in cold pressed *Camelina* oil are polyunsaturated. The major components are alpha-linolenic acid—C18:3 (omega-3-fatty acid, approx 35-45%) and linoleic acid—C18:2 (omega-6 fatty acid, approx 15-20%). FIG. 11 shows a representative composition of *Camelina* seed oil. The oil is also very rich in natural antioxidants, such as tocopherols, making this highly stable oil very resistant to oxidation and rancidity. It has 1-3% erucic

| Name | subcellular location | Fatty acid substrates | Site of double-bond insertion | Notes |
|---|---|---|---|---|
| FAD2 | ER | 18:1Δ9 | Δ12 | preferred substrate is phosphatidylcholine, oleate desaturase |
| FAD3 | ER | 18:2Δ9, 12 | ω3 | preferred substrate is phosphatidylcholine, linoleate desaturase |
| FAD4 | Chloroplast | 16:0 | Δ3 | produces 16:1-trans at sn-2 of phosphatidylglycerol |
| FAD5 | Chloroplast | 16:0 | Δ7 | desaturates 16:0 at sn-2 of monogalactosyldiacylglycerol |
| FAD6 | Chloroplast | 16:1Δ7 and 18:1Δ9 | ω6 | acts on all chloroplast glycerolipids, oleate desaturase |
| FAD7 | Chloroplast | 16:2Δ7, 11 and 18:2Δ9, 12 | ω3 | acts on all chloroplast glycerolipids, linoleate desaturase |
| FAD8 | Chloroplast | 16:2Δ7, 11 and 18:2Δ9, 12 | ω3 | isoenzyme of FAD7 induced by low temperature, linoleate desaturase |
| FAB2 | Chloroplast | 18:0 | Δ9 | stromal stearoyl-ACP desaturase | acid. The vitamin E content of *Camelina* oil is approximately 110 mg/100 g. The present invention relates to increasing oleic acid (18:1) level, decreasing the level of long chain fatty acids, and/or improving the seed oil quality of *Camelina*. As used herein, the term "level" refers to the relative percentage of a component in a mixture.

In the endoplasmic reticulum, oleic acid (18:1) is converted to linoleic acid (18:2) by a delta-12-desaturase, fatty acid desaturase 2 (FAD2). Mutations in *Arabidopsis thaliana* FAD2 have been shown to increase the levels of 18:1 in the seeds 2-3.4 fold while decreasing the levels of 18:2 fatty acids 4-10 fold. (Levels of 20:1 also increased approximately 1.5 fold—Okuley 1994.)

Very long chain fatty acids are synthesized in the cytosol by extension of an 18 carbon fatty acid. The rate limiting step is thought to be the initial condensation step, catalyzed in the seed by fatty acid elongase 1 (FAE1, Kunst 1992). In *Arabidopsis*, where approximately 25% of seed fatty acids can be long chain fatty acids, mutants in FAE1 have less than 1%. Interestingly, *Arabidopsis* fae1 mutants show a greater than 2-fold increase in 18:1 content in the seeds. (Katavic et al. (2002). "Restoring enzyme activity in nonfunctional low erucic acid *Brassica napus* fatty acid elongase 1 by a single amino acid substitution." Eur J Biochem 269(22): 5625-31.)

FAD2 and FAE1 Genes of *Camelina sativa*

The invention discloses the full genomic sequence of three FAD2 genes and three FAE1 genes from *Camelina sativa* with both upstream and downstream regions for FAD2 and upstream regions for FAE1 (deposited in Genbank at the NCBI, Genbank IDs: GU929417-GU929422, SEQ ID NOs. 1-6). These sequences include both the coding region as well as several hundred base pairs upstream and downstream of the genes. The coding sequences for the *Camelina sativa* FAD2 were obtained using primers from *Arabidopsis thaliana* FAD2 while the coding regions for the *Camelina sativa* FAE1 were obtained using primers from *Crambe abyssinica* FAE1. Also obtained are coding sequences for FAD2 and FAE1 genes from *Capsell rubella*, *A. Lyrata*, *Camelina hispida*, *Camelina laxa*, *Camelina microcarpa*, and *Camelina rumelica* (GU929423-GU929441, SEQ ID NOs 45-63), which were amplified using *C. Sativa* primers. The upstream regions for all the genes were obtained using a combination of RACE PCR and PCR with primers from upstream *Arabidopsis* sequences in conjunction with primers to *Camelina* sequences. The downstream regions of FAD2 were obtained using PCR with primers designed from a combination of downstream *Arabidopsis* sequence in conjunction with primers to *Camelina* sequences. The *Camelina sativa* FAD2 and FAE1 genes are highly homologous to both *Arabidopsis* and *Brassica napus* (e.g., canola, oilseed rape) FAD2 and FAE1. However, the disclosed sequences are specific to *Camelina sativa*.

The present invention provides an isolated nucleic acid sequence comprising a sequence selected from the group consisting of SEQ ID NOs: 1 to 6 and SEQ ID NOs: 45-63, and fragments and variations derived from thereof. In one embodiment, the present invention provides an isolated polynucleotide encoding plant fatty acid desaturase, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 1, 2, 3, 45, 46, 48, 51, 54, 55, 56, 60, and/or 61. In another embodiment, the present invention provides an isolated polynucleotide encoding fatty acid elongase, comprising a nucleic acid sequence that shares at least 90%, at least 91%, at least 92%, at least 93%, at least 94%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% identity to SEQ ID NO: 4, 5, 6, 47, 49, 50, 52, 53, 57, 58, 59, 62, and/or 63.

Methods of alignment of sequences for comparison are well known in the art. Various programs and alignment algorithms are described in: Smith and Waterman (*Adv. Appl. Math.*, 2:482, 1981); Needleman and Wunsch (*J. Mol. Biol.*, 48:443, 1970); Pearson and Lipman (*Proc. Natl. Acad. Sci.*, 85:2444, 1988); Higgins and Sharp (*Gene*, 73:237-44, 1988); Higgins and Sharp (*CABIOS*, 5:151-53, 1989); Corpet et al. (*Nuc. Acids Res.*, 16:10881-90, 1988); Huang et al. (*Comp. Appls Biosci.*, 8:155-65, 1992); and Pearson et al. (*Meth. Mol. Biol.*, 24:307-31, 1994). Altschul et al. (*Nature Genet.*, 6:119-29, 1994) presents a detailed consideration of sequence alignment methods and homology calculations.

The present invention also provides a chimeric gene comprising the isolated nucleic acid sequence of any one of the polynucleotides described above operably linked to suitable regulatory sequences.

The present invention also provides a recombinant construct comprising the chimeric gene as described above. In one embodiment, said recombinant construct is a gene silencing construct, such as used in RNAi gene silencing.

The expression vectors of the present invention will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Vectors that can be used with the invention comprise vectors for use in bacteria, which comprise pQE70, pQE60 and pQE-9, pBluescript vectors, Phagescript vectors, pNH8A, pNH16a, pNH18A, pNH46A, ptrc99a, pKK223-3, pKK233-3, pDR540, pRIT5. Among preferred eukaryotic vectors are pFastBac1 pWINEO, pSV2CAT, pOG44, pXT1 and pSG, pSVK3, pBPV, pMSG, and pSVL. Other suitable vectors will be readily apparent to the skilled artisan.

The present invention also provides a transformed host cell comprising the chimeric gene as described above. In one embodiment, said host cell is selected from the group consisting of bacteria, yeasts, filamentous fungi, algae, animals, and plants.

These sequences allow the design of gene-specific primers and probes for both FAD2 and FAE1. Additional data demonstrates that all three copies of each gene are expressed in the seed, i.e. no one copy is silent in the seed.

Primers are short nucleic acid molecules, for instance DNA oligonucleotides, usually 7 nucleotides or more in length, for example that hybridize to contiguous complementary nucleotides or a sequence to be amplified. Longer DNA oligonucleotides may be about 15, 20, 25, 30 or 50 nucleotides or more in length. Primers can be annealed to a complementary target DNA strand by nucleic acid hybridization to form a hybrid between the primer and the target DNA strand, and then the primer extended along the target DNA strand by a DNA polymerase enzyme. Primer pairs can be used for amplification of a nucleic acid sequence, for example, by the PCR or other nucleic-acid amplification methods known in the art, as described above.

A probe comprises an identifiable, isolated nucleic acid that recognizes a target nucleic acid sequence. A probe includes a nucleic acid that is attached to an addressable location, a detectable label or other reporter molecule and that hybridizes to a target sequence. Typical labels include radioactive isotopes, enzyme substrates, co-factors, ligands, chemiluminescent or fluorescent agents, haptens, and enzymes. Methods for labelling and guidance in the choice of labels appropriate for various purposes are discussed, for example, in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989 and Ausubel et al. *Short Protocols in Molecular Biology*, 4$^{th}$ ed., John Wiley & Sons, Inc., 1999.

Methods for preparing and using nucleic acid probes and primers are described, for example, in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989; Ausubel et al. *Short Protocols in Molecular Biology*, 4$^{th}$ ed., John Wiley & Sons, Inc., 1999; and Innis et al. *PCR Protocols, A Guide to Methods and Applications*, Academic Press, Inc., San Diego, Calif., 1990. Amplification primer pairs can be derived from a known sequence, for example, by using computer programs intended for that purpose such as PRIMER (Version 0.5, 1991, Whitehead Institute for Biomedical Research, Cambridge, Mass.). One of ordinary skill in the art will appreciate that the specificity of a particular probe or primer increases with its length. Thus, in order to obtain greater specificity, probes and primers can be selected that comprise at least 20, 25, 30, 35, 40, 45, 50 or more consecutive nucleotides of a target nucleotide sequences.

The inventor also obtained Real Time qPCR expression data that shows that FAD2 and FAE1 genes are expressed in the seed. In addition, SNP expression data demonstrated that all three copies of FAD2 and of FAE1 are expressed. Data that supports these SNP results was also obtained from sequencing a cDNA library from developing *Camelina* seed.

The invention also provides an EMS mutant library that has been created in *Camelina sativa* variety CS32 (commercial name as SO30). Initial TILLING® using primers designed to the three FAD2 genes yielded mutants in all three FAD2 genes (Hutcheon et al., TILLING® for Altered Fatty Acid Profiles in *Camelina sativa*, July 2009, American Society of Plant Biologists Annual Meeting, which is herein incorporated by reference in its entirety for all purposes). Preliminary analysis on lipid composition of these mutants using Gas Chromatography-Flame Ionization Detector (GC-FID) has also been conducted. In addition, Tilling mutants have been identified in FAE1 and preliminary analysis of lipid composition using GC-FID has been conducted on these mutants (Tables 19-20).

The close relationship between C. species and the model plant *Arabidopsis thaliana* (Al-Shehbaz, Beilstein et al. 2006; Beilstein, Al-Shehbaz et al. 2006; Beilstein, Al-Shehbaz et al. 2008) facilitates the manipulation of known pathways, such as the one regulating fatty acid biosynthesis. *C. sativa* seed oil is high in both polyunsaturated and long chain fatty acids (Budin, Breene et al. 1995; Zubr 1997; Gugel and Falk 2006), suggesting that both FAD2 and FAE1 are present and active. Three copies each of the FAD2 and FAE1 genes were isolated from an agronomic accession of *Camelina sativa* using primers designed from *Arabidopsis thaliana* or *Crambe abyssinica* sequence. Previously identified conserved sites in FAD2 (Tocher D R 1998; McCartney, Dyer et al. 2004; Belo, Zheng et al. 2008) and FAE1 (Ghanevati and Jaworski 2001; Moon, Smith et al. 2001; Ghanevati and Jaworski 2002) are present in all three copies of each gene and a 5' intron shown to be important in regulating FAD2 expression in sesame (Kim, Kim et al. 2006) was identified in all three CsFAD2 copies. Real Time qPCR data and Sequenom MassARRAY SNP analysis of the FAD2 and FAE1 cDNA showed that all three copies of each gene are expressed in developing seeds. Thus, it seems likely that all three copies of FAD2 and FAE1 in *C. sativa* are functional.

The cloning of three copies of FAD2 and FAE1 from the *C. sativa* genome, as well as the observation of three LFY hybridization signals by Southern analysis could be explained by at least two possible scenarios: segmental duplications of selected regions within a diploid genome either through tandem duplications or through transpositions, or whole genome duplications resulting from polyploidization. The possibility that ancient segmental duplications or transpositions affected all three examined loci seems less probable than polyploidy. Furthermore, no evidence of recent segmental duplication involving multiple genes has been observed in sequenced plant genomes (*Arabidopsis* genome (TAIR 2009, 2010); rice genome (TIGR Rice Database); maize genome (Maize Genome Browser 2010); and Soybean Genome (Phytozome, 2010)).

FAD2 and FAE1 Proteins of *Camelina sativa*

The present invention also provides polypeptides and amino acid sequences comprising at least a portion of the isolated protein selected from the group consisting of SEQ ID NOs: 7-12, and all variants thereof.

The present invention also provides an isolated amino acid sequence comprising a sequence selected from the group consisting of SEQ ID NOs: 7 to 12, and fragments and variations derived from thereof. In some embodiments, the present invention provides an isolated polypeptide comprising an amino acid sequence that shares at least about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 7, 8, 9, 64, 65, 67, 70, 73, 74, 75, 79, and/or 80. In one embodiment, the present invention provides an isolated polypeptide comprising an amino acid sequence which encodes an amino acid sequence that shares at least about 85%, about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to SEQ ID NO: 10, 11, 12, 66, 68, 69, 71, 72, 76, 77, 78, 81, and/or 82.

The invention also encompasses variants and fragments of proteins of FAD2 and FAE1 isolated in the present invention. The variants may contain alterations in the amino acid sequences of the constituent proteins. The term "variant" with respect to a polypeptide refers to an amino acid sequence that is altered by one or more amino acids with respect to a reference sequence. The variant can have "conservative" changes, or "nonconservative" changes, e.g., analogous minor variations can also include amino acid deletions or insertions, or both.

Functional fragments and variants of a polypeptide include those fragments and variants that maintain one or more functions of the parent polypeptide. It is recognized that the gene or cDNA encoding a polypeptide can be considerably mutated without materially altering one or more of the polypeptide's functions. First, the genetic code is well-known to be degenerate, and thus different codons encode the same amino acids. Second, even where an amino acid substitution is introduced, the mutation can be conservative and have no material impact on the essential function(s) of a protein. See, e.g., *Stryer Biochemistry* 3$^{rd}$ Ed., 1988. Third, part of a polypeptide chain can be deleted without impairing or eliminating all of its functions. Fourth, insertions or additions can be made in the polypeptide chain for example, adding epitope tags, without impairing or eliminating its functions (Ausubel et al. *J. Immunol.* 159(5): 2502-12, 1997). Other modifications that can be made without materially impairing one or more functions of a polypeptide can include, for example, in vivo or in vitro chemical and biochemical modifications or the incorporation of unusual amino acids. Such modifications include, but are not limited to, for example, acetylation, carboxylation, phosphorylation, glycosylation, ubiquination, labelling, e.g., with radionucleotides, and various enzymatic modifications, as will be readily appreciated by those well skilled in the art. A variety of methods for labelling polypeptides, and labels useful for such purposes, are well known in the art, and include radioactive isotopes such as $^{32}$P, ligands which bind to or are bound by labelled specific binding partners (e.g., antibodies), fluorophores, chemiluminescent agents, enzymes, and anti-ligands. Functional fragments and variants can be of varying length. For example, some fragments have at least 10, 25, 50, 75, 100, 200, or even more amino acid residues. These mutations can be natural or purposely changed. In some embodiments, mutations containing alterations that produce silent substitutions, additions, or deletions, but do not alter the properties or activities of the proteins or how the proteins are made are an embodiment of the invention.

Conservative amino acid substitutions are those substitutions that, when made, least interfere with the properties of the original protein, that is, the structure and especially the function of the protein is conserved and not significantly changed by such substitutions. Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain. Further information about conservative substitutions can be found, for instance, in Ben Bassat et al. (*J. Bacteriol.*, 169: 751-757, 1987), O'Regan et al. (*Gene*, 77:237-251, 1989), Sahin-Toth et al. (*Protein Sci.*, 3:240-247, 1994), Hochuli et al. (*Bio/Technology*, 6:1321-1325, 1988) and in widely used textbooks of genetics and molecular biology. The Blosum matrices are commonly used for determining the relatedness of polypeptide sequences. The Blosum matrices were created using a large database of trusted alignments (the BLOCKS database), in which pairwise sequence alignments related by less than some threshold percentage identity were counted (Henikoff et al., *Proc. Natl. Acad. Sci. USA*, 89:10915-10919, 1992). A threshold of 90% identity was used for the highly conserved target frequencies of the BLOSUM90 matrix. A threshold of 65% identity was used for the BLOSUM65 matrix. Scores of zero and above in the Blosum matrices are considered "conservative substitutions" at the percentage identity selected. The following table shows exemplary conservative amino acid substitutions.

| Original Residue | Very Highly - Conserved Substitutions | Highly Conserved Substitutions (from the Blosum90 Matrix) | Conserved Substitutions (from the Blosum65 Matrix) |
|---|---|---|---|
| Ala | Ser | Gly, Ser, Thr | Cys, Gly, Ser, Thr, Val |
| Arg | Lys | Gln, His, Lys | Asn, Gln, Glu, His, Lys |
| Asn | Gln; His | Asp, Gln, His, Lys, Ser, Thr | Arg, Asp, Gln, Glu, His, Lys, Ser, Thr |
| Asp | Glu | Asn, Glu | Asn, Gln, Glu, Ser |
| Cys | Ser | None | Ala |
| Gln | Asn | Arg, Asn, Glu, His, Lys, Met | Arg, Asn, Asp, Glu, His, Lys, Met, Ser |
| Glu | Asp | Asp, Gln, Lys | Arg, Asn, Asp, Gln, His, Lys, Ser |
| Gly | Pro | Ala | Ala, Ser |
| His | Asn; Gln | Arg, Asn, Gln, Tyr | Arg, Asn, Gln, Glu, Tyr |
| Ile | Leu; Val | Leu, Met, Val | Leu, Met, Phe, Val |
| Leu | Ile; Val | Ile, Met, Phe, Val | Ile, Met, Phe, Val |
| Lys | Arg; Gln; Glu | Arg, Asn, Gln, Glu | Arg, Asn, Gln, Glu, Ser, |
| Met | Leu; Ile | Gln, Ile, Leu, Val | Gln, Ile, Leu, Phe, Val |
| Phe | Met; Leu; Tyr | Leu, Trp, Tyr | Ile, Leu, Met, Trp, Tyr |
| Ser | Thr | Ala, Asn, Thr | Ala, Asn, Asp, Gln, Glu, Gly, Lys, Thr |
| Thr | Ser | Ala, Asn, Ser | Ala, Asn, Ser, Val |
| Trp | Tyr | Phe, Tyr | Phe, Tyr |
| Tyr | Trp; Phe | His, Phe, Trp | His, Phe, Trp |
| Val | Ile; Leu | Ile, Leu, Met | Ala, Ile, Leu, Met, Thr |

In some examples, variants can have no more than 3, 5, 10, 15, 20, 25, 30, 40, 50, or 100 conservative amino acid changes (such as very highly conserved or highly conserved amino acid substitutions). In other examples, one or several hydrophobic residues (such as Leu, Ile, Val, Met, Phe, or Trp) in a variant sequence can be replaced with a different hydrophobic residue (such as Leu, Ile, Val, Met, Phe, or Trp) to create a variant functionally similar to the disclosed FAD2 and FAE1 proteins.

In one embodiment, variants may differ from the disclosed sequences by alteration of the coding region to fit the codon usage bias of the particular organism into which the molecule is to be introduced. In other embodiments, the coding region may be altered by taking advantage of the degeneracy of the genetic code to alter the coding sequence such that, while the nucleotide sequence is substantially altered, it nevertheless encodes a protein having an amino acid sequence substantially similar to the disclosed FAD2 and FAE1 proteins.

*Camelina sativa* as an Allohexaploid Plant

The present inventors for the first time in the art demonstrates that *Camelina sativa* is an allohexaploid plant.

While not wishing to be bound to any particular theory, triplication of the *C. sativa* genome likely occurred through whole genome duplication, either through autopolyploidization or through allopolyploidization. An autopolyploidy event might have triplicated a single diploid genome resulting in an autohexaploid with a haploid genome of 18, 21, or 24 chromosomes. Given that *C. sativa* has a chromosome count of n=20, chromosome splitting or fusion could then have increased the chromosomes from 18 to 20, or decreased the chromosomes from 21 or 24 to 20.

Alternatively, triplication of the *C. sativa* genome might have resulted from two allopolyploidy events, resulting in first a tetraploid then a hexaploid, similar to the origin of cultivated wheat. According to this hypothesis, the three copies of each gene diverged in different diploid genomes before converging through polyploidy events. Taking into consideration the reported chromosome counts of various *Camelina* species, the basal chromosome number of the diploid parental species contributing to the *C. sativa* haploid genome of 20 chromosomes could be 7+7+6 or 8+6+6. The allopolyploid hypothesis is supported by the observation that *C. sativa* demonstrates diploid inheritance (Gehringer, Friedt et al. 2006; Lu 2008), as would be expected for an allopolyploid (Sybenga 1996). A hexaploid *C. sativa* could also be derived from the combination of an autotetraploid and a diploid species if, in an autopolyploidized genome, homologous chromosomes differentiated so that the subsequent chromosome-specific pairing mimicked an allopolyploid genome in its diploid inheritance patterns. Regardless of its evolutionary path, the *C. sativa* genome appears organized in three redundant and differentiated copies and can be formally considered to be an allohexaploid.

Results from the inventors' phylogenetic analyses support a history of duplication for both FAD2 and FAE1 in *Camelina*. For FAD2, duplications were only recovered for *C. sativa, C. microcarpa*, and *C. rumelica*. These data are consistent with genome size data, which indicate that all three genomes are larger than *C. laxa* and *C. hispida*, from which only a single FAD2 copy was recovered. Taken together, the results suggest that *C. sativa, C. microcarpa*, and *C. rumelica* are likely polyploids. Given the slightly smaller genome size of *C. rumelica*, and the fact that only two FAD2 copies were recovered from it, the *C. rumelica* sampled may be tetraploid while *C. sativa* and *C. microcarpa* are hexaploid. Interestingly, in both the FAD2 and FAE1 trees, one copy each of *C. rumelica* and *C. microcarpa* are strongly supported as sister. Thus, trees from these genes indicate that *C. rumelica* and *C. microcarpa* are closely related. The various placement of *C. microcarpa* FAD2 and FAE1 copies can be explained if *C. microcarpa* is the result of a hybridization event between *C. rumelica* and a currently unsampled, and thus unidentified species of *Camelina*. Two of the three copies of both FAD2 and FAE1 are identical, or nearly identical, in *C. sativa* and *C. microcarpa*, suggesting that *C. sativa* and *C. microcarpa* share a parental genome. Thus, the inventors suggest that an unsampled *Camelina* species contributed its genome to the hybrid formation of both *C. sativa* and *C. microcarpa*. In the case of *C. microcarpa*, the hybridization event likely involved *C. rumelica*. Given the chromosome count of n=6 for *C. rumelica*, the other putative parent would be expected to have an x=7 genome, and furthermore to be tetraploid at n=14. Such a cross would result in the observed *C. microcarpa* genome, with chromosome count n=20. Interestingly, *C. hispida* is the only species we sampled with a chromosome count of n=7; however no strong relationship between *C. hispida* and *C. microcarpa* is inferred in either gene tree. However, a weak relationship between *C. sativa* and *C. hispida* is inferred from the FAE1 tree, and thus the possibility that *C. hispida* is involved in the polyploid formation of *C. sativa* should be explored further.

The likely allohexaploid nature of the *Camelina sativa* genome has multiple implications. Its vigor and adaptability to marginal growth conditions may result at least in part from polyploidy. Polyploids are thought to be more adaptable to new or harsh environments, with the ability to expand into broader niches than either progenitor (Brochmann, Brysting et al. 2004; Salmon 2005). Indeed, *C. hispida* and *C. laxa*, both of which are likely diploids, are found only in Turkey, Iran, Armenia, and Azerbaijan, while *C. microcarpa* and *C. sativa* are distributed throughout Asia, Europe, and North Africa and are naturalized in North America (GRIN; Akeroyd 1993). The mechanisms behind this increased adaptability are not completely understood, but have been attributed to heterosis, genetic and regulatory network redundancies, and epigenetic factors (Comai 2005; Hegarty and Hiscock 2008).

Allohexaploidy might also affect any potential manipulations of the *C. sativa* genome, such as introgression of germplasm or induced mutations. Introgression of an exotic germplasm could be facilitated by the type of polyploidy-dependent manipulations that are possible in wheat, a potentially comparable allohexaploid (Gill and Friebe 1998; Dubcovsky and Dvorak 2007). In addition, polyploids have displayed excellent response to reverse genomics approaches such as Targeting Induced Local Lesions in Genomes (TILLING®) (Slade, Fuerstenberg et al. 2005; Cooper, Till et al. 2008). As in wheat, any recessive induced mutations could be masked by redundant homologous loci that have maintained function (Stadler 1929; Swaminathan and Rao 1960). This implies that multiple knockout alleles at different homologous sites can be combined to achieve partial or complete suppression of a targeted function (Muramatsu 1963; Li, Huang et al. 2008). We also expect that single locus traits, whether transgenic or not, will display diploid inheritance due to preferential intragenomic pairing.

Methods of Altering and/or Improving *Camelina* Seed Oil Composition

In light of the discovery that *Camelina* is an allohexaploid plant, the present invention provides methods of altering and/or improving *Camelina* seed oil composition. As used herein, the term "altering" refers to any change of fatty acid composition in the seed oil, including but not limited to compound structure, distribution, relative ratio, and yield, et al. The term "improving" refers to any change in seed oil composition that makes the seed oil composition better in one or more qualities for industrial or nutritional applications. Such improvement includes, but is not limited to, improved quality as meal, improved quality as raw material to produce biofuel, biodiesel, lubricant, more monounsaturated fatty acids and less polyunsaturated fatty acids, increased stability, lower cloud point, less NOx emissions, reduced trans-fatty acids, et al.

The quality of a biodiesel is greatly dependent upon its composition (Conley S P, Tao B: Biodiesel quality: Is All biodiesel Created Equal? Purdue University Extension; 2006). Polyunsaturated fatty acid methyl esters (FAME) have been shown to disproportionately increase oxidation of biodiesel. The temperatures at which biodiesel forms crystals (the cloud point) and at which it can no longer be poured (the pour point) are also affected by composition: saturated FAMEs and long chain FAMEs greatly increase cloud point and pour point. Biodiesel higher in unsaturated FAMEs are therefore better in colder environments, but have a lower oxidative stability than biodiesel higher in saturated FAMEs. Polyunsaturated FAMEs have also been shown to result in increased NOx emissions while long chain fatty acids result in a biodiesel with too high of a distillation temperature by ASTM standards. A biodiesel high in 18:1 and low in polyunsaturated FAMEs and long chain FAMEs is thought to be the best compromise, resulting in higher oxidative stability with a low enough cloud point and a high enough cetane number to meet biodiesel standards (ASTM D6751).

Meal is a significant byproduct of the extraction of the oil from oilseeds for biofuel. To be able to take advantage of this byproduct as a protein supplement for livestock is essential economically for biofuel producers. In order for meal from a particular oilseed to be included in livestock feed in the US, it must be approved by the Association of American Feed Control Officials (AAFCO). The approval takes into account feeding studies in livestock and published studies on the quality of the meal and formulates a definition for the meal that is included in the annually updated AAFCO manual. Currently soybean meal is the best source for animal feed because of its favorable amino acid content and high digestibility. Another widely used meal comes from Canola, an oilseed rape that has been bred to contain <2% erucic acid (22:1) and <30 µmol/g of glucosinolates. High amounts of erucic acid have been linked to fatty deposits in the heart muscles of animals and glucosinolates lend an unpalatable taste and confer adverse effects on growth in animals. *Camelina* oil has about 1-4% erucic acid, so the development of lines with consistently <2% erucic acid is still desirable. Thus the identification of FAE1 mutants with reduced very long chain fatty acids (VLCFA) such as 22:1 is valuable for the potential to create *Camelina* varieties having oil, and thus meal, with <2% erucic acid. *Camelina* meal has been tested at least in poultry, goat, cattle (Pilgeram et al., *Camelina sativa*, A montana omega-3 and fuel crop, Issues in new crops and new uses. 2007. J. Janick and A. Whipkey (eds.) and turkeys (Frame et al., Use of *Camelina sativa* in the Diets of Young Turkeys; J. Appl. Poult. Res. 16:381-386). ASHS Press, Alexandria, Va.). *Camelina* meal can currently be included in the diets of broiler chickens and feedlot beef cattle at no more than 10% (FDA, November 2009). Future feeding studies may enable the expansion of *Camelina* meal to swine, laying hens and dairy cattle.

In one embodiment, the methods relate to increasing monounsaturated fatty acids (e.g., oleic acids (18:1)) level and/or reducing polyunsaturated fatty acids level in the seed oil, wherein the method comprises disrupting and/or altering one or more copies of one or more *Camelina* fatty acids synthesis genes. In some embodiments, one, two, or all three copies of *Camelina* FAD2 and/or FAE1 genes are disrupted. For example, the methods comprise utilizing one or more *Camelina* mutants in any one of the mutations listed in Tables 7 to 12 described in Example 11.

In some embodiments, the methods related to increasing monounsaturated fatty acids (e.g., oleic acids (18:1)) level and/or decreasing very long chain fatty acids (>18 carbons), wherein the methods comprise disrupting and/or altering one or more copies of two or more *Camelina* fatty acids synthesis genes. In some embodiments, one, two, or all three copies of *Camelina* FAD2 and one, two, or all three FAE1 genes are disrupted.

In some embodiments, mutations in one or more copies of FAD2 genes and/or one or more copies of FAE1 genes described in the Tables 7 to 12 are integrated together to create mutant plants with double, triple, quadruple et al. mutations. Such mutants can be created by classic breeding methods.

In some embodiments, mutations described in the Tables 7-12 can be integrated into *Camelina* cultivars other than Cs32 by classic breeding methods, with or without the help of marker-facilitated gene transfer methods.

In some embodiments, mutations described in the Tables 7-12 can be integrated into species closely related to *Camelina sativa*, such as other species in the Brassicaceae family, such as *Brassica oleracea* (cabbage, cauliflower, etc.), *Brassica rapa* (turnip, Chinese cabbage, etc.), *Brassica napus* (rapeseed, etc.), *Raphanus sativus* (common radish), *Armoracia rusticana* (horseradish), *Matthiola* (stock), and many others, with or without the help of marker-facilitated inter-cultivar gene transfer methods.

In one embodiment, mutants in Tables 7 to 12, wherein the mutants are in evolutionarily conserved regions or sites can be used to produce *Camelina* plants with improved or altered seed oil. In one embodiment, mutants in Table 7 to 12, wherein the mutant is due to nonsense mutation (premature stop codon), can be used to produce *Camelina* plants with improved or altered seed oil.

In one embodiment, mutants in Tables 7 to 12, wherein the mutants are not in evolutionarily conserved regions or sites, can also be used to produce *Camelina* plants with improved or altered seed oil. Non-limiting examples of improved seed oil are those having increased oleic acid, increased fatty acids of C18 or less (C≤18), decreased very long chain fatty acid (C>18), and/or decreased polyunsaturated fatty acids, in ratio and/or in absolute weight. As used herein, the term "C≤18" refers to a chemical compound having not more than 18 carbons; as used herein, the term C>18 refers to a chemical compound that has more than 18 carbons.

In other embodiments, amino acids in conserved domains or sites of *Camelina* FAD2 or FAE1 proteins can be compared to FAD2 or FAE1 orthologs in other species, e.g., closely related Brassicaceae species, or plant species with known FAD/FAE sequences, which do not contain mutations listed in Tables 7 to 12. Then, the FAD/FAE genes in these related species can be substituted or deleted to make mutants with reduced or abolished activity.

In one embodiment, the oleic acid level in the seed oil produced from the *Camelina* plants of the present invention is increased as compared to the same plants known in the prior art (e.g., comparable wild type plant). For example, the level of oleic acid in the seed oil is increased by about 1%, about 2%, about 3%, about 4%, about 5%, about 6%, about 7%, about 8%, about 9%, about 10%, about 12%, about 14%, about 16%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 59%, about 60%, about 62%, about 64%, about 66%, about 68%, about 70%, about 75%, about 80%, about 85%, about 90%, about 95%, about 100%, about 150%, about 200%, about 250%, about 300%, about 350%, about 400%, about 450%, or about 500%.

In another embodiment, the oleic acid yield in the seed oil produced per *Camelina* plant of the present invention is increased as compared to the same plants known in the prior art (e.g., comparable wild type plant). As used herein, the term "yield" refers to amount of one or more types of fatty acids produced per plant, or per acre. For example, the yield of oleic acid in the seed oil is increased by about 1%, about 2%, about 3%, about 4%, about 5%, about 6%, about 7%, about 8%, about 9%, about 10%, about 12%, about 14%, about 16%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 59%, about 60%, about 62%, about 64%, about 66%, about 68%, about 70%, about 75%, about 80%, about 85%, about 90%, about 95%, about 100%, about 150%, about 200%, about 250%, about 300%, about 350%, about 400%, about 450%, or about 500%.

In another embodiment, the polyunsaturated fatty acid level and/or yield in the seed oil produced from the *Camelina* plants of the present invention is decreased as compared to the same plants known in the prior art (e.g., comparable wild type plant). For example, the level and/or yield of polyunsaturated fatty acid in the seed oil is decreased by about 1%, about 2%, about 3%, about 4%, about 5%, about 6%, about 7%, about 8%, about 9%, about 10%, about 12%, about 14%, about 16%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 59%, about 60%, about 62%, about 64%, about 66%, about 68%, about 70%, about 75%, about 80%, about 85%, about 90%, about 95%, about 100%, about 150%, about 200%, about 250%, about 300%, about 350%, about 400%, about 450%, or about 500%.

In another embodiment, the very long chain fatty acid (C>18) level and/or yield in the seed oil produced from the *Camelina* plants of the present invention is decreased as compared to the same plants known in the prior art (e.g., comparable wild type plant). For example, the level and/or yield of very long chain fatty acid in the seed oil is decreased by about 1%, about 2%, about 3%, about 4%, about 5%, about 6%, about 7%, about 8%, about 9%, about 10%, about 12%, about 14%, about 16%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 59%, about 60%, about 62%, about 64%, about 66%, about 68%, about 70%, about 75%, about 80%, about 85%, about 90%, about 95%, about 100%, about 150%, about 200%, about 250%, about 300%, about 350%, about 400%, about 450%, or about 500%.

In another embodiment, the fatty acids of C18 or less level and/or yield in the seed oil produced from the *Camelina* plants of the present invention is increased as compared to the same plants known in the prior art (e.g., comparable wild type plant). For example, the level and/or yield of fatty acids of C18 or less in the seed oil is increased by about 1%, about 2%, about 3%, about 4%, about 5%, about 6%, about 7%, about 8%, about 9%, about 10%, about 12%, about 14%, about 16%, about 18%, about 19%, about 20%, about 22%, about 24%, about 26%, about 28%, about 30%, about 32%, about 34%, about 36%, about 38%, about 40%, about 42%, about 44%, about 46%, about 48%, about 50%, about 52%, about 54%, about 56%, about 58%, about 59%, about 60%, about 62%, about 64%, about 66%, about 68%, about 70%, about 75%, about 80%, about 85%, about 90%, about 95%, about 100%, about 150%, about 200%, about 250%, about 300%, about 350%, or about 400%.

Molecular markers are used for the visualization of differences in nucleic acid sequences. This visualization is possible due to DNA-DNA hybridization techniques (RFLP) and/or due to techniques using the polymerase chain reaction (e.g. STS, microsatellites, AFLP, SNP, IMP et al.). All differences between two parental genotypes will segregate in a mapping population based on the cross of these parental genotypes. The segregation of the different markers may be compared and recombination frequencies can be calculated. The recombination frequencies of molecular markers on different chromosomes is generally 50%. Between molecular markers located on the same chromosome the recombination frequency depends on the distance between the markers. A low recombination frequency corresponds to a low distance between markers on a chromosome. Comparing all recombination frequencies will result in the most logical order of the molecular markers on the chromosomes. This most logical order can be depicted in a linkage map.

Molecular markers for the present invention, for example, can be generated by analyzing progeny of a cross between e.g., Cs32 cultivar to another *Camelina* species, e.g., *Camelina microcarpa*. The present inventors have generated such progeny and more Inter MITE Polymorphisms (IMP) markers can be generated following the procedures outlined in the present application. IMP markers are developed by and exclusive to DNA L and Marks Inc. IMP markers are based on Miniature Inverted-repeat Transposable Elements (MITEs), which are short interspersed DNA transposons with terminal inverted repeats (TIRs). They are small in size (<500 bp), conserved TIRs, high A+T content, and consist of several distinct families such as Tourist-like, Stowaway-like. They present in plants, fungi, vertebrates, fishes, insects. In plants, they are highly associated with genes (flanking regions, introns). They are also abundant in plants (several thousand copies per genome). IMP markers have many unique advantages:

Naturally multiplexed—Greatly lowers cost/data point
Reliable—PCR based, reproducible results
Portable—Markers are cross-applicable in all crops
Practical—Useful in a variety of marker-assisted breeding functions Similarly, Cs32 can be crossed to other species in the Brassicaceae family to generate molecular markers for further applications.

In some other embodiments, one, two, or all three copies of *Camelina* FAD2 and/or FAE1 genes, and one, two, or all three copies of other non-FAD2, non-FAE1 fatty acid synthesis genes are disrupted. As used herein, the phrase "non-FAD, non-FAE fatty acid synthesis genes" refers to polynucleotides encoding polypeptides that are involved in plant fatty acid synthesis, but share less than 95% identity to FAD2 or FAE1 polypeptide disclosed in the present invention. In still some embodiments, one, two, or all three copies of *Camelina* FAD2 and/or FAE1 genes are disrupted, while one or more non-FAD, non-FAE fatty acid synthesis genes are overexpressed. In still more embodiments, one, two, or all three copies of *Camelina* FAD2 and/or FAE1 genes are disrupted, while one or more non-fatty-acid-synthesis genes are overexpressed and/or disrupted. As used herein, the phrase "non-fatty-acid-synthesis genes" refers to polynucleotides encoding polypeptides that are not directly involved in the synthesis of fatty acids.

According to the present invention, one skilled in the art will be able to pick preferred target genes and decide when disruption or overexpression is needed to achieve certain goals, e.g., an induction or reduction of certain fatty acids composition, based on the plant fatty acid metabolic pathways and metabolic analysis tools known in the art (e.g., MetaCyc and AraCyc database, see Zhang et al., Plant Physiology, 2005, 138:27-37). For example, one skilled in the art would be able to combine FAD2 and/or FAE1 loss-of-function mutants (e.g., mutants with reduced, or abolished FAD2 and/or FAE1 protein activity), FAD2 and/or FAE1 gain-of-function mutants (e.g., mutants with altered or increased FAD2 and/or FAE1 protein activity), or FAD2 and/or FAE1 overexpression with overexpression or disruption of non-FAD, non-FAE fatty acid genes to modulate the fatty acid synthesis in a plant. While not wishing to be bound by any particular theory, knock-down of FAD2 can potentially lower 18:2 fatty acid; knock-down of FAD3 can potentially lower 18:3 fatty acid; overexpressing plastidial enzyme Δ9 will give higher 18:1; knock-down of both FAD2 and FAD3 will contribute to a higher cloud point of the oil; knock-down of thioesterases (e.g., FAT A and/or FAT B) will lower the amount of 16:0 fatty acids; knock-down of fatty acid elongase (FAE) will lower the amount of long-chain fatty acids; a dominant negative KRP protein or a REV protein can increase cell size and thus increase oil production (see US 2008/263727 and US 2007/056058, incorporated by reference in their entireties).

In addition, using the compositions and methods of the present invention, one skilled in the art will be able to combine disruption of FAD2 and/or FAE1 genes with other mutants and/or transgenes which can generally improve plant health, plant biomass, plant resistance to biotic and abiotic factors, plant yields, wherein the final preferred fatty acid production is increased. Such mutants and/or transgenes include, but are not limited to, cell cycle controlling genes, cell size controlling genes, cell division controlling genes, pathogen resistance genes, and genes controlling plant traits related to seed yield, which are well known to one skilled in the art (e.g., REV genes, KRP genes).

Methods of disrupting and/or altering a target gene have been known to one skilled in the art. These methods include, but are not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense and RNA interference. Various types of mutagenesis can be used to produce and/or isolate variant nucleic acids that encode for protein molecules and/or to further modify/mutate the proteins of the present invention. They include but are not limited to site-directed, random point mutagenesis, homologous recombination (DNA shuffling), mutagenesis using uracil containing templates, oligonucleotide-directed mutagenesis, phosphorothioate-modified DNA mutagenesis, mutagenesis using gapped duplex DNA or the like. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the present invention. In one embodiment, mutagenesis can be guided by known information of the naturally occurring molecule or altered or mutated naturally occurring molecule, e.g., sequence, sequence comparisons, physical properties, crystal structure or the like. For more information of mutagenesis in plants, such as agents, protocols, see Acquaah et al. (Principles of plant genetics and breeding, Wiley-Blackwell, 2007, ISBN 1405136464, 9781405136464, which is herein incorporated by reference in its entity). Methods of disrupting plant genes using RNA interference is described later in the specification.

The present invention provides methods of producing *Camelina* seed oil containing altered and/or increased levels of oleic acid (18:1), and/or altered or reduced levels of polyunsaturated fatty acids, and/or decreased very long chain fatty acids (C>18). Such methods comprise utilizing the *Camelina* plants comprising the chimeric genes as described above, or *Camelina* plants with disrupted FAD2 and/or FAE1 genes as described above.

The present invention also provides methods of breeding *Camelina* species producing altered levels of fatty acids in the seed oil and/or meal. In one embodiment, such methods comprise
i) making a cross between the *Camelina* mutants with mutations as described above to a second *Camelina* species to make F1 plants;
ii) backcrossing said F1 plants to said second *Camelina* species;
iii) repeating backcrossing step until said mutations are integrated into the genome of said second *Camelina* species. Optionally, such method can be facilitated by molecular markers.

The present invention provides methods of breeding species close to *Camelina sativa*, wherein said species produces altered levels of fatty acids in the seed oil and/or meal. In one embodiment, such methods comprise
i) making a cross between the *Camelina* mutants with mutations as described above to a species close to *Camelina sativa* to make F1 plants;
ii) backcrossing said F1 plants to said species that is close to *Camelina sativa*;
iii) repeating backcrossing step until said mutations are integrated into the genome of said species that is close to *Camelina sativa*. Special techniques (e.g., somatic hybridization) may be necessary in order to successfully transfer a gene from *Camelina sativa* to another species and/or genus, such as to *B. oleracea*. Optionally, such method can be facilitated by molecular markers.

Plant Transformation

The present polynucleotides of the present invention can be transformed into a *Camelina* plant, or other plants.

The most common method for the introduction of new genetic material into a plant genome involves the use of living cells of the bacterial pathogen *Agrobacterium tumefaciens* to literally inject a piece of DNA, called transfer or T-DNA, into individual plant cells (usually following wounding of the tissue) where it is targeted to the plant nucleus for chromosomal integration. There are numerous patents governing *Agrobacterium* mediated transformation and particular DNA delivery plasmids designed specifically for use with *Agrobacterium*—for example, U.S. Pat. No. 4,536,475, EP0265556, EP0270822, WO8504899, WO8603516, U.S. Pat. No. 5,591,616, EP0604662, EP0672752, WO8603776, WO9209696, WO9419930, WO9967357, U.S. Pat. No. 4,399,216, WO8303259, U.S. Pat. No. 5,731,179, EP068730, WO9516031, U.S. Pat. No. 5,693,512, U.S. Pat. No. 6,051,757 and EP904362A1. *Agrobacterium*-mediated plant transformation involves as a first step the placement of DNA fragments cloned on plasmids into living *Agrobacterium* cells, which are then subsequently used for transformation into individual plant cells. *Agrobacterium*-mediated plant transformation is thus an indirect plant transformation method. Methods of *Agrobacterium*-mediated plant transformation that involve using vectors with no T-DNA are also well known to those skilled in the art and can have applicability in the present invention. See, for example, U.S. Pat. No. 7,250,554, which utilizes P-DNA instead of T-DNA in the transformation vector.

Direct plant transformation methods using DNA have also been reported. The first of these to be reported historically is electroporation, which utilizes an electrical current applied to a solution containing plant cells (M. E. Fromm et al., Nature, 319, 791 (1986); H. Jones et al., Plant Mol. Biol., 13, 501 (1989) and H. Yang et al., Plant Cell Reports, 7, 421 (1988). Another direct method, called "biolistic bombardment", uses ultrafine particles, usually tungsten or gold, that are coated with DNA and then sprayed onto the surface of a plant tissue with sufficient force to cause the particles to penetrate plant cells, including the thick cell wall, membrane and nuclear envelope, but without killing at least some of them (U.S. Pat. No. 5,204,253, U.S. Pat. No. 5,015,580). A third direct method uses fibrous forms of metal or ceramic consisting of sharp, porous or hollow needle-like projections that literally impale the cells, and also the nuclear envelope of cells. Both silicon carbide and aluminium borate whiskers have been used for plant transformation (Mizuno et al., 2004; Petolino et al., 2000; U.S. Pat. No. 5,302,523 US Application 20040197909) and also for bacterial and animal transformation (Kaepler et al., 1992; Raloff, 1990; Wang, 1995). There are other methods reported, and undoubtedly, additional methods will be developed. However, the efficiencies of each of these indirect or direct methods in introducing foreign DNA into plant cells are invariably extremely low, making it necessary to use some method for selection of only those cells that have been transformed, and further, allowing growth and regeneration into plants of only those cells that have been transformed.

For efficient plant transformation, a selection method must be employed such that whole plants are regenerated from a single transformed cell and every cell of the transformed plant carries the DNA of interest. These methods can employ positive selection, whereby a foreign gene is supplied to a plant cell that allows it to utilize a substrate present in the medium that it otherwise could not use, such as mannose or xylose (for example, refer U.S. Pat. No. 5,767,378; U.S. Pat. No. 5,994,629). More typically, however, negative selection is used because it is more efficient, utilizing selective agents such as herbicides or antibiotics that either kill or inhibit the growth of nontransformed plant cells and reducing the possibility of chimeras. Resistance genes that are effective against negative selective agents are provided on the introduced foreign DNA used for the plant transformation. For example, one of the most popular selective agents used is the antibiotic kanamycin, together with the resistance gene neomycin phosphotransferase (nptII), which confers resistance to kanamycin and related antibiotics (see, for example, Messing & Vierra, Gene 19: 259-268 (1982); Bevan et al., Nature 304:184-187 (1983)). However, many different antibiotics and antibiotic resistance genes can be used for transformation purposes (refer U.S. Pat. No. 5,034,322, U.S. Pat. No. 6,174,724 and U.S. Pat. No. 6,255,560). In addition, several herbicides and herbicide resistance genes have been used for transformation purposes, including the bar gene, which confers resistance to the herbicide phosphinothricin (White et al., Nucl Acids Res 18: 1062 (1990), Spencer et al., Theor Appl Genet. 79: 625-631 (1990), U.S. Pat. No. 4,795,855, U.S. Pat. No. 5,378,824 and U.S. Pat. No. 6,107,549). In addition, the dhfr gene, which confers resistance to the anticancer agent methotrexate, has been used for selection (Bourouis et al., EMBO J. 2(7): 1099-1104 (1983).

The expression control elements used to regulate the expression of a given protein can either be the expression control element that is normally found associated with the coding sequence (homologous expression element) or can be a heterologous expression control element. A variety of homologous and heterologous expression control elements are known in the art and can readily be used to make expression units for use in the present invention. Transcription initiation regions, for example, can include any of the various opine initiation regions, such as octopine, mannopine, nopaline and the like that are found in the Ti plasmids of *Agrobacterium tumefaciens*. Alternatively, plant viral promoters can also be used, such as the cauliflower mosaic virus 19S and 35S promoters (CaMV 19S and CaMV 35S promoters, respectively) to control gene expression in a plant (U.S. Pat. Nos. 5,352,605; 5,530,196 and 5,858,742 for example). Enhancer sequences derived from the CaMV can also be utilized (U.S. Pat. Nos. 5,164,316; 5,196,525; 5,322,938; 5,530,196; 5,352,605; 5,359,142; and 5,858,742 for example). Lastly, plant promoters such as prolifera promoter, fruit specific promoters, Ap3 promoter, heat shock promoters, seed specific promoters, etc. can also be used.

Either a gamete-specific promoter, a constitutive promoter (such as the CaMV or Nos promoter), an organ-specific promoter (such as the E8 promoter from tomato), or an inducible promoter is typically ligated to the protein or antisense encoding region using standard techniques known in the art. The expression unit may be further optimized by employing supplemental elements such as transcription terminators and/or enhancer elements. For example, the 5' introns of FAD2 gene in sesame have been demonstrated to increase and/or regulate expression of certain genes (Kim et al. 2006. Mol Genet Genomics 276(4): 351-68). Thus, the 5' intron sequences of the FAD2 genes of the present invention can be used to increase expression of either a FAD2 or a non-FAD2 gene. The expression cassette can comprise, for example, a seed-specific promoter (e.g. the phaseolin promoter (U.S. Pat. No. 5,504,200). The term "seed-specific promoter", means that a gene expressed under the control of the promoter is predominantly expressed in plant seeds with no or no substantial expression, typically less than 10% of the overall expression level, in other plant tissues. Seed specific promoters have been well known in the art, for example, U.S. Pat. Nos. 5,623,067, 5,717,129, 6,403,371, 6,566,584, 6,642,437, 6,777,591, 7,081,565, 7,157,629, 7,192,774, 7,405,345, 7,554,006, 7,589,252, 7,595,384, 7,619,135, 7,642,346, and US Application Publication Nos. 20030005485, 20030172403, 20040088754, 20040255350, 20050125861, 20050229273, 20060191044, 20070022502, 20070118933, 20070199098, 20080313771, and 20090100551.

Thus, for expression in plants, the expression units will typically contain, in addition to the protein sequence, a plant promoter region, a transcription initiation site and a transcription termination sequence. Unique restriction enzyme sites at the 5' and 3' ends of the expression unit are typically included to allow for easy insertion into a pre-existing vector.

In the construction of heterologous promoter/structural gene or antisense combinations, the promoter is preferably positioned about the same distance from the heterologous transcription start site as it is from the transcription start site in its natural setting. As is known in the art, however, some variation in this distance can be accommodated without loss of promoter function.

In addition to a promoter sequence, the expression cassette can also contain a transcription termination region downstream of the structural gene to provide for efficient termination. The termination region may be obtained from the same gene as the promoter sequence or may be obtained from different genes. If the mRNA encoded by the structural gene is to be efficiently processed, DNA sequences which direct polyadenylation of the RNA are also commonly added to the vector construct. Polyadenylation sequences include, but are not limited to the *Agrobacterium* octopine synthase signal (Gielen et al., EMBO J. 3:835-846 (1984)) or the nopaline synthase signal (Depicker et al., Mol. and Appl. Genet. 1:561-573 (1982)). The resulting expression unit is ligated into or otherwise constructed to be included in a vector that is appropriate for higher plant transformation. One or more expression units may be included in the same vector. The vector will typically contain a selectable marker gene expression unit by which transformed plant cells can be identified in culture. Usually, the marker gene will encode resistance to an antibiotic, such as G418, hygromycin, bleomycin, kanamycin, or gentamicin or to an herbicide, such as glyphosate (Round-Up) or glufosinate (BASTA) or atrazine. Replication sequences, of bacterial or viral origin, are generally also included to allow the vector to be cloned in a bacterial or phage host; preferably a broad host range for prokaryotic origin of replication is included. A selectable marker for bacteria may also be included to allow selection of bacterial cells bearing the desired construct. Suitable prokaryotic selectable markers include resistance to antibiotics such as ampicillin, kanamycin or tetracycline. Other DNA sequences encoding additional functions may also be present in the vector, as is known in the art. For instance, in the case of *Agrobacterium* transformations, T-DNA sequences will also be included for subsequent transfer to plant chromosomes.

To introduce a desired gene or set of genes by conventional methods requires a sexual cross between two lines, and then repeated back-crossing between hybrid offspring and one of the parents until a plant with the desired characteristics is obtained. This process, however, is restricted to plants that can sexually hybridize, and genes in addition to the desired gene will be transferred.

Recombinant DNA techniques allow plant researchers to circumvent these limitations by enabling plant geneticists to identify and clone specific genes for desirable traits, such as improved fatty acid composition, and to introduce these genes into already useful varieties of plants. Once the foreign genes have been introduced into a plant, that plant can then be used in conventional plant breeding schemes (e.g., pedigree breeding, single-seed-descent breeding schemes, reciprocal recurrent selection) to produce progeny which also contain the gene of interest.

Genes can be introduced in a site directed fashion using homologous recombination. Homologous recombination permits site-specific modifications in endogenous genes and thus inherited or acquired mutations may be corrected, and/or novel alterations may be engineered into the genome. Homologous recombination and site-directed integration in plants are discussed in, for example, U.S. Pat. Nos. 5,451,513; 5,501,967 and 5,527,695.

Methods of producing transgenic plants are well known to those of ordinary skill in the art. Transgenic plants can now be produced by a variety of different transformation methods including, but not limited to, electroporation; microinjection; microprojectile bombardment, also known as particle acceleration or biolistic bombardment; viral-mediated transformation; and *Agrobacterium*-mediated transformation. See, for example, U.S. Pat. Nos. 5,405,765; 5,472,869; 5,538,877; 5,538,880; 5,550,318; 5,641,664; 5,736,369 and 5,736,369; International Patent Application Publication Nos. WO2002/038779 and WO/2009/117555; Lu et al., (Plant Cell Reports, 2008, 27:273-278); Watson et al., Recombinant DNA, Scientific American Books (1992); Hinchee et al., Bio/Tech. 6:915-922 (1988); McCabe et al., Bio/Tech. 6:923-926 (1988); Toriyama et al., Bio/Tech. 6:1072-1074 (1988); Fromm et al., Bio/Tech. 8:833-839 (1990); Mullins et al., Bio/Tech. 8:833-839 (1990); Hiei et al., Plant Molecular Biology 35:205-218 (1997); Ishida et al., Nature Biotechnology 14:745-750 (1996); Zhang et al., Molecular Biotechnology 8:223-231 (1997); Ku et al., Nature Biotechnology 17:76-80 (1999); and, Raineri et al., Bio/Tech. 8:33-38 (1990)), each of which is expressly incorporated herein by reference in their entirety.

*Agrobacterium tumefaciens* is a naturally occurring bacterium that is capable of inserting its DNA (genetic information) into plants, resulting in a type of injury to the plant known as crown gall. Most species of plants can now be transformed using this method, including cucurbitaceous species.

Microprojectile bombardment is also known as particle acceleration, biolistic bombardment, and the gene gun (Biolistic® Gene Gun). The gene gun is used to shoot pellets that are coated with genes (e.g., for desired traits) into plant seeds or plant tissues in order to get the plant cells to then express the new genes. The gene gun uses an actual explosive (.22 caliber blank) to propel the material. Compressed air or steam may also be used as the propellant. The Biolistic® Gene Gun was invented in 1983-1984 at Cornell University by John Sanford, Edward Wolf, and Nelson Allen. It and its registered trademark are now owned by E. I. du Pont de Nemours and Company. Most species of plants have been transformed using this method.

A transgenic plant formed using *Agrobacterium* transformation methods typically contains a single gene on one chromosome, although multiple copies are possible. Such transgenic plants can be referred to as being hemizygous for the added gene. A more accurate name for such a plant is an independent segregant, because each transformed plant represents a unique T-DNA integration event (U.S. Pat. No. 6,156,953). A transgene locus is generally characterized by the presence and/or absence of the transgene. A heterozygous genotype in which one allele corresponds to the absence of the transgene is also designated hemizygous (U.S. Pat. No. 6,008,437).

Breeding Methods

Classic breeding methods can be included in the present invention to introduce one or more mutations of the present invention into other *Camelina* varieties, or other close-related species of the Brassicaceae family that are compatible to be crossed with *Camelina*. In one embodiment, the mutations are on the FAD2 A, FAD2 B, and/or FAD2 C genes. In one embodiment, the mutations are on the FAE1 A, FAE1 B, and/or FAE1 C genes. In one embodiment, the mutations are on any FAD2 gene and/or any FAE1 gene.

Open-Pollinated Populations.

The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are several primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. Third, a method used in plant species that are largely self pollinated in nature, such as soybeans, wheat, rice, safflower, camelina and others is pedigree selection. In this situation, crosses are made and individual plants and lines from individual plants are selected for desired traits. These lines are thn advanced as genetically homogeneous varieties. Since the individuals are largely self pollinated these lines are analogous to an inbred line with favorable agronomic characteristics. These plant breeding procedures for improving open-pollinated populations are well known to those skilled in the art and comprehensive reviews of breeding procedures routinely used for improving cross-pollinated plants are provided in numerous texts and articles, including: Allard, *Principles of Plant Breeding*, John Wiley & Sons, Inc. (1960); Simmonds, *Principles of Crop Improvement*, Longman Group Limited (1979); Hallauer and Miranda, *Quantitative Genetics in Maize Breeding*, Iowa State University Press (1981); and, Jensen, *Plant Breeding Methodology*, John Wiley & Sons, Inc. (1988).

Mass Selection.

In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics.

A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (*Vicia*) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average. Broad based synthetics formed from 100 or more clones would be expected to be more stable during seed multiplication than narrow based synthetics.

Pedigreed Varieties.

A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids.

A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, *Commercial Hybrid Seed Production* 8:161-176, In Hybridization of Crop Plants.

RNA Interference (RNAi)

RNA interference (RNAi) is the process of sequence-specific, post-transcriptional gene silencing or transcriptional gene silencing in animals and plants, initiated by double-stranded RNA (dsRNA) that is homologous in sequence to the silenced gene. The preferred RNA effector molecules useful in this invention must be sufficiently distinct in sequence from any host polynucleotide sequences for which function is intended to be undisturbed after any of the methods of this invention are performed. Computer algorithms may be used to define the essential lack of homology between the RNA molecule polynucleotide sequence and host, essential, normal sequences.

The term "dsRNA" or "dsRNA molecule" or "double-strand RNA effector molecule" refers to an at least partially double-strand ribonucleic acid molecule containing a region of at least about 19 or more nucleotides that are in a double-strand conformation. The double-stranded RNA effector molecule may be a duplex double-stranded RNA formed from two separate RNA strands or it may be a single RNA strand with regions of self-complementarity capable of assuming an at least partially double-stranded hairpin conformation (i.e., a hairpin dsRNA or stem-loop dsRNA). In various embodiments, the dsRNA consists entirely of ribonucleotides or consists of a mixture of ribonucleotides and deoxynucleotides, such as RNA/DNA hybrids. The dsRNA may be a single molecule with regions of self-complementarity such that nucleotides in one segment of the molecule base pair with nucleotides in another segment of the molecule. In one aspect, the regions of self-complementarity are linked by a region of at least about 3-4 nucleotides, or about 5, 6, 7, 9 to 15 nucleotides or more, which lacks complementarity to another part of the molecule and thus remains single-stranded (i.e., the "loop region"). Such a molecule will assume a partially double-stranded stem-loop structure, optionally, with short single stranded 5' and/or 3' ends. In one aspect the regions of self-complementarity of the hairpin dsRNA or the double-stranded region of a duplex dsRNA will comprise an Effector Sequence and an Effector Complement (e.g., linked by a single-stranded loop region in a hairpin dsRNA). The Effector Sequence or Effector Strand is that strand of the double-stranded region or duplex which is incorporated in or associates with RISC. In one aspect the double-stranded RNA effector molecule will comprise an at least 19 contiguous nucleotide effector sequence, preferably 19 to 29, 19 to 27, or 19 to 21 nucleotides, which is a reverse complement to the RNA of *Camelina* genes (e.g., FAD2 and FAE1 genes), or an opposite strand replication intermediate. In one embodiment, said double-stranded RNA effector molecules are provided by providing to a *Camelina* plant, plant tissue, or plant cell an expression construct comprising one or more double-stranded RNA effector molecules. In one embodiment, the expression construct comprises a double-strand RNA derived from any one of SEQ ID NOs 1-6 and SEQ ID NOs 45-63. In other embodiments, the expression construct comprises a double-strand RNA derived from more than one sequences of SEQ ID NOs 1-6 and SEQ ID NOs 45-63. In further embodiments, the expression construct comprises a double-strand RNA derived from more than one sequences of SEQ ID NOs 1-6 and SEQ ID NOs 45-63, and one or more other genes involved in plant fatty acid synthesis. One skilled in the art will be able to design suitable double-strand RNA effector molecule based on the nucleotide sequences of *Camelina* FAD2 and FAE1 in the present invention and other *Camelina* fatty acid synthesis genes known in the art.

In some embodiments, the dsRNA effector molecule of the invention is a "hairpin dsRNA", a "dsRNA hairpin", "short-hairpin RNA" or "shRNA", i.e., an RNA molecule of less than approximately 400 to 500 nucleotides (nt), or less than 100 to 200 nt, in which at least one stretch of at least 15 to 100 nucleotides (e.g., 17 to 50 nt, 19 to 29 nt) is based paired with a complementary sequence located on the same RNA molecule (single RNA strand), and where said sequence and complementary sequence are separated by an unpaired region of at least about 4 to 7 nucleotides (or about 9 to about 15 nt, about 15 to about 100 nt, about 100 to about 1000 nt) which forms a single-stranded loop above the stem structure created by the two regions of base complementarity. The shRNA molecules comprise at least one stem-loop structure comprising a double-stranded stem region of about 17 to about 500 bp; about 17 to about 50 bp; about 40 to about 100 bp; about 18 to about 40 bp; or from about 19 to about 29 bp; homologous and complementary to a target sequence to be inhibited; and an unpaired loop region of at least about 4 to 7 nucleotides, or about 9 to about 15 nucleotides, about 15 to about 100 nt, about 250-500 bp, about 100 to about 1000 nt, which forms a single-stranded loop above the stem structure created by the two regions of base complementarity. It will be recognized, however, that it is not strictly necessary to include a "loop region" or "loop sequence" because an RNA molecule comprising a sequence followed immediately by its reverse complement will tend to assume a stem-loop conformation even when not separated by an irrelevant "stuffer" sequence.

The expression construct of the present invention comprising DNA sequence which can be transcribed into one or more double-stranded RNA effector molecules can be transformed into a *Camelina* plant, wherein the transformed plant produces different fatty acid compositions than the untransformed plant. The target sequence to be inhibited by the dsRNA effector molecule include, but are not limited to, coding region, 5' UTR region, 3' UTR region of fatty acids synthesis genes. In one embodiment, the target sequence is from one or more *Camelina* FAD2 and/or FAE1 genes.

The effects of RNAi can be both systemic and heritable in plants. In plants, RNAi is thought to propagate by the transfer of siRNAs between cells through plasmodesmata. The heritability comes from methylation of promoters targeted by RNAi; the new methylation pattern is copied in each new generation of the cell. A broad general distinction between plants and animals lies in the targeting of endogenously produced miRNAs; in plants, miRNAs are usually perfectly or nearly perfectly complementary to their target genes and induce direct mRNA cleavage by RISC, while animals' miRNAs tend to be more divergent in sequence and induce translational repression. Detailed methods for RNAi in plants are described in David Allis et al (Epigenetics, CSHL Press, 2007, ISBN 0879697245, 9780879697242), Sohail et al (Gene silencing by RNA interference: technology and application, CRC Press, 2005, ISBN 0849321417, 9780849321412), Engelke et al. (RAN Interference, Academic Press, 2005, ISBN 0121827976, 9780121827977), and Doran et al. (RNA Interference: Methods for Plants and Animals, CABI, 2009, ISBN 1845934105, 9781845934101), which are all herein incorporated by reference in their entireties for all purposes.

The present invention is further illustrated by the following examples that should not be construed as limiting. The contents of all references, patents, and published patent applications cited throughout this application, as well as the Figures, are incorporated herein by reference in their entirety for all purposes.

EXAMPLE

Example 1

Methods and Materials

Southern Blot

*Camelina sativa* Cs32 and Cs11, and *Arabidopsis thaliana* ecotype Col-0 (Table 2) seeds were germinated on *Arabidopsis* Growth Media (1× Murashige and Skoog (MS) mineral salts, 0.5 g/L MES, 0.8% PhytaBlend™ all from Caisson Labs, North Logan, Utah; pH5.7) and allowed to grow for ~2 weeks under 16/8 hours day/night, 22/18° C., and ~130 µE m$^{-2}$ s$^{-1}$ light intensity. Genomic DNA was isolated according to the CTAB method (Saghai-Maroof, Soliman et al. 1984) and 10 µg was digested overnight (~16 h) with EcoRI or a combination of EcoRI plus BamHI. DNA electrophoresis and blotting were carried out using standard molecular biology techniques (Tom Maniatis 1982). The probe was labelled with α-32P dCTP according to instructions of the DECAprime II kit (Ambion, Austin, Tex.). Hybridization was carried out overnight at 42° C. The blot was washed (30 minutes each) at 42° C. in 2×SSC, 0.1% SDS, followed by 55° C. in 2×SSC, 0.1% SDS, and then 55° C. in 0.1×SSC, 1% SDS, and exposed to a phosphorimager screen. The blot was hybridized with different probes after stripping the membrane in boiling 0.1% SDS for 20 minutes each time.

Cloning of *C. sativa* FAD2 and FAE1 Genes and Upstream Regions.

FAD2 and FAE1 genes were amplified from *C. sativa* Cs32 DNA isolated as described above, using Phusion polymerase (New England Biolabs, Ipswich, Mass.) and the primers listed in Table 3, according to the manufacturer's directions. The amplified fragments were cloned using the Zero Blunt PCR Cloning kit (Invitrogen, Carlsbad, Calif.)

FAD2 and FAE1 Sequence Alignments

Translated amino acid FAD2 and FAE1 sequences were aligned with AlignX (Invitrogen), with a gap opening penalty of 15, a gap extension penalty of 6.66, and a gap separation penalty range of 8. Alignments were imported into Boxshade (EMBnet) to highlight the conserved residues.

RNA Isolation and cDNA Preparation

*C. sativa* Cs32 plants were grown under 24/18° C. day/night conditions with a 16/8 hour photoperiod. Flowers were tagged and embryos harvested at the time points indicated. RNA was then isolated using the urea LiCl method described by Tai et al (Tai, Pelletier et al. 2004). cDNA were prepared from 0.5 µg of DNAsed RNA that was reverse transcribed with the High Capacity cDNA RT kit (Applied Biosystems, Foster City, Calif.) using random primers according to the manufacturer's instructions.

Quantitative Real-Time PCR

Relative expression of FAD2 and FAE1 cDNA was measured by real-time quantitative PCR and calculated according to the comparative $C_T$ method ($2^{-\Delta\Delta C_T}$). In brief, separate reactions were prepared in duplicate or triplicate for each of the genes to be measured. Each reaction contained 8 µl of the appropriate primers (200 nM each) and probe (900 nM) for Cs ACTIN (reference gene) or Cs FAD2 or FAE1 (target gene); 10 µl of Applied Biosystems 2× fast Taqman PCR mix; 2 µl of cDNA. The reactions were run on an Applied Biosystems 7900HT according to the manufacturer's fast PCR method. Real-time primers and probes are listed in Table 4.

Relative Expression Analysis

Three single nucleotide polymorphisms (SNPs) for each of FAD2 A, B, and C and FAE1 A, B, and C were identified. Each identified SNP distinguishes one copy from the other two. An additional SNP, which distinguishes FAE1 A, B, and C copies from each other, was also identified (Table 5). SNP frequencies were determined in cDNA isolated as described above by the Sequenom MassARRAY™ allele-specific expression analysis method with no competitor, as described in Park et al (Park, Correll et al. 2004).

Genome Size Estimation

*Camelina* lines (Table 2) were grown in the greenhouse at temperatures fluctuating between 16 and 26 C with 16 hour day length supplemented by halogen lights. The nuclei were extracted from leaves according to Henry et al [74]. Nuclei were also extracted from approximately 50 seeds of all species, except *C. laxa* and *C. hispida*, which are late flowering. The seeds were crushed with a pestle in 1.4 mL of the same extraction buffer used for the leaves. The fluid was then drawn through four layers of cheesecloth and strained and processed as for the leaf nuclei. Nuclei of diploid and tetraploids of *Arabidopsis thaliana* accession Col-0 (1 C genome size 157 Mb, and 314 Mb, respectively[75]), and tetraploid *Arabidopsis arenosa* accession Care-1 (1C genome size 480 Mb [Dilkes, unpublished results]) were used as standards for DNA content. Data was collected on two different days and normalized separately to account for daily fluctuations in flow cytometer performance. The 2C, 4C, and 8C nuclear peaks were used in a regression analysis of measured fluorescence intensity versus nuclear DNA content, producing equations of genome size versus fluorescence that were used to estimate the 2C content of *Camelina* nuclei.

Phylogenetic Inference

FAD2 and FAE1 were PCR amplified from several *Camelina* species and other species from the tribe Camelineae (Table 2) using primers designed from *C. sativa* FAD2 and FAE1 sequences (Table 3). Amplified fragments for FAD2 and FAE1 were cloned as described for *C. sativa* above, then aligned by translated amino acids sequences using MacClade 4.05 (Maddison 2004). ModelTest 3.7 (Posada and Crandall 1998) in PAUP*4.0b (Swofford 2001) was used to determine the model of sequence evolution favored by the data for each gene. Subsequent maximum likelihood (ML) analyses were performed in PAUP* 4.0b using a heuristic search with tree bisection reconnection (TBR) branch swapping. ML clade support using 100 bootstrap data sets were assessed and this support is presented on the most likely tree recovered from the ML heuristic search.

Camelina Alkaline Transesterification for FAMES Composition and Gas Chromatography (GC/FID) Analysis of *Camelina* Seeds Approximately 50 mg of seeds were ground up in liquid nitrogen with mortar and pestle. 5 mL of 0.2M KOH in methanol was added to each vial containing the ground seeds. Samples were capped, heated at 37 C for 1 hr and vortexed every 10 minutes. Reaction was stopped with addition of 1 mL 1M acetic acid and 2 mL heptanes. Samples were vortexed, and then centrifuged for 10 min at room temp at 2990 rpm and the upper organic phase was collected. Before GC analysis, samples were diluted 1/10 in heptanes.

The supernatant was transferred to a GC vial, in which 1 μL was used for GC analysis. Analysis was carried out on GC/FID 7890A series with a SP_2330 column. Injector and detector temperature were 250° C. and 300° C. respectively; oven temperature was held at 50° C. for 2 min, then programmed to 180° C. at a heating rate of 10° C./min, then programmed to hold for 5 min followed by an increase of 5° C./min to 240° C. Total run time was 32.5 min. Flow rates for hydrogen and air to the FID were 30 and 450 mL/min respectively. Helium as the carrier gas flowed at a rate of 1.69 mL/min and nitrogen as the make-up gas at 30 mL/min.

Example 2

Southern Blot Hybridizations Show Multiple Copies of Genes in *Camelina sativa*

As a first step to characterize genes involved in fatty acid biosynthesis, the inventors determined the copy number of FAD2 and FAE1 by Southern blot analysis. Since *C. sativa* is closely related to *Arabidopsis thaliana* (Al-Shehbaz, Beilstein et al. 2006; Beilstein, Al-Shehbaz et al. 2006; Beilstein, Al-Shehbaz et al. 2008), the inventors designed primers based on *Arabidopsis* that amplified conserved regions of FAD2 and FAE1. Using these primers, the inventors PCR amplified products of 225 base pairs (bp) (FAD2) and 403 by (FAE1) from *Arabidopsis* and from *C. sativa*. The *C. sativa* products were cloned, sequenced, and compared with *Arabidopsis* FAD2 and FAE1 sequences (TAIR 2009) to confirm their identities. The inventors used the *C. sativa* fragments as probes in Southern blot experiments (FIG. 1). Results of the Southern blots revealed three bands in *C. sativa* for both FAD2 (FIG. 1A) and FAE1 (FIG. 1B), whereas hybridization revealed only a single band in *Arabidopsis* for both genes (FIGS. 1A & B). These results suggest that FAD2 and FAE1 occur in at least three copies in *C. sativa*, while they are single copy in *Arabidopsis* (TAIR 2009). Fatty acid genes can be multi-copy in many species, including soybean (Schlueter, Lin et al. 2007), *Brassica napus* (Scheffler, Sharpe et al. 1997), olive (*Olea europaea*) (Hernandez, Mancha et al. 2005), maize (Mikkilineni and Rocheford 2003), and sunflower (Martínez-Rivas, Sperling et al. 2001). Therefore, the inventors designed a probe for Southern blot hybridization of the gene LEAFY (LFY), which is known to be single copy in a wide variety of species from several plant families (Frohlich and Estabrook 2000). Three bands were observed following hybridization using the LFY probe, suggesting LFY also exists as three copies in *C. sativa* (FIG. 1C).

Example 3

Copies of *C. sativa* FAD2 and FAE1 are Highly Similar to Each Other and to their Putative Orthologs from *Arabidopsis*

The inventors cloned and sequenced the full length genomic and cDNA sequences of *C. sativa* FAD2 and FAE1 (SEQ ID NOs: 1 to 6). Using primers designed from *Arabidopsis* FAD2 and *Crambe abyssinica* FAE1, the inventors PCR amplified a band of approximately 1.2 kb for FAD2 and 1.5 kb for FAE1 from C. sativa. For each gene, the inventors sequenced more than 60 clones. Three different versions of both FAD2 and FAE1 were recovered and designated A, B, and C. It should be noted that the A, B, and C copies were named independently for FAD2 and FAE1, and thus are not associated with a particular genome.

The three copies of C. sativa FAD2 are 1155 by long, lack introns in the coding regions, are 97% identical at the nucleotide level, and encode proteins that are 99% identical in sequence (Table 1). One of the FAD2 copies contains a BamHI site, and thus this copy likely produced the ~1.3 kb fragment in the Southern blot hybridization of FAD2 (FIG. 1A; BamHI+EcoRI digest). The C. sativa nucleotide sequences of FAD2 are greater than 93% identical to Arabidopsis FAD2, and the putative encoded proteins from the two species share greater than 96% identity (Table 1).

An approximately 1.4 kb intron found within the 5' untranslated region was also recovered from all three copies of C. sativa FAD2. A similarly sized intron is present in Arabidopsis (TAIR 2009) and in Sesamum indicum (sesame) where it has been shown to be involved in regulating FAD2 expression (Kim et al. 2006).

All three copies of FAE1 in C. sativa are 1518 by long and lack introns. When the nucleotide sequences and the putative encoded proteins of the three copies are compared they are more than 96% identical (Table 1). In comparison to Arabidopsis, the nucleotide sequences are more than 90% identical, while the encoded proteins are more than 91% identical (Table 1). Thus, the three copies of C. sativa FAD2 and the three copies of FAE1 are highly similar to each other and to their putative orthologs from Arabidopsis.

Example 4

Alignments of FAD2 and FAE1 Protein Sequences from Several Species Reveals Conserved and Non-Conserved Domains The inventors aligned translated amino acid sequences from the three copies of C. sativa FAD2 with the FAD2 protein sequences from Arabidopsis; Brassica rapa, an agronomically important member of the Brassicaceae family; Glycine max, an agronomically important dicot; and Zea mays, an agronomically important monocot (FIG. 2A). All three copies of C. sativa FAD2 have the three conserved HIS boxes found in all membrane-bound desaturases (Tocher D R 1998) as well as the ER localization signal described by McCartney et al (Belo, Zheng et al. 2008) (McCartney, Dyer et al. 2004). Furthermore, the conserved amino acids identified in an alignment of the FAD2 sequences from 34 different species [49] are also present in C. sativa with the exception of a positively-charged histidine at position number 44, which is substituted by a polar, uncharged glutamine in C. sativa. When the inventors amplified the FAD2 gene from several species in the tribe Camelineae (Table 2) and aligned the translated amino acid sequences, the inventors found that the FAD2 proteins from Capsella rubella, Camelina microcarpa, Camelina laxa, and one copy from Camelina rumelica contain a glutamine at amino acid position 44, while the FAD2 proteins from Arabidopsis lyrata, Camelina hispida, and a second copy from Camelina rumelica contained a histidine (data not shown).

TABLE 1

Nucleotide and Amino Acid identity of Camelina sativa and Arabidopsis thaliana FAD2 and FAE1 genes.

| Gene | | % Nucleotide Identity* | | | | % Amino Acid Identity | | | |
|---|---|---|---|---|---|---|---|---|---|
| | | AtFAD2 | CsFAD2A | CsFAD2B | CsFAD2C | AtFAD2 | CsFAD2A | CsFAD2B | CsFAD2C |
| FAD2 | AtFAD2 | 100 | 93.6 | 93.8 | 93.4 | 100 | 96.9 | 96.6 | 96.4 |
| | CsFAD2A | | 100 | 97.3 | 98.3 | | 100 | 99.0 | 99.5 |
| | CsFAD2B | | | 100 | 97.7 | | | 100 | 99.5 |
| | CsFAD2C | | | | 100 | | | | 100 |
| | | AtFAE1 | CsFAE1A | CsFAE1B | CsFAE1C | AtFAE1 | CsFAE1A | CsFAE1B | CsFAE1C |
| FAE1 | AtFAE1 | 100 | 90.7 | 91.2 | 91.0 | 100 | 91.9 | 91.7 | 91.7 |
| | CsFAE1A | | 100 | 97.8 | 96.8 | | 100 | 97.6 | 96.4 |
| | CsFAE1B | | | 100 | 97.2 | | | 100 | 96.8 |
| | CsFAE1C | | | | 100 | | | | 100 |

*Nucleotide identity is in coding region only.

TABLE 2

Plant species and sources

| Species | Source | Catalogue number |
|---|---|---|
| Camelina sativa Cs32 | USDA | PI 311732 |
| Camelina sativa Cs11 | Ames | 26668 |
| Arabidopsis thaliana, ecotype Col-0 | ABRC | CS28166 |
| Arabidopsis lyrata | ABRC | CS22696 |
| Camelina laxa | USDA | PI 650132 |
| Camelina microcarpa | wild collection; Harvard Herbarium | number "01-22" |
| Camelina microcarpa | USDA | PI 633188 |
| Capsella bursa-pastoris | Wild collection; Harvard Herbarium collection | number "08-188" |
| Capsella rubella | ABRC | CS22561 |
| Camelina hispida var grandiflora | Ames | 21324 |
| Camelina alyssum | Ames | 26658 |
| Camelina rumelica | Ames | 21327 |

TABLE 3

Primers used for amplification of genomic regions of C. sativa

| | Primer Name | Primer sequence (5'-3') |
|---|---|---|
| Southern analysis of FAD2 | FAD2_631F | TCAACAACCCTCTTGGACGCATCA (SEQ ID NO: 13) |
| | FAD2_832R | CTTGTGCAGCAGCGTAACGGTAAA (SEQ ID NO: 14) |
| Southern analysis of FAE1 | AtFAE1 probe F | AGACGGTCCAAGTACAAGCTAGTTC (SEQ ID NO: 15) |
| | AtFAE1 probe R | CCAAATCTATGTAACGTTGATCT (SEQ ID NO: 16) |
| Southern analysis of LFY | AtLFY probe F | GATGCGGCGGGGAATAACGGCGGAG (SEQ ID NO: 17) |
| | AtLFY probe R | CCTGAAGAAGGAACTCACGGCATT (SEQ ID NO: 18) |
| Cloning of FAD2 coding region | AtFAD2_start | AACATGGGTGCAGGTGGAAGAATG (SEQ ID NO: 19) |
| | AtFAD2_stop2 | TCATAACTTATTGTTGTACCAGTAC (SEQ ID NO: 20) |
| Cloning of FAE1 coding region | CaFAE1 start | ATGACGTCCATTAACGTAAAGCTC (SEQ ID NO: 21) |
| | CaFAE1 stop | TTAGGACCGACCGTTTTGGGC (SEQ ID NO: 22) |
| KCS17-FAE1 intergenic region "A" and "C" (initial clones) | AtKCS F | GGGTGGCTCTTCGCAATGTCGAGCCC (SEQ ID NO: 23) |
| | CsFAE1 5' RACE | GAGGCTTTTCCGGCAAGTAACGCCG (SEQ ID NO: 24) |
| KCS17-FAE1 intergenic region "A" | AtKCS cons F | GGTATGAATTGGCTTACACGGAAG (SEQ ID NO: 25) |
| | CsKCSA_F | TATGAATTGGCTTACACGGAAGCC (SEQ ID NO: 26) |
| | CsFAE1A_R2 | TATATTGCCAATATAAGTATTAAAGGTCC (SEQ ID NO: 27) |
| KCS17-FAE intergenic region "B" | AtKCS cons F | GGTATGAATTGGCTTACACGGAAG (SEQ ID NO: 28) |
| | CsFAE1B_R | TATATTGCCAATATAAGTATTAAAGGTCC (SEQ ID NO: 29) |
| KCS17-FAE intergenic region "C" | AtKCS cons F | GGTATGAATTGGCTTACACGGAAG (SEQ ID NO: 30) |
| | CsFAE1C_R | GGTAGAGATCGTTTGTGGTAAGCG (SEQ ID NO: 31) |
| Camelinae FAD2 | CsFAD2 start | ATGGGTGCAGGTGGAAGAATGC (SEQ ID NO: 32) |
| | CsFAD2 stop | TCATAACTTATTGTTGTACCAGTACACACC (SEQ ID NO: 33) |
| Camelinae FAE1 | CsFAE1 start | ATGACGTCCGTTAACGCAAAGCTC (SEQ ID NO: 34) |
| | CsFAE1 stop | TTAGGACCGACCGTTTTTGACATG (SEQ ID NO: 35) |

TABLE 4

Primers used for qPCR analyses

| | Primer or Probe Name | Sequence (5'-3') |
|---|---|---|
| qPCR of CsACTIN | CsACT For | ACA ATT TCC CGC TCT GCT GTT GTG (SEQ ID NO: 36) |
| | CsACT Rev | AGG GTT TCT CTC TTC CAC ATG CCA (SEQ ID NO: 37) |

TABLE 4-continued

Primers used for qPCR analyses

|  | Primer or Probe Name | Sequence (5'-3') |
|---|---|---|
|  | CsACT probe | FAM- TGT TTC AAA CGC TCT ATC CCT CGC TC -IABLFQ (SEQ ID NO: 38) |
| qPCR of CsFAD2 | CsFAD2 A For1 | CTG CGA GAA ACC ACC GTT CAC CC (SEQ ID NO: 39) |
|  | CsFAD2 all Rev | CAC GAG TAG TCA ACG AGG TAA ACC GG (SEQ ID NO: 40) |
|  | CsFAD2 all probe | FAM- CCA CTT CTA TTC CCA TCT CCA ACA CAA CC -IABLFQ (SEQ ID NO: 41) |
| qPCR of CsFAE1 | CsFAE1 all For | AAC CTT TGC TTG TTT CCG TTA ACG GC (SEQ ID NO: 42) |
|  | CsFAE1 all Rev | CAC GAG TAG TCA ACG AGG TAA ACC GG (SEQ ID NO: 43) |
|  | CsFAE1 all probe | FAM- CCA CTT CTA TTC CCA TCT CCA ACA CAA CC -IABLFQ (SEQ ID NO: 44) |

TABLE 5

SNPs distinguishing each copy of FAD2 and FAE1

| SNP_ID | Nucleotide position from beginning of coding region |
|---|---|
| FAD2_A4 | 51 |
| FAD2_A2 | 453 |
| FAD2_A6 | 549 |
| FAD2_B4 | 288 |
| FAD2_B5 | 687 |
| FAD2_B8 | 1109 |
| FAD2_C1 | 78 |
| FAD2_C5 | 615 |
| FAD2_C3 | 966 |
| FAE1_A4 | 624 |
| FAE1_A3 | 1368 |
| FAE1_A7 | 1475 |
| FAE1_B4 | 414 |
| FAE1_B5 | 783 |
| FAE1_B8 | 1438 |
| FAE1_C1 | 336 |
| FAE1_C2 | 721 |
| FAE1_C7 | 1419 |
| FAE1_ABC1 | 104 |

Figure 2B:
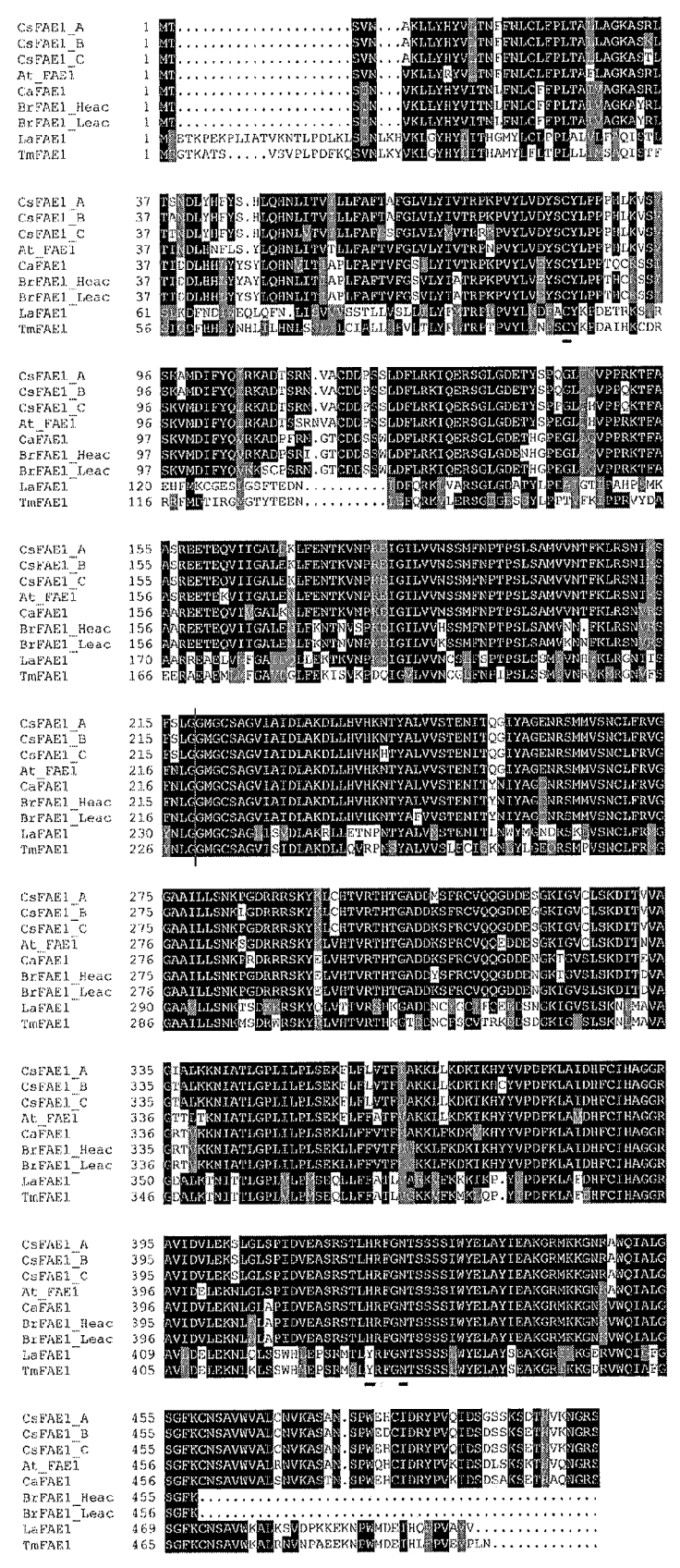

The inventors aligned the translated amino acid sequences from the three copies of C. sativa FAE1 with the seed-specific FAE1 proteins from A. thaliana, Crambe abyssinica, a high and low erucic acid Brassica rapa, Limnanthes alba, and Tropaeolum majus (FIG. 2B). L. alba and T. majus are both in the order Brassicales and their seeds accumulate high levels of very long chain fatty acids (Cahoon, Marillia et al. 2000; Mietkiewska, Giblin et al. 2004). Four conserved histidine residues and six conserved cysteine residues, including the active site at cysteine 223, as well as an asparagine residue at 424 required for FAE1 activity were previously identified by Ghanevati and Jaworski (Ghanevati and Jaworski 2001; Ghanevati and Jaworski 2002). All conserved residues were found to be present in all three copies of C. sativa FAE1. More differences were apparent between the three C. sativa FAE1 sequences and the other FAE1 sequences than observed in the FAD2 comparison (FIGS. 2A and B), an observation consistent with the level of amino acid identity seen between Arabidopsis and C. sativa FAD2 versus FAE1 (Table 1).

Example 5

Figure 3:
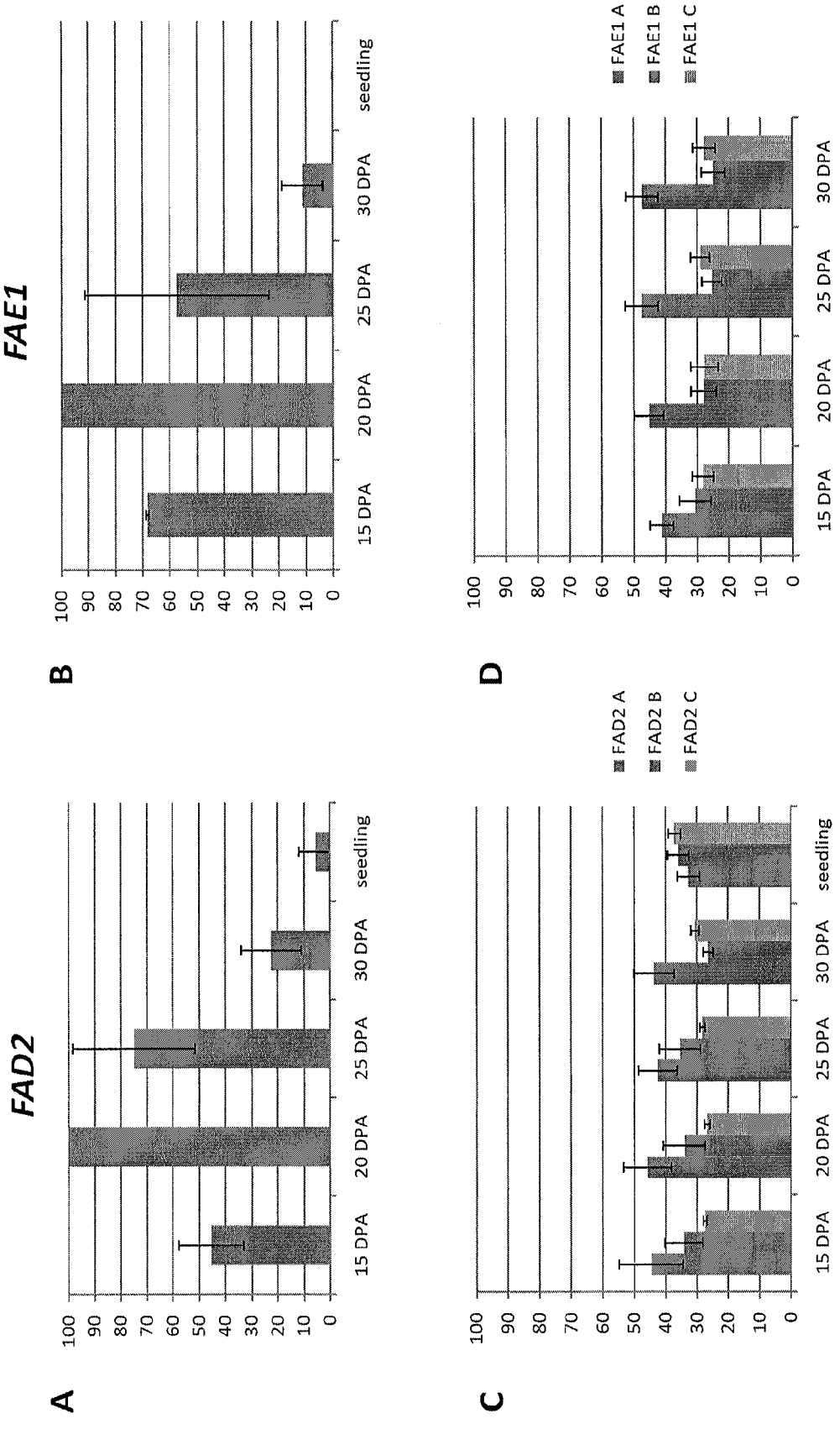
FIG. 3 depicts FAD2 and FAE1 Expression in Developing Seeds. Relative combined expression of all three copies of (A) FAD2 and (B) FAE1 measured by real time quantitative PCR at 15, 20, 25, and 30 days post anthesis (DPA) and in 2 week old seedlings. The 20 DPA sample, which expressed FAD2 and FAE1 at the highest amount, was used as the calibrator. Error bars represent the standard deviation of 3 replicate experiments. Sequenom SNP analysis demonstrating the expression of each version of (C) FAD2 or (D) FAE1 relative to the other versions. Error bars represent the standard deviation of three (for FAD2) or four (for FAE1) SNP analyses. Because FAE1 is not expressed in *C. sativa* seedlings (B), the relative expression of the 3 copies of FAE1 in seedling tissue is not shown (D).

All Three Copies of FAD2 and FAE1 are Expressed in Developing Seeds of C. sativa The conservation of amino acids as well as the presence of the 5' regulatory intron in FAD2 suggests that all three copies of FAD2 and of FAE1 could be functional. To determine whether these genes are also expressed, the inventors first evaluated total FAD2 and FAE1 gene expression in developing seeds and in seedling tissue using quantitative real time PCR (qPCR) with primer/probe combinations designed to detect all three copies of each gene. FAD2 expression in seedling tissue is present but minimal (0.4% of that seen in seeds at 20 days post-anthesis (DPA)), while FAE1 expression could not be detected in seedlings (FIGS. 3A and B). In developing seeds, both FAD2 and FAE1 expression peaks at 20 DPA and is reduced by 30 DPA (FIGS. 3A and B). In Arabidopsis, FAD2 peaks earlier and decreases sooner than FAE1 (Ruuska, Girke et al. 2002).

The inventors wondered whether the expression of each of the FAD2 and FAE1 copies present in C. sativa are equally or differentially expressed in the seed. Duplicated genes are frequently silenced either throughout the plant or in a tissue-specific manner (Comai, Tyagi et al. 2000; Kashkush, Feldman et al. 2002; He, Friebe et al. 2003; Adams, Percifield et al. 2004); hence the inventors hypothesized that one or more of the copies of each gene could be significantly down-regulated. The inventors used the Sequenom MassARRAY™ method for determining allele-specific expression of a gene (Park, Correll et al. 2004) to evaluate the relative expression of each of the copies of FAD2 and FAE1. The inventors identified at least three single nucleotide polymorphisms (SNPs) specific to each of the FAD2 A, B, and C and the FAE1 A, B, and C copies and then calculated the frequency of each SNP in seed cDNA. Controls consisting of the cloned FAE1 A, B, and C copies combined to known frequencies showed that the method is greater than 80% accurate (Table 6). No evidence of silencing of any particular copy of either FAE1 or FAD2 was discovered. The inventors did observe differential expression, especially of FAE1 A, which accounts for approx 40-50% of FAE1 expression in seeds at 20-30 DPA (FIGS. 3C and D).

Six cloned DNA positive controls were also included in the analysis and the relative amount of "B" version in each measured with the FAE1_B5 SNP and all 3 versions with the FAE1_ABC SNP:

TABLE 6

Expression level of FAE1 genes relative to FAE1 B

|  |  | FAE1_B5 | FAE1 ABC | | |
|---|---|---|---|---|---|
|  |  | relative B | relative A | relative B | relative C |
| C1 | 100% Version A | 0.00 | 1 | 0 | 0 |
| C2 | 100% Version B | 1.00 | 0 | 1 | 0 |
| C3 | 100% Version C | 0.00 | 0 | 0 | 1 |
| C4 | 60% A, 20% B, 20% C | 0.20 | 0.59 | 0.20 | 0.22 |
| C5 | 20% A, 60% B, 20% C | 0.54 | 0.29 | 0.48 | 0.23 |
| C6 | 20% A, 20% B, 60% C | 0.20 | 0.24 | 0.28 | 0.48 |

As the results indicate, all three FAE1 genes are expressed in the seed. A dosage effect may still be expected, however, since FAE1 B appears to account for only approximately 25-30% of FAE1 expression in the seeds. A mutation in FAE1 A would be expected to have a greater effect on fatty acids composition in the seeds since it accounts for ~41-48% of FAE1 expression.

Example 6

Characterization of Sequences Upstream of *C. sativa* FAE1 and Downstream of *C. sativa* FAD2 Suggests Colinearity with *A. thaliana*

Figure 4:
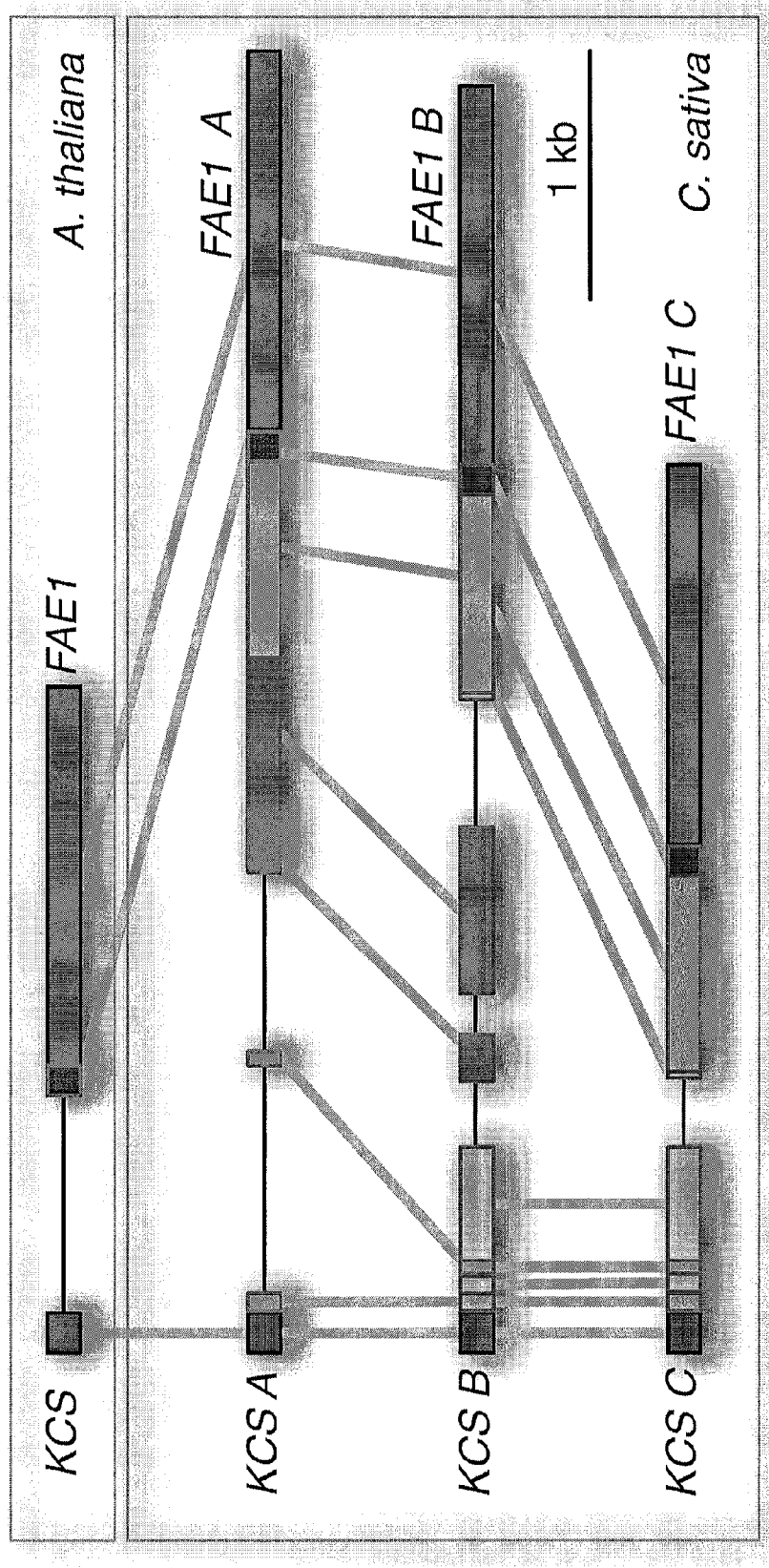
FIG. 4 depicts structure and conservation of the KCS17-FAE1 intergenic region in *Camelina sativa*. The three putative homologous regions in allohexaploid *C. sativa* are aligned to the orthologous region of *Arabidopsis* to display blocks of homology identified on a dot matrix by perfect conservation of a sliding window of 9 bases. The KCS17 and FAE1 gene, respectively blue and red, flank a variable region in which conserved blocks common to two or more genomes are marked by different shades of brown. Lined regions display reduced or no conservation. The large variation in the intergenic region of the triplicated KCS17-FAE1 DNA of *C. sativa* is consistent with independent evolution before reunion of diverged genomes by allohexaploidization.

To investigate whether the different copies of *C. sativa* FAD2 and FAE1 are the result of allelic variation or are in fact independent loci, the inventors obtained sequence from the region upstream of FAE1 and downstream of FAD2. Assuming colinearity between *C. sativa* and *Arabidopsis* for the region around FAE1, the inventors PCR amplified the region 5' to FAE1 using a forward primer for the upstream gene KCS17 with reverse primers for *C. sativa* FAE1. The resulting sequences obtained for the putative *C. sativa* KCS17 were highly similar to the last 189 by of *Arabidopsis* KCS17, suggesting that the inventors had in fact amplified the orthologous *C. sativa* region upstream of FAE1, confirming colinearity between the two species. The inventors then used a dot plot (see details for Nucleic Acid Dot Plots in Maizel et al., 1981; Pustell et al. 1982; Quigley et al., 1984) to compare the three *C. sativa* upstream sequences to each other and to *Arabidopsis* with parameters set for perfect match on a sliding window of 9 bases. The coordinates from the dot plot were used to define blocks of homology between *Arabidopsis* and the three *C. sativa* copies (FIG. 4). The results show a variable intergenic region containing conserved blocks common to two or more genomes.

Co-linearity with *Arabidopsis* was also found for a region downstream of FAD2 containing the ACTIN11 (ACT11) gene for two out of the three *C. sativa* copies (data not shown). For the third copy, the region downstream of FAD2 A could have been missed if the length of the amplified product was too large. Alternatively, the region downstream of FAD2 A might not exhibit colinearity with *Arabidopsis*.

Example 7

Figure 5:
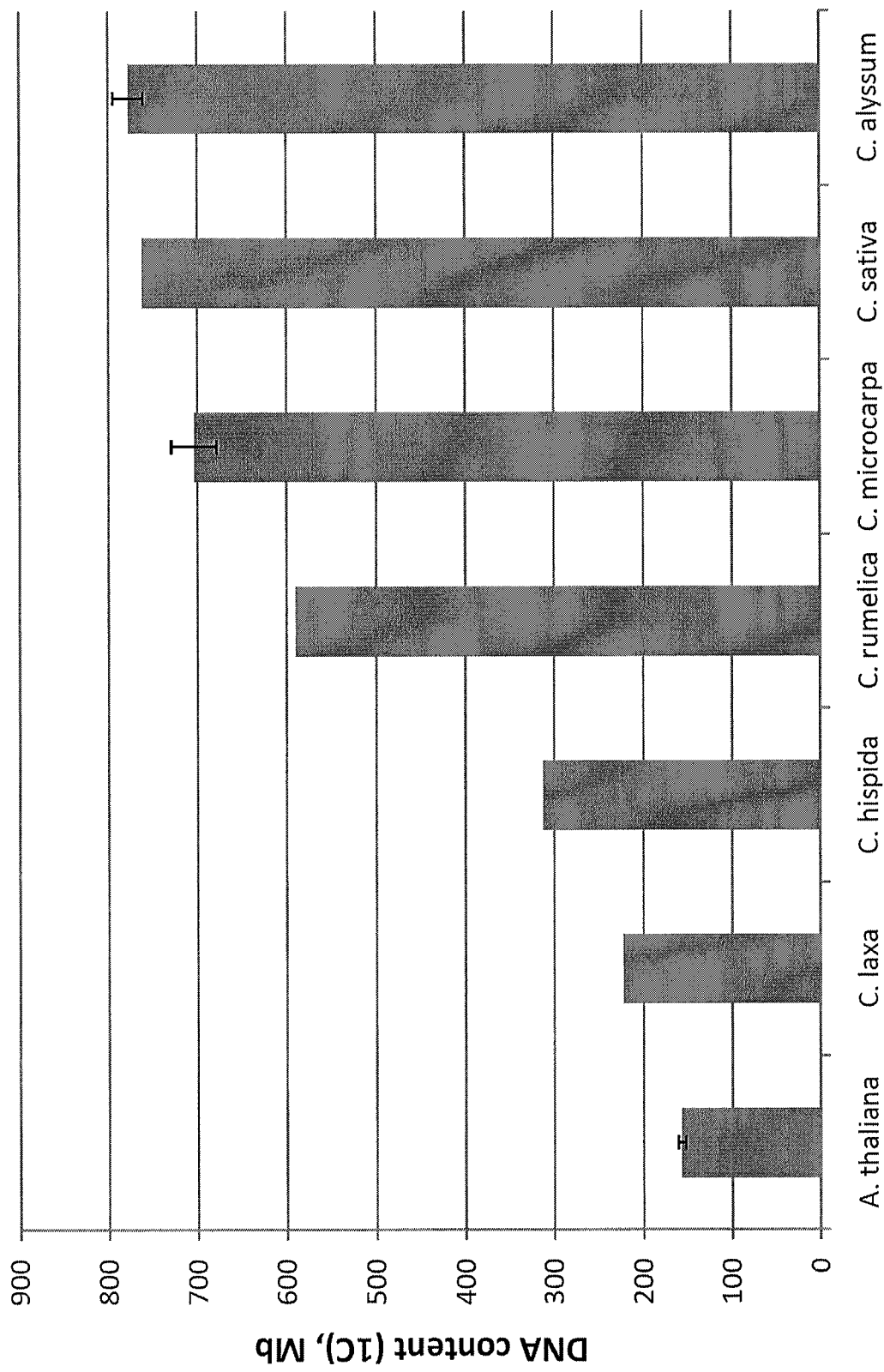
FIG. 5 depicts genome content of *Camelina* species. 1C nuclei were stained with propidium iodide and analyzed by flow cytometry. Error bars represent the standard deviation of 2-4 replicate samples.

The Genomes of *C. sativa*, *C. alyssum*, and *C. microcarpa* are Larger than the Genomes of other *Camelina* Species The inventors calculated DNA content in several accessions of *C. sativa* and related species from flow cytometry analyses using propidium iodide-stained nuclei. The inventors used *Arabidopsis* accession Col-0 (2×) and its tetraploid (4×) derivative as genome size standards. *C. sativa*, *C. alyssum*, and *C. microcarpa* diploid (2C) genomes had a haploid content between 650 and 800 Mb (FIG. 5). *C. sativa* accessions uniformly displayed a genome size close to 750 Mb. North American isolates of *C. sativa*, *C. alyssum*, and *C. microcarpa* have reported chromosome counts of n=20 (Francis and Warwick 2009). The genomes of *C. rumelica* (600 Mb), *C. hispida* (300 Mb) and *C. laxa* (210 Mb) are smaller than those of *C. sativa*, *C. alyssum*, and *C. microcarpa*. Chromosome counts of both n=6 (Baksay 1957; Brooks 1985) and n=12 (Maassoumi 1980) have been recorded for *C. rumelica*, while only a single count of n=7 exists for *C. hispida* (Maassoumi 1980). To our knowledge, no published counts exist for *C. laxa*.

Example 8

Figure 6A:
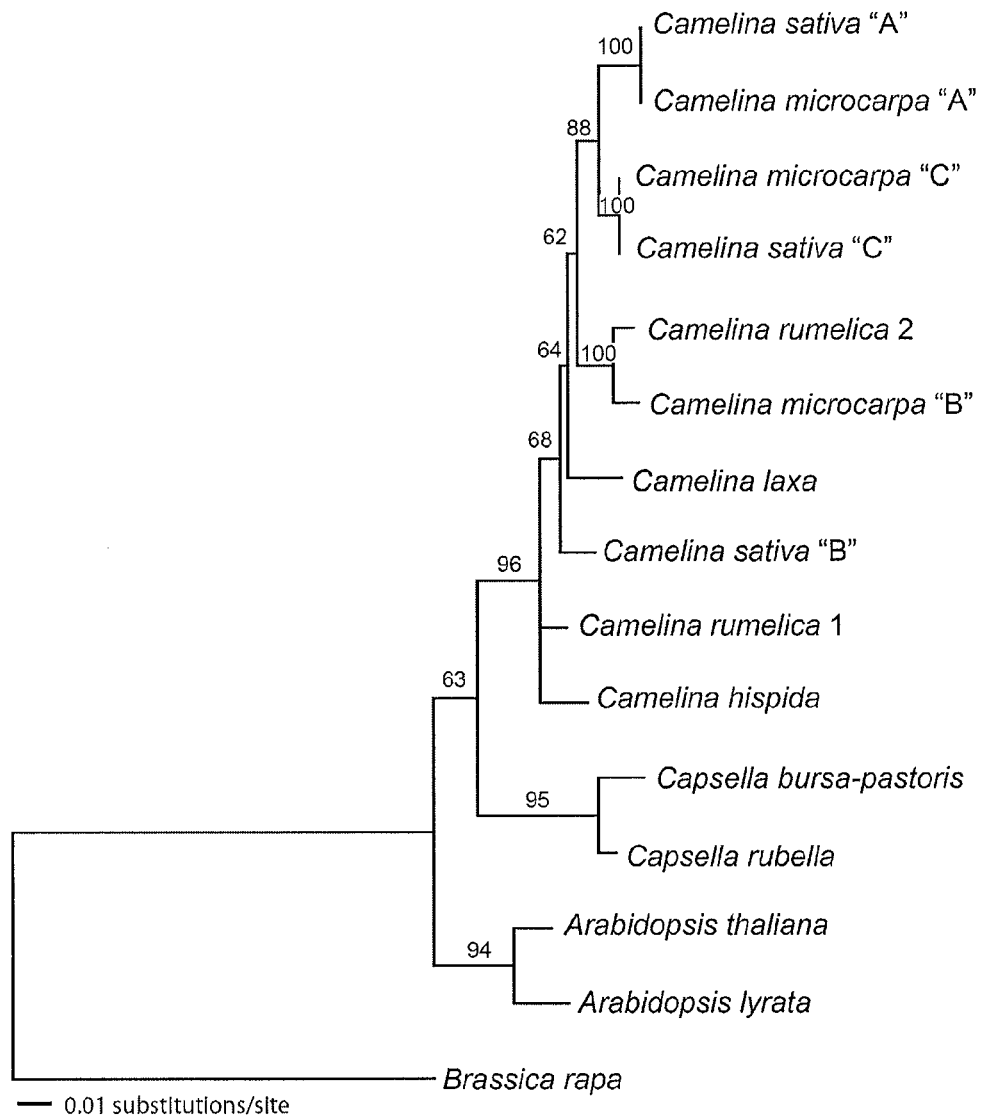
FIG. 6 depicts phylogenetic analyses of Camelineae FAD2 and FAE1. Maximum-likelihood trees showing branch length and bootstrap support (100 bootstrap replicates) for (A) 15 FAD2 sequences from species from the tribe Camelineae calculated using the TVM+I+Γ model in PAUP* and rooted with *Brassica rapa* FAD2 (−LnL 3665.277); and for (B) 15 FAE1 sequences from species from the tribe Camelineae calculated using the HKY+I+Γ model in PAUP* and rooted with *Crambe abyssinica* FAE1 (−LnL 5051.552). Sequences obtained from Genbank are *Capsella bursa-pastoris* FAD2 [Genbank: DQ518293], *Arabidopsis thaliana* FAD2 [Genbank: NM_112047], *Brassica rapa* FAD2 [Genbank: AJ459107], *Arabidopsis thaliana* FAE1 [Genbank: NM_119617], and *Crambe abyssinica* FAE1 [Genbank: AY793549].
Figure 6B:
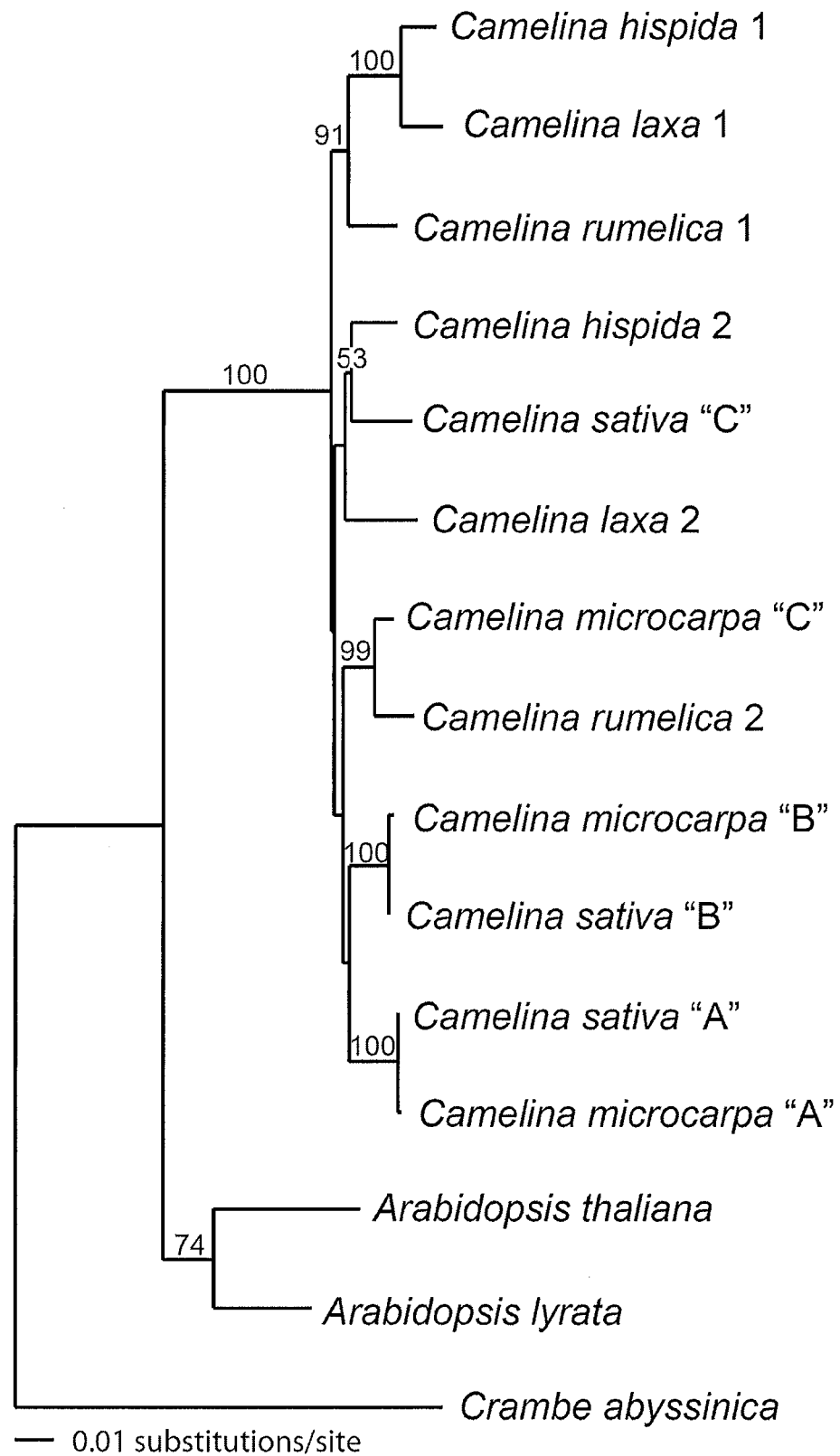

Phylogenetic Analysis of FAD2 and FAE1 Indicate that *C. sativa* and *C. microcarpa* are Closely Related To understand the duplication history of the multiple FAD2 and FAE1 copies recovered from *C. sativa*, the inventors amplified the FAD2 and FAE1 genes from several species in the tribe Camelineae (Table 2), and inferred phylogeny for each gene. The sampling of taxa chosen allowed the inventors to test whether FAD2 and FAE1 duplication events occurred after *Camelina* diverged from its closest relatives or within the genus. Results from the evaluation of 55 different models of sequence evolution using Modeltest 3.7 (Posada and Crandall 1998) indicated that the FAD2 sequence data are best described by the TVM+I+Γ model, while the FAE1 data are best described by the HKY+I+Γ model. Likelihood phylogenetic analyses in PAUP*4.0 (Swofford 2001) produced a single FAD2 tree (−LnL 3665.277; FIG. 6A), and a single FAE1 tree (−LnL 5051.552; FIG. 6B).

Phylogenies inferred from FAD2 and FAE1 data indicate a history of duplication for both markers. Both *C. microcarpa* and *C. sativa* have three distinct copies of FAD2 and FAE1. Moreover, for FAD2, the A and C copies from these two species are monophyletic with strong (100%) bootstrap support (bs); for FAE1 the A and B copies from these species are strongly monophyletic (100% bs). In contrast, neither the FAD2 B copies of *C. sativa* and *C. microcarpa*, nor the FAE1 C copies of these species form a monophyletic group with each other. Instead, results indicate that *C. rumelica* has two distinct copies of FAD2 and that one of these copies (FAD2-2) is strongly monophyletic with *C. microcarpa* FAD2 B. The inventors recovered only a single FAD2 copy for *C. laxa* and *C. hispida*. In contrast, at least two distinct copies of FAE1 were recovered from all sampled *Camelina* species. The FAE1-1 copy of *C. laxa*, *C. hispida*, and *C. rumelica* form a monophyletic group (91% bs), with the former two species sister to one another with strong support (100% bs). Similar to the results from FAD2, *C. rumelica* FAE1-2 is sister to one of the *C. microcarpa* copies (FAE1 C; 99% bs). Neither the *C. sativa* FAD2 B copy, nor the *C. sativa* FAE1 C copy, shows a well supported sister relationship to other FAD2 or FAE1 sequences. However, in the FAE1 tree, *C. sativa* FAE1 C is very weakly supported as sister to *C. hispida* FAE1-2 (53%). Finally, all recovered FAD2 and FAE1 copies from species of the genus *Camelina* are monophyletic and sister to other sampled members of the tribe Camelineae, consistent with phylogenies based on other markers (Beilstein, Al-Shehbaz et al. 2006; Beilstein, Al-Shehbaz et al. 2008).

Example 9

*Camelina* Breeding Program

Since *Camelina* has not been intensively bred and the germplasm is somewhat limited genetically, the inventors established three strategies for long term development of *Camelina* germplasm. These three, non-mutually exclusive strategies for *Camelina* germplasm enhancement include: transgenic approach, classical and molecular breeding, and mutation breeding. The long term goals are to achieve increased yield, increased seed oil content and improved fatty acid composition (e.g., higher percentage oleic acid (18:1), which is an optimal fatty acid for biodiesel and/or lower percentage of very long chain fatty acids (VLCFA, such as 20:1, 20:2, 22:1, etc)).

In the transgenic approach, REV and KRP yield technology (US 2008/263727 and US 2007/056058, incorporated by reference in their entireties) can be introduced into *Camelina* to obtain events with increased seed yield or seed size, agronomic properties beneficial to obtaining *Camelina* germplasm with increased oil yield per unit land for biofuel purposes. Efficient transformation of *Camelina* has been established before (WO 2009/117555, incorporated by reference in its entirety).

In the classical and molecular breeding approach, broad field evaluations of more than 100 accessions of *Camelina* in Northern United States and Canada was initiated across multiple field locations and over multiple years. Different accessions were evaluated for seed yield, oil yield, fatty acid composition, and agronomic performance under different environmental conditions. Superior lines with higher yield identified in the evaluations are used in the breeding program. In addition, molecular breeding studies are also in progress. Preliminary results show that existing *Camelina* cultivars are closely related, as indicated by AFLP analysis in which 379 markers were scored. Jaccard analysis suggested there is more than 90% genetic similarity across existing cultivars. Therefore, there is much room for improvement of *Camelina* germplasm, which will be realized by classical and molecular breeding programs. In the mutation breeding approach, an EMS mutagenized population was created in a selected *Camelina* cultivar, and Targeting Induced Local Lesions In Genomes (TILLING®) method was used to find mutations in known gene sequences. Especially, mutations with altered fatty acid compositions and improved yield as expressed in amount of oil produced per acre are of the most interest. M2 plants/M3 seed were harvested, and gene sequences for select targets were isolated and characterized. Preferred fatty acids include 16:1 and 18:1 monounsaturated fatty acids, since they have the best combination of proper cetane number, cloud point, oxidative stability, and less NOx emissions, as compared to saturated fatty acids (e.g., 12:0, 14:0, 16:0, 18:0, 20:0, and 22:0), or poly unsaturated fatty acids (e.g., 18:2, 18:3).

Example 10

TILLING® Method to Isolate *Camelina* Mutants in FAD2 and FAE1 Genes

As described above, the goal is to improve *Camelina sativa* fatty acid composition for biodiesel. For example, since oleic acid (18:1) is optimal for fatty acid biodiesel, one specific goal is to increase 18:1 and decrease polyunsaturated fatty acids and long chain fatty acids. One way is to lower the activity of FAD2 and of FAE1, as indicated by the fatty acids synthesis pathway shown in FIG. 7.

Figure 8:
FIG. 8 depicts an exemplary field growth of EMS mutagenized *Camelina* M2 population (upper-panel), and exemplary mutant M2 plants with morphological changes (lower-panel).
Figure 8:
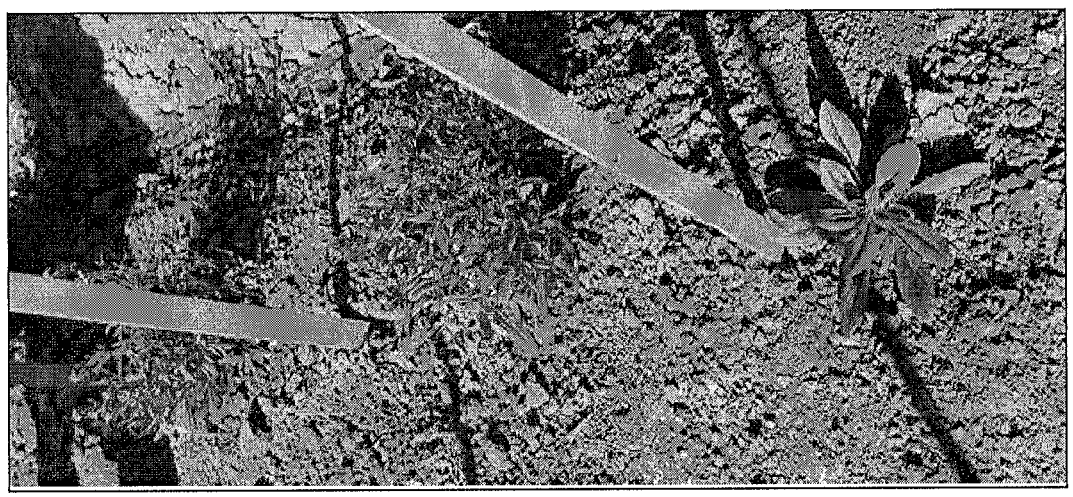

An EMS mutant library has been created in *Camelina sativa* line CS32. This library has a population of about 8000 mutants and was used to screen for mutants of FAD2 genes (FIG. 8). Initial TILLING® using primers designed to the three FAD2 genes yielded mutants in all three FAD2 genes. Later, TILLING® using primers designed to the three FAE1 genes also yielded mutants in all three FAE1 genes. Lu et al (*Camelina sativa*: A Potential Oilseed Crop for Biofuels and Genetically Engineered Products, Information Systems for Biotechnology New Report, January 2008) describes a preliminary mutant screen where a random screen was carried out for fatty acid composition *Camelina* mutant using gas chromatography (GC). The TILLING® method of the present invention is superior to this because it is not necessary to GC screen thousands of mutants; rather, mutants in known fatty acid genes are identified (Hutcheon et al., TILLING® for Altered Fatty Acid Profiles in *Camelina sativa*, July 2009, American Society of Plant Biologists Annual Meeting, which is herein incorporated by reference in its entirety for all purposes). Also the identification of *Camelina* sequences allows for the design of gene-specific TILLING® primers which can make it much easier to get mutations in all three versions of any given gene, FAD2 or FAE1.

Figure 9:
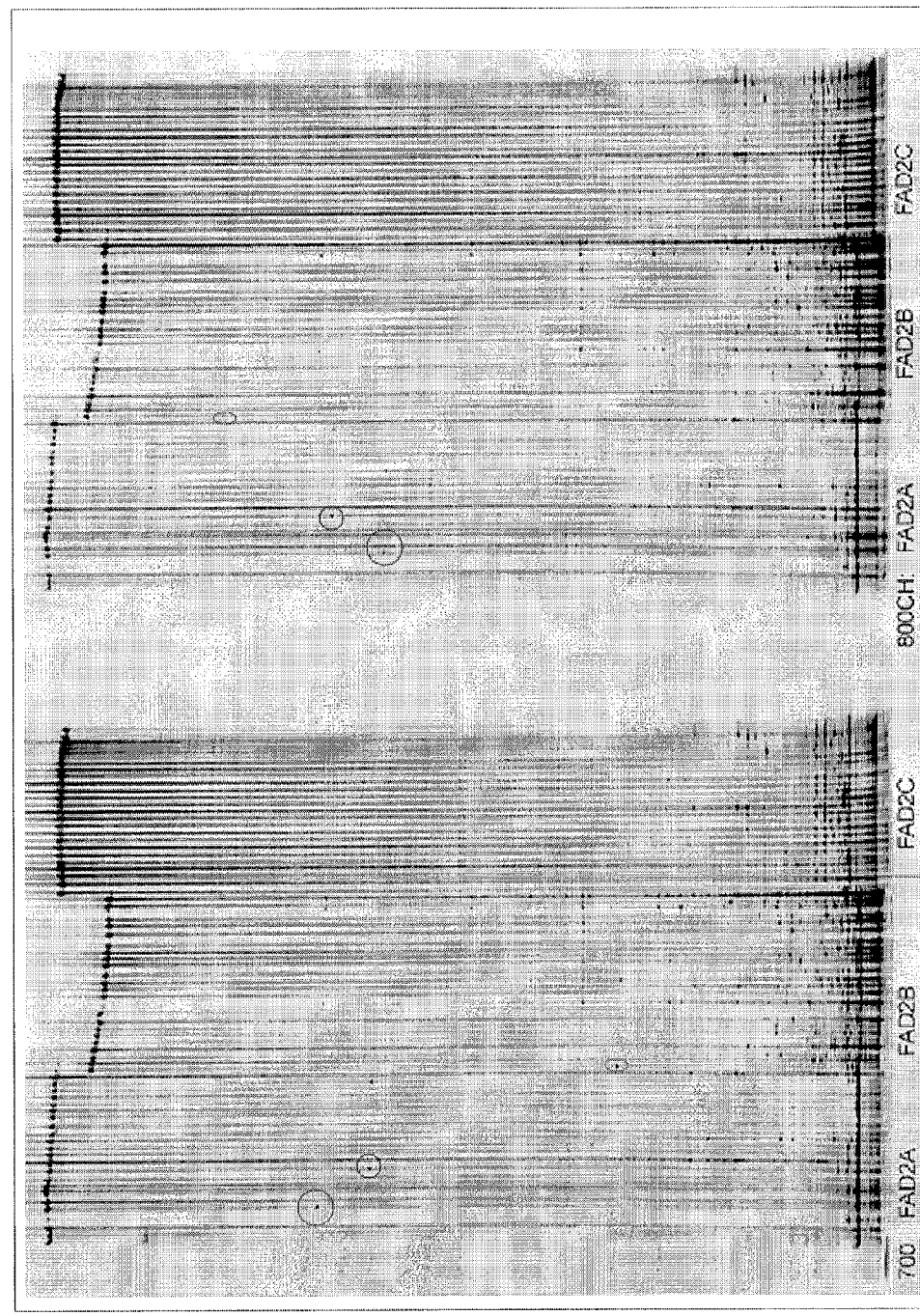
FIG. 9 depicts an exemplary LI-COR® gel identifying mutants in *Camelina* FAD2 genes.
Figure 10:
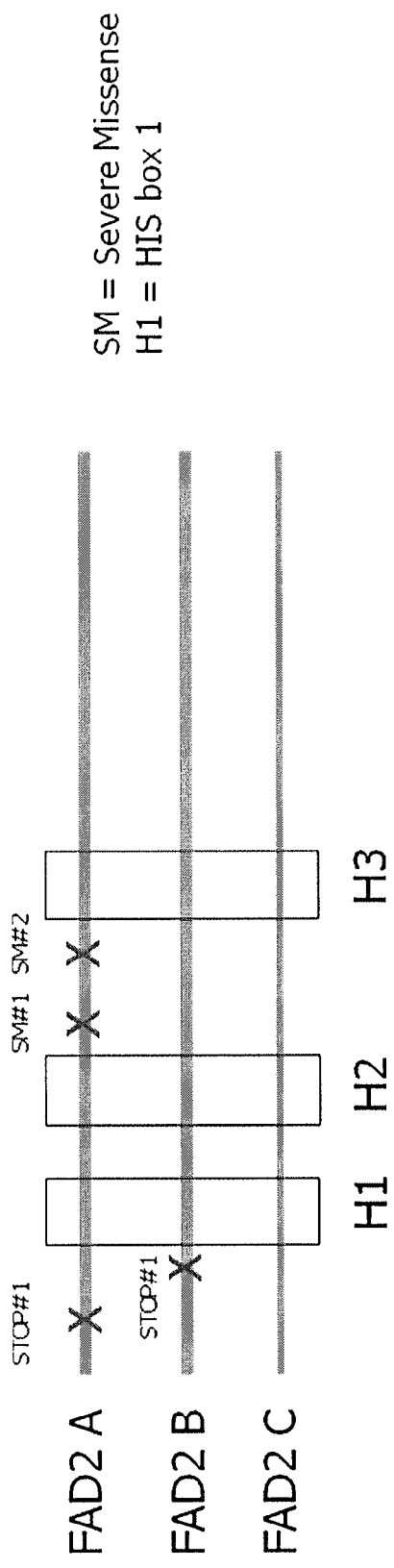
FIG. 10 depicts proximate locations of mutations in FAD2 A and B, which were used in the preliminary GC analysis. "H" identifies a His box.

A non-limiting exemplary protocol of TILLING® is described below:

1. Seeds are mutagenized to induce point mutations throughout the genome.
2. A founder population is grown from mutagenized seeds.
3. Founder population is self-fertilized to produce a crossed population.
4. DNA samples from the crossed population are collected in 96-well plates and seeds from the crossed population are stored.
5. Up to eight 96-well plates are pooled into one and the samples (768) subjected to PCR with two gene-specific primers labelled with different IRDye® infrared dyes.
6. Resulting amplicons are heated and cooled, resulting in heteroduplexes between wild type and mutant samples.
7. CEL I nuclease is used to cleave at base mismatches.
8. Samples are denatured and electrophoresed on a LI-COR® DNA Analysis System.
9. In lanes that have a mutation in the pool, a band will be visible below the wild type band on the IRDye® 700 infrared dye image. A counterpart band will be visible in the same lane on the IRDye® 800 infrared dye image. This band is the cleavage product labeled with IRDye® 800 infrared dye from the complementary DNA strand. The sum of the length of the two counterpart bands is equal to the size of the amplicon, which makes it easy to distinguish mutations from amplification artifacts. An exemplary LI-COR gel identifying mutants in *Camelina* FAD2 genes is shown in FIG. 9.

10. After detection of a mutation in a pool (lane), the individual DNA samples in the pool are screened again to find out which of the eight pooled samples from the crossed population has the mutation.

More information on TILLING® is described by Colbert et al. (2001. High Throughput Screening for Induced Point Mutations. *Plant Physiology* 126: 480-484); McCallum et al. (2000. Target Induced Local Lesions In Genomes (TILLING) for Plant Functional Genomics. *Plant Physiology* 123:439-442); Henikoff et al. (Single-Nucleotide Mutations for Plant Functional Genomics. *Annual Review of Plant Biology*. 54:15.1-15.27); and Till et al. (2003. Large-Scale Discovery of Induced Point Mutations With High-Throughput TILLING. *Genome Research* 13:524-530).

A pilot study determined that the mutation density of the inventors' mutant *Camelina* population was 1/25 kb. TILLING® of an initial 768 M2 individuals for FAD2 has identified 60 mutants, 60% of which are non-silent mutations. Of the non-silent mutations, about 30% are predicted to be severe missense or truncation mutations. Mutations were identified in all 3 copies of *Camelina* FAD2. The inventors' previous finding that *Camelina sativa* may be polyploid is further supported by the high density of lesions this plant is willing to tolerate in its genome. The mutant M3 plants were grown and a preliminary analysis of their fatty acid profiles by GC was performed.

Example 11

Mutations of *Camelina* FAD2 and FAE1 Genes Identified in TILLING®

Initial screening of the TILLING® population for FAD2 mutants resulted in plants with silent, STOP (nonsense) and/or severe missense mutations in FAD2 A, B, and C; and FAE1 A, B and C genes.

Positions and effects of mutations in FAD2 A, B, and C genes and FAE1 A, B and C genes are displayed in Tables 7 to 12 below (* indicates the mutation results in a stop codon, =indicates silent mutation).

TABLE 7

Summary of *Camelina* FAD2 A mutants

| Nucleotide Change | Effect | Primer set | Plant ID | Mutation Score |
|---|---|---|---|---|
| G1516A | G35R | FAD2A | 2480 | severe missense |
| C1645T | L78F | FAD2A | 2487 | severe missense |
| C1746T | H111= | FAD2A | 2782 | silent |
| C1813T | P134S | FAD2A | 2085 | severe missense |
| G1844A | R144H | FAD2A | 2764 | severe missense |
| C1977T | V188= | FAD2A | 2484 | silent |
| G2015A | G201D | FAD2A | 2993 | severe missense |
| C2099T | S229F | FAD2A | 2579 | severe missense |
| G2155A | G248R | FAD2A | 2200 | severe missense |
| G1495A, G2272A | E28K, E287K | FAD2A | 2983 | missense, severe missense |
| G2138A | R242H | FAD2A | 2986 | missense |

TABLE 8

Summary of *Camelina* FAD2 B mutants

| Nucleotide Change | Effect | Primer set | Plant ID | Mutation Score |
|---|---|---|---|---|
| C207T | S53F | FAD2B | 2474 or 2199 | severe missense |
| C213T | S55F | FAD2B | 3142 | Severe Missense |
| G785A | A246T | FAD2B | 3363 | Missense |
| C476T | R143C | FAD2B | 3314 | Severe Missense |
| C176T | P43S | FAD2B | 3325 | Severe Missense |
| G462A | W138* | FAD2B | 3489 | Nonsense |
| G498A | G150E | FAD2B | 3702 | Severe Missense |
| G779A | A244T | FAD2B | 3732 | Missense |
| G737A | D230N | FAD2B | 3814 | Missense |
| C812T | L255F | FAD2B | 4245 | Missense |
| C882T | P278L | FAD2B | 4408 | Missense |
| G410A | D121N | FAD2B | 4875 | Missense |
| G675A | C209Y | FAD2B | 4916 | Missense |
| C459T | S137F | FAD2B | 5155 | Severe Missense |
| C528T | P160L | FAD2B | 5746 | Severe Missense |
| C987T | T313M | FAD2B | 6023 | Severe Missense |
| C284T | P79S | FAD2B | 6107 | Severe Missense |
| G416A | V123I | FAD2B | 6122 | Severe Missense |
| G650A | G201S | FAD2B | 6105 | Severe Missense |
| C656T | P203S | FAD2B | 6277 | Missense |
| C203T | R52C | FAD2B | 6493 | Severe Missense |
| G582A | G178E | FAD2B | 6486 | Severe Missense |
| G372A | C108Y | FAD2B | 6479 | Severe Missense |
| G322A | W91* | FAD2B | 6490 | Nonsense |
| G374A | G109S | FAD2B | 6752 | Severe Missense |
| G926A | G293R | FAD2B | 6778 | Severe Missense |
| C490T | S147= | FAD2B | 3207 | silent |
| C940T | T297= | FAD2B | 3423 | silent |
| G148A | T33= | FAD2B | 3521 | silent |

TABLE 9

Summary of *Camelina* FAD2 C mutants

| Nucleotide Change | Effect | Primer set | plant ID | Mutation Score |
|---|---|---|---|---|
| G1429A | E28K | FAD2C | 6431 | Missense |
| C1501T | R52C | FAD2C | 3168 | Severe Missense |
| C1542T | S65= | FAD2C | 5756 | silent |
| C1576T | L77F | FAD2C | 5550 | Missense |
| C1582T | P79S | FAD2C | 5655 | Severe Missense |
| G1607A | W87* | FAD2C | 4506 | Nonsense |
| C1609T | P88S | FAD2C | 3210 | Severe Missense |
| G1619A | W91* | FAD2C | 3284 | Nonsense |
| G1672A | G109S | FAD2C | 3690 | Severe Missense |
| G1717A | G124S | FAD2C | 5644 | Severe Missense |
| C1720T | L125F | FAD2C | 4933 | Missense |
| C1741T | L132F | FAD2C | 4995 | Missense |
| G1795A | G150R | FAD2C | 3147 | Severe Missense |
| G1796A | G150E | FAD2C | 4608 | Severe Missense |
| C1799T | S151F | FAD2C | 3275 | Severe Missense |
| G1808A | R154K | FAD2C | 3490 | Missense |
| G1810A | D155N | FAD2C | 2578, 2586 | Severe Missense |
| C1857T | G170= | FAD2C | 4716 | silent |
| C1873T | P176S | FAD2C | 3267 | Severe Missense |
| G1880A | G178E | FAD2C | 5903 | Severe Missense |
| G1883A | R179H | FAD2C | 4846 | Severe Missense |
| G1890A | M181I | FAD2C | 4400 | Missense |
| G1915A | G190R | FAD2C | 5524 | Severe Missense |
| G1948A | G201S | FAD2C | 6120 | Severe Missense |
| G1963A | G206R | FAD2C | 4556 | Missense |
| C2029T | L228F | FAD2C | 4802 | Missense |
| G2072A | R242H | FAD2C | 5122 | Missense |
| G2080A | A245T | FAD2C | 3152 | Missense |
| C2081T | A245V | FAD2C | 5318 | Missense |
| C2084T | A246V | FAD2C | 4884 | Missense |
| C2096T | A250V | FAD2C | 3318 | Missense |
| C2110T | L255F | FAD2C | 5734 | Missense |
| C2112T | L255= | FAD2C | 4677 | silent |
| G2117A | G257E | FAD2C | 5491 | Severe Missense |
| G2117A | G257E | FAD2C | 6470 | Severe Missense |

TABLE 9-continued

Summary of *Camelina* FAD2 C mutants

| Nucleotide Change | Effect | Primer set | plant ID | Mutation Score |
|---|---|---|---|---|
| G2140A | A265T | FAD2C | 3924 | Missense |
| G2149A | V268I | FAD2C | 6068 | Severe Missense |
| C2188T | P281S | FAD2C | 4864 | Severe Missense |
| C2204T | S286F | FAD2C | 5183 | Severe Missense |
| G2255A | G303E | FAD2C | 4467 | Severe Missense |
| G2268A | K307= | FAD2C | 6509 | silent |
| C2285T | T313M | FAD2C | 5426 | Severe Missense |
| C2293T | H316Y | FAD2C | 2785, 2487, 2488, or 2786 | Severe Missense |
| C2315T | S323L | FAD2C | 6060 | Severe Missense |
| G2422A | E359K | FAD2C | 4997 | Severe Missense |
| G2443A | V366I | FAD2C | 6579 | Missense |
| C1595T | S83F | FAD2C | 4138 | Severe Missense |
| C2383T | Q346* | FAD2C | 6077 | Nonsense |

TABLE 10

Summary of *Camelina* FAE1 A mutants

| Nucleotide Change | Effect | Primer set | Plant ID | Mutation Score |
|---|---|---|---|---|
| G621A | V55I | FAE1-A | 4696 | Missense |
| C695T | L79= | FAE1-A | 3920 | silent |
| C714T | L86F | FAE1-A | 4489 | Severe Missense |
| G798A | V114M | FAE1-A | 5495 | Missense |
| G801A | A115T | FAE1-A | 3436 | Missense |
| G805A | C116Y | FAE1-A | 3533 | Missense |
| G810A | D118N | FAE1-A | 3424 | Missense |
| G810A | D118N | FAE1-A | 5977 | Missense |
| C817T | S120F | FAE1-A | 3821 | Severe Missense |
| C820T | S121L | FAE1-A | 4703 | Missense |
| G821A | S121= | FAE1-A | 6126 | silent |
| G867A | E137K | FAE1-A | 6361 | Missense |
| G877A | S140N | FAE1-A | 3284 | Severe Missense |
| G997A | R180K | FAE1-A | 3390 | Missense |
| G997A | R180K | FAE1-A | 5346 | Missense |
| G1005A | G183S | FAE1-A | 6655 | Severe Missense |
| C1042T | T195I | FAE1-A | 5557 | Severe Missense |
| G1061A | M201I | FAE1-A | 4088 | Severe Missense |
| G1065A | V203I | FAE1-A | 4469 | Missense |
| C1072T | T205I | FAE1-A | 4500 | Severe Missense |
| C1083T | R209* | FAE1-A | 3395 | Nonsense |
| C1091T | N211= | FAE1-A | 5486 | silent |
| G1120A | G221D | FAE1-A | 6386 | Severe Missense |
| C1141T | A228V | FAE1-A | 4467 | Severe Missense |
| C1167T | H237Y | FAE1-A | 4164 | Severe Missense |
| C1167T | H237Y | FAE1-A | 4318 | Severe Missense |
| G1254A | V266I | FAE1-A | 3365 | Missense |
| G1258A | S267N | FAE1-A | 3783 | Severe Missense |
| C1272T | R272C | FAE1-A | 5401 | Severe Missense |
| G1311A | G285R | FAE1-A | 3799 | Missense |
| G1354A | R299Q | FAE1-A | 5095 | Severe Missense |
| G1366A | G303E | FAE1-A | 3820 | Severe Missense |
| G1387A | R310Q | FAE1-A | 6528 | Missense |
| G1390A | C311Y | FAE1-A | 3631 | Severe Missense |
| G1401A | G315R | FAE1-A | 4257 | Missense |
| G1402A | G315E | FAE1-A | 6186 | Missense |
| G1402A | G315E | FAE1-A | 6446 | Missense |
| G1407A | D317N | FAE1-A | 3897 | Severe Missense |
| G1416A | G320S | FAE1-A | 5197 | Severe Missense |
| G1426A | G323E | FAE1-A | 5680 | Severe Missense |
| G1426A | G323E | FAE1-A | 6284 | Severe Missense |
| C1450T | T331I | FAE1-A | 4412 | Missense |
| G1463A | G335= | FAE1-A | 5117 | silent |
| G1518A | E354K | FAE1-A | 3597 | Severe Missense |

TABLE 11

Summary of *Camelina* FAE1 B mutants

| Nucleotide Change | Effect | Primer set | PLANT ID | Mutation Score |
|---|---|---|---|---|
| C710T | P76L | FAE1B | 5778 | Severe Missense |
| C718T | L79F | FAE1B | 5840 | Severe Missense |
| G724A | D81N | FAE1B | 6324 | Severe Missense |
| C731T | S83L | FAE1B | 4318 | Severe Missense |
| C817T | R112W | FAE1B | 4140 | Severe Missense |
| G823A | V114M | FAE1B | 3768 | Missense |
| G823A | V114M | FAE1B | 5966 | Missense |
| C845T | S121L | FAE1B | 3758 | Missense |
| G858A | L125= | FAE1B | 3709 | silent |
| G887A | G135D | FAE1B | 4015 | Severe Missense |
| C907T | Q142* | FAE1B | 5951 | Nonsense |
| C928T | P149S | FAE1B | 5107 | Severe Missense |
| C952T | R157C | FAE1B | 4840 | Severe Missense |
| G953A | R157H | FAE1B | 4239 | Severe Missense |
| G958A | E159K | FAE1B | 6322 | Severe Missense |
| G969A | Q162= | FAE1B | 3529 | silent |
| G988A | E169K | FAE1B | 3734 | Severe Missense |
| C1019T | P179L | FAE1B | 3873 | Severe Missense |
| G1031A | G183D | FAE1B | 4135 | Missense |
| G1042A | V187M | FAE1B | 6517 | Severe Missense |
| C1063T | P194S | FAE1B | 6478 | Severe Missense |
| C1082T | A200V | FAE1B | 3986 | Severe Missense |
| G1086A | M201I | FAE1B | 3895 | Missense |
| G1109A | R209Q | FAE1B | 4139 | Severe Missense |
| C1154T | A224V | FAE1B | 3352 | Severe Missense |
| C1229T | T249I | FAE1B | 4169 | Severe Missense |
| G1231A | E250K | FAE1B | 6678 | Severe Missense |
| C1271T | S263F | FAE1B | 3829 | Severe Missense |
| C1271T | S263F | FAE1B | 6700 | Severe Missense |
| G1275A | M264I | FAE1B | 6308 | Severe Missense |
| G1306A | G275R | FAE1B | 5333 | Severe Missense |
| C1310T | A276V | FAE1B | 3241 | Severe Missense |
| G1314A | A277= | FAE1B | 4884 | silent |
| C1310T | A276V | FAE1B | 3284 | Severe Missense |
| C1325T | S281F | FAE1B | 5343 | Severe Missense |
| G1337A | G285E | FAE1B | 3358 | Missense |
| G1337A | G285E | FAE1B | 3821 | Missense |
| G1343A | R287Q | FAE1B | 5930 | Silent |
| C1352T | S290F | FAE1B | 4882 | Severe Missense |
| C1384T | H301Y | FAE1B | 4687 | Severe Missense |
| C1389T | T302= | FAE1B | 5840 | silent |
| G1412A | R310Q | FAE1B | 3936 | Missense |
| G1417A | V312M | FAE1B | 3173 | Severe Missense |
| G1427A | G315E | FAE1B | 3926 | Missense |
| G1435A | E318K | FAE1B | 6479 | Missense |
| G1441A | G320S | FAE1B | 3842 | Severe Missense |
| C1493T | A337V | FAE1B | 4630 | Severe Missense |
| C1522T | P347S | FAE1B | 3912 | Severe Missense |

TABLE 12

Summary of *Camelina* FAE1 C mutants

| Nucleotide Change | Effect | Primer set | Plant ID | Mutation Score |
|---|---|---|---|---|
| A506T | T15S | FAE1-C | 3688 | Missense |
| A506T | T15S | FAE1-C | 4325 | Missense |
| A506T | T15S | FAE1-C | 4907 | Missense |
| A506T | T15S | FAE1-C | 6025 | Missense |
| A506T | T15S | FAE1-C | 6695 | Missense |
| C564T | S34F | FAE1-C | 4965 | Missense |
| C605T | L48F | FAE1-C | 6835 | Missense |
| G704A | D81N | FAE1-C | 4510 | Severe Missense |
| C719T | L86F | FAE1-C | 5015 | Severe Missense |
| G798A | R112Q | FAE1-C | 4184 | Missense |
| C802T | N113= | FAE1-C | 6130 | silent |
| C822T | S120F | FAE1-C | 3886 | Severe Missense |

TABLE 12-continued

Summary of Camelina FAE1 C mutants

| Nucleotide Change | Effect | Primer set | Plant ID | Mutation Score |
|---|---|---|---|---|
| C825T | S121L | FAE1-C | 4255 | Missense |
| G840A | R126K | FAE1-C | 5936 | Missense |
| G855A | R131H | FAE1-C | 3725 | Severe Missense |
| G855A | R131H | FAE1-C | 4813 | Severe Missense |
| C858T | S132L | FAE1-C | 5951 | Severe Missense |
| C887T | P142S | FAE1-C | 3918 | Missense |
| C887T | P142S | FAE1-C | 4198 | Missense |
| C906T | P148L | FAE1-C | 4068 | Severe Missense |
| C911T | Q150* | FAE1-C | 5566 | Nonsense |
| C911T | Q150* | FAE1-C | 6139 | Nonsense |
| G926A | A155T | FAE1-C | 3923 | Missense |
| G933A | R157H | FAE1-C | 5576 | Severe Missense |
| G982A | E173= | FAE1-C | 3367 | silent |

TABLE 12-continued

Summary of Camelina FAE1 C mutants

| Nucleotide Change | Effect | Primer set | Plant ID | Mutation Score |
|---|---|---|---|---|
| C987T | T175I | FAE1-C | 3247 | Severe Missense |
| G1010A | G183S | FAE1-C | 3365 | Severe Missense |
| C1047T | T195I | FAE1-C | 5891 | Severe Missense |
| G1067A | V202I | FAE1-C | 5975 | Missense |
| C1088T | R209* | FAE1-C | 6476 | Nonsense |
| G1115A | G218R | FAE1-C | 3970 | Severe Missense |
| G1137A | G225D | FAE1-C | 3911 | Severe Missense |
| C1154T | L231F | FAE1-C | 6643 | Severe Missense |
| G1175A | V238I | FAE1-C | 3380 | Missense |
| C1251T | S263F | FAE1-C | 5793 | Severe Missense |
| C1252T | S263= | FAE1-C | 3885 | silent |
| G1255A | M264I | FAE1-C | 5422 | Severe Missense |
| G1283A | G274S | FAE1-C | 4945 | Severe Missense |
| G1287A | G275E | FAE1-C | 3749 | Severe Missense |
| C1305T | S281F | FAE1-C | 3401 | Severe Missense |
| C1305T | S281F | FAE1-C | 4608 | Severe Missense |
| G1316A | G285R | FAE1-C | 4123 | Missense |
| C1353T | T297M | FAE1-C | 3427 | Severe Missense |
| G1359A | R299Q | FAE1-C | 3166 | Severe Missense |
| C1400T | Q313* | FAE1-C | 5114 | Nonsense |
| C1403T | Q314* | FAE1-C | 4162 | Nonsense |
| G1406A | G315R | FAE1-C | 3776 | Missense |
| G1472A | A337T | FAE1-C | 4852 | Missense |
| C1486T | N341= | FAE1-C | 4399 | silent |
| C1494T | T344M | FAE1-C | 5013 | Severe Missense |
| C1502T | P347S | FAE1-C | 6553 | Severe Missense |

As tables 7-12 indicate, multiple mutants were isolated in each FAD2 or FAE1 gene copy. The types of mutants include missense, severe missense, nonsense and silent mutations.

Example 12

Fatty Acids Composition in FAD2 and FAE1 Mutants

Fatty acid methyl ester (FAME) composition in Camelina FAD2 mutants was analyzed in a preliminary test by gas chromatography (GC) following the protocol described in Example 1. The results were shown in Table 13.

TABLE 13

% FAME content in Camelina FAD2 mutants

| Mutation | Cs 32 wild type | Combined Null Population | FAD2A Q44* HOMO | FAD2A missense G150E HOMO | FAD2A missense G150E NULL | FAD2A missense S229F HOMO | FAD2A missense S229F NULL | FAD2B W91* HOMO | FAD2B W91* NULL |
|---|---|---|---|---|---|---|---|---|---|
| sample size | 10 | 14 | 8 | 7 | 4 | 5 | 4 | 6 | 6 |
| C18:1 | 14.4 ± 0.4 | 14.3 ± 2.0 | 22.6 ± 1.2 | 24.0 ± 1.2 | 17.1 ± 0.9 | 19.2 ± 1.3 | 13.9 ± 0.9 | 18.4 ± 0.6 | 12.8 ± 0.5 |
| C18:2 | 21.4 ± 0.8 | 28.8 ± 2.8 | 20.3 ± 1.1 | 19.0 ± 0.5 | 26.9 ± 1.2 | 22.2 ± 1.1 | 26.8 ± 1.4 | 28.7 ± 0.4 | 31.5 ± 2.0 |
| C18:3 | 33.7 ± 0.6 | 25.4 ± 1.9 | 26.2 ± 1.8 | 26.1 ± 1.6 | 26.0 ± 1.1 | 25.7 ± 1.2 | 26.5 ± 1.3 | 23.8 ± 1.5 | 24.2 ± 2.2 |
| C20:1 | 15.5 ± 1.0 | 10.7 ± 1.4 | 12.2 ± 1.0 | 13.1 ± 1.4 | 10.5 ± 1.3 | 13.4 ± 1.0 | 10.8 ± 1.3 | 10.2 ± 1.6 | 10.7 ± 1.2 |
| % increase in 18:1 relative to wild type seeds | | | 56.9% | 66.7% | | 33.3% | | 27.8% | |

Note:
HOMO means the plants are all homozygous mutants at the specified locus.
NULL means there is no mutation at the specified locus.
% means % of FAME composition As the results indicate, an obvious increase of oleic acid (18:1) was observed in certain FAD2 mutants tested compared to NULL control plants. Thus, the data supports the inventors' prediction very well that disruption in one, two or more FAD2 gene in Camelina is sufficient to alter its fatty acid composition, and more specifically, to increase the oleic acid (18:1) concentration.

More mutants in FAD2 genes and FAE1 genes were subjected to GC analysis. To select mutants with potentially the most profound phenotype, FAD2 A, B, and C, or FAE1 A, B, and C protein sequences were analyzed against orthologs in Arabidopsis, Crambe, B. rapa HEAC, B. rapa LEAC, meadow foam, and nasturtium. It is preferred that a mutation happens at the position which is conserved through reference species, and/or a position described before as conserved in orthologs or close-related genes in other species (e.g., see reference 52, Ghanevati and Jaworski, 2002, and Jet et al., Dissection of malonyl-coenzyme A decarboxylation from polyketide formation in the reaction mechanism of a plant polyketide synthase, Biochemistry, 39:890-902). For example, the G150E, Q44* (nonsense), S229F and W91* (nonsense) mutations in FAD2 genes are potentially very promising as are the following mutants in FAE1: Q142* (nonsense), R209* (nonsense), G221D and H301Y.

Figure 12:
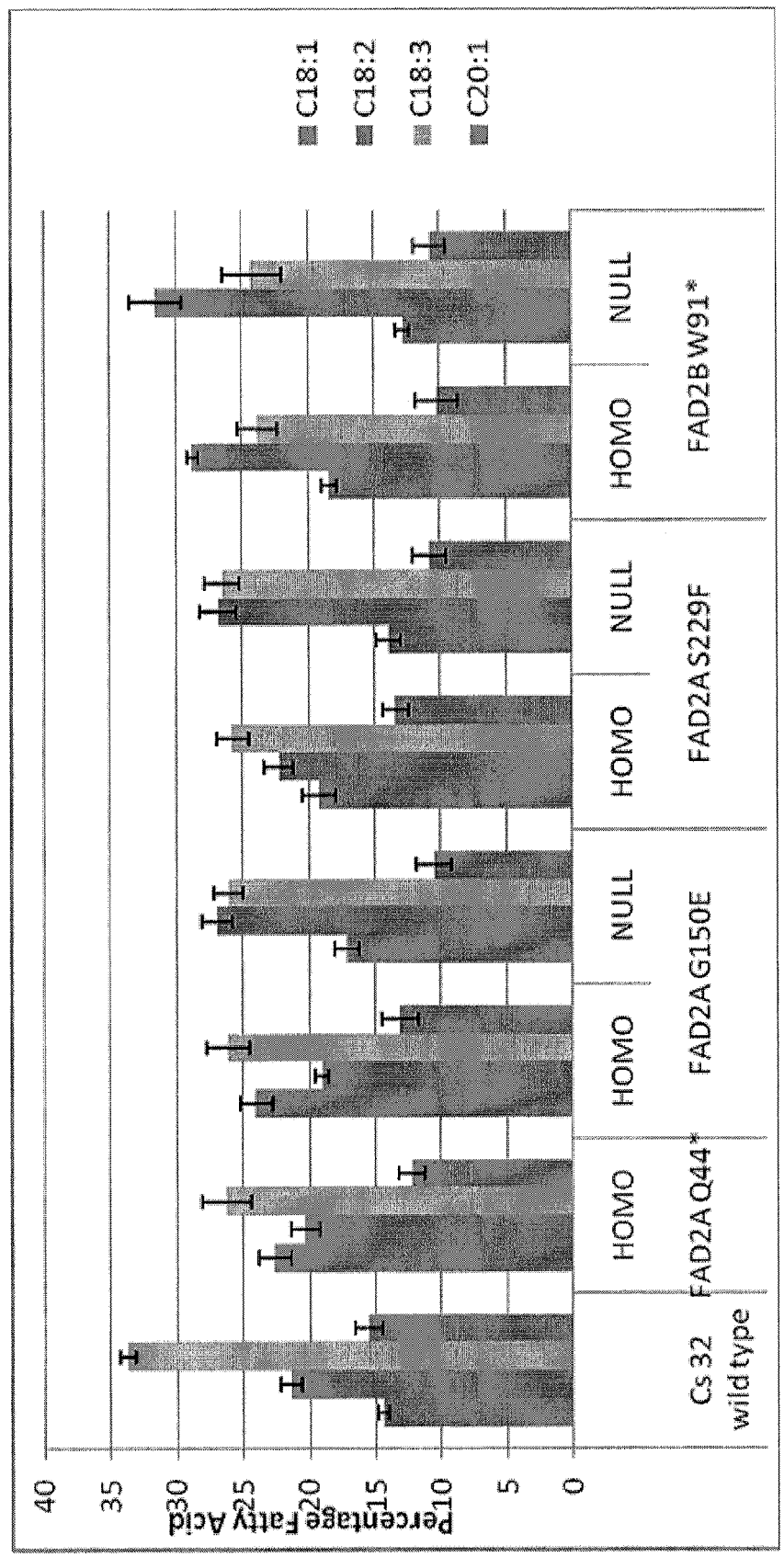
FIG. 12 depicts fatty acid compositions in FAD2 mutants (12A) and in FAE1 mutants (12B) measured by gas chromatography. Note.

Two independent GC analyses of fatty acid compositions in FAD2 A and FAD2 B mutants were conducted, and the results are shown in Tables 14 and 15. Mutants with clear increases in oleic acid were selected, and their results from both GC runs were averaged together to produce Table 16. Some of these tested mutations have obvious increased oleic acid (18:1), such as FAD2 A mutants G150E, Q44*, S229F, and FAD2 B mutants W91* compared to NULL population or wild-type Cs32 control plants, while no significant difference was found between NULL population and wild type Cs32 plants. Table 17 shows the fatty acid compositions of selected FAD2 mutants for one of the independent GC analyses. The result of Table 16 is further summarized in FIG. 12A. As the results indicate, these mutants have evident increased oleic acid (18:1) and reduced polyunsaturated fatty acids (e.g., 18:2 and 18:3) in seed oil, just as the inventors predicted.

A third independent GC analysis was conducted in which FAD2 C mutants were included. This was a preliminary analysis where seeds from heterozygous plants were used, resulting in a mixed population containing null, heterozygous and homozygous seeds. The results (see Table 18 in U.S. Provisional Application No. 61/318,273, incorporated by reference in its entirety) showed that all tested FAD2 C mutants do not have significant induction of 18:1 fatty acid, as compared to Cs32 control plants. While not wishing to be bound by any particular theory, the results suggest that any potential increase in 18:1 in a FAD2 C mutant plant is not detectable in progeny from heterozygous plants, where the mixture of wild type, heterozygous and homozygous seeds may dilute the effects of the homozygous seed.

The same preliminary third GC run analyzed mutants at the FAE1 loci. Though results (see Table 19 and Table 20 in U.S. Provisional Application No. 61/318,273) showed that some of these tested mutants, for example FAE1 A mutant R272C, FAE1 B mutants S281F and R209Q, and FAE1C mutants Q313* and Q150* had obvious decreased 20:1 and/or 22:1 in seed oil relative to wild type Cs32 plants, the inclusion of a significant number of heterozygous lines may have confounded the results as was the case with the FAD2 C results above.

A fourth independent GC analysis (results shown in Tables 18a and 19a of the present specification) was conducted on M4 or M5 generation FAD2 A, FAD2 B, FAD2 C, FAE1 A, FAE1 B and FAE1 C mutants. This analysis included multiple homozygous lines for a given FAD2 or FAE1 mutation, which conferred more confidence in the results due to multiple samples for a given mutation. In addition, the inventors limited the number of heterozygous lines analyzed where the seeds were a mixture of homozygous (designated 'hom'), heterozygous (designated 'het') and null because of ambiguous results in the third GC run. In test 4, *Arabidopsis* FAD2 and FAE1 mutants, wild type *Camelina sativa* CS32, and null sibling lines not carrying a FAD2 or FAE1 mutation were included as controls. From this analysis, some FAD2 A Q44* and G150E, FAD2 B W91* and G150E, and FAD2C W87* homozygous or heterozygous lines clearly had greater 18:1 fatty acid levels compared to their null sibling lines or the CS32 control.

Figure 12B:
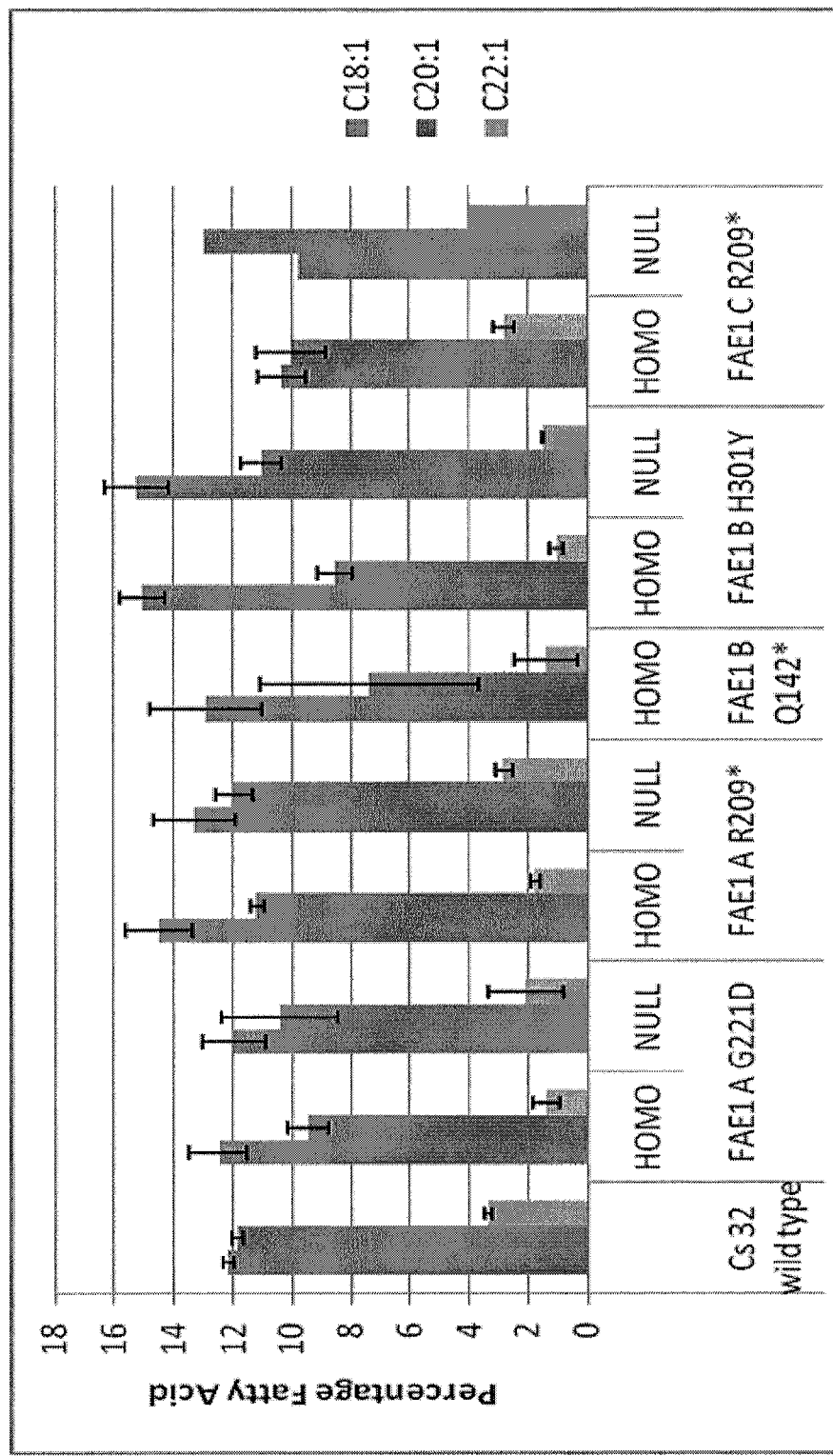
FIG. 12B is summarized FAE1 data from GC test 4 and replaces FIG. 14B from U.S. Provisional Application No. 61/318,273, which summarized FAE1 data from GC test 3.

For FAE1, some FAE1 A G221D, FAE1 B Q142* and H301 Y, and FAE1 C R209* homozygous or heterozygous lines clearly had lower 20:1 fatty acid levels and/or lower 22:1 fatty acid levels compared to their null sibling lines or the CS32 control. The FAE1 data from the fourth GC run is summarized in FIG. 12B (this Figure replaces FIG. 14B from U.S. Provisional Application No. 61/318,273, which summarized FAE1 data from the third GC run). This data supports the inventors' prediction that disruption in one, two or more FAE1 genes in *Camelina* is sufficient to alter its fatty acid composition, and more specifically, to decrease the very long chain (for example 20:1 and 22:1) fatty acid content.

The fourth GC analysis did not include some FAD2 C, FAE1 A, FAE1 B and FAE1 C mutants included in the third GC analysis due to pursuance of a select number of mutant lines in the breeding program for FAD2 (A, B and C) and FAE1 (A, B and C) mutants. In particular, FAD2 C mutants Q346*, G150R, R242H, G190R were included in the third but not the fourth GC analysis. Similarly, FAE1 A mutants G183S, R272C, C311Y, FAE1 B mutants P76L, L79F, R157H, R209Q, E250K, W91*, and FAE1 C mutants R157H, G225D, L231F, G274S, Q313*, Q314* were included in the third but not the fourth GC analysis. The FAE1 C Q150* mutant, which was analyzed in test 3 but not test 4, will be tested for fatty acid composition in future GC runs. In test 3, homozygous FAE1 C Q150* mutant plants were used for analysis. According to the GC data in test 3, the fatty acids composition in homozygous FAE1 C Q150* mutant is as following: C16:0, 6.19%; C18:0, 2.74%; C18:1, 13.81%; C18:2, 24.05%; C20:0, 0.97%; C18:3, 33.28%; C20:1, 14.25%; C20:2, 1.79%; C20:3, 0.70%; and C22:1, 2.23%.

TABLE 14

Fatty Acids Composition in FAD2 mutants, sorted by mutation, Test No. 1

| Line | Gene | SNP | mutation | Plant # | genotype | C16:0 | C18:0 | C18:1 | C18:2 | C20:0 | C18:3 | C20:1 | C20:2 | C20:3 | C22:1 |
|---|---|---|---|---|---|---|---|---|---|---|---|---|---|---|---|
| 2362 | FAD2A | 5 | G150E | 4 | HOMO | 7.9% | 4.3% | 22.9% | 19.1% | 1.9% | 28.1% | 12.3% | 0.8% | 0.7% | 2.1% |
| 2362 | FAD2A | 5 | G150E | 5 | HOMO | 7.8% | 3.8% | 23.0% | 19.1% | 1.8% | 28.1% | 13.1% | 0.7% | 0.6% | 2.1% |
| 2362 | FAD2A | 5 | G150E | 1 | HET | 7.3% | 3.8% | 22.3% | 20.7% | 2.1% | 25.7% | 14.3% | 0.9% | 0.6% | 2.3% |
| 2362 | FAD2A | 5 | G150E | 2 | HET | 11.0% | 5.4% | 13.6% | 15.0% | 2.8% | 34.6% | 12.9% | 1.4% | 0.8% | 2.4% |
| 2362 | FAD2A | 5 | G150E | 11 | Null | 8.3% | 5.2% | 17.9% | 25.3% | 2.7% | 27.4% | 10.0% | 1.0% | 0.5% | 1.7% |
| 2362 | FAD2A | 5 | G150E | 18 | Null | 9.0% | 5.1% | 17.8% | 28.2% | 3.2% | 24.9% | 8.9% | 1.2% | 0.6% | 1.1% |
| 2510 | FAD2A | 4 | S147F | 3 | HOMO | 7.2% | 5.1% | 15.9% | 24.4% | 3.8% | 28.4% | 10.3% | 1.3% | 0.8% | 2.7% |
| 2510 | FAD2A | 4 | S147F | 10 | HOMO | 9.0% | 6.4% | 15.9% | 29.2% | 3.5% | 25.0% | 7.1% | 1.2% | 0.6% | 2.1% |
| 2510 | FAD2A | 4 | S147F | 1 | HET | 8.2% | 5.5% | 15.1% | 27.2% | 3.3% | 27.9% | 8.0% | 1.3% | 0.8% | 2.8% |
| 2510 | FAD2A | 4 | S147F | 4 | HET | 8.4% | 5.7% | 15.8% | 30.1% | 3.7% | 23.7% | 8.5% | 1.3% | 0.3% | 2.4% |
| 2510 | FAD2A | 4 | S147F | 2 | Null | 8.5% | 4.7% | 12.6% | 28.2% | 3.5% | 27.7% | 9.2% | 1.7% | 0.9% | 2.9% |
| 2510 | FAD2A | 4 | S147F | 5 | Null | 7.7% | 3.5% | 14.0% | 26.9% | 2.5% | 29.3% | 10.7% | 1.5% | 0.9% | 3.0% |
| 2579 | FAD2A | 7 | S229F | 1 | HOMO | 7.3% | 3.4% | 19.3% | 23.6% | 1.7% | 26.5% | 13.0% | 1.2% | 0.7% | 3.2% |
| 2579 | FAD2A | 7 | S229F | 5 | HOMO | 8.0% | 4.4% | 20.9% | 22.3% | 2.2% | 27.4% | 10.6% | 1.1% | 0.4% | 2.8% |
| 2579 | FAD2A | 7 | S229F | 2 | HET | 7.5% | 3.6% | 17.0% | 25.8% | 0.1% | 31.7% | 10.1% | 1.6% | 0.4% | 2.3% |
| 2579 | FAD2A | 7 | S229F | 3 | HET | 7.7% | 4.6% | 16.5% | 25.0% | 0.1% | 30.5% | 11.2% | 1.3% | 0.8% | 2.4% |
| 2579 | FAD2A | 7 | S229F | 10 | Null | 8.4% | 3.6% | 12.0% | 26.8% | 2.6% | 28.9% | 11.9% | 1.9% | 0.9% | 3.1% |
| 2579 | FAD2A | 7 | S229F | 12 | Null | 8.0% | 5.2% | 14.4% | 26.1% | 3.5% | 28.9% | 8.9% | 1.5% | 0.8% | 2.8% |
| 2764 | FAD2A | 3 | R144H | 5 | HOMO | 7.5% | 3.8% | 22.1% | 26.3% | 0.1% | 26.0% | 10.5% | 1.1% | 0.5% | 2.1% |
| 2764 | FAD2A | 3 | R144H | 8 | HOMO | 7.5% | 3.3% | 17.0% | 21.6% | 0.1% | 34.4% | 11.3% | 1.2% | 0.9% | 2.9% |
| 2764 | FAD2A | 3 | R144H | 10 | HOMO | 6.9% | 4.3% | 17.6% | 22.5% | 2.9% | 28.4% | 12.3% | 1.2% | 0.8% | 3.2% |

TABLE 14-continued

Fatty Acids Composition in FAD2 mutants, sorted by mutation, Test No. 1

| Line | Gene | SNP | mutation | Plant # | genotype | C16:0 | C18:0 | C18:1 | C18:2 | C20:0 | C18:3 | C20:1 | C20:2 | C20:3 | C22:1 |
|---|---|---|---|---|---|---|---|---|---|---|---|---|---|---|---|
| 2764 | FAD2A | 3 | R144H | 16 | HOMO | 6.5% | 3.0% | 18.7% | 24.5% | 1.7% | 26.9% | 13.3% | 1.3% | 0.7% | 3.4% |
| 2764 | FAD2A | 3 | R144H | 1 | HET | 6.9% | 3.4% | 18.4% | 24.5% | 1.5% | 27.7% | 12.7% | 1.3% | 0.5% | 3.0% |
| 2764 | FAD2A | 3 | R144H | 2 | HET | 7.7% | 3.9% | 15.7% | 25.5% | 0.1% | 32.5% | 10.1% | 1.4% | 0.8% | 2.3% |
| 2764 | FAD2A | 3 | R144H | 3 | HET | 7.3% | 3.5% | 17.6% | 26.5% | 0.1% | 29.1% | 11.4% | 1.4% | 0.7% | 2.4% |
| 2764 | FAD2A | 3 | R144H | 6 | HET | 7.7% | 3.3% | 16.8% | 22.3% | 0.1% | 34.5% | 10.8% | 1.1% | 0.9% | 2.6% |
| 2764 | FAD2A | 3 | R144H | 4 | Null | 6.8% | 3.5% | 17.1% | 27.8% | 1.7% | 24.9% | 12.8% | 1.5% | 0.7% | 3.1% |
| 2764 | FAD2A | 3 | R144H | 7 | Null | 7.1% | 3.2% | 17.1% | 25.2% | 1.5% | 28.2% | 12.5% | 1.5% | 0.5% | 3.3% |
| 2785 | FAD2C | 11 | H316Y | 3 | HOMO | 8.1% | 3.7% | 16.6% | 20.5% | 2.6% | 32.1% | 11.2% | 1.3% | 0.8% | 3.2% |
| 2785 | FAD2C | 11 | H316Y | 10 | HOMO | 8.3% | 3.7% | 15.2% | 16.7% | 2.3% | 34.2% | 14.3% | 1.2% | 1.1% | 3.1% |
| 2785 | FAD2C | 11 | H316Y | 12 | HOMO | 8.5% | 3.5% | 14.3% | 18.0% | 2.7% | 32.8% | 14.1% | 1.2% | 1.2% | 3.7% |
| 2785 | FAD2C | 11 | H316Y | 18 | HOMO | 8.1% | 3.9% | 14.8% | 19.1% | 2.1% | 35.0% | 11.0% | 1.3% | 1.3% | 3.4% |
| 2785 | FAD2C | 11 | H316Y | 1 | HET | 8.8% | 4.0% | 14.3% | 22.0% | 2.0% | 33.3% | 9.9% | 1.6% | 0.8% | 3.4% |
| 2785 | FAD2C | 11 | H316Y | 6 | HET | 8.9% | 3.9% | 14.4% | 20.5% | 0.1% | 36.0% | 11.1% | 1.3% | 1.1% | 2.8% |
| 2785 | FAD2C | 11 | H316Y | 7 | HET | 8.2% | 3.9% | 14.4% | 20.5% | 0.1% | 36.1% | 11.1% | 1.3% | 1.1% | 3.1% |
| 2785 | FAD2C | 11 | H316Y | 8 | HET | 9.0% | 3.9% | 12.6% | 21.0% | 0.1% | 38.2% | 10.2% | 1.5% | 1.0% | 2.5% |
| 2785 | FAD2C | 11 | H316Y | 2 | Null | 8.6% | 3.8% | 11.3% | 20.6% | 2.8% | 35.1% | 11.1% | 1.6% | 1.4% | 3.7% |
| 2785 | FAD2C | 11 | H316Y | 5 | Null | 8.8% | 4.7% | 12.8% | 20.7% | 3.0% | 34.2% | 10.3% | 1.4% | 1.1% | 3.0% |
| 2812 | FAD2B | 9 | H145Y | 1 | HOMO | 8.3% | 4.1% | 15.1% | 27.4% | 2.9% | 24.6% | 12.4% | 1.5% | 0.7% | 3.1% |
| 2812 | FAD2B | 9 | H145Y | 2 | HOMO | 9.9% | 3.6% | 13.3% | 28.7% | 2.4% | 27.0% | 9.3% | 1.5% | 0.8% | 3.5% |
| 2812 | FAD2B | 9 | H145Y | 12 | HET | 7.8% | 3.9% | 16.6% | 29.1% | 2.6% | 24.6% | 10.7% | 1.5% | 0.7% | 2.6% |
| 2812 | FAD2B | 9 | H145Y | 25 | HET | 7.8% | 4.1% | 15.9% | 30.5% | 2.2% | 25.8% | 9.0% | 1.6% | 0.7% | 2.4% |
| 2826 | FAD2A | 2 | Q44* | 1 | HOMO | 7.7% | 4.9% | 22.2% | 20.1% | 2.1% | 28.4% | 11.0% | 0.8% | 0.6% | 2.1% |
| 2826 | FAD2A | 2 | Q44* | 2 | HOMO | 7.8% | 4.9% | 19.9% | 19.2% | 2.6% | 29.5% | 11.7% | 1.0% | 0.8% | 2.6% |
| 2826 | FAD2A | 2 | Q44* | 3 | HOMO | 7.5% | 4.6% | 22.9% | 19.8% | 2.1% | 27.7% | 11.7% | 0.8% | 0.6% | 2.3% |
| 2826 | FAD2A | 2 | Q44* | 4 | HOMO | 7.7% | 5.4% | 24.7% | 20.3% | 2.5% | 25.7% | 10.6% | 0.7% | 0.5% | 1.9% |
| 2826 | FAD2A | 2 | Q44* | 5 | HOMO | 7.6% | 5.2% | 22.9% | 19.1% | 2.2% | 28.1% | 11.5% | 0.8% | 0.6% | 2.0% |
| 2826 | FAD2A | 2 | Q44* | 37 | HET | 7.3% | 4.8% | 22.9% | 19.1% | 2.0% | 28.5% | 12.2% | 0.7% | 0.6% | 1.9% |
| 3006 | FAD2B | 8 | W91* | 1 | HOMO | 7.9% | 4.6% | 18.9% | 28.5% | 1.7% | 26.8% | 8.9% | 1.0% | 0.5% | 1.1% |
| 3006 | FAD2B | 8 | W91* | 2 | HOMO | 8.2% | 5.3% | 18.8% | 29.2% | 1.7% | 26.3% | 7.8% | 0.9% | 0.4% | 1.3% |
| 3006 | FAD2B | 8 | W91* | 3 | HOMO | 8.0% | 5.5% | 18.4% | 28.9% | 2.7% | 24.4% | 8.6% | 1.1% | 0.5% | 1.8% |
| 3006 | FAD2B | 8 | W91* | 4 | HOMO | 7.5% | 5.1% | 18.0% | 28.9% | 2.9% | 22.9% | 10.6% | 1.3% | 0.5% | 2.3% |
| 3006 | FAD2B | 8 | W91* | 5 | Null | 7.8% | 4.2% | 12.3% | 33.5% | 2.9% | 23.8% | 9.3% | 2.1% | 0.7% | 3.5% |
| 3006 | FAD2B | 8 | W91* | 7 | Null | 7.9% | 4.4% | 17.6% | 30.0% | 2.1% | 24.9% | 9.7% | 1.2% | 0.5% | 1.6% |
| 3006 | FAD2B | 8 | W91* | 8 | HET | 8.0% | 3.9% | 13.4% | 30.6% | 2.2% | 26.9% | 9.3% | 2.0% | 0.5% | 3.1% |

Note:
*stands for nonsense mutation;
HOMO means the plants are all homozygous mutants at the specified locus.
HET means the plants are heterozygous mutants at the specified locus.
NULL means there is no mutation at the specified locus.
% means % of FAME composition

TABLE 15

Fatty Acids Composition in FAD2 mutants, sorted by mutation, Test No. 2

| Gene | SNP | muta-tion | Plant # | geno-type | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|---|
| none | none | | 1 | CS32 controls | 10 | 5.8% | 2.3% | 14.9% | 20.3% | 34.0% | 1.2% | 16.2% | 1.8% | 0.9% | 2.7% |
| none | none | | 2 | CS32 controls | | 6.1% | 2.3% | 14.6% | 21.3% | 33.3% | 1.2% | 15.6% | 1.8% | 1.2% | 2.6% |
| none | none | | 3 | CS32 controls | | 6.2% | 2.3% | 14.1% | 21.7% | 34.2% | 1.1% | 15.5% | 1.8% | 1.0% | 2.1% |
| none | none | | 4 | CS32 controls | | 6.0% | 2.4% | 14.2% | 20.8% | 34.5% | 1.2% | 15.8% | 1.6% | 1.0% | 2.4% |
| none | none | | 5 | CS32 controls | | 6.7% | 2.6% | 14.6% | 23.1% | 33.5% | 0.7% | 12.9% | 1.8% | 1.3% | 2.7% |
| none | none | | 6 | CS32 controls | | 6.2% | 2.5% | 14.6% | 21.6% | 33.4% | 1.0% | 15.4% | 1.8% | 1.1% | 2.5% |
| none | none | | 7 | CS32 controls | | 5.9% | 2.4% | 14.6% | 22.2% | 32.7% | 1.3% | 15.7% | 1.8% | 1.0% | 2.5% |
| none | none | | 8 | CS32 controls | | 6.0% | 2.3% | 13.6% | 21.0% | 34.3% | 1.4% | 16.0% | 1.9% | 1.0% | 2.6% |
| none | none | | 9 | CS32 controls | | 5.9% | 2.4% | 14.3% | 20.6% | 33.6% | 1.3% | 16.2% | 1.9% | 1.1% | 2.7% |
| none | none | | 10 | CS32 controls | | 6.2% | 2.4% | 13.9% | 21.4% | 33.2% | 1.3% | 15.9% | 1.9% | 1.2% | 2.6% |
| FAD2B/C | 51 | D60N | Y1 | 605 | 1 | 8.7% | 2.5% | 10.4% | 29.0% | 28.4% | 1.7% | 13.3% | 2.1% | 0.9% | 3.0% |
| FAD2A | 5 | G150E | 4 | HOMO | 1 | 8.0% | 4.4% | 22.5% | 18.8% | 27.5% | 2.2% | 12.7% | 0.5% | 1.7% | 1.7% |
| FAD2A | 5 | G150E | 5 | HOMO | 1 | 7.8% | 4.2% | 23.2% | 18.4% | 26.6% | 2.2% | 14.2% | 0.7% | 0.6% | 2.2% |
| FAD2A | | G150E | 20 | Null | 2 new | 8.7% | 4.2% | 16.2% | 26.7% | 25.7% | 2.2% | 12.0% | 1.3% | 0.4% | 2.4% |
| FAD2A | | G150E | 24 | Null | | 8.7% | 5.1% | 16.4% | 27.4% | 26.0% | 2.2% | 10.9% | 1.1% | 0.6% | 1.6% |
| FAD2A | | G150E | 6 | HOMO | 5 new | 7.7% | 4.2% | 26.1% | 18.8% | 25.2% | 1.9% | 13.3% | 0.6% | 0.5% | 1.7% |
| FAD2A | | G150E | 8 | HOMO | | 8.1% | 4.6% | 24.2% | 18.7% | 28.1% | 2.2% | 10.2% | 0.7% | 0.5% | 2.7% |
| FAD2A | | G150E | 14 | HOMO | | 8.2% | 4.5% | 24.6% | 19.4% | 24.7% | 2.0% | 13.7% | 0.6% | 0.3% | 1.9% |
| FAD2A | | G150E | 23 | HOMO | | 8.6% | 4.7% | 23.0% | 19.0% | 26.7% | 2.1% | 13.1% | 0.6% | 0.5% | 1.8% |
| FAD2A | | G150E | 25 | HOMO | | 8.0% | 4.0% | 24.2% | 20.0% | 23.7% | 1.8% | 14.6% | 0.7% | 0.5% | 2.5% |
| FAD2A | | G150E | 3 | Het | 3 new at least | 7.9% | 4.4% | 21.1% | 22.2% | 27.2% | 2.0% | 12.4% | 0.8% | 0.3% | 1.7% |

TABLE 15-continued

Fatty Acids Composition in FAD2 mutants, sorted by mutation, Test No. 2

| Gene | SNP | mutation | Plant # | genotype | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|---|
| FAD2A |   | G150E | 7  | Het  |       | 8.5% | 4.5% | 19.1% | 24.3% | 24.8% | 2.1% | 12.8% | 1.0% | 0.6% | 2.2% |
| FAD2A |   | G150E | 9  | Het  |       | 8.4% | 4.7% | 17.9% | 23.3% | 27.5% | 2.5% | 12.2% | 1.0% | 0.6% | 1.8% |
| FAD2A | 2 | Q44*  | 2  | HOMO | 1     | 8.3% | 5.1% | 22.8% | 20.8% | 26.7% | 2.0% | 11.1% | 0.8% | 0.4% | 2.0% |
| FAD2A | 2 | Q44*  | 1  | HOMO | 1     | 7.8% | 4.9% | 19.7% | 18.9% | 28.3% | 2.6% | 13.9% | 0.9% | 0.7% | 2.4% |
| FAD2A | 2 | Q44*  | 4  | HOMO | 1     | 7.6% | 5.1% | 23.7% | 20.2% | 25.7% | 2.4% | 12.8% | 0.6% | 0.4% | 1.5% |
| FAD2A |   | Q44*  | 40 | Null | 1     | 8.2% | 6.1% | 25.6% | 20.4% | 24.3% | 2.4% | 10.8% | 0.6% | 0.3% | 1.4% |
| FAD2A |   | Q44*  | 36 | HOMO | 3     | 7.8% | 5.5% | 23.2% | 21.4% | 23.8% | 2.5% | 13.0% | 0.7% | 0.2% | 1.8% |
| FAD2A |   | Q44*  | 38 | HOMO |       | 8.0% | 6.2% | 22.3% | 20.4% | 25.4% | 2.9% | 12.4% | 0.7% | 0.3% | 1.5% |
| FAD2A |   | Q44*  | 39 | HOMO |       | 9.2% | 5.6% | 22.9% | 22.0% | 23.7% | 2.3% | 11.0% | 0.7% | 0.4% | 2.0% |
| FAD2A | 3 | R144H | 16 | HOMO | 1     | 6.9% | 2.9% | 18.5% | 26.2% | 26.5% | 1.6% | 13.1% | 1.2% | 0.3% | 2.9% |
| FAD2A | 3 | R144H | 5  | HOMO | 1     | 7.1% | 4.0% | 21.7% | 26.0% | 23.2% | 2.4% | 12.1% | 0.9% | 0.3% | 2.3% |
| FAD2A |   | R144H | 19 | Null | 2 (34)| 7.1% | 3.0% | 17.8% | 27.1% | 26.0% | 1.7% | 12.8% | 1.3% | 0.4% | 2.7% |
| FAD2A |   | R144H | 25 | Null |       | 7.4% | 4.3% | 15.2% | 25.6% | 29.6% | 2.4% | 11.5% | 1.2% | 0.4% | 2.4% |
| FAD2A | 7 | S229F | 5  | HOMO | 1     | 7.6% | 3.8% | 19.6% | 21.4% | 27.4% | 2.0% | 13.9% | 1.0% | 0.6% | 2.6% |
| FAD2A | 7 | S229F | 3  | HET  | 1     | 7.9% | 5.1% | 18.2% | 26.0% | 25.7% | 2.0% | 10.4% | 1.2% | 0.7% | 2.6% |
| FAD2A | 7 | S229F | 12 | Null | 1     | 8.6% | 5.6% | 15.0% | 27.8% | 26.6% | 3.4% | 8.2%  | 1.4% | 0.7% | 2.8% |
| FAD2A | 7 | S229F | 10 | Null | 1     | 9.3% | 5.7% | 12.8% | 28.1% | 25.4% | 3.7% | 10.1% | 1.8% | 0.4% | 2.7% |
| FAD2A |   | S229F | 7  | HOMO | 3     | 8.4% | 5.8% | 18.4% | 22.7% | 24.5% | 3.5% | 11.8% | 1.1% | 0.6% | 3.2% |
| FAD2A |   | S229F | 9  | HOMO |       | 7.3% | 5.1% | 17.8% | 22.4% | 25.2% | 3.6% | 14.0% | 1.1% | 0.6% | 2.9% |
| FAD2A |   | S229F | 19 | HOMO |       | 6.9% | 5.0% | 21.0% | 20.9% | 24.8% | 2.7% | 14.3% | 0.9% | 0.6% | 2.9% |
| FAD2A |   | S229F | 13 | Null | 2     | 7.8% | 5.6% | 14.1% | 26.4% | 25.6% | 3.6% | 12.2% | 1.5% | 0.7% | 2.5% |
| FAD2A |   | S229F | 14 | Null |       | 7.6% | 4.8% | 13.8% | 25.0% | 28.3% | 3.2% | 12.6% | 1.2% | 0.8% | 2.6% |
| FAD2A |   | S229F | 4  | Het  | 3 (46)| 7.6% | 3.5% | 15.6% | 23.8% | 27.3% | 2.3% | 14.2% | 1.6% | 0.8% | 3.2% |
| FAD2A |   | S229F | 6  | Het  |       | 7.7% | 2.8% | 14.8% | 24.5% | 29.4% | 1.9% | 13.5% | 1.5% | 0.8% | 3.1% |
| FAD2A |   | S229F | 8  | Het  |       | 7.3% | 5.0% | 14.2% | 22.6% | 28.2% | 3.7% | 13.5% | 1.4% | 1.0% | 3.2% |
| FAD2A |   | S229F | Y1 | 610  | 7     | 5.3% | 2.3% | 16.5% | 21.8% | 29.8% | 1.5% | 16.2% | 2.0% | 1.2% | 3.4% |
| FAD2A |   | S229F | Y2 | 610  |       | 5.5% | 2.3% | 16.1% | 22.0% | 30.6% | 1.2% | 16.2% | 1.9% | 1.2% | 2.9% |
| FAD2A |   | S229F | Y3 | 610  |       | 6.5% | 2.2% | 17.0% | 23.3% | 29.5% | 1.1% | 15.3% | 1.7% | 0.9% | 2.4% |
| FAD2A |   | S229F | Y4 | 610  |       | 5.9% | 2.0% | 14.8% | 21.8% | 34.2% | 0.9% | 14.7% | 2.0% | 1.1% | 2.5% |
| FAD2A |   | S229F | Y5 | 610  |       | 5.9% | 2.0% | 14.4% | 22.3% | 34.7% | 1.0% | 14.7% | 1.8% | 1.0% | 2.3% |
| FAD2A |   | S229F | Y6 | 610  |       | 5.5% | 2.2% | 16.7% | 21.6% | 31.9% | 1.2% | 15.2% | 1.8% | 1.1% | 2.8% |
| FAD2A |   | S229F | Y7 | 610  |       | 6.3% | 2.5% | 17.8% | 23.7% | 28.4% | 1.4% | 14.8% | 1.6% | 0.9% | 2.6% |
| FAD2B |   | W91*  | 1  | HOMO | 1     | 7.7% | 5.1% | 19.4% | 28.6% | 23.9% | 1.9% | 10.9% | 0.9% | 0.4% | 1.2% |
| FAD2B |   | W91*  | 8  | HET  | 1     | 7.8% | 5.5% | 18.5% | 27.5% | 24.4% | 2.5% | 10.9% | 0.9% | 0.5% | 1.5% |
| FAD2B |   | W91*  | 7  | Null | 1     | 7.6% | 3.9% | 12.4% | 32.4% | 23.9% | 2.6% | 11.5% | 1.9% | 0.7% | 3.1% |
| FAD2B |   | W91*  | 5  | Null | 1     | 7.9% | 4.2% | 12.8% | 29.4% | 26.1% | 2.6% | 11.8% | 1.7% | 0.7% | 2.9% |
| FAD2B |   | W91*  | 10 | Null | 4     | 8.4% | 5.0% | 12.1% | 28.8% | 26.9% | 2.8% | 11.4% | 1.7% | 0.8% | 2.0% |
| FAD2B |   | W91*  | 13 | Null |       | 7.6% | 4.8% | 13.0% | 33.7% | 21.9% | 2.8% | 10.8% | 1.8% | 0.6% | 2.9% |
| FAD2B |   | W91*  | 23 | Null |       | 8.3% | 5.8% | 13.4% | 31.9% | 21.4% | 4.0% | 10.6% | 1.7% | 0.4% | 2.6% |
| FAD2B |   | W91*  | 24 | Null |       | 9.1% | 5.1% | 13.1% | 32.8% | 24.8% | 2.2% | 8.4%  | 1.8% | 0.3% | 2.5% |
| FAD2B |   | W91*  | 21 | HOMO | 2     | 7.9% | 5.0% | 17.9% | 28.5% | 23.5% | 2.2% | 11.5% | 1.1% | 0.5% | 1.8% |
| FAD2B |   | W91*  | 22 | HOMO |       | 7.7% | 6.0% | 18.1% | 28.1% | 21.8% | 3.3% | 11.5% | 1.1% | 0.4% | 2.0% |
| FAD2B |   | W91*  | Y1 | 1105 | 9     | 5.9% | 2.5% | 19.7% | 22.9% | 33.6% | 0.6% | 12.3% | 1.0% | 0.7% | 0.8% |
| FAD2B |   | W91*  | Y2 | 1105 |       | 6.4% | 2.5% | 19.0% | 24.5% | 30.4% | 1.0% | 13.0% | 1.2% | 0.7% | 1.3% |
| FAD2B |   | W91*  | Y3 | 1105 |       | 6.8% | 2.7% | 18.8% | 25.4% | 31.6% | 0.6% | 11.5% | 1.2% | 0.5% | 1.0% |
| FAD2B |   | W91*  | Y4 | 1105 |       | 7.1% | 3.0% | 19.8% | 26.8% | 28.0% | 1.0% | 11.9% | 1.0% | 0.5% | 0.9% |
| FAD2B |   | W91*  | Y5 | 1105 |       | 6.4% | 2.4% | 19.8% | 25.1% | 29.7% | 0.8% | 12.7% | 1.1% | 0.6% | 1.5% |
| FAD2B |   | W91*  | Y6 | 1105 |       | 6.8% | 2.6% | 18.1% | 26.1% | 29.6% | 1.1% | 12.7% | 1.3% | 0.5% | 1.3% |
| FAD2B |   | W91*  | Y7 | 1105 |       | 6.0% | 2.7% | 14.6% | 24.5% | 30.3% | 1.0% | 14.9% | 2.0% | 1.1% | 2.9% |
| FAD2B |   | W91*  | Y8 | 1105 |       | 5.9% | 2.5% | 19.0% | 23.0% | 32.0% | 0.9% | 13.7% | 1.2% | 0.5% | 1.2% |
| FAD2B |   | W91*  | Y9 | 1105 |       | 6.5% | 2.5% | 17.2% | 24.2% | 31.7% | 1.1% | 13.4% | 1.1% | 0.7% | 1.5% |

Note:
*stands for nonsense mutation;
HOMO means the plants are all homozygous mutants at the specified locus.
HET means the plants are heterozygous mutants at the specified locus.
NULL means there is no mutation at the specified locus.
% means % of FAME composition

TABLE 16

Fatty Acids Composition in selected FAD2 mutants, sorted by mutation, Average of Test No. 1 and Test No. 2

| Gene | SNP | mutation | Plant # | genotype | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|---|
| none | none | CS32 controls | 1 | CS32 controls | 10 | 5.79% | 2.28% | 14.91% | 20.26% | 34.01% | 1.20% | 16.16% | 1.75% | 0.92% | 2.71% |
| none | none | CS32 controls | 2 | CS32 controls |    | 6.07% | 2.30% | 14.63% | 21.35% | 33.27% | 1.19% | 15.64% | 1.80% | 1.17% | 2.56% |
| none | none | CS32 controls | 3 | CS32 controls |    | 6.17% | 2.30% | 14.13% | 21.74% | 34.22% | 1.08% | 15.46% | 1.79% | 1.02% | 2.09% |

TABLE 16-continued

Fatty Acids Composition in selected FAD2 mutants, sorted by mutation, Average of Test No. 1 and Test No. 2

| Gene | SNP | mutation | Plant # | genotype | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|---|
| none | none | CS32 controls | 4 | CS32 controls | | 6.03% | 2.40% | 14.23% | 20.78% | 34.53% | 1.23% | 15.81% | 1.56% | 1.01% | 2.41% |
| none | none | CS32 controls | 5 | CS32 controls | | 6.73% | 2.57% | 14.63% | 23.08% | 33.52% | 0.75% | 12.87% | 1.83% | 1.34% | 2.67% |
| none | none | CS32 controls | 6 | CS32 controls | | 6.22% | 2.46% | 14.57% | 21.59% | 33.42% | 0.98% | 15.40% | 1.84% | 1.05% | 2.47% |
| none | none | CS32 controls | 7 | CS32 controls | | 5.88% | 2.42% | 14.58% | 22.23% | 32.70% | 1.26% | 15.70% | 1.79% | 0.97% | 2.46% |
| none | none | CS32 controls | 8 | CS32 controls | | 6.03% | 2.26% | 13.61% | 20.96% | 34.27% | 1.35% | 15.97% | 1.89% | 1.04% | 2.62% |
| none | none | CS32 controls | 9 | CS32 controls | | 5.93% | 2.38% | 14.34% | 20.60% | 33.61% | 1.26% | 16.23% | 1.85% | 1.11% | 2.70% |
| none | none | CS32 controls | 10 | CS32 controls | | 6.19% | 2.42% | 13.93% | 21.40% | 33.20% | 1.35% | 15.85% | 1.88% | 1.20% | 2.57% |
| FAD2A | | | | Cs32 AVE | | | | 14.36% | 21.40% | 33.67% | | 15.51% | | | |
| FAD2A | | | | Cs32 SD | | | | 0.39% | 0.83% | 0.57% | | 0.96% | | | |
| FAD2A | 5 | G150E | 4 | HOMO | 1 | 7.98% | 4.39% | 22.51% | 18.83% | 27.52% | 2.20% | 12.69% | 0.47% | 1.71% | 1.71% |
| FAD2A | 5 | G150E | 5 | HOMO | 1 | 7.80% | 4.19% | 23.22% | 18.43% | 26.56% | 2.16% | 14.17% | 0.68% | 0.56% | 2.24% |
| FAD2A | | G150E | 6 | HOMO | 5 new | 7.68% | 4.22% | 26.13% | 18.78% | 25.20% | 1.94% | 13.30% | 0.55% | 0.46% | 1.74% |
| FAD2A | | G150E | 8 | HOMO | | 8.09% | 4.58% | 24.20% | 18.71% | 28.10% | 2.24% | 10.23% | 0.73% | 0.46% | 2.66% |
| FAD2A | | G150E | 14 | HOMO | | 8.24% | 4.46% | 24.63% | 19.43% | 24.68% | 2.02% | 13.72% | 0.64% | 0.29% | 1.89% |
| FAD2A | | G150E | 23 | HOMO | | 8.60% | 4.73% | 22.96% | 19.00% | 26.72% | 2.07% | 13.07% | 0.58% | 0.52% | 1.76% |
| FAD2A | | G150E | 25 | HOMO | | 8.05% | 4.01% | 24.16% | 19.98% | 23.65% | 1.84% | 14.60% | 0.72% | 0.52% | 2.46% |
| FAD2A | | G150E | | Homo AVE | | | | 23.97% | 19.02% | 26.06% | | 13.11% | | | |
| FAD2A | | G150E | | Homo SD | | | | 1.22% | 0.52% | 1.60% | | 1.43% | | | |
| FAD2A | | G150E | 20 | Null | 2 new | 8.73% | 4.20% | 16.24% | 26.75% | 25.73% | 2.17% | 12.03% | 1.30% | 0.44% | 2.41% |
| FAD2A | 5 | G150E | 11 | Null | | 8.29% | 5.23% | 17.87% | 25.33% | 27.41% | 2.72% | 9.99% | 0.98% | 0.49% | 1.69% |
| FAD2A | 5 | G150E | 18 | Null | | 8.98% | 5.13% | 17.82% | 28.18% | 24.86% | 3.19% | 8.92% | 1.20% | 0.57% | 1.14% |
| FAD2A | | G150E | 24 | Null | | 8.74% | 5.08% | 16.38% | 27.40% | 26.04% | 2.17% | 10.88% | 1.09% | 0.63% | 1.59% |
| FAD2A | | G150E | | Null AVE | | | | 17.08% | 26.91% | 26.01% | | 10.46% | | | |
| FAD2A | | G150E | | null SD | | | | 0.89% | 1.21% | 1.06% | | 1.32% | | | |
| FAD2A | 2 | Q44* | 2 | HOMO | 1 | 8.29% | 5.10% | 22.83% | 20.76% | 26.73% | 2.03% | 11.13% | 0.78% | 0.39% | 1.96% |
| FAD2A | 2 | Q44* | 1 | HOMO | 1 | 7.80% | 4.89% | 19.67% | 18.86% | 28.30% | 2.61% | 13.90% | 0.87% | 0.73% | 2.36% |
| FAD2A | 2 | Q44* | 4 | HOMO | 1 | 7.63% | 5.05% | 23.75% | 20.19% | 25.73% | 2.39% | 12.83% | 0.60% | 0.38% | 1.45% |
| FAD2A | 2 | Q44* | 5 | HOMO | | 7.61% | 5.25% | 22.91% | 19.10% | 28.07% | 2.20% | 11.49% | 0.78% | 0.62% | 1.95% |
| FAD2A | 2 | Q44* | 3 | HOMO | | 7.50% | 4.63% | 22.86% | 19.84% | 27.72% | 2.09% | 11.66% | 0.80% | 0.63% | 2.26% |
| FAD2A | | Q44* | 36 | HOMO | 3 | 7.79% | 5.55% | 23.24% | 21.36% | 23.80% | 2.46% | 13.03% | 0.71% | 0.22% | 1.84% |
| FAD2A | | Q44* | 38 | HOMO | | 7.98% | 6.21% | 22.35% | 20.37% | 25.41% | 2.87% | 12.40% | 0.66% | 0.28% | 1.47% |
| FAD2A | | Q44* | 39 | HOMO | | 9.19% | 5.64% | 22.93% | 22.02% | 23.75% | 2.34% | 10.96% | 0.74% | 0.42% | 2.00% |
| FAD2A | | Q44* | | Homo AVE | | | | 22.57% | 20.31% | 26.19% | | 12.18% | | | |
| FAD2A | | Q44* | | homo SD | | | | 1.24% | 1.07% | 1.82% | | 1.04% | | | |
| FAD2A | 7 | S229F | 5 | HOMO | 1 | 7.60% | 3.79% | 19.62% | 21.37% | 27.42% | 2.01% | 13.94% | 0.97% | 0.63% | 2.64% |
| FAD2A | 7 | S229F | 1 | HOMO | | 7.31% | 3.36% | 19.34% | 23.61% | 26.47% | 1.74% | 13.03% | 1.25% | 0.73% | 3.17% |
| FAD2A | | S229F | 7 | HOMO | 3 | 8.44% | 5.78% | 18.39% | 22.68% | 24.53% | 3.52% | 11.78% | 1.09% | 0.56% | 3.22% |
| FAD2A | | S229F | 9 | HOMO | | 7.32% | 5.15% | 17.75% | 22.35% | 25.15% | 3.56% | 14.04% | 1.11% | 0.65% | 2.91% |
| FAD2A | | S229F | 19 | HOMO | | 6.92% | 4.96% | 21.02% | 20.89% | 24.77% | 2.73% | 14.28% | 0.92% | 0.63% | 2.87% |
| FAD2A | | S229F | 20 | HOMO AVE | | | | 19.23% | 22.18% | 25.67% | | 13.42% | | | |
| FAD2A | | S229F | 21 | HOMO SD | | | | 1.25% | 1.08% | 1.23% | | 1.03% | | | |
| FAD2A | 7 | S229F | 12 | Null | 1 | 8.62% | 5.59% | 14.98% | 27.76% | 26.56% | 3.41% | 8.20% | 1.36% | 0.69% | 2.82% |
| FAD2A | 7 | S229F | 10 | Null | 1 | 9.35% | 5.67% | 12.84% | 28.10% | 25.37% | 3.68% | 10.10% | 1.77% | 0.41% | 2.71% |
| FAD2A | | S229F | 13 | Null | 2 | 7.77% | 5.64% | 14.08% | 26.36% | 25.64% | 3.59% | 12.18% | 1.49% | 0.75% | 2.51% |
| FAD2A | | S229F | 14 | Null | | 7.57% | 4.84% | 13.78% | 24.96% | 28.33% | 3.24% | 12.64% | 1.21% | 0.85% | 2.59% |
| FAD2A | | S229F | 15 | Null AVE | | | | 13.92% | 26.80% | 26.47% | | 10.78% | | | |
| FAD2A | | S229F | 16 | Null SD | | | | 0.88% | 1.44% | 1.34% | | 2.05% | | | |
| FAD2B | | W91* | 1 | HOMO | 1 | 7.72% | 5.07% | 19.39% | 28.57% | 23.91% | 1.93% | 10.91% | 0.92% | 0.44% | 1.15% |
| FAD2B | | W91* | 21 | HOMO | 2 | 7.85% | 5.02% | 17.95% | 28.51% | 23.54% | 2.22% | 11.50% | 1.10% | 0.53% | 1.78% |
| FAD2B | | W91* | 22 | HOMO | | 7.73% | 5.99% | 18.08% | 28.11% | 21.75% | 3.34% | 11.49% | 1.09% | 0.44% | 1.97% |
| FAD2B | 8 | W91* | 2 | HOMO | | 8.23% | 5.35% | 18.80% | 29.20% | 26.29% | 1.68% | 7.84% | 0.86% | 0.41% | 1.34% |
| FAD2B | 8 | W91* | 3 | HOMO | | 8.05% | 5.50% | 18.37% | 28.87% | 24.40% | 2.69% | 8.63% | 1.15% | 0.53% | 1.82% |
| FAD2B | 8 | W91* | 4 | HOMO | | 7.54% | 5.09% | 17.96% | 28.89% | 22.95% | 2.92% | 10.62% | 1.25% | 0.51% | 2.27% |
| FAD2B | | W91* | 5 | HOMO AVE | | | | 18.43% | 28.69% | 23.80% | | 10.17% | | | |
| FAD2B | | W91* | 6 | HOMO SD | | | | 0.57% | 0.38% | 1.52% | | 1.55% | | | |
| FAD2B | | W91* | 7 | Null | 1 | 7.61% | 3.94% | 12.42% | 32.37% | 23.94% | 2.61% | 11.48% | 1.87% | 0.68% | 3.09% |
| FAD2B | | W91* | 5 | Null | 1 | 7.93% | 4.16% | 12.77% | 29.39% | 26.08% | 2.58% | 11.78% | 1.68% | 0.74% | 2.89% |
| FAD2B | | W91* | 10 | Null | 4 | 8.35% | 5.04% | 12.13% | 28.77% | 26.89% | 2.84% | 11.44% | 1.69% | 0.82% | 2.04% |
| FAD2B | | W91* | 13 | Null | | 7.61% | 4.83% | 12.99% | 33.71% | 21.94% | 2.81% | 10.77% | 1.84% | 0.62% | 2.88% |
| FAD2B | | W91* | 23 | Null | | 8.31% | 5.84% | 13.38% | 31.92% | 21.35% | 4.00% | 10.55% | 1.66% | 0.36% | 2.62% |
| FAD2B | | W91* | 24 | Null | | 9.08% | 5.10% | 13.10% | 32.82% | 24.75% | 2.16% | 8.39% | 1.77% | 0.34% | 2.49% |

TABLE 16-continued

Fatty Acids Composition in selected FAD2 mutants, sorted by mutation, Average of Test No. 1 and Test No. 2

| Gene | SNP | mutation | Plant # | genotype | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|---|
| FAD2B | | W91* | 25 | Null AVE | | | | 12.80% | 31.50% | 24.16% | | 10.73% | | | |
| FAD2B | | W91* | 26 | Null SD | | | | 0.46% | 1.97% | 2.21% | | 1.24% | | | |

Note:
*stands for nonsense mutation;
HOMO means the plants are all homozygous mutants at the specified locus.
HET means the plants are heterozygous mutants at the specified locus.
NULL means there is no mutation at the specified locus.
% means % of FAME composition

TABLE 17

Fatty Acids Composition in selected FAD2 mutants, sorted by mutation, Test 2

| Gene | SNP | mutation | Plant # | genotype | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|---|
| none | none | CS32 controls | 1 | CS32 controls | 10 | 5.8% | 2.3% | 14.9% | 20.3% | 34.0% | 1.2% | 16.2% | 1.8% | 0.9% | 2.7% |
| none | none | CS32 controls | 2 | CS32 controls | | 6.1% | 2.3% | 14.6% | 21.3% | 33.3% | 1.2% | 15.6% | 1.8% | 1.2% | 2.6% |
| none | none | CS32 controls | 3 | CS32 controls | | 6.2% | 2.3% | 14.1% | 21.7% | 34.2% | 1.1% | 15.5% | 1.8% | 1.0% | 2.1% |
| none | none | CS32 controls | 4 | CS32 controls | | 6.0% | 2.4% | 14.2% | 20.8% | 34.5% | 1.2% | 15.8% | 1.6% | 1.0% | 2.4% |
| none | none | CS32 controls | 5 | CS32 controls | | 6.7% | 2.6% | 14.6% | 23.1% | 33.5% | 0.7% | 12.9% | 1.8% | 1.3% | 2.7% |
| none | none | CS32 controls | 6 | CS32 controls | | 6.2% | 2.5% | 14.6% | 21.6% | 33.4% | 1.0% | 15.4% | 1.8% | 1.1% | 2.5% |
| none | none | CS32 controls | 7 | CS32 controls | | 5.9% | 2.4% | 14.6% | 22.2% | 32.7% | 1.3% | 15.7% | 1.8% | 1.0% | 2.5% |
| none | none | CS32 controls | 8 | CS32 controls | | 6.0% | 2.3% | 13.6% | 21.0% | 34.3% | 1.4% | 16.0% | 1.9% | 1.0% | 2.6% |
| none | none | CS32 controls | 9 | CS32 controls | | 5.9% | 2.4% | 14.3% | 20.6% | 33.6% | 1.3% | 16.2% | 1.9% | 1.1% | 2.7% |
| none | none | CS32 controls | 10 | CS32 controls | | 6.2% | 2.4% | 13.9% | 21.4% | 33.2% | 1.3% | 15.9% | 1.9% | 1.2% | 2.6% |
| FAD2A | 5 | G150E | 4 | HOMO | 1 | 8.0% | 4.4% | 22.5% | 18.8% | 27.5% | 2.2% | 12.7% | 0.5% | 1.7% | 1.7% |
| FAD2A | 5 | G150E | 5 | HOMO | 1 | 7.8% | 4.2% | 23.3% | 18.4% | 26.6% | 2.2% | 14.2% | 0.7% | 0.6% | 2.2% |
| FAD2A | | G150E | 6 | HOMO | 5 new | 7.7% | 4.2% | 26.1% | 18.8% | 25.2% | 1.9% | 13.3% | 0.6% | 0.5% | 1.7% |
| FAD2A | | G150E | 8 | HOMO | | 8.1% | 4.6% | 24.2% | 18.7% | 28.1% | 2.2% | 10.2% | 0.7% | 0.5% | 2.7% |
| FAD2A | | G150E | 14 | HOMO | | 8.2% | 4.5% | 24.6% | 19.4% | 24.7% | 2.0% | 13.7% | 0.6% | 0.3% | 1.9% |
| FAD2A | | G150E | 23 | HOMO | | 8.6% | 4.7% | 23.0% | 19.0% | 26.7% | 2.1% | 13.1% | 0.6% | 0.5% | 1.8% |
| FAD2A | | G150E | 25 | HOMO | | 8.0% | 4.0% | 24.2% | 20.0% | 23.7% | 1.8% | 14.6% | 0.7% | 0.5% | 2.5% |
| FAD2A | 2 | Q44* | 2 | HOMO | 1 | 8.3% | 5.1% | 22.8% | 20.8% | 26.7% | 2.0% | 11.1% | 0.8% | 0.4% | 2.0% |
| FAD2A | 2 | Q44* | 1 | HOMO | 1 | 7.8% | 4.9% | 19.7% | 18.9% | 28.3% | 2.6% | 13.9% | 0.9% | 0.7% | 2.4% |
| FAD2A | 2 | Q44* | 4 | HOMO | 1 | 7.6% | 5.1% | 23.7% | 20.2% | 25.7% | 2.4% | 12.8% | 0.6% | 0.4% | 1.5% |
| FAD2A | 2 | Q44* | 5 | HOMO | | | | | | | | | | | |
| FAD2A | 2 | Q44* | 3 | HOMO | | | | | | | | | | | |
| FAD2A | | Q44* | 36 | HOMO | 3 | 7.8% | 5.5% | 23.2% | 21.4% | 23.8% | 2.5% | 13.0% | 0.7% | 0.2% | 1.8% |
| FAD2A | | Q44* | 38 | HOMO | | 8.0% | 6.2% | 22.3% | 20.4% | 25.4% | 2.9% | 12.4% | 0.7% | 0.3% | 1.5% |
| FAD2A | | Q44* | 39 | HOMO | | 9.2% | 5.6% | 22.9% | 22.0% | 23.7% | 2.3% | 11.0% | 0.7% | 0.4% | 2.0% |
| FAD2A | 7 | S229F | 5 | HOMO | 1 | 7.6% | 3.8% | 19.6% | 21.4% | 27.4% | 2.0% | 13.9% | 1.0% | 0.6% | 2.6% |
| FAD2A | 7 | S229F | 1 | HOMO | | | | | | | | | | | |
| FAD2A | | S229F | 7 | HOMO | 3 | 8.4% | 5.8% | 18.4% | 22.7% | 24.5% | 3.5% | 11.8% | 1.1% | 0.6% | 3.2% |
| FAD2A | | S229F | 9 | HOMO | | 7.3% | 5.1% | 17.8% | 22.4% | 25.2% | 3.6% | 14.0% | 1.1% | 0.6% | 2.9% |
| FAD2A | | S229F | 19 | HOMO | | 6.9% | 5.0% | 21.0% | 20.9% | 24.8% | 2.7% | 14.3% | 0.9% | 0.6% | 2.9% |
| FAD2B | | W91* | 1 | HOMO | 1 | 7.7% | 5.1% | 19.4% | 28.6% | 23.9% | 1.9% | 10.9% | 0.9% | 0.4% | 1.2% |
| FAD2B | | W91* | 21 | HOMO | 2 | 7.9% | 5.0% | 17.9% | 28.5% | 23.5% | 2.2% | 11.5% | 1.1% | 0.5% | 1.8% |
| FAD2B | | W91* | 22 | HOMO | | 7.7% | 6.0% | 18.1% | 28.1% | 21.8% | 3.3% | 11.5% | 1.1% | 0.4% | 2.0% |
| FAD2B | 8 | W91* | 2 | HOMO | | | | | | | | | | | |
| FAD2B | 8 | W91* | 3 | HOMO | | | | | | | | | | | |
| FAD2B | 8 | W91* | 4 | HOMO | | | | | | | | | | | |
| FAD2A | | G150E | 20 | Null | 2 | 8.7% | 4.2% | 16.2% | 26.7% | 25.7% | 2.2% | 12.0% | 1.3% | 0.4% | 2.4% |
| FAD2A | 5 | G150E | 11 | Null | | 8.3% | 5.2% | 17.9% | 25.3% | 27.4% | 2.7% | 10.0% | 1.0% | 0.5% | 1.7% |
| FAD2A | 5 | G150E | 18 | Null | | 9.0% | 5.1% | 17.8% | 28.2% | 24.9% | 3.2% | 8.9% | 1.2% | 0.6% | 1.1% |
| FAD2A | | G150E | 24 | Null | | 8.7% | 5.1% | 16.4% | 27.4% | 26.0% | 2.2% | 10.9% | 1.1% | 0.6% | 1.6% |
| FAD2A | 7 | S229F | 12 | Null | 1 | 8.6% | 5.6% | 15.0% | 27.8% | 26.6% | 3.4% | 8.2% | 1.4% | 0.7% | 2.8% |
| FAD2A | 7 | S229F | 10 | Null | 1 | 9.3% | 5.7% | 15.0% | 28.1% | 25.4% | 3.7% | 10.1% | 1.8% | 0.4% | 2.7% |
| FAD2A | | S229F | 13 | Null | 2 | 7.8% | 5.6% | 14.1% | 26.4% | 25.6% | 3.6% | 12.2% | 1.5% | 0.7% | 2.5% |
| FAD2A | | S229F | 14 | Null | | 7.6% | 4.8% | 13.8% | 25.0% | 28.3% | 3.2% | 12.6% | 1.2% | 0.8% | 2.6% |
| FAD2B | | W91* | 7 | Null | 1 | 7.6% | 3.9% | 12.4% | 32.4% | 23.9% | 2.6% | 11.5% | 1.9% | 0.7% | 3.1% |
| FAD2B | | W91* | 5 | Null | 1 | 7.9% | 4.2% | 12.8% | 29.4% | 26.1% | 2.6% | 11.8% | 1.7% | 0.7% | 2.9% |

TABLE 17-continued

Fatty Acids Composition in selected FAD2 mutants, sorted by mutation, Test 2

| Gene | SNP mutation | Plant # | geno-type | # of samples | C16:0 | C18:0 | C18:1 | C18:2 | C18:3 | C20:0 | C20:1 | C20:2 | C20:3 | C22:1 |
|---|---|---|---|---|---|---|---|---|---|---|---|---|---|---|
| FAD2B | W91* | 10 | Null | 4 | 8.4% | 5.0% | 12.1% | 28.8% | 26.9% | 2.8% | 11.4% | 1.7% | 0.8% | 2.0% |
| FAD2B | W91* | 13 | Null | | 7.6% | 4.8% | 13.0% | 33.7% | 21.9% | 2.8% | 10.8% | 1.8% | 0.6% | 2.9% |
| FAD2B | W91* | 23 | Null | | 8.3% | 5.8% | 13.4% | 31.9% | 21.4% | 4.0% | 10.6% | 1.7% | 0.4% | 2.6% |
| FAD2B | W91* | 24 | Null | | 9.1% | 5.1% | 13.1% | 32.8% | 24.8% | 2.2% | 8.4% | 1.8% | 0.3% | 2.5% |

Note:
*stands for nonsense mutation;
HOMO means the plants are all homozygous mutants at the specified locus.
HET means the plants are heterozygous mutants at the specified locus.
NULL means there is no mutation at the specified locus.
% means % of FAME composition TABLE 18a Fatty Acids Composition in selected FAD2 mutants, sorted by gene, Test 4

| Sample | Geno-type | Seed generation | gene | muta-tion | C16:0 | C18:0 | C18:1 | C18:2 | C20:0 | C18:3 | C20:1 | C20:2 | C20:3 | C22:1 |
|---|---|---|---|---|---|---|---|---|---|---|---|---|---|---|
| 2362-Q10 | HOM | M5 | FAD2A | G150E | 8.0% | 4.3% | 21.6% | 16.2% | 2.3% | 30.3% | 13.4% | 0.8% | 0.7% | 2.2% |
| 2362-Q11 | HOM | M5 | FAD2A | G150E | 8.0% | 3.6% | 20.4% | 17.1% | 1.8% | 32.3% | 13.1% | 0.8% | 0.7% | 2.2% |
| 2362-Q12 | HOM | M5 | FAD2A | G150E | 8.3% | 3.6% | 19.4% | 17.9% | 1.5% | 32.5% | 13.0% | 0.9% | 0.7% | 2.2% |
| 2362-Q13 | HOM | M5 | FAD2A | G150E | 8.2% | 4.2% | 20.4% | 17.3% | 2.3% | 31.0% | 13.1% | 0.9% | 0.6% | 2.1% |
| 2826-P1 | Het | M5 | FAD2A | Q44* | 7.1% | 3.4% | 16.3% | 16.3% | 2.2% | 35.1% | 14.6% | 1.2% | 1.1% | 2.8% |
| 2826-P2 | Het | M5 | FAD2A | Q44* | 7.7% | 4.0% | 17.2% | 16.4% | 2.5% | 33.7% | 14.1% | 1.0% | 0.9% | 2.5% |
| 2826-P3 | Het | M5 | FAD2A | Q44* | 8.4% | 4.0% | 17.8% | 19.8% | 2.7% | 28.9% | 12.4% | 1.4% | 1.2% | 3.3% |
| 2826-P4 | Het | M5 | FAD2A | Q44* | 7.7% | 3.9% | 15.5% | 16.6% | 2.5% | 34.4% | 14.5% | 1.2% | 1.0% | 2.6% |
| 3006-R1 | HOM | M5 | FAD2B | W91* | 7.7% | 3.5% | 11.9% | 21.5% | 2.3% | 35.6% | 12.3% | 1.6% | 1.1% | 2.6% |
| 3006-R2 | HOM | M5 | FAD2B | W91* | 7.8% | 3.6% | 12.1% | 22.6% | 2.3% | 33.4% | 12.7% | 1.6% | 1.0% | 2.7% |
| 3006-R3 | HOM | M5 | FAD2B | W91* | 8.1% | 3.5% | 12.3% | 22.5% | 2.1% | 34.5% | 12.0% | 1.6% | 1.1% | 2.4% |
| 3006-R4 | HOM | M5 | FAD2B | W91* | 7.8% | 3.6% | 12.7% | 22.2% | 2.1% | 34.4% | 12.2% | 1.6% | 1.0% | 2.4% |
| 3489-N2 | HOM | M4 | FAD2B | W138* | 8.0% | 3.4% | 11.9% | 23.2% | 2.5% | 31.7% | 12.8% | 1.9% | 1.1% | 3.6% |
| 3489-N5 | HOM | M4 | FAD2B | W138* | 8.2% | 3.5% | 11.5% | 23.7% | 2.6% | 31.0% | 12.8% | 2.0% | 1.0% | 3.6% |
| 3489-N9 | HOM | M4 | FAD2B | W138* | 7.9% | 3.3% | 12.3% | 22.2% | 2.6% | 31.0% | 13.7% | 1.9% | 1.2% | 3.8% |
| 3489-N12 | HOM | M4 | FAD2B | W138* | 7.8% | 3.4% | 11.9% | 22.9% | 2.6% | 30.7% | 14.0% | 2.0% | 1.1% | 3.8% |
| 3489-N16 | HOM | M4 | FAD2B | W138* | 7.8% | 3.5% | 11.9% | 22.7% | 2.6% | 31.2% | 13.6% | 2.0% | 1.1% | 3.8% |
| 3702-O2 | HOM | M4 | FAD2B | G150E | 7.7% | 4.2% | 12.8% | 23.5% | 3.0% | 31.1% | 12.0% | 1.8% | 1.0% | 2.9% |
| 3702-O3 | HOM | M4 | FAD2B | G150E | 9.7% | 5.6% | 17.1% | 34.2% | 3.7% | 18.0% | 8.2% | 1.0% | 0.3% | 2.0% |
| 3702-O4 | Het | M4 | FAD2B | G150E | 7.5% | 4.4% | 11.6% | 24.7% | 4.5% | 31.1% | 10.4% | 1.8% | 0.9% | 3.2% |
| 3702-O6 | HOM | M4 | FAD2B | G150E | 7.8% | 4.4% | 12.0% | 24.4% | 3.0% | 31.4% | 11.5% | 1.8% | 0.9% | 2.7% |
| 3702-O7 | HOM | M4 | FAD2B | G150E | 8.0% | 5.8% | 13.6% | 25.2% | 4.2% | 29.7% | 9.1% | 1.4% | 0.7% | 2.2% |
| 3702-O9 | Het | M4 | FAD2B | G150E | 7.1% | 4.0% | 12.1% | 23.7% | 3.2% | 31.2% | 12.4% | 1.9% | 1.0% | 3.3% |
| 6490-M1 | HOM | M4 | FAD2B | W91* | 6.3% | 3.2% | 13.2% | 21.8% | 2.3% | 32.1% | 14.4% | 1.8% | 1.2% | 3.7% |
| 6490-M2 | HOM | M4 | FAD2B | W91* | 6.1% | 2.9% | 12.0% | 20.2% | 2.2% | 34.2% | 14.8% | 2.1% | 1.3% | 4.1% |
| 6490-M3 | HOM | M4 | FAD2B | W91* | 6.2% | 3.0% | 12.5% | 20.8% | 2.3% | 33.5% | 14.5% | 2.0% | 1.3% | 4.0% |
| 6490-M4 | HOM | M4 | FAD2B | W91* | 8.3% | 3.2% | 12.3% | 21.3% | 2.3% | 32.0% | 14.0% | 1.8% | 1.2% | 3.6% |
| 6490-M5 | HOM | M4 | FAD2B | W91* | 8.0% | 2.5% | 12.0% | 20.5% | 1.8% | 33.8% | 14.7% | 1.9% | 1.3% | 3.6% |
| 6490-M10 | null | M4 | FAD2B | W91* | 9.0% | 2.6% | 10.9% | 18.5% | 2.1% | 35.5% | 14.4% | 2.1% | 1.4% | 3.3% |
| 3284-B11 | null | M4 | FAD2C | W91* | 8.9% | 4.7% | 10.1% | 22.3% | 2.8% | 35.8% | 10.3% | 2.0% | 1.2% | 2.0% |
| 3284-B12 | Het | M4 | FAD2C | W91* | 8.6% | 5.2% | 11.9% | 23.2% | 3.2% | 33.4% | 10.2% | 1.6% | 0.9% | 1.7% |
| 3284-B13 | Het | M4 | FAD2C | W91* | 8.1% | 4.4% | 11.6% | 21.1% | 2.7% | 36.3% | 11.1% | 1.7% | 1.2% | 1.9% |
| 3284-B15 | null | M4 | FAD2C | W91* | 9.0% | 4.2% | 9.3% | 22.1% | 2.9% | 36.9% | 10.5% | 1.9% | 1.3% | 1.9% |
| 3284-B21 | Het | M4 | FAD2C | W91* | 8.4% | 4.5% | 10.6% | 20.3% | 2.9% | 36.5% | 11.7% | 1.7% | 1.2% | 2.2% |
| 4506-A2 | null | M4 | FAD2C | W87* | 7.5% | 3.5% | 11.9% | 23.6% | 3.0% | 30.8% | 12.9% | 2.1% | 1.1% | 3.5% |
| 4506-A10 | Hom | M4 | FAD2C | W87* | 6.9% | 3.6% | 14.7% | 20.7% | 2.6% | 31.5% | 14.1% | 1.6% | 1.0% | 3.3% |
| 4506-A12 | Hom | M4 | FAD2C | W87* | 7.3% | 4.0% | 15.9% | 20.4% | 2.9% | 30.0% | 14.1% | 1.4% | 0.9% | 3.2% |
| 4506-A15 | Hom | M4 | FAD2C | W87* | 8.2% | 3.3% | 7.1% | 24.1% | 2.5% | 33.8% | 14.0% | 1.9% | 1.1% | 4.1% |
| 4506-A16 | null | M4 | FAD2C | W87* | 8.0% | 3.5% | 12.8% | 23.6% | 3.0% | 30.9% | 12.5% | 1.7% | 1.0% | 3.1% |
| 4608-C4 | Hom | M4 | FAD2C | G150E | 8.8% | 3.5% | 9.2% | 23.3% | 2.9% | 35.0% | 11.2% | 1.9% | 1.2% | 2.9% |
| 4608-C12 | Hom | M4 | FAD2C | G150E | 9.3% | 4.0% | 10.0% | 25.9% | 3.0% | 31.6% | 10.8% | 1.9% | 1.0% | 2.7% |
| 4608-C13 | Het | M4 | FAD2C | G150E | 9.0% | 3.9% | 9.2% | 25.4% | 2.8% | 32.8% | 11.0% | 2.1% | 1.1% | 2.8% |
| 4608-C15 | null | M4 | FAD2C | G150E | 8.9% | 3.9% | 8.9% | 26.0% | 2.9% | 32.7% | 10.7% | 2.2% | 1.1% | 2.7% |
| 4608-C17 | Het | M4 | FAD2C | G150E | 9.0% | 3.8% | 8.7% | 23.6% | 3.1% | 34.1% | 11.1% | 2.2% | 1.3% | 3.1% |
| Cs32-1 | | | | | 7.8% | 4.7% | 12.4% | 27.1% | 4.3% | 25.5% | 12.1% | 2.0% | 0.8% | 3.3% |
| Cs32-2 | | | | | 8.0% | 4.5% | 12.0% | 26.7% | 3.9% | 27.1% | 11.8% | 2.0% | 0.8% | 3.2% |
| Cs32-3 | | | | | 8.0% | 4.1% | 12.1% | 26.6% | 3.7% | 27.7% | 11.7% | 2.1% | 0.9% | 3.2% |
| Cs32-4 | | | | | 7.9% | 3.9% | 12.2% | 26.2% | 3.4% | 28.7% | 11.7% | 2.0% | 0.9% | 3.0% |
| At FAD2_1 | | | | | 5.4% | 3.0% | 49.9% | 4.2% | 1.5% | 10.3% | 24.2% | 0.0% | 0.0% | 1.5% |
| At FAD2_2 | | | | | 5.6% | 3.6% | 50.5% | 4.5% | 0.0% | 10.3% | 24.1% | 0.1% | 0.0% | 1.4% |

TABLE 18a-continued

Fatty Acids Composition in selected FAD2 mutants, sorted by gene, Test 4

| Sample | Geno-type | Seed generation | gene | muta-tion | C16:0 | C18:0 | C18:1 | C18:2 | C20:0 | C18:3 | C20:1 | C20:2 | C20:3 | C22:1 |
|---|---|---|---|---|---|---|---|---|---|---|---|---|---|---|
| At FAE1_1 | | | | | 10.3% | 4.7% | 28.8% | 34.2% | 1.0% | 20.9% | 0.1% | 0.0% | 0.0% | 0.0% |
| At FAE1_2 | | | | | 10.2% | 5.2% | 28.7% | 33.9% | 1.0% | 20.9% | 0.1% | 0.0% | 0.0% | 0.0% |

Note:

*stands for nonsense mutation;

Hom means the plants are all homozygous mutants at the specified locus.

Het means the plants are heterozygous mutants at the specified locus.

Null means there is no mutation at the specified locus.

% means % of FAME composition

Gene indicates in which gene the mutation is located

TABLE 19a

Fatty Acids Composition in selected FAE1 mutants, sorted by gene, Test 4

| Sample | Geno-type | Seed generation | gene | muta-tion | C16:0 | C18:0 | C18:1 | C18:2 | C20:0 | C18:3 | C20:1 | C20:2 | C20:3 | C22:1 |
|---|---|---|---|---|---|---|---|---|---|---|---|---|---|---|
| 3395-D10 | Hom | M4 | FAE1A | R209* | 9.7% | 4.2% | 13.2% | 20.8% | 2.4% | 33.6% | 11.4% | 1.6% | 1.1% | 2.0% |
| 3395-D12 | Hom | M4 | FAE1A | R209* | 8.3% | 4.7% | 15.8% | 21.0% | 2.4% | 32.7% | 11.0% | 1.3% | 1.0% | 1.6% |
| 3395-D13 | Hom | M4 | FAE1A | R209* | 7.8% | 4.2% | 14.1% | 20.7% | 2.2% | 35.7% | 11.0% | 1.5% | 1.1% | 1.7% |
| 3395-D17 | null | M4 | FAE1A | R209* | 9.8% | 3.4% | 11.7% | 20.8% | 2.1% | 34.6% | 11.7% | 1.8% | 1.3% | 2.8% |
| 3395-D18 | null | M4 | FAE1A | R209* | 7.4% | 4.3% | 14.0% | 21.4% | 2.5% | 33.5% | 11.6% | 1.6% | 1.2% | 2.6% |
| 3395-D19 | null | M4 | FAE1A | R209* | 7.7% | 3.5% | 14.2% | 20.2% | 2.4% | 33.5% | 12.7% | 1.6% | 1.1% | 3.1% |
| 3395-D20 | Hom | M4 | FAE1A | R209* | 7.8% | 4.4% | 14.8% | 21.4% | 2.4% | 33.8% | 11.3% | 1.4% | 1.0% | 1.7% |
| 6386-F1 | Het | M4 | FAE1A | G221D | 11.1% | 5.0% | 10.6% | 32.7% | 3.6% | 23.4% | 9.2% | 1.7% | 0.5% | 2.1% |
| 6386-F2 | HOM | M4 | FAE1A | G221D | 9.2% | 4.7% | 13.3% | 26.8% | 2.2% | 31.3% | 9.1% | 1.3% | 0.7% | 1.2% |
| 6386-F7 | Hom | M4 | FAE1A | G221D | 8.8% | 4.6% | 12.7% | 26.3% | 2.4% | 32.7% | 9.0% | 1.5% | 0.8% | 1.1% |
| 6386-F9 | Hom | M4 | FAE1A | G221D | 9.0% | 4.4% | 11.5% | 26.8% | 2.6% | 30.9% | 10.2% | 1.8% | 0.9% | 1.9% |
| 6386-F13 | null | M4 | FAE1A | G221D | 8.9% | 4.6% | 12.7% | 25.4% | 2.3% | 33.6% | 9.0% | 1.4% | 0.8% | 1.2% |
| 6386-F15 | null | M4 | FAE1A | G221D | 8.1% | 4.2% | 11.2% | 25.3% | 3.4% | 30.1% | 11.8% | 1.9% | 1.0% | 2.9% |
| 6386-F19 | Het | M4 | FAE1A | G221D | 8.2% | 4.2% | 11.4% | 24.8% | 2.7% | 32.8% | 10.9% | 1.8% | 1.0% | 2.2% |
| 4687-I4 | HOM | M4 | FAE1B | H301Y | 7.1% | 2.6% | 14.6% | 20.7% | 1.2% | 41.0% | 9.2% | 1.3% | 1.1% | 1.3% |
| 4687-I10 | null | M4 | FAE1B | H301Y | 7.3% | 3.2% | 14.5% | 21.0% | 1.8% | 37.8% | 10.5% | 1.4% | 1.1% | 1.5% |
| 4687-I11 | HOM | M4 | FAE1B | H301Y | 7.7% | 3.2% | 15.9% | 21.8% | 1.4% | 38.9% | 8.2% | 1.1% | 0.9% | 0.9% |
| 4687-I14 | null | M4 | FAE1B | H301Y | 7.6% | 3.6% | 16.0% | 21.6% | 1.8% | 34.1% | 11.5% | 1.4% | 1.0% | 1.5% |
| 4687-I17 | HOM | M4 | FAE1B | H301Y | 7.2% | 3.0% | 14.7% | 19.6% | 1.3% | 43.0% | 8.2% | 1.1% | 1.0% | 0.9% |
| 5343-H6 | null | M4 | FAE1B | S281F | 7.6% | 3.5% | 11.5% | 19.6% | 2.5% | 36.5% | 12.6% | 1.8% | 1.4% | 3.0% |
| 5343-H7 | null | M4 | FAE1B | S281F | 7.8% | 3.6% | 11.6% | 20.1% | 2.6% | 35.7% | 12.5% | 1.8% | 1.2% | 3.1% |
| 5343-H10 | HOM | M4 | FAE1B | S281F | 7.9% | 4.0% | 13.2% | 22.9% | 2.3% | 34.5% | 10.6% | 1.5% | 1.0% | 2.1% |
| 5343-H14 | HOM | M4 | FAE1B | S281F | 8.3% | 3.2% | 11.2% | 20.6% | 1.8% | 39.3% | 10.6% | 1.7% | 1.3% | 2.1% |
| 5343-H15 | HOM | M4 | FAE1B | S281F | 8.1% | 4.0% | 12.0% | 22.1% | 2.2% | 36.5% | 10.4% | 1.6% | 1.1% | 2.0% |
| 5343-H16 | HOM | M4 | FAE1B | S281F | 7.9% | 3.0% | 11.0% | 19.4% | 1.7% | 40.6% | 10.9% | 1.8% | 1.5% | 2.3% |
| 5951-G1 | HOM | M4 | FAE1B | Q142* | 8.7% | 3.6% | 14.1% | 22.4% | 1.1% | 43.0% | 4.9% | 0.8% | 0.7% | 0.7% |
| 5951-G2 | HOM | M4 | FAE1B | Q142* | 8.1% | 3.8% | 14.4% | 22.3% | 1.4% | 40.7% | 6.6% | 0.9% | 0.8% | 0.9% |
| 5951-G3 | HOM | M4 | FAE1B | Q142* | 7.9% | 3.1% | 11.3% | 20.0% | 2.1% | 39.0% | 11.0% | 1.7% | 1.5% | 2.4% |
| 5951-G4 | HOM | M4 | FAE1B | Q142* | 9.4% | 3.3% | 14.3% | 23.8% | 0.9% | 44.0% | 3.0% | 0.5% | 0.5% | 0.3% |
| 5951-G5 | HOM | M4 | FAE1B | Q142* | 8.0% | 2.8% | 10.5% | 20.4% | 2.2% | 39.0% | 11.4% | 1.7% | 1.4% | 2.7% |
| 6476-K2 | Hom | M4 | FAE1C | R209* | 7.8% | 3.2% | 9.2% | 23.2% | 2.2% | 38.7% | 9.4% | 1.9% | 1.3% | 2.9% |
| 6476-K4 | HOM | M4 | FAE1C | R209* | 7.3% | 3.8% | 10.6% | 23.1% | 2.4% | 38.3% | 9.1% | 1.7% | 1.2% | 2.3% |
| 6476-K6 | HOM | M4 | FAE1C | R209* | 8.3% | 4.0% | 10.2% | 22.9% | 2.5% | 36.3% | 9.8% | 1.9% | 1.2% | 2.9% |
| 6476-K7 | null | M4 | FAE1C | R209* | 7.1% | 3.6% | 9.8% | 23.6% | 3.0% | 32.1% | 13.0% | 2.5% | 1.2% | 4.0% |
| 6476-K15 | HOM | M4 | FAE1C | R209* | 7.5% | 4.0% | 11.2% | 21.6% | 2.2% | 35.6% | 11.7% | 1.9% | 1.2% | 3.0% |
| Cs32-1 | | | | | 7.8% | 4.7% | 12.4% | 27.1% | 4.3% | 25.5% | 12.1% | 2.0% | 0.8% | 3.3% |
| Cs32-2 | | | | | 8.0% | 4.5% | 12.0% | 26.7% | 3.9% | 27.1% | 11.8% | 2.0% | 0.8% | 3.2% |
| Cs32-3 | | | | | 8.0% | 4.1% | 12.1% | 26.6% | 3.7% | 27.7% | 11.7% | 2.1% | 0.9% | 3.2% |
| Cs32-4 | | | | | 7.9% | 3.9% | 12.2% | 26.2% | 3.4% | 28.7% | 11.7% | 2.0% | 0.9% | 3.0% |
| At FAE1_1 | | | | | 10.3% | 4.7% | 28.8% | 34.2% | 1.0% | 20.9% | 0.1% | 0.0% | 0.0% | 0.0% |
| At FAE1_2 | | | | | 10.2% | 5.2% | 28.7% | 33.9% | 1.0% | 20.9% | 0.1% | 0.0% | 0.0% | 0.0% |

Note:

*stands for nonsense mutation;

Hom means the plants are all homozygous mutants at the specified locus.

Het means the plants are heterozygous mutants at the specified locus.

Null means there is no mutation at the specified locus.

% means % of FAME composition

Gene indicates in which gene the mutation is located

Example 13

Fatty Acids Composition in Plants with Multiple Mutations in FAD2 and/or FAE1 Genes To further increase the oleic acid (18:1) level and/or yield and improve *Camelina* seed oil quality, mutations in one or more copies of FAD2 genes and/or one or more copies of FAE1 genes are integrated together to create mutant plants with double, triple, quadruple et al. mutations. Such mutants can be created by classic breeding methods. Table 20 below shows a list of non-limiting examples of such mutants.

TABLE 20

Plants with more than one mutation in Fatty Acid Synthesis Genes

| Plant ID | Genotype | | | | | |
|---|---|---|---|---|---|---|
| | FAD2A | FAD2B | FAD2C | FAE1A | FAE1B | FAE1C |
| A1 | HOMO | HOMO | NULL | NULL | NULL | NULL |
| A2 | HOMO | NULL | HOMO | NULL | NULL | NULL |
| A3 | NULL | HOMO | HOMO | NULL | NULL | NULL |
| A4 | HOMO | HOMO | HOMO | NULL | NULL | NULL |
| A5 | NULL | NULL | NULL | HOMO | HOMO | NULL |
| A6 | NULL | NULL | NULL | HOMO | NULL | HOMO |
| A7 | NULL | NULL | NULL | NULL | HOMO | HOMO |
| A8 | NULL | NULL | NULL | HOMO | HOMO | HOMO |
| A9 | HOMO | NULL | NULL | HOMO | NULL | NULL |
| A10 | HOMO | NULL | NULL | HOMO | HOMO | NULL |
| A11 | HOMO | NULL | NULL | HOMO | HOMO | HOMO |
| A12 | HOMO | HOMO | NULL | HOMO | NULL | NULL |
| A13 | HOMO | HOMO | NULL | HOMO | HOMO | NULL |
| A14 | HOMO | HOMO | NULL | HOMO | HOMO | HOMO |
| A15 | HOMO | HOMO | HOMO | HOMO | NULL | NULL |
| A16 | HOMO | HOMO | HOMO | HOMO | HOMO | NULL |
| A17 | HOMO | HOMO | HOMO | HOMO | HOMO | HOME |

Note:
HOMO means the plants are all homozygous mutants at the specified locus.
NULL means there is no mutation at the specified locus.

Fatty acid compositions in these mutants are then analyzed by gas chromatography (GC). The results will show that one or more of these mutants produce seed oil with higher oleic acid (18:1) levels and/or lower VLCFA levels when compared to Cs32 control plants or to one or more single mutants that have only one mutation in a FAD2 gene and/or a FAE1 gene.

Thus, mutations in more than one FAD2 and/or FAE1 genes further increase oleic acid (18:1) levels and/or lower VLCFA levels, and improve *Camelina* seed oil quality.

Example 14

Fatty Acids Composition in RNAi Transgenic *Camelina* Plants

As described in the present invention, RNAi technology can be used to disrupt one or more fatty acid synthesis genes (e.g., FAD2, FAE1, and other genes) in *Camelina* to obtain an increase in oleic acid (18:1) and/or a decrease in VLCFA in the seed oil as measured by relative percent or absolute yield. The advantage of this method is that an RNAi expression vector can contain a double strand RNA that simultaneously suppresses one or more homologous genes. This is extremely helpful in *Camelina* as the inventors proved it is an allohexaploid species.

Using RNAi technology to knock down expression of all FAD2 genes and/or all FAE1 genes may be more convenient than classic breeding method. Whereas both sense- and antisense-mediated gene silencing have proven fruitful for PTGS in plant cells, RNAi induction can be more efficiently achieved by specialized expression cassettes that produce self-complementary hairpin (hp)-like RNA molecules. Such cassettes typically include plant promoter and terminator sequences that control the expression of two inversely repeated sequences of the target genes that are separated by a specific spacer.

Upon delivery to plant cells, expression of an RNAi cassette will result in a dsRNA molecule composed of two distinct regions: a single-stranded loop, encoded by the spacer region, and a double-stranded stem, encoded by the inverted repeats. It is the stem region that is used as a substrate by the dicer, but, because the spacer itself can potentially be recognized as a substrate as well, intron sequences are often used in the construction of such RNAi vectors (e.g. Meyer et al., 2004, Vectors for RNAi technology in poplar. Plant Biol (Stuttg) 6: 100-103). These vectors include, but are not limited to, pHANNIBAL, pKANNIBAL, pHELLSGATE, pSAT, pCAMBIA, pGREEN, et al. RNAi (or hpRNA) plant expression can potentially be delivered to plant cells by various means of transformation but are typically used by incorporating into binary plasmids to be delivered to plant cells by *Agrobacterium*-mediated transformation.

Fatty acid synthesis genes that are potential targets include, any one of FAD2 genes and/or any one of FAE1 genes as provided in the present invention, or alternatively along with any other genes involved in *Camelina* fatty acid synthesis as described herein or elsewhere.

A non-limiting example of using RNAi technology to suppress *Camelina* FAD2 genes is described below. A complete hpRNA expression cassette is composed of four distinct regions: a promoter and terminator sequence, the ChsA intron sequence, and a dual MCS. The dual MCS results from cloning of the ChsA intron sequence into pSAT6-MCS and dividing the original MCS into two new, distinct regions, designated MCS-I and MCS-II, which contain the following unique restriction endonuclease recognition sites: NcoI, BspEI, BglII, XhoI, SacI, and EcoRI in MCS-I and PstI, SalI, KpnI, SacII, ApaI, XmaI, SmaI, BamHI, and XbaI in MCS-II. The two MCS regions allow the successive cloning of the target gene sequence in reverse orientation and assembly of a hpRNA sequence. In pSAT6.35S.RNAi, expression of hpRNA is controlled by tandem CaMV 35S promoter (35SP) and CaMV 35S terminator (35ST), conferring a complete expression cassette. In pSAT6.Napin.RNAi, expression of hpRNA is controlled by Napin plant seed-specific promoter. hpRNA designed according to conserved, specific 19 to 29, 19 to 27, or 19 to 21 polynucleotides of FAD2 A, FAD2 B, and FAD2 C genes, which does not share homology to other genes, are introduced into either pSAT6.35S.RNAi or pSAT6.Napin.RNA vector to make the final RNAi construct. Such conserved, specific 15-21 polynucleotides sequences can be designed by one of ordinary skill in the art based on FAD2 genes disclosed in the present invention and known *Camelina* non-FAD2 gene sequences deposited in the GenBank.

Further, pSAT6.35S.RNAi or pSAT6.Napin.RNA vector containing the hpRNA targeting FAD2 genes is transformed into *Camelina* plant using the method described in WO2009/117555, and positive transformants are selected. Northern blot or qPCR is used to verify if one or more FAD2 genes are suppressed in the transformants. The transgenic lines with the most efficient suppression in all FAD2 genes are subjected to fatty acid composition analysis by GC, and the results indicate such transgenic *Camelina* plants have an increased oleic acid (18:1) level and/or reduced polyunsaturated fatty acids level in the seed oil compared to transgenic *Camelina* plants with empty control vector.

In addition, another pSAT6.35S.RNAi or pSAT6.Napin.RNA vector containing the hpRNA targeting FAE1 genes is transformed into *Camelina* plant using the method described in WO2009/117555, and positive transformants are selected. Northern blot or qPCR is used to verify if one or more FAE1 genes are suppressed in the transformants. The transgenic lines with the most efficient suppression in all FAE1 genes are subjected to fatty acid composition analysis by GC, and the results indicate such transgenic *Camelina* plants have a decreased long chain fatty acid level, and/or reduced long chain polyunsaturated fatty acids level in the seed oil compared to transgenic *Camelina* plants with empty control vector.

Example 15

Fatty Acid Composition in *Camelina* Plants Having Suppressed FAD2 and/or FAE1 Gene Functions in Combination with Overexpression or Suppression of Other Non-FAD and Non-FAE Fatty Acid Synthesis Genes Other fatty acid synthesis enzymes may be manipulated in the fatty acid synthesis pathways to increase the amount of oleic acid (18:1) or decrease the amount of palmitic acid (16:0) to create *Camelina* oil with fatty acid profiles optimal for biodiesel production. Lower amounts of 16:0 saturated fatty acid and higher amounts of 18:1 monounsaturated fatty acid is desirable for a good balance of proper cetane number, cloud point, oxidative stability, and reduced NOx emissions, as mentioned in the Background and Example 9.

Three key enzymes regulate the amount of 16:0, 18:0 and 18:1 fatty acids (FIG. 13): acyl-acyl carrier protein thioesterase (also known as FATB), β-ketoacyl-acyl carrier protein (ACP) synthase II (KAS II) and Δ-9 desaturase. FATB hydrolyzes the fatty acyl group from acyl carrier protein (ACP) and thus determines the amount and type of fatty acid that is exported from the plastid. Suppression of FATB leads to a reduction in 16:0 and 18:0 (stearic acid) released to the cytoplasm. KAS II converts palmitoyl-ACP (16:0-ACP) to stearoyl-ACP (18:0 ACP), and thus the overexpression of KAS II leads to an increase in the amount of 16:0 being converted to 18:0. Δ-9 desaturase converts 18:0-ACP to oleoyl-ACP (18:1-ACP), and thus the overexpression of Δ-9 desaturase leads to an increase in the amount of 18:0 being converted to 18:1. Since the product of KAS II activity (18:0-ACP) is the substrate for Δ-9 desaturase, the overexpression of both KAS II and Δ-9 desaturase will lead to a further decrease in 16:0 and 18:0 and an increase in 18:1.

*Camelina* lines having suppressed FAD2 and/or FAE1 gene functions, as described in the present invention, obtained either by TILLING or transgenic means (e.g., antisense, RNAi), may be combined with overexpression or suppression of the non-FAD and non-FAE genes described in this example to create new *Camelina* lines with even greater percentages of 18:1 fatty acid and/or lesser percentages of 16:0 and/or 18:0 fatty acids compared to lines with only FAD2/FAE1 modifications or only non-FAD/non-FAE modifications.

For example, *Camelina* FAD2 and/or FAE1 mutant plants, permutations of which are described in Example 13, may be combined by breeding with a *Camelina* plant overexpressing KAS II in a seed-specific manner to create a new *Camelina* line where the amount of 18:1 is higher and the amount of 16:0 is lower compared to either parent plant alone. The seed-specific overexpression of KAS II may also indirectly decrease the amount of 18:2 and/or 18:3 polyunsaturated fatty acids.

Alternatively, *Camelina* FAD2 and/or FAE1 mutant plants may be combined by breeding with a *Camelina* plant overexpressing Δ-9 desaturase in a seed-specific manner to create a new *Camelina* line where the amount of 18:1 is higher and the amount of 16:0 is lower compared to either parent plant alone. This combination may also decrease the amount of very long chain fatty acids.

In addition, *Camelina* FAD2 and/or FAE1 mutant plants may be combined by breeding with a *Camelina* plant overexpressing both KAS II and Δ-9 desaturase in a seed-specific manner to create a new *Camelina* line where the amount of 18:1 is higher and the amount of 16:0 is lower compared to any of the original parent modifications (FAD2/FAE1 suppression, KAS II overexpression or Δ-9 desaturase overexpression) alone.

Optionally, *Camelina* FAD2 and/or FAE1 mutant plants may be combined by breeding with a *Camelina* plant knocked out for FATB function (either by TILLING or transgenic means with a seed-specific promoter) to create a new *Camelina* line where the amount of 18:1 is higher and the amount of 16:0 is lower compared to either parent plant alone. *Arabidopsis* FATB knockout plants are compromised in growth and produce less viable seeds (Bonaventure et al, The Plant Cell, Vol. 15, 1020-1033, April 2003). This detrimental phenotype may be alleviated in a polyploid like *Camelina*, where the presence of multiple copies for a given gene may allow greater flexibility in manipulating the levels of camelina FATB. Alternatively, the detrimental FATB knockout phenotype may be alleviated by only suppressing or knocking out FATB function using a FATB antisense or RNAi construct driven by a seed-specific promoter.

Other combinations of FAD2/FAE1 suppression, KAS II seed-specific overexpression, Δ-9 desaturase seed-specific overexpression and/or FATB suppression may be envisioned to obtain *Camelina* plants with increased 18:1 and decreased 16:0 and/or 18:0.

Example 16

*Camelina* Plants Having Mutations in FAD2 and/or FAE1 Genes in Combination with Overexpression of REV/KRP Genes for Altered Fatty Acid Composition and Increased Seed Yield The purpose of suppressing *Camelina* FAD2 and/or FAE1 functions is to obtain an altered fatty acid profile of *Camelina* oil more suitable for conversion to biodiesel. Another attribute that would contribute to improvement of the oilseed crop for biofuel purposes would be an increase in seed yield, either by an increase in total seed number or seed size, in order to increase the amount of oil recovered per unit of land. Two yield technologies, REV and KRP dominant negative, have been described (US 2008/263727 and US 2007/056058, incorporated by reference in their entireties) that give increased seed yield when overexpressed under early embryo-specific promoters.

*Camelina* FAD2 and/or FAE1 mutant plants, permutations of which are described in Example 13, may be combined by breeding with a *Camelina* plant overexpressing REV in an early embryo-specific manner to create a new *Camelina* line with greater seed yield and high 18:1 and/or low VLCFAs compared to either parent plant alone.

Similarly, *Camelina* FAD2 and/or FAE1 mutant plants may be combined by breeding with a *Camelina* plant overexpressing KRP dominant negative in an early embryo-specific or constitutive manner to create a new *Camelina* line with greater seed yield and high 18:1 and/or low VLCFAs compared to either parent plant alone.

Additionally, *Camelina* FAD2 and/or FAE1 mutant plants may be combined by breeding with a *Camelina* plant overexpressing both REV and KRP dominant negative in an early embryo-specific (or constitutive for KRP) manner to create a new *Camelina* line with greater seed yield and high 18:1 and/or low VLCFAs compared to any of the original parent modifications (FAD2/FAE1 suppression, early embryo-specific REV overexpression or embryo-specific or constitutive KRP dominant negative overexpression) alone.

In view of the many possible embodiments to which the principles of the disclosed invention may be applied, it should be recognized that the illustrated embodiments are only examples and should not be taken as limiting the scope of the invention.

Unless defined otherwise, all technical and scientific terms herein have the same meaning as commonly understood by one of ordinary skill in the art to which this invention belongs. Definitions of common terms in molecular biology may be found in Benjamin Lewin, *Genes IX*, published by Oxford University Press, 2007 (ISBN-10 0131439812); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: A Comprehensive Desk Reference*, published by VCH Publishers, Inc., 1995 (ISBN 1-56081-569-8); *Oxford Dictionary of Biochemistry and Molecular Biology*, Revised Edition, 2000. Although any methods and materials, similar or equivalent to those described herein, can be used in the practice or testing of the present invention, the preferred methods and materials are described herein.

All publications, patents, and patent publications cited are incorporated by reference herein in their entirety for all purposes. Also incorporated by reference herein are nucleic acid sequences and polypeptide sequences deposited into the GenBank, which are cited in this specification.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES (2010). "Maize Genome Browser." from http://maizesequence.org/index.html.
(2010). "Phytozome." from http://www.phytozome.net/index.php.
(2010). "TIGR Rice Database." from http://rice.tigr.org/.
Abramovic, H. and V. Abram (2005). "Physico-chemical properties, composition and oxidative stability of *Camelina sativa* oil." *Food Technology and Biotechnology* 43: 63-70.
Adams, K. L., R. Percifield, et al. (2004). "Organ-specific silencing of duplicated genes in a newly synthesized cotton allotetraploid." *Genetics* 168(4): 2217-26.
Akeroyd, J. (1993). *Camelina in Flora Europaea*. Cambridge, UK, Cambridge University Press.
Al-Shehbaz, I., M. Beilstein, et al. (2006). "Systematics and phylogeny of the Brassicaceae (Cruciferae): an overview." *Plant Systematics and Evolution* 259(2): 89-120.
ASTM D6751-09: Standard Specification for Biodiesel Fuel Blend Stock (B100) for Middle Distillate Fuels. West Conshohocken, Pa., ASTM.
Baksay, L. (1957). "The chromosome numbers and cytotaxonomical relations of some European plant species." *Ann. Hist.-Nat. Mus. Natl. Hung*(8): 169-174.
Beilstein, M. A., I. A. Al-Shehbaz, et al. (2006). "Brassicaceae phylogeny and trichome evolution." *Am. J. Bot.* 93(4): 607-619.
Beilstein, M. A., I. A. Al-Shehbaz, et al. (2008). "Brassicaceae phylogeny inferred from phytochrome A and ndhF sequence data: tribes and trichomes revisited." *Am. J. Bot.* 95(10): 1307-1327.
Belo, A., P. Zheng, et al. (2008). "Whole genome scan detects an allelic variant of fad2 associated with increased oleic acid levels in maize." *Mol Genet Genomics* 279(1): 1-10.
Bernardo, A., R. Howard-Hildige, et al. (2003). "*Camelina* oil as a fuel for diesel transport engines." *Industrial Crops and Products* 17(3): 191-197.
Brochmann, C., A. K. Brysting, et al. (2004). "Polyploidy in arctic plants." *Biological Journal of the Linnean Society* 82(4): 521-536.
Brooks, R. E. (1985). "Chromosome number reports LXXXVII" *Taxon* 34: 346-351.
Budin, J., W. Breene, et al. (1995). "Some compositional properties of camelina (*camelina sativa* L. Crantz) seeds and oils" *Journal of the American Oil Chemists' Society* 72(3): 309-315.
Cahoon, E. B., E. F. Marillia, et al. (2000). "Production of fatty acid components of meadowfoam oil in somatic soybean embryos." *Plant Physiol* 124(1): 243-51.
Comai, L. (2005). "The advantages and disadvantages of being polyploid." *Nat Rev Genet.* 6(11): 836-46.
Comai, L., A. P. Tyagi, et al. (2000). "Phenotypic instability and rapid gene silencing in newly formed *arabidopsis* allotetraploids." *Plant Cell* 12(9): 1551-68.
Cooper, J., B. Till, et al. (2008). "TILLING to detect induced mutations in soybean." *BMC Plant Biology* 8(1): 9.
Dubcovsky, J. and J. Dvorak (2007). "Genome plasticity a key factor in the success of polyploid wheat under domestication." *Science* 316(5833): 1862-6.
Durrett, T. P., C. Benning, et al. (2008). "Plant triacylglycerols as feedstocks for the production of biofuels." *Plant J* 54(4): 593-607.
EMBnet, S. "Boxshade." from <http://www.ch.embnet.org/>.
Flannery, M. L., F. J. Mitchell, et al. (2006). "Plastid genome characterisation in *Brassica* and Brassicaceae using a new set of nine SSRs." *Theor Appl Genet.* 113(7): 1221-31.
Francis, A. and S. Warwick (2009). "The Biology of Canadian Weeds. 142. *Camelina alyssum* (Mill.) Thell.; *C. microcarpa* Andrz. ex DC.; *C. sativa* (L.) Crantz." *Canadian Journal of Plant Science* 89: 791-810.
Frohlich, A. and B. Rice (2005). "Evaluation of *Camelina sativa* oil as a feedstock for biodiesel production." *Industrial Crops and Products* 21(1): 25-31.
Frohlich, M. W. and G. F. Estabrook (2000). "Wilkinson support calculated with exact probabilities: an example using Floricaula/LEAFY amino acid sequences that compares three hypotheses involving gene gain/loss in seed plants." *Mol Biol Evol* 17(12): 1914-25.

Gehringer, A., W. Friedt, et al. (2006). "Genetic mapping of agronomic traits in false flax (*Camelina sativa* subsp. *sativa*)." *Genome* 49(12): 1555-63.

Ghanevati, M. and J. G. Jaworski (2001). "Active-site residues of a plant membrane-bound fatty acid elongase beta-ketoacyl-CoA synthase, FAE1 KCS." *Biochim Biophys Acta* 1530(1): 77-85.

Ghanevati, M. and J. G. Jaworski (2002). "Engineering and mechanistic studies of the *Arabidopsis* FAE1 beta-ketoacyl-CoA synthase, FAE1 KCS." *Eur J Biochem* 269(14): 3531-9.

Gill, B. S, and B. Friebe (1998). "Plant cytogenetics at the dawn of the 21st century" *Current Opinion in Plant Biology* 1(2): 109-115.

GRIN, U. "USDA Germplasm Resources Information Network." from http://www.ars-grin.gov/cgi-bin/npgs/html/index.pl?language=en.

Gugel, R. K. and K. C. Falk (2006). "Agronomic and seed quality evaluation of *Camelina sativa* in western Canada." *Canadian journal of plant science* 86(4): 1047-1058

Han, J., W. Labs, et al. (2001). "Functional characterization of β-ketoacyl-CoA synthase genes from *Brassica napus* L." *Plant Mol Biol* 46(2): 229-239.

He, P., B. R. Friebe, et al. (2003). "Allopolyploidy alters gene expression in the highly stable hexaploid wheat." *Plant Mol Biol* 52(2): 401-14.

Hegarty, M. J. and S. J. Hiscock (2008). "Genomic Clues to the Evolutionary Success of Polyploid Plants." 18(10): R435-R444.

Hernandez, M. L., M. Mancha, et al. (2005). "Molecular cloning and characterization of genes encoding two microsomal oleate desaturases (FAD2) from olive." *Phytochemistry* 66(12): 1417-26.

Hongtrakul, V., M. B. Slabaugh, et al. (1998). "A Seed Specific {Delta}-12 Oleate Desaturase Gene Is Duplicated, Rearranged, and Weakly Expressed in High Oleic Acid Sunflower Lines." *Crop Sci* 38(5): 1245-1249.

Hu, X., M. Sullivan-Gilbert, et al. (2006). "Mapping of the loci controlling oleic and linolenic acid contents and development of fad2 and fad3 allele-specific markers in canola (*Brassica napus* L.)." *Theor Appl Genet.* 113(3): 497-507.

James Jr, D. W., E. Lim, et al. (1995). "Directed Tagging of the *Arabidopsis* FATTY ACID ELONGATION1 (FAE1) Gene with the Maize Transposon Activator." *Plant Cell* 7(3): 309-319.

Kashkush, K., M. Feldman, et al. (2002). "Gene loss, silencing and activation in a newly synthesized wheat allotetraploid." *Genetics* 160(4): 1651-9.

Katavic, V., E. Mietkiewska, et al. (2002). "Restoring enzyme activity in nonfunctional low erucic acid *Brassica napus* fatty acid elongase 1 by a single amino acid substitution." *Eur J Biochem* 269(22): 5625-31.

Kim, M. J., H. Kim, et al. (2006). "Seed-specific expression of sesame microsomal oleic acid desaturase is controlled by combinatorial properties between negative cis-regulatory elements in the SeFAD2 promoter and enhancers in the 5'-UTR intron." *Mol Genet Genomics* 276(4): 351-68.

Knothe, G. (2005). "Dependence of biodiesel fuel properties on the structure of fatty acid alkyl esters" *Fuel Processing Technology* 86(10): 1059-1070.

Knothe, G. and R. Dunn (2003). "Dependence of oil stability index of fatty compounds on their structure and concentration and presence of metals." *Journal of the American Oil Chemists' Society* 80(10): 1021-1026.

Kunst, L., D. Taylor, et al. (1992). "Fatty acid elongation in developing seeds of *Arabidopsis thaliana*." *Plant Physiol Biochem* 30(4): 425-434.

Li, W., L. Huang, et al. (2008). "Recurrent Deletions of Puroindoline Genes at the Grain Hardness Locus in Four Independent Lineages of Polyploid Wheat1." *Plant Physiol.* 146(1): 200-212.

Lu, C., Kang, J (2008). "Generation of transgenic plants of a potential oilseed crop *Camelina sativa* by *Agrobacterium*-mediated transformation." *Plant Cell Reports* 27: 273-278.

Maassoumi, A. (1980). Cruciferes de la flore d'Iran: etude caryosystematique. Strasbourg, France, Strasbourg, France. Thesis.

Maddison, W., and Maddison, D R (2004). MacClade: analysis of phylogeny and character evolution. Sunderland, MA, Sinauer.

Maizel J V and Lenk R P: Enhanced graphic matrix analysis of nucleic acid and protein sequences. Proc Natl Acad Sci USA 78:7665, 1981.

Martínez-Rivas, J. M., P. Sperling, et al. (2001). "Spatial and temporal regulation of three different microsomal oleate desaturase genes (FAD2) from normal-type and high-oleic varieties of sunflower (*Helianthus annuus* L.)." *Molecular Breeding* 8(2): 159-168.

Martynov, V. V., I. L. Tsvetkov, et al. (2004). "Orthologs of arabidopsis CLAVATA 1 gene in cultivated Brassicaceae plants." *Ontogenez* 35(1): 41-6.

McCartney, A. W., J. M. Dyer, et al. (2004). "Membrane-bound fatty acid desaturases are inserted co-translationally into the ER and contain different ER retrieval motifs at their carboxy termini." *Plant J* 37(2): 156-73.

McCormick, R. L., M. S. Graboski, et al. (2001). "Impact of Biodiesel Source Material and Chemical Structure on Emissions of Criteria Pollutants from a Heavy-Duty Engine." *Environmental Science & Technology* 35(9): 1742-1747.

Mietkiewska, E., E. M. Giblin, et al. (2004). "Seed-specific heterologous expression of a nasturtium FAE gene in *Arabidopsis* results in a dramatic increase in the proportion of erucic acid." *Plant Physiol* 136(1): 2665-75.

Mikkilineni, V. and T. R. Rocheford (2003). "Sequence variation and genomic organization of fatty acid desaturase-2 (fad2) and fatty acid desaturase-6 (fad6) cDNAs in maize." *Theor Appl Genet.* 106(7): 1326-32.

Mirek, Z. (1981). "Genus *Camelina* in Poland—Taxonomy, Distribution and Habitats." *Fragmenta Floristica et Geobotanica* 27: 445-503.

Moon, H., M. A. Smith, et al. (2001). "A Condensing Enzyme from the Seeds of Lesquerella fendleri That Specifically Elongates Hydroxy Fatty Acids." *Plant Physiol.* 127(4): 1635-1643.

Muramatsu, M. (1963). "Dosage Effect of the Spelta Gene q of Hexaploid Wheat." *Genetics* 48(4): 469-482.

Ní Eidhin, D., J. Burke, et al. (2003). "Oxidative Stability of C9; 3-rich *Camelina* Oil and *Camelina* Oil-based Spread Compared with Plant and Fish Oils and Sunflower Spread." *Journal of Food Science* 68(1): 345-353

Okuley, J., J. Lightner, et al. (1994). "*Arabidopsis* FAD2 gene encodes the enzyme that is essential for polyunsaturated lipid synthesis." *Plant Cell* 6(1): 147-58.

Park, C., D. Correll, et al. (2004). Measuring Allele-Specific Expression Using MassARRAY. *Sequenom Application Note.* Doc No. 8876-005 R01.

Patel, M., S. Jung, et al. (2004). "High-oleate peanut mutants result from a MITE insertion into the FAD2 gene." *TAG Theoretical and Applied Genetics* 108(8): 1492-1502.

Posada, D. and K. Crandall (1998). "Modeltest: testing the model of DNA substitution."*Bioinformatics* 14(9): 817-818.

Pustell J and Kafatos F C: A high speed, high capacity homology matrix: Zooming through SV40 and polyoma. Nucleic Acids Res 10:4765, 1982.

Putnam, D., J. Budin, et al. (1993). *Camelina*: a promising low-input oilseed. *New crops*. J. Janick, and Simon, J E New York, Wiley: 314-322.

Quigley G J, Gehrke L, Roth D A and Auron P E: Computer-aided nucleic acid secondary structure modeling incorporating enzymatic digestion data. Nucleic Acids Res 12:347, 1984.

Rice, B., A. Frohlich, et al. (1997). Biodiesel production based on waste cooking oil: Promotion of the Establishment of an Industry in Ireland. Dublin, Ireland, Teagasc Agriculture and Food Development Authority.

Ruuska, S. A., T. Girke, et al. (2002). "Contrapuntal networks of gene expression during *Arabidopsis* seed filling." *Plant Cell* 14(6): 1191-206.

Saghai-Maroof, M. A., K. M. Soliman, et al. (1984). "Ribosomal DNA spacer-length polymorphisms in barley: mendelian inheritance, chromosomal location, and population dynamics." *Proc Natl Acad Sci USA* 81(24): 8014-8.

Salmon, A., Ainouche, M L, Wendel, J F, (2005). "Genetic and epigenetic consequences of recent hybridization and polyploidy in *Spartina* (Poaceae)." *Molecular Ecology* 14(4): 1163-1175.

Scheffler, J. A., A. G. Sharpe, et al. (1997). "Desaturase multigene families of *Brassica napus* arose through genome duplication." *Theoretical and Applied Genetics* 94(5): 583-591.

Schlueter, J. A., J. Y. Lin, et al. (2007). "Gene duplication and paleopolyploidy in soybean and the implications for whole genome sequencing." *BMC Genomics* 8: 330.

Serdari, A., E. Lois, et al. (1999). "Impact of Esters of Mono- and Dicarboxylic Acids on Diesel Fuel Quality." *Industrial & Engineering Chemistry Research* 38(9): 3543-3548.

Slade, A. J., S. I. Fuerstenberg, et al. (2005). "A reverse genetic, nontransgenic approach to wheat crop improvement by TILLING." *Nat Biotechnol* 23(1): 75-81.

Stadler, L. J. (1929). "Chromosome Number and the Mutation Rate in Avena and Triticum." *Proc Natl Acad Sci USA* 15(12): 876-81.

Stournas, S., Lois, E., Serdari, A. (1995). "Effects of fatty acid derivatives on the ignition quality and cold flow of diesel fuel" *Journal of the American Oil Chemists' Society* 72(4): 433-437.

Swaminathan, M. S, and M. V. Rao (1960). "Frequency of Mutations Induced by Radiations in Hexaploid Species of Triticum." *Science* 132(3442): 1842.

Swofford, D. (2001). PAUP*4.0 beta 5: Phylogenetic Analysis Using Parsimony and Other Methods. Sunderland, MA, Sinauer.

Sybenga, J. (1996). "Chromosome pairing affinity and quadrivalent formation in polyploids: do segmental allopolyploids exist?" *Genome* 39: 1176-1184.

Tai, H. H., C. Pelletier, et al. (2004). "Total RNA isolation from *Picea mariana* dry seed" *Plant Molecular Biolgy Reporter* 22(1): 93a-93e.

TAIR. (2009). "The *Arabidopsis* Information Resource." from http://www.arabidopsis.org.

Tedin, O. (1925). "Vererbung, Variation and Systematik in der Gattung *Camelina.*" *Hereditas* 6: 19-386.

Tocher D R, L. M., Hodgson P A (1998). "Recent advances in the biochemistry and molecular biology of fatty acyl desaturases" *Progress in Lipid Research* 37(2-3): 73-117.

Tom Maniatis, J. S., E. F. Fritsch (1982). *Molecular cloning: a laboratory manual*. Cold Spring Harbor, N.Y., Cold Spring Harbor Laboratory.

Vollmann, J., H. Grausgruber, et al. (2005). "Genetic diversity in camelina germplasm as revealed by seed quality characteristics and RAPD polymorphism." *Plant Breeding* 124(5): 446-453.

Wang, N., Y. Wang, et al. (2008). "A functional genomics resource for *Brassica napus*: development of an EMS mutagenized population and discovery of FAE1 point mutations by TILLING." *New Phytol* 180(4): 751-65.

Worgetter, M., H. Prankl, et al. (2006). Local and Innovative Biodiesel. Wieselburg, Austria, FJ-BLT Wieselburg.

Wu, G., Y. Wu, et al. (2008). "Zero erucic acid trait of rapeseed (*Brassica napus* L.) results from a deletion of four base pairs in the fatty acid elongase 1 gene." *Theor Appl Genet.* 116(4): 491-9.

Zubr, J. (1997). "Oil-seed crop: *Camelina sativa.*" Industrial Crops and Products 6(2): 113-119.

Zubr, J., Matthaus, B. (2002). "Effects of growth conditions on fatty acids and tocopherols in *Camelina sativa* oil." *Industrial Crops and Products* 15: 155-162.

Pustell J and Kafatos F C: A high speed, high capacity homology matrix: Zooming through SV40 and polyoma. *Nucleic Acids Res* 10:4765, 1982.

Quigley G J, Gehrke L, Roth D A and Auron P E: Computer-aided nucleic acid secondary structure modeling incorporating enzymatic digestion data. *Nucleic Acids Res* 12:347, 1984.

The invention claimed is:

1. A method of altering and/or improving fatty acid composition of a *Camelina* plant cell, plant part, tissue culture or whole plant, the method comprising disrupting one, two, or three copies of FAD2 genes and/or one, two or three copies of FAE1 genes in said *Camelina* plant cell, plant part, tissue culture or whole plant.

2. The method of claim 1, wherein the disruption is achieved by one or more mutations selected from the mutations listed in Tables 7 to 12 for a particular FAD2 or FAE1 gene.

3. A method of breeding *Camelina* plants to produce altered levels of fatty acids in seed oil and/or meal, wherein the method comprises
   i) making a cross between a *Camelina* plant with one or more mutations listed in Tables 7-12 with a second *Camelina* plant to produce an F1 plant;
   ii) backcrossing the F1 plant to the second *Camelina* plant; and
   iii) repeating the backcrossing step to generate a near isogenic line, wherein the one or more mutations are integrated into the genome of the second *Camelina* plant; wherein the near isogenic line derived from the second *Camelina* plant with the integrated mutations has altered seed oil composition compared to that of the second *Camelina* plant without the integrated mutations; wherein the mutations disrupt two or three homologous copies of endogenous FAD2 and/or two or three homologous copies of FAE1 genes.

4. The method of claim 3, wherein the near isogenic line has an increased oleic acid (18:1) level, and/or reduced polyunsaturated fatty acids level and/or reduced very long chain fatty acids (C>18) level in the seed oil and/or meal compared to that of the second *Camelina* plant without the integrated mutation or mutations.

* * * * *

UNITED STATES PATENT AND TRADEMARK OFFICE
CERTIFICATE OF CORRECTION

| | | |
|---|---|---|
| PATENT NO. | : 9,035,131 B2 | Page 1 of 1 |
| APPLICATION NO. | : 13/072122 | |
| DATED | : May 19, 2015 | |
| INVENTOR(S) | : Carolyn Hutcheon et al. | |

It is certified that error appears in the above-identified patent and that said Letters Patent is hereby corrected as shown below:

In the Specification

Column 2,
Line 67, "(Han, Labs" should read --(Han, Lühs--.

Column 3,
Line 27, "la fore" should read --la flore--.

Column 43,
Line 9, "1155 by" should read --1155 bp--.

Column 43,
Line 46, "1518 by" should read --1518 bp--.

Column 49,
Line 53, "189 by" should read --189 bp--.

Column 79,
Line 24, "W. Labs," should read --W. Lühs,--.

Signed and Sealed this
Twenty-sixth Day of January, 2016

Michelle K. Lee
*Director of the United States Patent and Trademark Office*